(12) United States Patent
Takagi et al.

(10) Patent No.: US 8,470,798 B2
(45) Date of Patent: Jun. 25, 2013

(54) CANCER CELL-SPECIFIC APOPTOSIS-INDUCING AGENTS THAT TARGET CHROMOSOME STABILIZATION-ASSOCIATED GENES

(75) Inventors: Motoki Takagi, Shinagawa-ku (JP);
Kazunobu Futami, Fujisawa (JP);
Akira Shimamoto, Hiroshima (JP);
Yasuhiro Furuichi, Kamakura (JP)

(73) Assignee: Genecare Research Institute Co., Ltd., Kanagawa (JP)

( * ) Notice: Subject to any disclaimer, the term of this patent is extended or adjusted under 35 U.S.C. 154(b) by 0 days.

(21) Appl. No.: 13/473,328

(22) Filed: May 16, 2012

(65) Prior Publication Data

US 2012/0225928 A1 Sep. 6, 2012

Related U.S. Application Data

(62) Division of application No. 11/547,770, filed as application No. PCT/JP2005/006914 on Apr. 8, 2005, now Pat. No. 8,193,332.

(30) Foreign Application Priority Data

Apr. 9, 2004 (JP) ................................ 2004-115404

(51) Int. Cl.
*C12N 15/11* (2006.01)
*C12N 15/00* (2006.01)
*C07H 21/02* (2006.01)

(52) U.S. Cl.
USPC ..................... 514/44 A; 536/24.5; 435/320.1

(58) Field of Classification Search
None
See application file for complete search history.

(56) References Cited

U.S. PATENT DOCUMENTS

| | | | |
|---|---|---|---|
| 5,919,643 | A | 7/1999 | Kelley et al. |
| 2005/0255487 | A1 | 11/2005 | Khvorova et al. |
| 2007/0031844 | A1 | 2/2007 | Khvorova et al. |
| 2007/0243570 | A1 | 10/2007 | Takagi et al. |
| 2009/0028861 | A1 | 1/2009 | Takagi et al. |
| 2009/0215867 | A1 | 8/2009 | Takagi et al. |
| 2010/0168209 | A1 | 7/2010 | Takagi et al. |

FOREIGN PATENT DOCUMENTS

| | | |
|---|---|---|
| WO | 01/62964 A2 | 8/2001 |
| WO | 02/09573 A2 | 2/2002 |
| WO | 02/102981 A2 | 12/2002 |
| WO | 03/046207 A2 | 6/2003 |
| WO | 03/073826 A2 | 9/2003 |
| WO | 03/074654 A2 | 9/2003 |
| WO | 03/105891 A2 | 12/2003 |
| WO | 2004/033666 A2 | 4/2004 |
| WO | 2004/091548 A2 | 10/2004 |
| WO | 2004/094636 A1 | 11/2004 |
| WO | 2004/100990 A1 | 11/2004 |

OTHER PUBLICATIONS

Akimitsu, N. et al., "Induction of apoptosis by depletion of DNA topoisomerase IIα in mammalian cells," *Biochemical and Biophysical Research Communications* 307: 301-307, 2003.
Carney, J. et al., "The hMre11/hRad50 Protein Complex and Nijmegen Breakage Syndrome: Linkage of Double-Strand Break Repair to the Cellular DNA Damage Response," *Cell* 93: 477-486, May 1, 1998.
Chen, Z. et al., "Human Chk1 Expression Is Dispensable for Somatic Cell Death and Critical for Sustaining G2 DNA Damage Checkpoint," *Molecular Cancer Therapeutics* 2: 543-548, Jun. 2003.
Cheng, T.-J. et al., "Kinetic studies of human tyrosyl-DNA phosphodiesterase, an enzyme in the topoisomerase I DNA repair pathway," *Eur. J. Biochem.* 269: 3697-3704, 2002.
Habelhah, H. et al., "Ubiquitination and translocation of TRAF2 is required for activation of JNK but not of p38 or NF-κB," *The EMBO Journal* 23(2): 322-332, 2004.
Hiraoka, L. et al., "Sequence of Human FEN-1, a Structure-Specific Endonuclease, and Chromosomal Localization of the Gene (*FEN1*) in Mouse and Human," *Genomics* 25: 220-225, 1995.
Jilani, A. et al., "Molecular Cloning of the Human Gene, *PNKP*, Encoding a Polynucleotide Kinase 3'-Phosphatase and Evidence for Its Role in Repair of DNA Strand Breaks Caused by Oxidative Damage," *The J. of Biol. Chem.* 274(34): 24176-24186, Aug. 20, 1999.
Koike, G. et al., "Purification, Structure, and Biochemical Properties of Human $O^6$-Methylguanine-DNA Methyltransferase," *The J. of Biol. Chem.* 265(25): 14754-14762, Sep. 5, 1990.
Li, Z. et al., "The *XRCC4* Gene Encodes a Novel Protein Involved in DNA Double-Strand Break Repair and V(D)J Recombination," *Cell* 83: 1079-1089, Dec. 29, 1995.
Merkle, C. et al., "Cloning and Characterization of hCTF18, hCTF8, and hDCC1," *The J. of Biol. Chem.* 278(32): 30051-30056, Aug. 8, 2003.
Mimori, T. et al., "Isolation and characterization of cDNA encoding the 80-kDa subunit protein of the human autoantigen Ku (p70/p80) recognized by autoantibodies from patients with scleroderma-polymyositis overlap syndrome," *Proc. Natl. Acad. Sci. USA* 87: 1777-1781, Mar. 1990.
Nakatsu, Y. et al., "XAB2, a Novel Tetratricopeptide Repeat Protein Involved in Transcription-coupled DNA Repair and Transcription," *The J. of Biol. Chem.* 275(45):.34931-34937, Nov. 10, 2000.
Nigg, E., "Centrosome Aberrations: Cause or Consequence of Cancer Progression?" *Nature Reviews—Cancer* 2: 1-11, Nov. 2002.
North, B. et al., "The Human Sir2 Ortholog, SIRT2, Is an NAD+-Dependent Tubulin Deacetylase," *Mol. Cell* 11: 437-444, Feb. 2003.
O'Donovan, A. et al., "XPG endonuclease makes the 3' incision in human DNA nucleotide excision repair," *Nature* 371: 432-435, Sep. 29, 1994.

(Continued)

*Primary Examiner* — Richard Schnizer
(74) *Attorney, Agent, or Firm* — Seed IP Law Group PLLC

(57) ABSTRACT

The present inventors discovered that inhibition of the expression of various genes associated with chromosome stabilization induces cancer cell-specific apoptosis and inhibits cell proliferation. Compounds that inhibit expression of a gene associated with chromosome stabilization or inhibit the function of a protein encoded by such a gene are thought to have cancer cell-specific apoptosis-inducing effects.

10 Claims, 36 Drawing Sheets

OTHER PUBLICATIONS

Parker, A. et al., "A Human Homologue of the *Schizosaccharomyces pombe rad1+* Checkpoint Gene Encodes an Exonuclease," *The J. of Biol. Chem.* 273(29): 18332-18339, Jul. 17, 1998.

Takanami, T. et al., "*Caenorhabditis elegans Ce-rdh-1/rad-51* functions after double-strand break formation of meiotic recombination," *Chromosome Research* 11: 125-135, 2003.

Tombline, G. et al., "Biochemical Characterization of the Human RAD51 Protein: II. Adenosine Nucleotide Binding and Competition," *The J. of Biol. Chem.* 277(17): 14426-14433, Apr. 26, 2002.

Tugal, T. et al., "The Orc4p and Orc5p Subunits of the *Xenopus* and Human Origin Recognition Complex Are Related to Orc1p and Cdc6p," *The J. of Biol. Chem.* 273(49): 32421-32429, Dec. 4, 1998.

Vaisman, A. et al., "Human DNA Polymerase ι Promiscuous Mismatch Extension," *The J. of Biol. Chem.* 276(33): 30615-30622, Aug. 17, 2001.

Volkmer, E. et al., "Human Homologs of *Schizosaccharomyces pombe* Rad1, Hus1, and Rad9 Form a DNA Damage-responsive Protein Complex," *The J. of Biol. Chem.* 274(2): 567-570, Jan. 8, 1999.

Wang, F. et al., "*Caenorhabditis elegans* EVL-14/PDS-5 and SCC-3 Are Essential for Sister Chromatid Cohesion in Meiosis and Mitosis," *Mol. and Cell. Biol.* 23(21): 7698-7707, Nov. 2003.

Wang, X. et al., "An Overactivated ATR/CHK1 Pathway Is Responsible for the Prolonged $G_2$ Accumulation in Irradiated AT Cells," *The J. of Biol. Chem.* 278(33): 30869-30874, Aug. 15, 2003.

Wilson III, D. et al., "Hex1: a new human Rad2 nuclease family member with homology to yeast exonuclease 1," *Nucleic Acids Research* 26(16): 3762-3768, 1998.

Babu et al., "Rae1 is an essential mitotic checkpoint regulator that cooperates with Bub3 to prevent chromosome missegregation," *The Journal of Cell Biology* 160(3):341-353, 2003.

U.S. Appl. No. 13/629,226, filed Sep. 27, 2012, entitled "Apoptosis Inducer for Cancer Cell," 58 pages.

Chen et al., "HEC, a Novel Nuclear Protein Rich in Leucine Heptad Repeats Specifically Involved in Mitosis," *Molecular and Cellular Biology* 17(10):6049-6056, 1997.

Cummings et al., "Modulation of cisplatin resistance by siRNA-mediated targeting of NER genes." *Proc Amer Assoc Cancer Res* 45:709, 2004. (Abstract Only).

Machida et al., "Hepatitis C virus induces a mutator phenotype. Enhanced mutations of immunoglobulin and protooncogenes," *PNAS* 101(12):4262-4267, 2004.

Takagi et al., "Cancer-Cell-Specific Cytostatic Agent," U.S. Appl. No. 13/671,118, filed Nov. 7, 2012, 32 pages.

Wang et al., "Pol ι Is a Candidate for the Mouse Pulmonary Adenoma Resistance 2 Locus, a Major Modifier of Chemically Induced Lung Neoplasia," *Cancer Research* 64:1924-1931, 2004.

Yang et al., "Altered DNA Polymerase ι Expression in Breast Cancer Cells Leads to a Reduction in DNA Replication Fidelity and a Higher Rate of Mutagenesis," *Cancer Research* 64:5597-5607, 2004.

Afshar, G. et al., "Characterization of a human gene with sequence homology to *Saccharomyces cerevisiae SIR2*," *Gene* 234: 161-168, 1999.

Akimitsu, N. et al., "Induction of apoptosis by depletion of DNA topoisomerase IIα in mammalian cells," *Biochemical and Biophysical Research Communications* 307: 301-307, 2003.

Aspinwall, R. et al., "Cloning and characterization of a functional human homolog of *Escherichia coli* endonuclease III," *Proc. Natl. Acad. Sci. USA* 94: 109-114, Jan. 1997.

Barnes, D. et al., "Human DNA ligase I cDNA: Cloning and functional expression in *Saccharomyces cerevisiae*," *Proc. Natl. Acad. Sci. USA* 87: 6679-6683, Sep. 1990.

Bernstein, H. et al., "A Mammalian Homolog of Fission Yeast Cdc5 Regulates G2 Progression and Mitotic Entry," *The Journal of Biological Chemistry* 273(8): 4666-4671, Feb. 20, 1998.

Bharadwaj, R. et al., "Identification of Two Novel Components of the Human NDC80 Kinetochore Complex," *The Journal of Biological Chemistry* 279(13): 13076-13085, Mar. 26, 2004.

Bochkarev, A. et al., "Structure of the single-stranded-DNA-binding domain of replication protein A bound to DNA," *Nature* 385: 176-181, Jan. 9, 1997.

Bruun, D. et al., "siRNA depletion of BRCA1, but not BRCA2, causes increased genome instability in Fanconi anemia cells," *DNA Repair* 2: 1007-1013, 2003.

Budd, M. et al., "A yeast gene required for DNA replication encodes a protein with homology to DNA helicases," *Proc. Natl. Acad. Sci. USA* 92: 7642-7646, Aug. 1995.

Budd, M. et al., "*DNA2* Encodes a DNA Helicase Essential for Replication of Eukaryotic Chromosomes," *The Journal of Biological Chemistry* 270(45): 26766-26769, Nov. 10, 1995.

Carney, J. et al., "The hMre11/hRad50 Protein Complex and Nijmegen Breakage Syndrome: Linkage of Double-Strand Break Repair to the Cellular DNA Damage Response," *Cell* 93: 477-486, May 1, 1998.

Casper, A. et al., "ATR Regulates Fragile Site Stability," *Cell* 111: 779-789, Dec. 13, 2002.

Chen, Z. et al., "Human Chk1 Expression Is Dispensable for Somatic Cell Death and Critical for Sustaining G2 DNA Damage Checkpoint," *Molecular Cancer Therapeutics* 2: 543-548, Jun. 2003.

Cheng, T.-J. et al., "Kinetic studies of human tyrosyl-DNA phosphodiesterase, an enzyme in the topoisomerase I DNA repair pathway," *Eur. J. Biochem.* 269:3697-3704, 2002.

Christensen, T. et al., "*Drosophila* Mcm10 Interacts with Members of the Prereplication Complex and Is Required for Proper Chromomsome Condensation," *Molecular Biology of the Cell* 14: 2206-2215, Jun. 2003.

Collis, S. et al., "Enhanced Radiation and Chemothereapy-mediated Cell Killing of Human Cancer Cells by Small Inhibitory RNA Silencing of DNA Repair Factors," *Cancer Research* 63: 1550-1554, Apr. 1, 2003.

D'Arpa, P. et al., "cDNA cloning of human DNA topoisomerase I: Catalytic activity of a 67.7-kDa carboxyl-terminal fragment," *Proc. Natl. Acad. Sci. USA* 85: 2543-2547, Apr. 1988.

Erdile, L. et al., "The Primary Structure of the 32-kDa Subunit of Human Replication Protein A," *The Journal of Biological Chemistry* 265(6): 3177-3182, Feb. 25, 1990.

Feng, D. et al., "Inhibiting the Expression of DNA Replication-Initiation Proteins Induces Apoptosis in Human Cancer Cells," *Cancer Research* 63: 7356-7364, Nov. 1, 2003.

Fishel, M. et al., "Imbalancing the DNA Base Excision Repair Pathway in the Mitochondria; Targeting and Overexpressing *N*-Methylpurine DNA Glycosylase in Mitochondria Leads to Enhanced Cell Killing," *Cancer Research* 63: 608-615, Feb. 1, 2003.

Fishel, R. et al., "Purified Human MSH2 Proteing Binds to DNA Containing Mismatched Nucleotides," *Cancer Research* 54: 5539-5542, Nov. 1, 1994.

Glockzin, S. et al., "Involvment of the DNA Repair Protein hHR23 in p53 Degradation," *Molecular and Cellular Biology* 23(24): 8960-8969, Dec. 2003.

Gozuacik, D. et al., "Identification and functional characterization of a new member of the human Mcm protein family: hMcm8," *Nucleic Acids Research* 31(2): 570-579, 2003.

Habelhah, H. et al., "Ubiquitination and translocation of TRAF2 is required for activation of JNK but not of p38 or NF-κB," *The EMBO Journal* 23(2): 322-332, 2004.

Hadi, M. et al., "Determinants in Nuclease Specificity of Ape1 and Ape2, Human Homologues of *Escherichia coli* Exonuclease III," *J. Mol. Biol.* 316: 853-866, 2002.

Hazra, T. et al., "Identification and Characterization of a Novel Human DNA Glycosylase for Repair of Cytosine-derived Lesions," *The J. of Biol. Chem.* 277(34): 30417-30420, Aug. 23, 2002.

Hendrich, B. et al., "Identification and Characterization of a Family of Mammalian Methyl-CpG Binding Proteins," *Molecular and Cellular Biology* 18(11): 6538-6547, Nov. 1998.

Henning, K. et al., "The Cockayne Syndrome Group A Gene Encodes a WD Repeat Protein That Interacts with CSB Protein and a Subunit of RNA Polymerase II TFIIH," *Cell* 82: 555-564, Aug. 25, 1995.

Hiraoka, L. et al., "Sequence of Human FEN-1, a Structure-Specific Endonuclease, and Chromosomal Localization of the Gene (*FEN1*) in Mouse and Human," *Genomics* 25:220-225, 1995.

Hofmann, R. et al., "Noncanonical *MMS2*-Encoded Ubiquitin-Conjugating Enzyme Functions in Assembly of Novel Polyubiquitin Chains for DNA Repair," *Cell* 96: 645-653, Mar. 5, 1999.

Ikejima, M. et al., "The Zinc Fingers of Human Poly(ADP-ribose) Polymerase Are Differentially Required for the Recognition of DNA Breaks and Nicks and the Consequent Enzyme Activation," *The J. of Biol. Chem.* 265(35): 21907-21913, Dec. 15, 1990.

Ishimi, Y. et al., "A DNA Helicase Activity Is Associated with an MCM4, -6, and -7 Protein Complex," *The J. of Biol. Chem.* 272(39): 24508-24513, Sep. 26, 1997.

Ishimi, Y. et al., "Biochemical Function of Mouse Minichromosome Maintenance 2 Protein," *The J. of Biol. Chem.* 273(14): 8369-8375, Apr. 3, 1998.

Jezewska, M. et al., "Dynamics of Gapped DNA Recognition by Human Polymerase β," *The J. of Biol. Chem.* 277(23): 20316-20327, Jun. 7, 2002.

Jilani, A. et al., "Molecular Cloning of the Human Gene, *PNKP*, Encoding a Polynucleotide Kinase 3'-Phosphatase and Evidence for Its Role in Repair of DNA Strand Breaks Caused by Oxidative Damage," *The J. of Biol. Chem.* 274(34): 24176-24186, Aug. 20, 1999.

Johnson, R. et al., "Mammalian XRCC2 promotes the repair of DNA double-strand breaks by homologous recombination," *Nature* 401: 397-399, Sep. 23, 1999.

Kanaar, R. et al., "Human and mouse homologs of the *Saccharomyces cerevisiae RAD54* DNA repair gene: evidence for functional conservation," *Current Biology* 6(7): 828-838, May 20, 1996.

Keeney, S. et al., "Characterization of a Human DNA Damage Binding Protein Implicated in Xeroderma Pigmentosum E," *The J. of Biol. Chem.* 268(28): 21293-21300, Oct. 5, 1993.

Kim, J. et al., "The Novel Human DNA Helicase hFBH1 Is an F-box protein," *The J. of Biol. Chem.* 277(27): 24530-24537, Jul. 5, 2002.

Kim, S. et al., "TIN2, a new regulator of telomere length in human cells," *Nature Genetics* 23: 405-412, Dec. 1999.

Koike, G. et al., "Purification, Structure, and Biochemical Properties of Human $O^6$ Methylguanine-DNA Methyltransferase," *The J. of Biol. Chem.* 265(25): 14754-14762, Sep. 5, 1990.

Koken, M. et al., "Structural and functional conservation of two human homologs of the yeast DNA repair *RAD6*," *Proc. Natl. Acad. Sci. USA* 88: 8865-8869, Oct. 1991.

Kollmannsberger, C. et al., "Topotecan—A Novel Topoisomerase I Inhibitor: Pharmacology and Clinical Experience," *Oncology* 56: 1-12, 1999.

Krause, D. et al., "Suppression of Tousled-like kinase activity after DNA damage or replication block requires ATM, NBS1 and Chk1," *Oncogene* 22: 5927-5937, 2003.

Krishna, T. et al., "Crystal Structure of the Eukaryotic DNA Polymerase Processivity Factor PCNA," *Cell* 79: 1233-1243, Dec. 30, 1994.

Kubota, Y. et al., "A novel ring-like complex of *Xenopus* proteins essential for the initiation of DNA replication," *Genes & Development* 17: 1141-1152, 2003.

Kukimoto, I. et al., "Human CDC45 protein binds to minichromosome maintenance 7 protein and the p70 subunit of DNA polymerase α," *Eur. J. Biochem.* 265: 936-943, 1999.

Ladner, R. et al., "Characterization of Distinct Nuclear and Mitochondrial Forms of Human Deoxyuridine Triphosphate Nucleotidohydrolase," *The J. of Biol. Chem.* 271(13): 7745-7751, Mar. 29, 1996.

Lee, K.-H. et al., "Dna2 Requirement for Normal Reproduction of *Caenorhabditis elegans* Is Temperature-dependent," *Mol. Cells* 15(1): 81-86, Nov. 28, 2002.

Leonard, J. et al., "Reduction of Stability of Arabidopsis Genomic and Transgenic DNA-Repeat Sequences (Microsatellites) by Inactivation of AtMSH2 Mismatch-Repair Function," *Plant Physiology* 133: 328-338, Sep. 2003.

Li, Y. et al., "Identification and Cloning of Two Histone Fold Motif-containing Subunits of HeLa DNA Polymerase ε," *The J. of Biol. Chem.* 275(30): 23247-23252, Jul. 28, 2000.

Li, Z. et al., "The XRCC4 Gene Encodes a Novel Protein Involved in DNA Double-Strand Break Repair and V(D)J Recombination," *Cell* 83:1079-1089, Dec. 29, 1995.

Liu, L. et al., "Identification of a Fourth Subunit of Mammalian DNA Polymerase δ," *The J. of Biol. Chem.* 275(25): 18739-18744, Jun. 23, 2000.

Martin-Lluesma, S. et al., "Role of Hec1 in Spindle Checkpoint Signaling and Kinetochore Recruitment of Mad1/Mad2," *Science* 297: 2267-2270, Sep. 27, 2002.

Masson, J.-Y. et al., "Identification and purification of two distinct complexes containing the five RAD51 paralogs," *Genes & Development* 15: 3296-3307, 2001.

Masutani, C. et al., "Purification and cloning of a nucleotide excision repair complex involving the xeroderma pigmentosum group C protein and a human homologue of yeast RAD23," *The EMBO Journal* 13(8): 1831-1843, 1994.

McGarry, T. et al., "Geminin, an Inhibitor of DNA Replication, Is Degraded during Mitosis," *Cell* 93: 1043-1053, Jun. 12, 1998.

Merchant, A. et al., "A Lesion in the DNA Replication Initiation Factor Mcm10 Induces Pausing of Elongation Forks through Chromosomal Replication Origins in *Saccharomyces cerevisiae*," *Molecular and Cellular Biology* 17(6): 3261-3271, Jun. 1997.

Merkle, C. et al., "Cloning and Characterization of hCTF18, hCTF8, and hDCC1," *The J. of Biol. Chem.* 278(32):30051-30056, Aug. 8, 2003.

Mihaylov, I. et al., "Control of DNA Replication and Chromosome Ploidy by Geminin and Cyclin A," *Molecular and Cellular Biology* 22(6): 1868-1880, Mar. 2002.

Miller, H. et al., "Hot Topics in DNA Repair No. 6: DNA repair investigations using siRNA," *DNA Repair* 2: 759-763, 2002.

Mimori, T. et al., "Isolation and characterization of cDNA encoding the 80-kDa subunit protein of the human autoantigen Ku (p70/p80) recognized by autoantibodies from patients with scleroderma-polymyositis overlap syndrome," *Proc. Natl. Acad. Sci. USA* 87:1777-1781, Mar. 1990.

Morland, I. et al., "Human DNA glycosylases of the bacterial Fpg/MutM superfamily: an alternative pathway for the repair of 8-oxoguanine and other oxidation products in DNA," *Nucleic Acids Research* 30(22): 4926-4936, 2002.

Nakatsu, Y. et al., "XAB2, a Novel Tetratricopeptide Repeat Protein Involved in Transcription-coupled DNA Repair and Transcription," *The J. of Biol. Chem.* 275(45): 34931-34937, Nov. 10, 2000.

Neddermann, P. et al., "The Purification of a Mismatch-specific Thymine-DNA Glycosylase from HeLa Cells," *The J. of Biol. Chem.* 268(28): 21218-21224, Oct. 5, 1993.

Nigg, E., "Centrosome Aberrations: Cause or Consequence of Cancer Progression?" *Nature Reviews —Cancer* 2: 1-11, Nov. 2002.

North, B. et al., "The Human Sir2 Ortholog, SIRT2, Is an $NAS^+$-Dependent Tubulin Deacetylase," *Mol. Cell* 11: 437-444, Feb. 2003.

Nyberg, K. et al., "Toward Maintaining the Genome: DNA Damage and Replication Checkpoints," *Annu. Rev. Genet.* 36: 617-656, 2002.

O'Donovan, A. et al., "XPG endonuclease makes the 3' incision in human DNA nucleotide excision repair," *Nature* 371: 432-435, Sep. 29, 1994.

Ohta, S. et al., "The ORC1 Cycle in Human Cells," *The J. of Biol. Chem.* 278(42): 41535-41540, Oct. 17, 2003.

Olsen, L. et al., "Molecular cloning of human uracil—DNA glycosylase, a highly conserved DNA repair enzyme," *The EMBO Journal* 8(10): 3121-3125, 1989.

Parker, A. et al., "A Human Homologue of the *Schizosaccharomyces pombe rad1*[+]Checkpoint Gene Encodes an Exonuclease," *The J. of Biol. Chem.* 273(29): 18332-18339, Jul. 17, 1998.

Poot, R. et al., "HuCHRAC, a human ISWI chromatin remodeling complex contains hACF1 and two novel histone-fold proteins," *The EMBO Journal* 19(13): 3377-3387, 2000.

Pouliot, J. et al., "Yeast Gene for a Tyr-DNA Phosphodiesterase that Repairs Topoisomerase I Complexes," *Science* 286: 552-555, Oct. 15, 1999.

Quinn, J. et al., "BRCA1 Functions as a Differential Modulator of Chemotherapy-induced Apoptosis," *Cancer Research* 63: 6221-6228, Oct. 1, 2003.

Rich, T. et al., "Defying death after DNA damage," *Nature* 407: 777-783, Oct. 12, 2000.

Rodriguez, J. et al., "Nuclear-cytoplasmic shuttling of BARD1 contributes to its proapoptotic activity and is regulated by dimerization with BRCA1," *Oncogene* 23: 1809-1820, 2004.

Sanchez, Y. et al., "Conservation of the Chk1 Checkpoint Pathway in Mammals: Linkage of DNA Damage to Cdk Regulation Through Cdc25," *Science* 277: 1497-1501, Sep. 5, 1997.

Sangoram, A. et al., "Mammalian Circadian Autoregulatory Loop: A *Timeless* Ortholog and *mPer1* Interact and Negatively Regulate CLOCK-BMAL1-Induced Transcription," *Neuron* 21: 1101-1113, Nov. 1998.

Schauber, C. et al., "Rad23 links DNA repair to the ubiquitin/proteasome pathway," *Nature* 391: 715-718, Feb. 12, 1998.

Selby, C. et al., "Human Transcription-Repair Coupling Factor CSB/ERCC6 Is a DNA-stimulated ATPase but Is Not a Helicase and Does Not Disrupt the Ternary Transcription Complex of Stalled RNA Polymerase II," *The J. of Biol. Chem.* 272(3): 1885-1890, Jan. 17, 1997.

Shiloh, Y., "ATM and ATR: networking cellular responses to DNA damage," *Current Opinion in Genetics & Development* 11: 71-77, 2001.

Sijbers, A. et al., "Xeroderma Pigmentosum Group F Caused by a Defect in a Structure-Specific DNA Repair Endonuclease," *Cell* 86: 811-822, Sep. 6, 1996.

Sogo, J. et al., "Fork Reversal and ssDNA Accumulation at Stalled replication Forks Owing to Checkpoint Defects," *Science* 297: 599-602, Jul. 26, 2002.

Sordet, O. et al., "Apoptosis Induced by Topoisomerase Inhibitors," *Curr. Med. Chem.—Anti-Cancer Agents* 3: 271-290, 2003.

Stadlbauer, F. et al., "DNA replication *in vitro* by recombinant DNA-polymerase-α-primase," *Eur. J. Biochem.* 222: 781-793, 1994.

Stoeber, K. et al., "Cdc6 protein causes premature entry into S phase in a mammalian cell-free system," *The EMBO Journal* 17(24): 7219-7229, 1998.

Sumara, I. et al., "Characterization of Vertebrate Cohesin Complexes and Their Regulation in Prophase," *The J. of Cell Biol.* 151(4): 749-761, Nov. 13, 2000.

Takanami, T. et al., "*Caenorhabditis elegans* Ce-rdh-I/rad-51 functions after double-strand break formation of meiotic recombination," *Chromosome Research* 11: 125-135, 2003.

Takata, K. et al., "*Drosophila* damage-specific DNA-binding protein 1 (D-DDB1) is controlled by the DRE-DREF system," *Nucleic Acids Research* 30(17): 3795-3808, 2002.

Tang, J. et al., "Xeroderma pigmentosum complementation group E and UV-damaged DNA-binding protein," *DNA Repair* 1: 601-616, 2002.

Tombline, G. et al., "Biochemical Characterization of the Human RAD51 Protein: I. ATP Hydrolysis," *The J. of Biol. Chem.* 277(17): 14417-14425, Apr. 26, 2002.

Tombline, G. et al., "Biochemical Characterization of the Human RAD51 Protein: II. Adenosine Nucleotide Binding and Competition," *The J. of Biol. Chem.* 277(17): 1442614433, Apr. 26, 2002.

Tombline, G. et al., "Biochemical Characterization of the Human RAD51 Protein: III. Modulation of DNA Binding by Adenosine Nucleotides," *The J. of Biol. Chem.* 277(17): 14434-14442, Apr. 26, 2002.

Tugal, T. et al., "The Orc4p and Orc5p Subunits of the *Xenopus* and Human Origin Recognition Complex Are Related to Orc1p and Cdc6p," *The J. of Biol. Chem.* 273(49): 32421-32429, Dec. 4, 1998.

Ulane, C. et al., "Paramyxoviruses SV5 and HPIV2 Assemble STAT Protein Ubiquitin Ligase Complexes from Cellular Components," *Virology* 304: 160-166, 2002.

Vaisman, A. et al., "Human DNA Polymerase ι Promiscuous Mismatch Extension," *The J. of Biol. Chem.* 276(33):30615-30622, Aug. 17, 2001.

Vandenberg, C. et al., "BRCA1-Independent Ubiquitination of FANCD2," *Molecular Cell* 12: 247-254, Jul. 2003.

Volkmer, E. et al., "Human Homologs of *Schizosaccharomyces pombe* Rad1, Hus1, and Rad9 Form a DNA Damage-responsive Protein Complex," *The J. of Biol. Chem.* 274(2):567-570, Jan. 8, 1999.

Wang, F. et al., "*Caenorhabditis elegans* EVL-14/PDS-5 and SCC-3 Are Essential for Sister Chromatid Cohesion in Meiosis and Mitosis," *Mol. and Cell. Biol.* 23(21):7698-7707, Nov. 2003.

Wang, X. et al., "An Overactivated ATR/CHK1 Pathway Is Responsible for the Prolonged $G_2$ Accumulation in Irradiated AT Cells," *The J. of Biol. Chem.* 278(33):30869-30874, Aug. 15, 2003.

Wang, Y. et al., "Knockdown of Chk1, Wee1 and Myt1 by RNA Interference Abrogates $G_2$ Checkpoint and Induces Apoptosis," *Cancer Bio. & Therapy* 3(3): 305-313, Mar. 2004.

Wilson III, D. et al., "Hex 1: a new human Rad2 nuclease family member with homology to yeast exonuclease 1," *Nucleic Acids Research* 26(16): 3762-3768, 1998.

Wohlschlegel, J. et al., "Inhibition of Eukaryotic DNA Repolication by Geminin Binding to Cdt1," *Science* 290: 2309-2312, Dec. 22, 2000.

Wood, R. et al., "Human DNA Repair Genes," *Science* 291: 1284-1289, Feb. 16, 2001.

Xiao, Z. et al., "Chk1 Mediates S and $G_2$ Arrests through Cdc25A Degradation in Response to DNA-damaging Agents," *The J. of Biol. Chem.* 278(24): 21767-21773, Jun. 13, 2003.

Xin, H. et al., "The human *RAD18* gene product interacts with HHR6A and HHR6B," *Nucleic Acids Research* 28(14): 2847-2854, 2000.

Yarden, R. et al., "BRCA1 regulates the G2/M checkpoint by activating Chk1 kinase upon DNA damage," *Nature Genetics* 30: 285-289, Mar. 2002.

Yuan, Z. et al., "Polymorhphisms and HNPCC: PMS2-MLH1 Protein Interactions Diminished by Single Nucleotide Polymorphisms," *Human Mutation* 19: 108-113, 2002.

Zhang, X. et al., "Hoechst 33342-Induced Apoptosis Is Associated With Intracellular Accumulation of E2F-1 Protein in BC3H-1 Myocytes and HL-60 Cells," *Arch. Pathol. Lab Med.* 125: 99-104, Jan. 2001.

Zhao, H. et al., "Disruption of the checkpoint kinase 1/cell division cycle 25A pathway abrogates ionizing radiation-induced S and $G_2$ checkpoints," *PNAS* 99(23): 14795-14800, Nov. 12, 2002.

Zhou, B.-B. et al., "Targeting the Checkpoint Kinases: Chemosensitization Versus Chemoprotection," *Nature Reviews—Cancer* 4: 1-10, Mar. 2004.

Ziv, I. et al., "Neuronal Apoptosis Induced by Dopamine Is Associated With Cell Cycle-Related Events: Clues for Nigral Degeneration in Parkinson's Disease?" *Neurology* 46: A269-A270, Feb. 1996.

Ishimi, Y., "A DNA Helicase Activity Is Associated with an MCM4, -6, and -7 Protein Complex," *The J. of Biol. Chem.* 272(39): 24508-24513, Sep. 26, 1997.

Kanaar, R. et al., "Human and mouse homologs of the *Saccharomyces cerevisiae* RAD54 DNA repair gene: evidence for functional conservation," *Current Biology* 6(7): 828-838, Jul. 1, 1996.

Lee, K.-H. et al., "Dna2 Requirement for Normal Reproduction of *Caenorhabditis elegans* Is Temperature-dependent," *Mol. Cells* 15(1): 81-86, Feb. 28, 2003.

Miller, H. et al., "Hot Topics in DNA Repair No. 6: DNA repair investigations using siRNA," *DNA Repair* 2: 759-763, Jun. 11, 2003.

Sato, N. et al., "Human and *Xenopus* cDNAs encoding budding yeast Cdc7-related kinases: *in vitro* phosphorylation of MCM subunits by a putative human homologue of Cdc7," *The EMBO Journal* 16(14): 4340-4351, Jul. 16, 1997.

Hans et al., "Overexpression of dominant negative PARP interferes with tumor formation of HeLa cells in nude mice: Evidence for increased tumor cell apoptosis in vivo," Oncogene 18:7010-7015, 1999.

Ide et al., "Characterization of the genomic structure and expression of the mouse *Apex2* gene," Genomics 81:47-57, 2003.

Patry et al., "Small Interfering RNA-Mediated Reduction in Heterogeneous Nuclear Ribonucleoparticule A1/A2 Proteins Induces Apoptosis in Human Cancer Cells but not in Normal Mortal Cell Lines," Cancer Research 63:7679-7688, Nov. 15, 2003.

Babu et al., "Rael is an essential mitotic checkpoint regulator that cooperates with Bub3 to prevent chromosome missegregation," *The Journal of Cell Biology* 160(3):341-353, 2003.

Dai et al., "Slippage of Mitotic Arrest and Enhanced Tumor Development in Mice with *BubR1* Haploinsufficiency," Cancer Res 64:440-445, 2004.

Michel et al., "MAD2 haplo-insufficiency causes premature anaphase and chromosome instability in mammalian cells," Nature 409:355-359, 2001.

FIG. 1

| FUNCTION | GENE NAME | ACCESSION NUMBER | siRNA SEQUENCE | SEQ ID NO | INHIBITION OF GENE EXPRESSION IN HELA CELLS | MTT ASSAY (HELA CELLS) | TUNEL METHOD | INHIBITION OF GENE EXPRESSION IN TIG3 CELLS | MTT ASSAY (TIG CELLS) |
|---|---|---|---|---|---|---|---|---|---|
| REPLICATION INITIATION | Mcm10 | NM_182751, NM_018518 | ggAAAAUCUggCCACUCUCdTdT | 724 | 2% | 52% | YES | 15% | 110% |
| | Orc1 | NM_004153 | ggUUgUUCCACCgAgAUUCdTdT | 725 | 2% | 29% | YES | 9% | 111% |
| | Orc3 | NM_181837, NM_012381 | ggAUgAACUgAUgACCAUAdTdT | 726 | 17% | 54% | YES | 20% | 132% |
| | Cdc6 | NM_001254 | ggCAAgAAAgAgAAUggUCdTdT | 727 | 0% | 58% | YES | 6% | 122% |
| | Cdt1 | NM_030928 | gCAgCUggCACAgAUgACgdTdT | 728 | 9% | 56% | YES | 19% | 111% |
| | Geminin | NM_015895 | ggCgCUgUAUgAAgCACUUdTdT | 729 | 1% | 69% | YES | 2% | 112% |
| | Mcm3 | NM_002388 | gAUgCAggAUgACAAUCAgdTdT | 730 | 2% | 43% | YES | 18% | 109% |
| | Mcm4 | NM_005914, X74794 | CAAAUgCAUUCUCAgCUAdTdT | 731 | 15% | 49% | YES | 24% | 107% |
| | Mcm5 | NM_006739 | ggAgUUCCUgCggCAgUACdTdT | 732 | 7% | 47% | YES | 10% | 95% |
| | Mcm6 | NM_005915 | gACCgUAAAgAgAUCCCUCdTdT | 733 | 0% | 25% | YES | 12% | 53% |
| | Mcm7 | NM_005916 | gCUCAUgAggCgUUACAUAdTdT | 734 | 1% | 48% | YES | 16% | 111% |
| | Mcm8 | NM_032485 | gUCUCAAAUgCggAAgAAgdTdT | 735 | 2% | 32% | YES | 8% | 66% |
| | Cdc7 | NM_003503 | gUAUgCCUUggUAgACUUUdTdT | 736 | 6% | 36% | YES | 16% | 93% |
| | Cdc5 | AK128737, NM_001253 | gAAgACgUUCAgCgACAACdTdT | 737 | 0% | 29% | YES | 17% | 106% |
| | Psf1 | NM_021067 | gUUCUggAggAgAUgAAAgdTdT | 738 | 0% | 49% | YES | 13% | 69% |
| | Psf2 | AF201939 | gCUggAUAAACUUgACCUgdTdT | 739 | 0% | 54% | YES | 10% | 63% |
| | Psf3 | BC005879 | ggACUUUUgACAACAAgCdTdT | 740 | 5% | 69% | YES | 20% | 94% |
| | Cdc45 | BC005879 | gAUgAUgACCUUgAAgUUCdTdT | 741 | 17% | 69% | YES | 18% | 69% |

FIG. 2

| FORK PROGRESSION | | | | | | | | | |
|---|---|---|---|---|---|---|---|---|---|
| | Polα p180 | X06745 | gAgCCAACCUgUCgCAAUCdTdT | 742 | 2% | 53% | YES | 18% | 96% |
| | Polα p70 | L24559, NM_002689 | gCAUgAACAggUggAgAAUdTdT | 743 | 9% | 24% | YES | 3% | 45% |
| | Polα Spp1 (Prim2a) | NM_000947 | ggAUAAAAUUCAggAUUUCdTdT | 744 | 0% | 65% | YES | 4% | 101% |
| | RPA70 | NM_002945 | gACggAAggAgAgUAgUUAdTdT | 745 | 0% | 25% | YES | 7% | 96% |
| | RPA34 | NM_002946 | gUggCAggCCACCUgAgAUdTdT | 746 | 5% | 69% | YES | 12% | 99% |
| | PCNA | NM_002592 | AAAgCCACUCCACUCUCUUdTdT | 747 | 2% | 33% | YES | 2% | 84% |
| | Elg1 | AJ314648 | gACUgUACgACACCUUUggdTdT | 748 | 11% | 61% | YES | 3% | 63% |
| | FEN1 | NM_004111 | gCACAAgAgCAUCgAggAgAdTdT | 749 | 2% | 63% | YES | 26% | 61% |
| | DNA2 | XM_166103 | gAUAAAUgCCgCUgAACUdTdT | 750 | 12% | 47% | YES | 31% | 49% |
| | Ligase1 | NM_000234 | gUCCUggAAgAgAgAgUgdTdT | 751 | 0% | 57% | YES | 7% | 80% |
| | Polδ p125 | M80397 | ggUgCAgAgCUACgAgAgdTdT | 752 | 7% | 55% | YES | 39% | 100% |
| | Polε Pol2 | L09561, NM_006231 | ggUggCUUUgCCCUAUAAAdTdT | 753 | 0% | 36% | YES | 16% | 65% |
| | Polε Dpb3 | AF226077, NM_017443 | gAggAAgAAgUAgACAACUdTdT | 754 | 2% | 29% | YES | 11% | 68% |
| | Polε Dpb4 | AF261688, NM_019896 | gAUgCCUACUgUUgCgCUCdTdT | 755 | 1% | 20% | YES | 21% | 40% |
| | Topoisomerase I | NM_003286 | gUUCCUgAgCCAgAUAACAdTdT | 756 | 0% | 40% | YES | 12% | 92% |
| | TDP1 | NM_018319 | gACgAgUAUgAgACAUCAgdTdT | 757 | 9% | 45% | YES | 12% | 44% |

FIG. 3

| | | | | | | | | |
|---|---|---|---|---|---|---|---|---|
| SISTER CHROMATID SEPARATION | Ctf18 | NM_022092 | gUggAAgAgCCACgAACAgdTdT | 758 | 10% | 41% | YES | 22% | 66% |
| | Scc1 | NM_006265 | gAACCgUACAgUgACAUCAgdTdT | 759 | 1% | 58% | YES | 9% | 57% |
| | Scc3 | Z75330, NM_005802 | gAgAgUgCUAACUgCCAAAdTdT | 760 | 0% | 61% | YES | 12% | 53% |
| CELL CYCLE CHECK POINT | ATR | NM_001184 | gACgUgUgCUCAUgCggCdTdT | 761 | 1% | 61% | YES | 19% | 88% |
| | Chk1 | NM_001274 | gCgUgCCgUAgACUgUCCAdTdT | 762 | 7% | 40% | YES | 2% | 96% |
| | NBS1 | NM_002485 | gCAgUACCAgAAAgUAgCAdTdT | 763 | 6% | 28% | YES | 12% | 55% |
| | Hus1 | NM_004507 | gCUggCUAAUggAggAgUgdTdT | 764 | 13% | 26% | YES | 18% | 59% |
| | Rad1 | NM_002853 | gCUAUUCAUUUCCgAgAACdTdT | 765 | 7% | 62% | YES | 13% | 51% |
| | Topoisomerase IIIb | AF053082, NM_003935 | ggUUAAACACUgACAAAgACdTdT | 766 | 8% | 59% | YES | 12% | 76% |
| | Rad6A | NM_003336 | gAAUAUCCAAAUAAACCACdTdT | 767 | 8% | 66% | YES | 12% | 98% |
| | Rad18 | NM_020165 | gAAAUAgUgUUCUACAUdTdT | 768 | 4% | 47% | YES | 11% | 129% |
| | Ubc13 | NM_003348 | gUACgUUUCAUgACCAAAAdTdT | 769 | 1% | 33% | YES | 4% | 94% |
| | FBH1 | AF380349 | gUAAACACUCAggAUUCCAdTdT | 770 | 2% | 37% | YES | 16% | 88% |
| | Mad2 | NM_002358 | gAUUggUUAUACAAgUUdTdT | 771 | 0% | 29% | YES | 10% | 69% |
| NUCLEOTIDE EXCISION REPAIR | XPC | NM_004628 | gAAgAgCCUUCUCUCCAAAdTdT | 772 | 1% | 29% | YES | 29% | 35% |
| | Rad23A | NM_005053 | gAUAgAAgCUgAgAAgggUdTdT | 773 | 3% | 28% | YES | 8% | 81% |
| | Rad23B | NM_002874 | gAUgCAACgAgUgCACUUgdTdT | 774 | 0% | 66% | YES | 10% | 80% |
| | CSA | NM_000082 | gUCACAAgCUgUUgAAUCAdTdT | 775 | 6% | 49% | YES | 14% | 76% |
| | CSB | NM_000124 | gCCUAAgAACUCUAAgCAUdTdT | 776 | 2% | 34% | YES | 12% | 148% |
| | XPG | NM_000123 | gAAgGCAUUAACAAAUACCdTdT | 777 | 0% | 21% | YES | 17% | 85% |
| | XPF | NM_005236 | CAgUCgCUAUgAAgUUUACdTdT | 778 | 5% | 37% | YES | 18% | 104% |
| | DDB1 | NM_001923 | ggUUgUggAggAgCUAACUdTdT | 779 | 4% | 24% | YES | 5% | 76% |
| | DDB2 | NM_000107 | gAgCgAgAUCCgAgUUUACdTdT | 780 | 0% | 56% | YES | 0% | 104% |
| | XAB2 | NM_020196 | gUUUUAUAggAGCAACggAdTdT | 781 | 3% | 23% | YES | 10% | 77% |

FIG. 4

| | | | Sequence | # | | | | | |
|---|---|---|---|---|---|---|---|---|---|
| BASE EXCISION REPAIR | UNG | NM_003362 | gUCuggCAAgAAgCCCAUUdTdT | 782 | 4% | 37% | YES | 15% | 88% |
| | MBD4 | NM_003925 | ggAUgUAggAAgAgCUgUUdTdT | 783 | 5% | 39% | YES | 14% | 85% |
| | TGD | NM_003211 | gAggCUCCAAAAggAAgAAdTdT | 784 | 17% | 40% | YES | 45% | 61% |
| | NTH1 | NM_002528 | ggAUgCACCUggACCAUdTdT | 785 | 4% | 53% | YES | 10% | 98% |
| | NEIL2 | NM_145043 | gUUCCAUCgAggACAAgCCdTdT | 786 | 0% | 51% | YES | 4% | 91% |
| | NEIL3 | NM_018248 | gCUACCgACUAgAAAUACUdTdT | 787 | 8% | 47% | YES | 9% | 95% |
| | APE2 | NM_014481 | gAUgCgCUUCUAUCgUUUgdTdT | 788 | 6% | 67% | YES | 27% | 97% |
| | PARP1 | NM_001618 | gCCACAgCUAggCAUgAUUdTdT | 789 | 1% | 42% | YES | 25% | 75% |
| | PNK | NM_007254 | gAAgCgUAUgCggAAgUCAdTdT | 790 | 14% | 54% | YES | 35% | 96% |
| | Polb | NM_002690 | gAAUUCCUCgUgAAgAgAUdTdT | 791 | 13% | 41% | YES | 12% | 71% |
| MISMATCH REPAIR | MSH2 | NM_000251 | ggUgUcUgUgAUCAAAgUUdTdT | 792 | 3% | 29% | YES | 25% | 67% |
| | PMS1 | NM_000534 | gAACggCUgCUgAUAUAUUdTdT | 793 | 10% | 69% | YES | 36% | 81% |
| | PMS2 | NM_000535 | ggUUggAACUCgACUgAUgdTdT | 794 | 7% | 63% | YES | 9% | 68% |
| | MLH3 | NM_014381 | gUUgUgCAgUgUgUUAACAdTdT | 795 | 6% | 67% | YES | 10% | 80% |
| | Exonuclease1 | NM_003686 | gAgACUggUUgACCAgAUdTdT | 796 | 2% | 44% | YES | 11% | 84% |
| SPECIALIZED DNA POLYMERASE | Poli | NM_007195 | ggACCUAAAgAACCUCAAgdTdT | 797 | 3% | 44% | YES | 23% | 74% |
| DOUBLE STRAND BREAK REPAIR | Rad51 | NM_002875 | gCUAUgUUCgCCAUUAAUgdTdT | 798 | 0% | 42% | YES | 7% | 101% |
| | Rad51D | NM_002878 | gAgrUAgCUCAgAAAUgUgdTdT | 799 | 13% | 54% | YES | 27% | 81% |
| | Xrcc2 | NM_005431 | gCCUCgAgCAUCAgAAgAUdTdT | 800 | 8% | 25% | YES | 29% | 83% |
| | Rad54 | NM_003579 | gUgUUggUCUggUCAUAUgdTdT | 801 | 11% | 43% | YES | 7% | 97% |
| | BRCA1 | NM_007295 | gCAgAUAgUUCUACCAgUAdTdT | 802 | 0% | 46% | YES | 13% | 71% |
| | Ku80 | NM_021141 | ggAUgAgAUUgCUUUAgUCdTdT | 803 | 1% | 65% | YES | 3% | 91% |
| | XRCC4 | NM_003401 | gAgUCUUgUUAUUUCUCUdTdT | 804 | 1% | 46% | YES | 9% | 91% |
| TELOMERE MAINTENANCE | Tin2 | NM_012461 | ggAAgAACAUgCgAUAUACdTdT | 805 | 4% | 56% | YES | 16% | 85% |
| | Sir2 | AF095714 | CAACCUAgAgAAgUACCAUdTdT | 805 | 8% | 61% | YES | 26% | 69% |
| OTHERS | MGMT | NM_002412 | gUgAUUCUUACCAgCAAUdTdT | 807 | 3% | 58% | YES | 13% | 93% |
| | DUT | NM_001948 | gAAgUUCAAgCCUUggAUgdTdT | 808 | 4% | 45% | YES | 17% | 101% |
| | TIMELESS | NM_003920, BC050557 | ggAgCUACCAgCAgAAUAgdTdT | 809 | 0% | 31% | YES | ND | 86% |

ND: NOT DETECTABLE

FIG. 9
Ku80 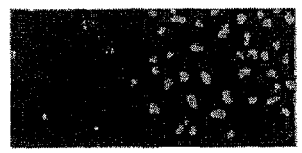
XRCC4 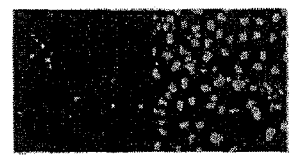
Tin2 
Sir2 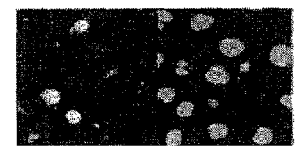
MGMT 
DUT 
Timeless 

FIG. 12
Mcm6
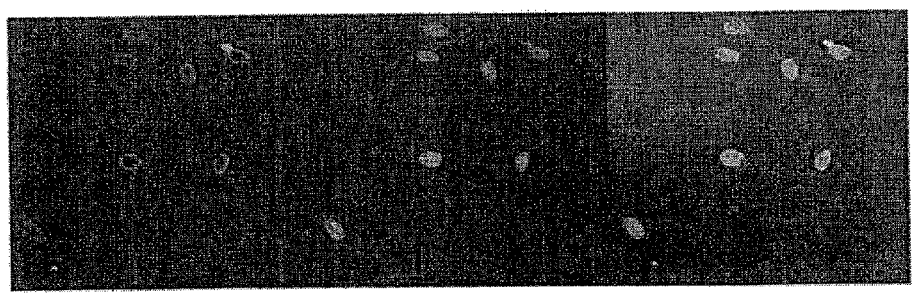
Mcm7
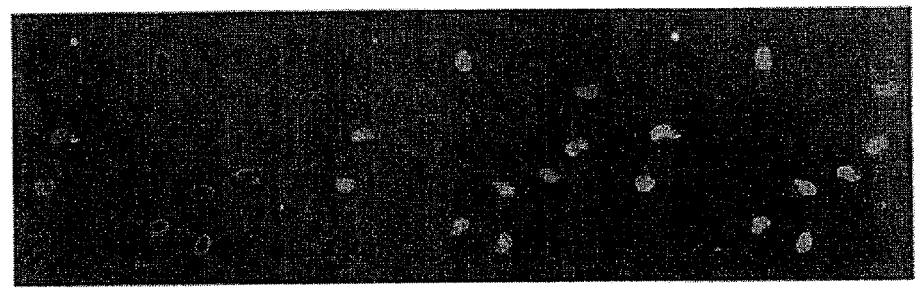
Mcm8
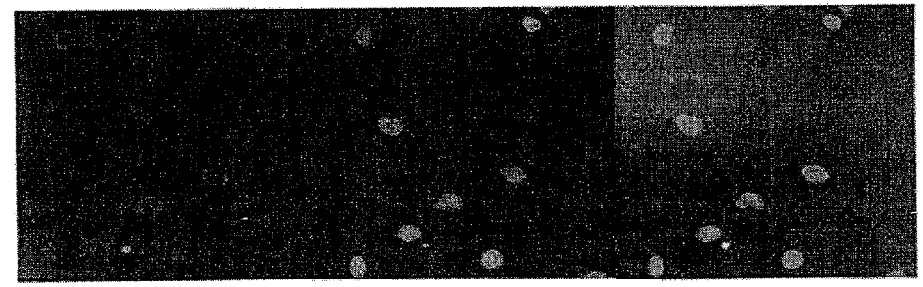
Cdc7
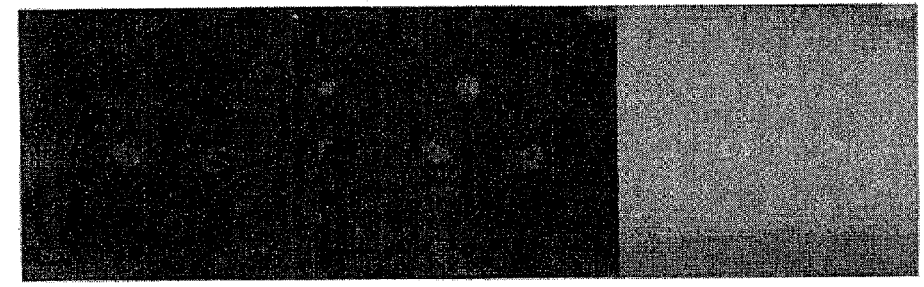
Cdc5
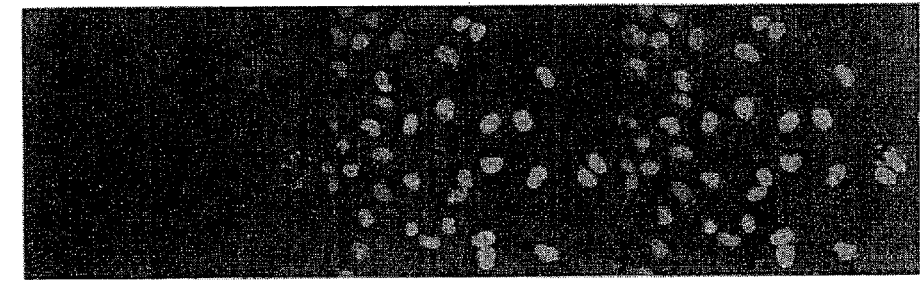

FIG. 19
Rad18
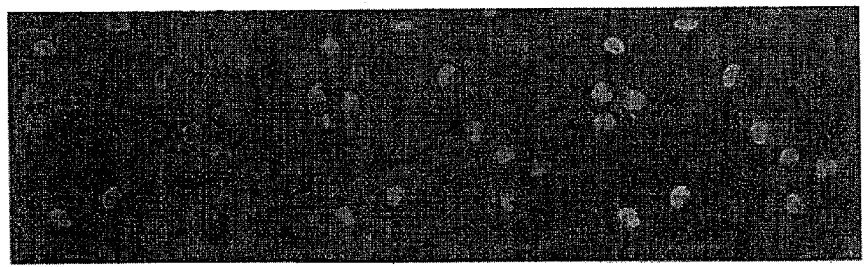
UBC13
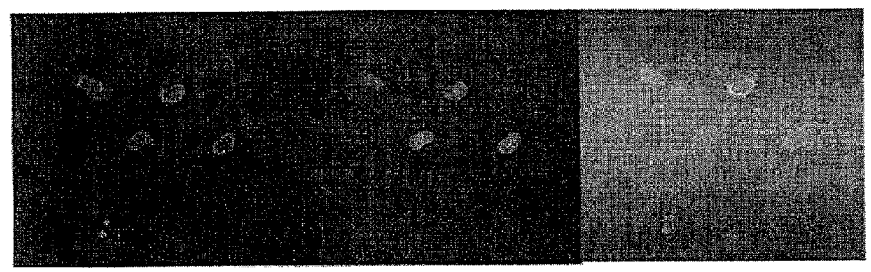
FBH
MAD2
XPC

FIG. 20
Rad23A
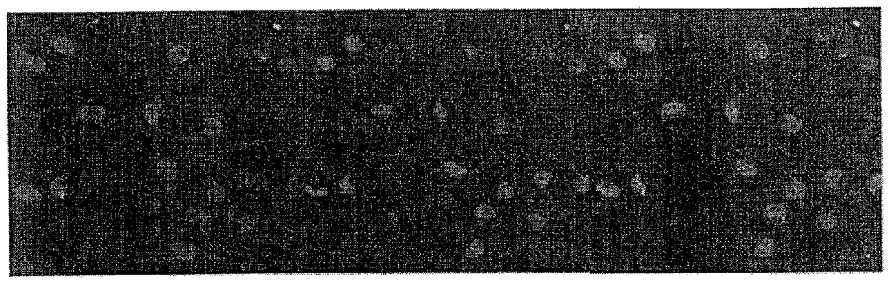
Rad23B
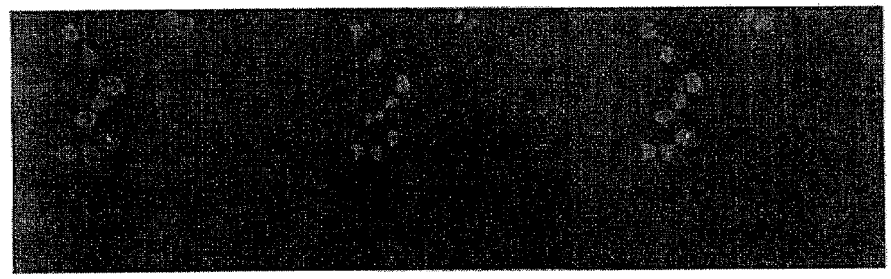
CSA
CSB
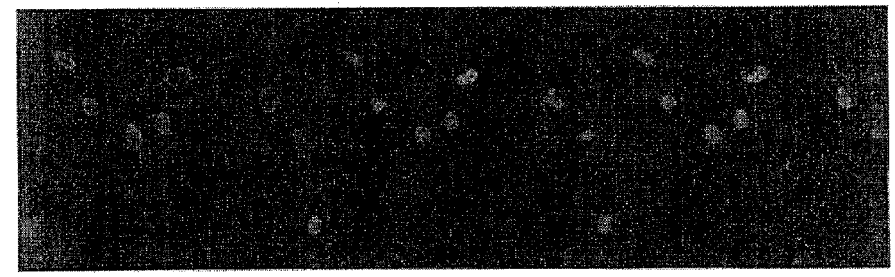
XPG

FIG. 23
APE2
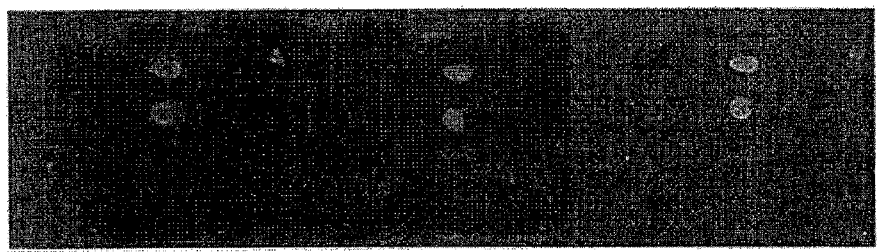
PARP1
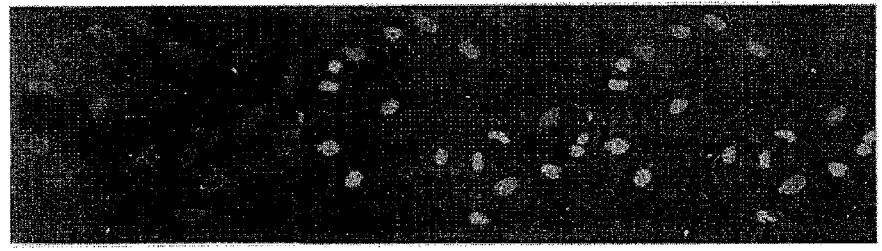
PNK
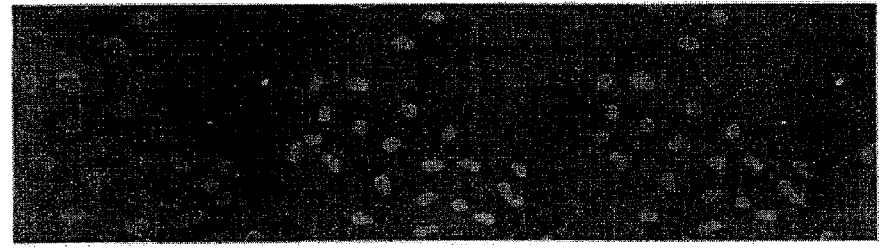
Polb
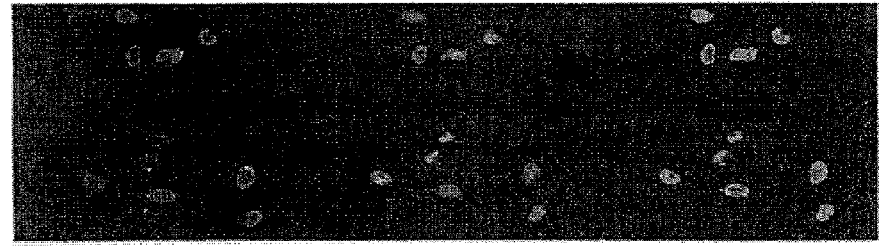
MSH2
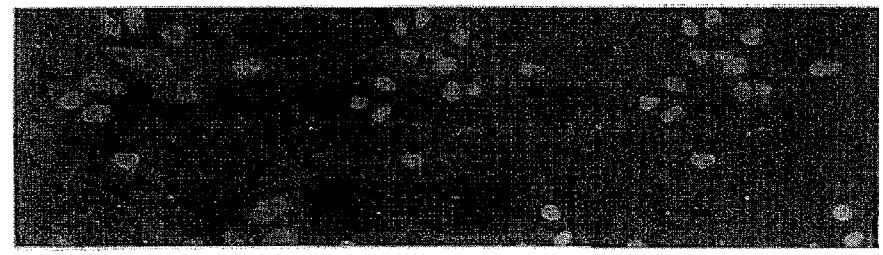

FIG. 24
PMS1
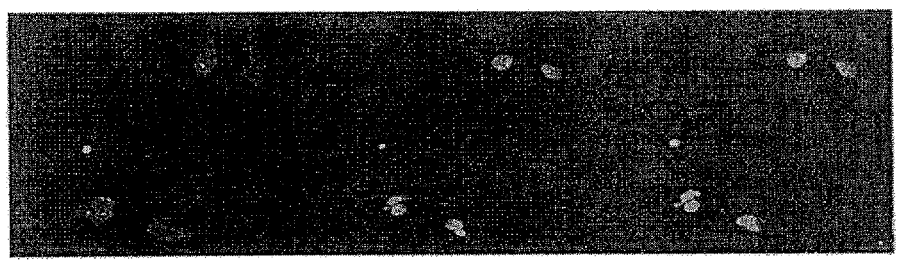
PMS2
MLH3
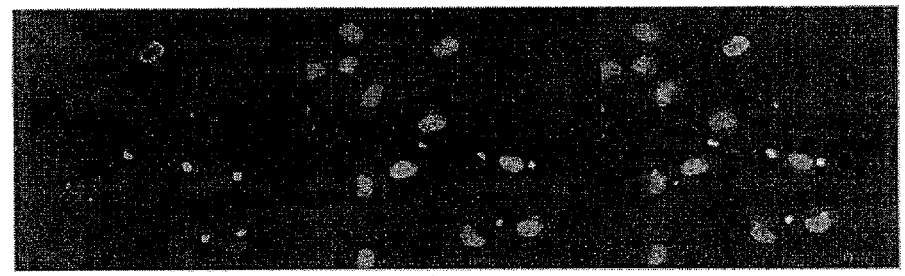
Exo1
Pol i
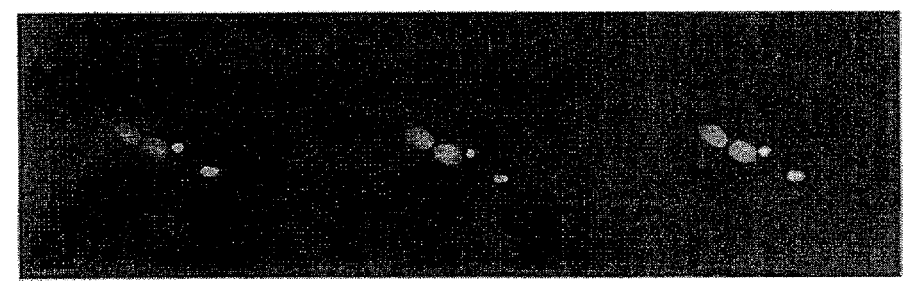

FIG. 25
Rad51
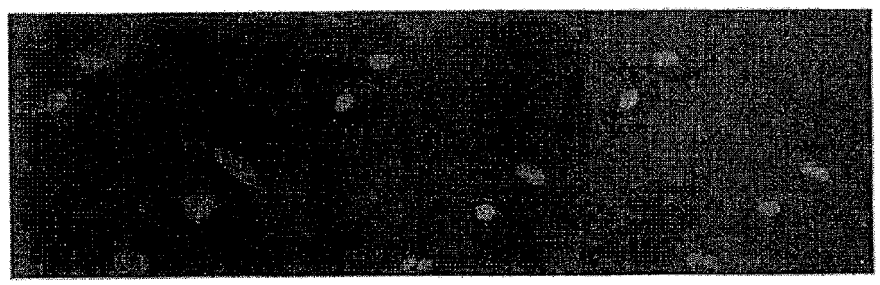
Rad51D
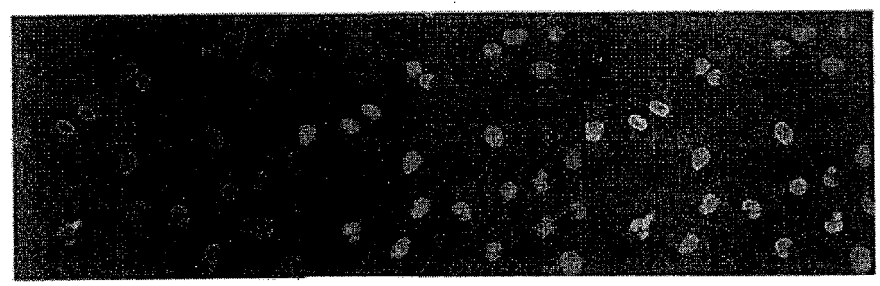
XRCC2
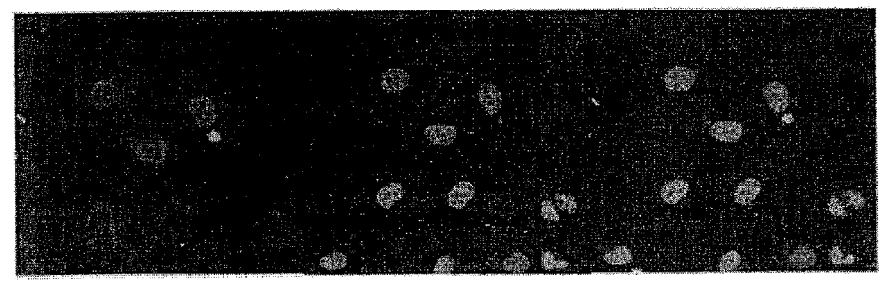
Rad54
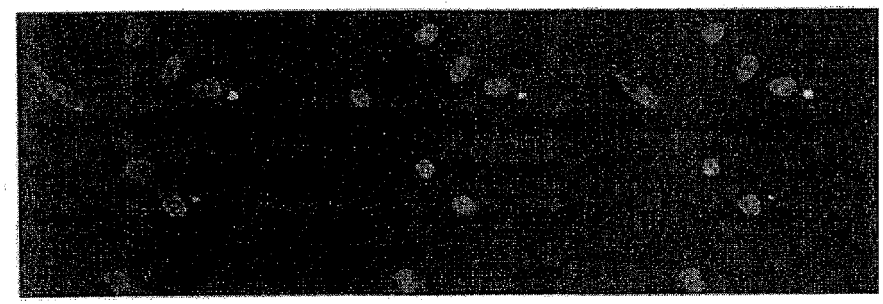
BRCA1
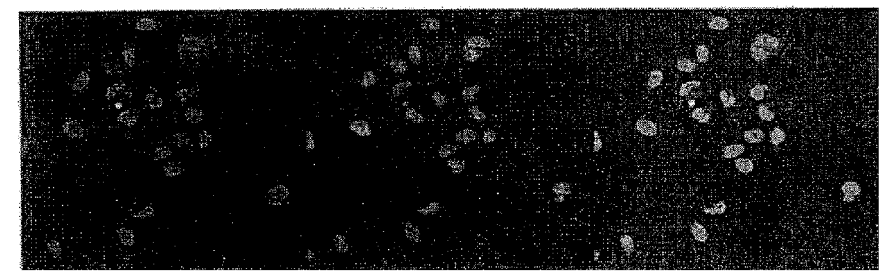

FIG. 28

| FUNCTION | GENE NAME | ACCESSION NUMBER | OTHER ACCESION NUMBERS | siRNA SEQUENCE | SEQ ID NO | INHITIBION OF GENE EXPRESSION IN 40nM HELA CELLS | INHIBITION OF PROLIFERATION IN 40nM HELA CELLS | INHITIBION OF GENE EXPRESSION IN 40nM TIG3 CELLS | INHIBITION OF PROLIFERATION IN 40nM TIG3 CELLS |
|---|---|---|---|---|---|---|---|---|---|
| PROGRESSION OF REPLICATION FORK | Pif1 | NM_025049.1 | AF108138.1 | ggCCAgAgCAUCUUCUUCA | 974 | 24% | 73% | ** | ** |
| | | | BC033254.1 | gAgCUggAAgAggUgUgUg | 975 | 19% | 61% | ** | ** |
| | | | AK026345.1 | ggCAUgACCCUggAUUgUg | 976 | 11% | 50% | 6% | 73% |
| | | | BC018978.2 | | | | | | |
| DNA DAMAGE CHECK POINTS | Mms4 | NM_152463.1 | AK021607.1 | AAUUgUgCAgAgCUggAAA | 977 | 24% | 60% | ** | ** |
| | | | BC016470.2 | AAgAAgCUCCgAgAAUgAAA | 978 | 30% | 57% | ** | ** |
| | | | AK055926.1 | gggAAAgAgAAgAUUgUAgU | 979 | 9% | 43% | 22% | 72% |
| | Topoisomerase IIIa | NM_004618.2 | BC051748.1 | gAUggUAUCgUAgAAUUCA | 980 | 11% | 60% | 9% | 100% |
| | | | AK128869.1 | ggCAUCgACUCUUUAACCA | 981 | 8% | 67% | ** | ** |
| | | | U43431.1 | gCUggCUUCUCgAAAgUUg | 982 | 16% | 84% | ** | ** |
| | Mus81 | NM_025128 | AK128820.1 | CCAUCAAgAAUAAggCCCA | 983 | 25% | 52% | 14% | 93% |
| | | | CR604400.1 | AggCCUgAgCUUgCUgAAU | 984 | 27% | 37% | ** | ** |
| | | | CR601399.1 | CACCAACACUCAggUCAUU | 985 | 19% | 45% | ** | ** |
| | | | AL353934.1 | gACACUgCUgAgCACCAUU | 986 | 22% | 58% | ** | ** |
| | | | AK024665.1 | | | | | | |
| | | | NM_025128.3 | | | | | | |
| | | | BC009999.2 | | | | | | |
| | | | AF425646.1 | | | | | | |
| | | | AK095326.1 | | | | | | |
| CHROMATIN STRUCTURE MAINTENANCE | SIRT1 (Sirtuin) | NM_012238.3 | BX648554.1 | gCCACggAUAggUCCAUAU | 987 | 34% | 69% | 29% | 77% |
| | | | AF083106.2 | gCgAUgUUUUgAUAUUgAA | 988 | 6% | 72% | ** | ** |
| | | | AF235040.1 | | | | | | |
| | | | AL136741.1 | | | | | | |
| | | | AK027686.1 | | | | | | |
| | | | BC012499.1 | | | | | | |
| | | | AK074805.1 | | | | | | |

FIG. 29

| | | | | | | | | |
|---|---|---|---|---|---|---|---|---|
| SISTER CHROMATID AGGLUTINATION AND SEPARATION | Esp1 | NM_012291 | | BC047603.1, | AAAgAgAACAgCAgCUgUA | 989 | 23% | 34% | 21% | 79% |
| | | | | AK128350.1, | AAgCCAAAUACAggAAgg | 990 | 28% | 45% | ** | ** |
| | | | | AK128350.1, | gCUgUCAgAUAgUUgAUUU | 991 | 21% | 35% | ** | ** |
| | | | | AY455930.1, | gCUCUgCUCUggAUgCUAU | 992 | 17% | 32% | ** | ** |
| | | | | D79987.1 | gUUUgUAgCAgCACggAUA | 993 | 17% | 59% | ** | ** |
| BASE EXCISION REPAIR | MPG | NM_002434 | | M99626.1, | UgAAgAAACCAAAgCAgUU | 994 | 5% | 45% | ** | ** |
| | | | | NM_002434.1, | gAUgAAgAAACCAAAgCAg | 995 | 4% | 40% | 33% | 82% |
| | | | | CR619346.1, | gggUgUUUgUgCCUCAUAA | 996 | 10% | 55% | ** | ** |
| | | | | CR612592.1, | | | | | | |
| | | | | CR606356.1, | | | | | | |
| | | | | CR600098.1, | | | | | | |
| | | | | CR598824.1, | | | | | | |
| | | | | L10752.1, | | | | | | |
| | | | | M74905.1, | | | | | | |
| | | | | X56528.1, | | | | | | |
| | | | | BC014991.1, | | | | | | |
| | | | | M71215.1, | | | | | | |
| | | | | S51033.1 | | | | | | |

FIG. 30

| | | | | | | | | |
|---|---|---|---|---|---|---|---|---|
| DNA POLYMERASE | PolI | NM_013274 | AK128521.1 | gCAgAAAUUCAUgCUgAU | 997 | 22% | 57% | 26% | 82% |
| | | | AK127896.1 | UgCggAAgCUggACCAUAU | 998 | 27% | 67% | ** | ** |
| | | | BC068529.1 | gggCAUgAgUCUgUCAgAA | 999 | 25% | 49% | ** | ** |
| | | | AJ131890.1 | AggCAAAAgAAgCACCAAA | 1000 | 26% | 64% | ** | ** |
| | | | CR619817.1 | | | | | |
| | | | CR615868.1 | | | | | |
| | | | NM_013274.2 | | | | | |
| | | | AF161019.1 | | | | | |
| | | | AK021600.1 | | | | | |
| | | | AK022476.1 | | | | | |
| | | | AF218027.1 | | | | | |
| | | | AF283478.1 | | | | | |
| | | | BC003548.1 | | | | | |
| | | | AK094956.1 | | | | | |
| | PolM | NM_013284 | BC049202.1 | bAgAgAAgUUUCUgCAUUU | 1001 | 23% | 30% | 24% | 85% |
| | | | BC062590.1 | CUggACAUAgUCUggUUAA | 1002 | 4% | 65% | ** | ** |
| | | | BC026306.1 | CCCgUCgCAgAgCCCUUUA | 1003 | 7% | 52% | ** | ** |
| | | | AJ131891.2 | | | | | |
| | | | CR620839.1 | | | | | |
| | | | CR606869.1 | | | | | |
| | | | NM_013284.1 | | | | | |
| | | | AF176097.1 | | | | | |
| | | | AK023002.1 | | | | | |
| | | | AK092903.1 | | | | | |
| | | | AK092801.1 | | | | | |
| | | | BC035685.1 | | | | | |
| NUCLEASE | EndoV | NM_173627 | NM_173627.2 | UgUggAUggAAACgggUA | 1004 | 7% | 62% | 13% | 90% |
| | | | BC045824.1 | | | | | |
| | | | BX647411.1 | | | | | |
| | | | AK123689.1 | | | | | |
| | | | BC059781.1 | | | | | |
| | | | BC064545.1 | | | | | |
| | | | CR617882.1 | | | | | |
| | | | CR599326.1 | | | | | |
| | | | AK056045.1 | | | | | |
| | | | AK096802.1 | | | | | |
| | | | AK096344.1 | | | | | |
| | | | AK092539.1 | | | | | |
| | | | BC037889.2 | | | | | |

FIG. 31

| FUNCTION | GENE NAME | ALTERNATIVE NAMES | NCBI ACCESSION NUMBER | mRNA REGISTRATION NUMBERS | | siRNA ID | siRNA SEQUENCE | SEQ ID NO | HeLa | | | HDF | |
|---|---|---|---|---|---|---|---|---|---|---|---|---|---|
| | | | | | | | | | mRNA EXPRESSION | INHIBITION OF PROLIFERATION | APOPTOSIS | mRNA EXPRESSION | INHIBITION OF PROLIFERATION | APOPTOSIS |
| SISTER CHROMATID AGGLUTINATION AND SEPARATION | KNTC2 (NDC80) | KNTC2 HEC HEC1 | NM_006101 | NM_006101.1 CR609890.1 BC010171.2 BC005239.1 BC035617.1 AF017790.1 | (Nagayama) 40nM / (Futami) 20nM | hNDC80-1 | AAUCAAggACCcgAgACCACUAAU | 1005 | 7% | 9% | Yes | 13% | 29% | NOT DETECTABLE |
| | | | | | | hNDC80-2 | CCAgAAgUACUCAgUUgCAgACAUU | 1006 | 15% | 5% | Yes | 16% | 12% | NOT DETECTABLE |
| | | | | | | hNDC80-3 | AgAAgUUCAAAAgCUggAUgAUCCUU | 1007 | 15% | 10% | Yes | 14% | 16% | NOT DETECTABLE |
| | | | | | | KNTC2-N1 | ggAgUUAAgAUCCAggAU | 1008 | 21% | 27% | Yes | 19% | 52% | NOT DETECTABLE |
| | | | | | | KNTC2-N2 | CCACUUAAUgACAAAgCAU | 1009 | 9% | 18% | Yes | 25% | 40% | NOT DETECTABLE |
| | | | | | | KNTC2-N3 | gCAgCCUUAgUUUggCUAA | 1010 | 23% | 59% | Yes | 44% | 80% | DETECTABLE |
| | | | | | | KNTC2-N4 | ggAAAUUgCUAgAgUAgAA | 1011 | 20% | 17% | Yes | 15% | 33% | NOT DETECTABLE |
| | | | | | | KNTC2-N5 | gCUAgAgUAgAACUAgAAU | 1012 | 21% | 15% | Yes | 9% | 60% | DETECTABLE |
| | | | | | | KNTC2-N6 | gCAgACAUUgAgCgAAUAA | 1013 | 24% | 17% | Yes | 7% | 39% | NOT DETECTABLE |
| | | | | | | KNTC2-N7 | ggAgAUACUUUAgAACAA | 1014 | 21% | 17% | Yes | 6% | 50% | NOT DETECTABLE |
| | | | | | | KNTC2-N8 | CCAgUgAgCUUgAgUCCUU | 1015 | 25% | 18% | Yes | 9% | 59% | NOT DETECTABLE |
| | | | | | | KNTC2-N9 | gCUUgAgUCCUUggAgAAA | 1016 | 20% | 18% | Yes | 28% | 45% | NOT DETECTABLE |
| | | | | | | KNTC2-N10 | ggAgCAgAUUgCUAAAgU | 1017 | 18% | 20% | Yes | 39% | 65% | DETECTABLE |

FIG. 32

| GENE NAME | siRNA ID | siRNA SEQUENCE | SEQ ID NO | HeLa EXPRESSION | HeLa PROLIFERATION | HeLa APOPTOSIS | HDF EXPRESSION | HDF PROLIFERATION | HDF APOPTOSIS |
|---|---|---|---|---|---|---|---|---|---|
| Mcm3 | mcm3-N2 | gCUUCUgAACAAUgCCUUU | 1018 | 5% | 54% | + | 12% | 69% | − |
| | mcm3-N3 | ggACgUCAUUCUggAUgAU | 1019 | 15% | 19% | + | 20% | 41% | − |
| | mcm3-N6 | gCUUCUgCggUAUgUgCUU | 1020 | 8% | 49% | + | 24% | 59% | − |
| | mcm3-N7 | gCAggUAUgACCAgUAUAA | 1021 | 11% | 45% | + | 23% | 65% | − |
| | mcm3-N8 | gCAUgACAACCUUCUACAU | 1022 | 10% | 55% | + | 13% | 51% | − |
| | mcm3-N10 | gCAAgAUgCAggAUgACAA | 1023 | 7% | 28% | + | 10% | 57% | − |
| Cdc5 | cdc5-N1 | ggAAgAAgCAAgACgUCUU | 1024 | 12% | 20% | + | 28% | 40% | − |
| | cdc5-N2 | ggAgUggAACAACUCCCAA | 1025 | 29% | 35% | + | 49% | 64% | − |
| | cdc5-N3 | CCUCUUCgAgACAAgUUAA | 1026 | 5% | 45% | + | 19% | 55% | − |
| | cdc5-N4 | gCCAAgACCAUCAgAAgUA | 1027 | 7% | 44% | + | 16% | 66% | − |
| | cdc5-N5 | gCUUCAUUAUgACCUUCUA | 1028 | 2% | 46% | + | 13% | 50% | − |
| | cdc5-N6 | CCUUCUACAUCACCCUUAU | 1029 | 3% | 34% | + | 13% | 45% | − |
| | cdc5-N7 | CCAAUAAUUCAgAgCACAU | 1030 | 4% | 40% | + | 14% | 60% | − |
| | cdc5-N8 | ggAAgAAUgCUACAgUCAA | 1031 | 7% | 40% | + | 13% | 45% | − |
| | cdc5-N9 | ggACAgAAAUUgAAUCACUU | 1032 | 8% | 22% | + | 12% | 45% | − |
| | cdc5-N10 | gCUCAUgAAACAgUUgAAU | 1033 | 7% | 30% | + | 15% | 50% | − |
| Pole Dpb3 | dpb3-N1 | CCACAUCCUgUgCUAACAA | 1034 | 12% | 54% | + | 32% | 58% | − |
| | dpb3-N3 | gggAgCAgAAAAggCAAgAA | 1035 | 11% | 37% | + | 45% | 44% | − |
| Pole Dpb4 | dpb4-N1 | UgCgCUCAgCAgggAAAAA | 1036 | 2% | 63% | + | 9% | 97% | − |
| | dpb4-N2 | gAggAgAgACUUggAUAAU | 1037 | 1% | 65% | + | 1% | 90% | − |
| | dpb4-N3 | ggCCUUggUgAAggCAgAU | 1038 | 12% | 42% | + | 9% | 64% | − |
| | dpb4-N5 | CCgggAUAAgCAgAgAUCU | 1039 | 1% | 57% | + | 2% | 72% | − |
| | dpb4-N6 | AgAggAgAgACUUggAUAA | 1040 | 0% | 47% | + | 0% | 87% | − |
| | dpb4-N7 | UgCAAggUCUUCCACUAU | 1041 | 1% | 62% | + | 5% | 92% | − |
| | dpb4-N9 | AggCCUCAgCUUUgAAgAA | 1042 | 3% | 65% | + | 9% | 67% | − |
| | dpb4-N10 | gAgCAgAgAUgAAgAAAgU | 1043 | 2% | 38% | + | 7% | 53% | − |
| Esp1 | ESP1-N1 | gCgggAUgAUggUgUgUAU | 1044 | 17% | 35% | + | 39% | 40% | − |
| | ESP1-N2 | gCUgUCAgAUAgUUgAUUU | 1045 | 20% | 58% | + | 34% | 66% | − |
| | ESP1-N3 | gCUUCUUACACCAgUAAUU | 1046 | 16% | 29% | + | 31% | 65% | − |
| | ESP1-N4 | gCUCUgCUCUggAUgCUAU | 1047 | 14% | 25% | + | 21% | 40% | − |
| | ESP1-N5 | gCUCUCAUAgACUCCCAUA | 1048 | 10% | 35% | + | 13% | 48% | − |
| | ESP1-N6 | gCUgAUgggCAgUgACAUU | 1049 | 18% | 41% | + | 19% | 53% | − |
| | ESP1-N7 | ggAUgAgAUCUUggCUCAA | 1050 | 32% | 44% | + | 41% | 47% | − |
| | ESP1-N8 | gCCAAgAAggUggCAUCAA | 1051 | 8% | 17% | + | 13% | 38% | − |
| | ESP1-N9 | gCCUgACAgUACCAAgCAA | 1052 | 28% | 23% | + | 27% | 36% | − |
| | ESP1-N10 | gCAUCgUgCUCAAgUACAU | 1053 | 22% | 57% | + | 27% | 45% | − |
| XAB2 | xab2-N1 | ggACCUUgUCUUCgAggAA | 1054 | 11% | 22% | + | 10% | 50% | − |
| | xab2-N2 | ggAAAUCAUgCggAACCAA | 1055 | 27% | 23% | + | 22% | 45% | − |
| | xab2-N3 | ggAACCAAUUCUCUgUCAA | 1056 | 6% | 18% | + | 12% | 50% | − |
| | xab2-N4 | CCUCgUCUgUggCUAgAUU | 1057 | 6% | 19% | + | 8% | 60% | − |
| | xab2-N5 | gggACUUCACACAggUgUU | 1058 | 7% | 19% | + | 14% | 22% | − |
| | xab2-N6 | CCACCAAggUgAACUUCAA | 1059 | 5% | 15% | + | 10% | 18% | − |
| | xab2-N7 | gCCgAgUACUUUgAUggUU | 1060 | 7% | 27% | + | 14% | 25% | − |
| | xab2-N8 | CCCAgCAgUAUgACAUgUU | 1061 | 38% | 49% | + | 35% | 40% | − |
| | xab2-N9 | gCAUCUACCAgAAggCCAU | 1062 | 9% | 12% | + | 10% | 23% | − |
| | xab2-N10 | gCAgACgUggAAggACUUU | 1063 | 35% | 65% | + | 16% | 35% | − |

FIG. 34
Esp1
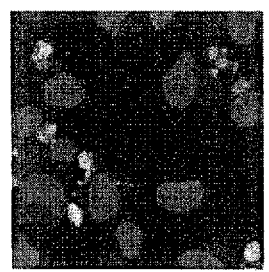 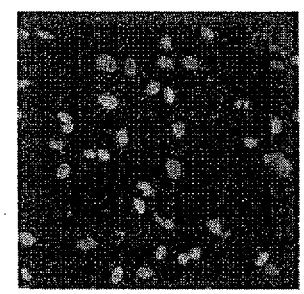
MPG
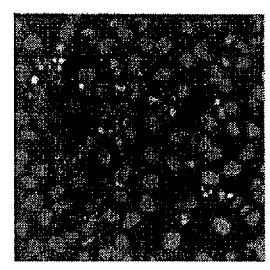 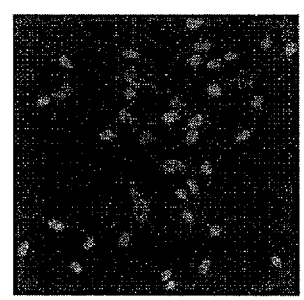
Pol l
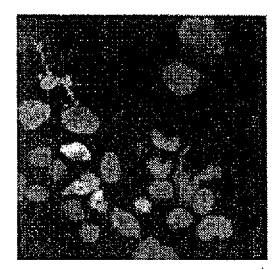 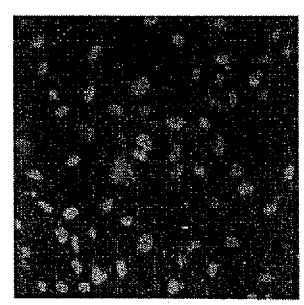
Pol m
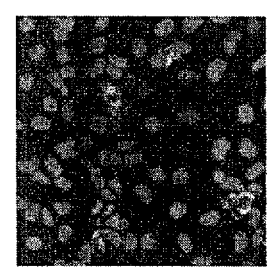 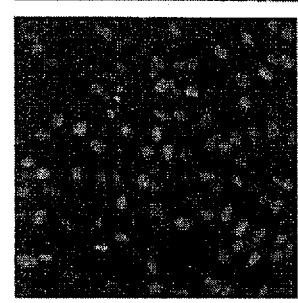
EndoV
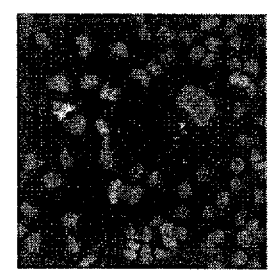 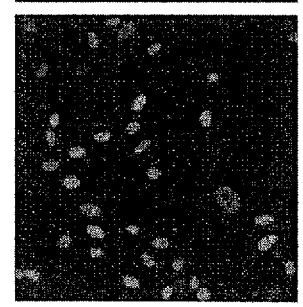

CANCER CELL-SPECIFIC APOPTOSIS-INDUCING AGENTS THAT TARGET CHROMOSOME STABILIZATION-ASSOCIATED GENES

CROSS-REFERENCES TO RELATED APPLICATIONS

This application is a divisional of U.S. patent application Ser. No. 11/547,770, filed Sep. 30, 2008, now allowed, which is a national stage application filed under 35 U.S.C. §371 of International Patent Application No. PCT/JP2005/006914, accorded an international filing date of Apr. 8, 2005, which claims the benefit of priority to Japan (JP) Patent Application Serial No. 2004-115404, filed Apr. 9, 2004. All the aforementioned patent applications are herein incorporated by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 390081_402D1_SEQUENCE_LISTING.txt. The text file is 3 MB, was created on May 7, 2012, and is being submitted electronically via EFS-Web.

BACKGROUND

1. Technical Field

The present invention relates to cancer cell-specific apoptosis-inducing agents that target chromosome stabilization-associated genes and methods of screening for the apoptosis-inducing agents.

2. Background Art

Chromosomes are maintained in a stable state within cells by the action of various cellular functions (genes). Examples of typical cellular functions (genes) that contribute to this chromosome stabilization are as follows:

(a) Genes Associated with Human Chromosomal Instability Disorders

Chromosome breakage, deletion, translocation, and aneuploidy are observed in cells from patients with human chromosomal instability disorders, and these cells are also sensitive to DNA damage-inducing drugs. The occurrence of such instabilities indicates that human chromosomal instability disorder-associated genes are involved in chromosome stabilization.

(b) Chromosomal DNA Replication Reaction Including Initiation of Chromosomal DNA Replication and Progression of Replication Fork The chromosomal DNA replication reaction plays the role of replicating chromosomal DNA during cell proliferation. It has the function of maintaining the number of chromosomes by accurately doubling the chromosomes when a cell divides into two cells.

(c) DNA Damage Checkpoints

DNA damage checkpoints play the role of checking for DNA damage, including breakage, chemical modification, and crosslinking, in chromosomes when the cell cycle advances from each of G1, S, G2, and M phases to the next phase. These checkpoints have the function of removing chromosomal DNA damage before proceeding to the next stage of the cell cycle.

(d) Sister Chromatid Agglutination and Separation

Sister chromatid agglutination and separation play the role of accurately separating, into daughter cells, sister chromatids in somatic cells in which replication has been completed.

(e) Base Excision Repair

Base excision repair plays the role of removing modified bases when a chemical modification damage, including oxidation and methylation, has occurred in bases in chromosomal DNA.

(f) Mismatch Excision Repair

Mismatch excision repair plays the role of recognizing mismatched base pairs other than the correct G-C and A-T base pairs present in chromosomal DNA, and repairing them to the correct base pairs.

(g) Nucleotide Excision Repair

Nucleotide excision repair plays the role of repairing DNA by recognizing and removing DNA damage such as cyclobutane pyrimidine dimers and 6-4 photoproducts, which occur in chromosomal DNA due to ultraviolet irradiation, and DNA internal crosslinking, which occurs between adjacent bases in chromosomal DNA due to cisplatin.

(h) Homologous Recombination Repair

Using an undamaged homologous chromosome as a template, homologous recombination repair plays the role of repairing various DNA damage, including breaks and gaps occurring in chromosomal DNA, and DNA damage resulting from incomplete repair by mechanisms such as base excision repair, mismatch excision repair, and nucleotide excision repair.

(i) Non-Homologous End Joining Repair (Non-Homologous Recombination Repair)

Non-homologous end joining repair (non-homologous recombination repair) plays the role of repairing double-strand breaks in chromosomal DNA by joining the ends.

(j) Double-Strand DNA Break Repair

Double-strand DNA break repair plays the role of repairing double-strand breaks occurring in chromosomal DNA. This repair mechanism includes homologous recombination repair and non-homologous end joining repair (non-homologous recombination repair).

(k) DNA Post-Replication Repair (DNA Damage Tolerance)

DNA post-replication repair (DNA damage tolerance) is a mechanism that enables repair of a damaged DNA strand when damaged chromosomal DNA is replicated. Residual DNA damage is repaired following replication by this mechanism.

(l) DNA Crosslink Damage Repair

DNA crosslink damage repair plays the role of repairing DNA crosslink damage within and between chromosomes caused by crosslinking agents such as cisplatin.

(m) DNA-Protein Crosslink Damage Repair

DNA-protein crosslink damage repair plays the role of removing covalently bonded complexes and crosslinked complexes when a covalently bonded enzyme protein-DNA complex, which is a reaction intermediate of DNA repair, has been formed, or a crosslinked complex between a base in chromosomal DNA and a protein has formed.

(n) DNA Polymerase

DNA polymerases play the role of carrying out DNA synthesis reactions in chromosome stabilization mechanisms such as replication, recombination, and repair.

(o) Nuclease

Nucleases play the role of decomposing DNA in chromosome stabilization mechanisms such as replication, recombination, and repair.

(p) Nucleotide Cleansing

Nucleotide cleansing plays the role of removing modified bases when chemical modification damage, including oxidation and methylation, has occurred in a base of a nucleotide serving as the substrate of a DNA synthesis reaction.

(q) Chromatin Structure Maintenance

Chromatin structure maintenance plays a role in chromosome stabilization mechanisms such as replication, recombination, and repair, through maintaining the higher order chromosomal structure.

(r) Telomere Structure Maintenance

Telomere structure maintenance plays an important role in chromosome stabilization via the control of chromosome end telomere length and the formation and maintenance of special higher order structures in telomere regions.

In addition, various genes related to the aforementioned functions have been reported to be involved in chromosome stabilization. For example, various findings have been reported regarding various genes involved in chromosome stabilization (see Non-Patent Documents 1 to 83).

However, the correlation between the aforementioned functions (genes) involved in chromosome stabilization and the induction of cancer-cell specific apoptosis was so far unknown.

[Non-patent Document 1] Wood, R. D., Mitchell, M., Sgourou, J. and Lindahl, T. (2001). Human DNA repair genes Science, 291, 1284-1289.

[Non-patent Document 2] Nyberg, K. A., Michelson, R. J., Putnam, C. W. and Weinert, T. A. (2002). Toward maintaining the genome: DNA damage and replication checkpoints Annu. Rev. Genet. 36, 617-656.

[Non-patent Document 3] Sogo, J. M., Lopes, M. and Foiani, M. (2002). Fork reversal and ssDNA accumulation at stalled replication forks owing to checkpoint defects Science, 297, 599-602.

[Non-patent Document 4] Casper, A. M., Ngheim, P., Arlt, M. F. and Glover, T. W. (2002). ATR regulates fragile site stability Cell, 111, 779-789.

[Non-patent Document 5] Zhou, B.-B. S. and Bartek, J. (2004). Targeting the checkpoint kinases: chemosensitization versus chemoprotection Nature Review, 4, 1-10.

[Non-patent Document 6] Rich, T., Allen, R. and Wyllie, A. H. (2000). Defying death after DNA damage Nature, 407, 777-783.

[Non-patent Document 7] Nigg, E. A. (2002). Centrosome aberrations:cause or consequence of cancer progression Nature Review, 2, 815-825.

[Non-patent Document 8] Miller, H. and Grollman, A. P. (2003). DNA repair investigations using siRNA DNA repair, 2, 759-763.

[Non-patent Document 9] Merchant, A. M., Kawasaki, Y., Chen, Y., Lei, M., Tye, B. K. (1997). A lesion in the DNA replication initiation factor Mcm10 induces pausing of elongation forks through chromosomal replication origins in *Saccharomyces cerevisiae*. Mol Cell Biol., 17, 3261-3271.

[Non-patent Document 10] Tugal, T., Zou-Yang, X. H., Gavin, K., Pappin, D., Canas, B., Kobayashi, R., Hunt, T. and Stillman, B. (1998). The Orc4p and Orc5p subunits of the *Xenopus* and human origin recognition complex are related to Orc1p and Cdc6p J. Biol. Chem., 273, 32421-32429.

[Non-patent Document 11] Stoeber, K., Mills, A. D., Kubota, Y., Krude, T., Romanowski, P., Marheineke, K., Laskey, R. A. and Williams, G. (1998). Cdc6 protein causes premature entry into S phase in a mammalian cell-free system EMBO J., 17, 7219-7229.

[Non-patent Document 12] Wohlschlegel, J. A., Dwyer, B. T., Dhar, S., Cvetic, C., Walter, J. C. and Dutta, A. (2000). Inhibition of eukaryotic DNA replication by Geminin binding to Cdt1 Science, 290, 2309-2312.

[Non-patent Document 13] McGarry, T. and Kirschner, M. W. (1998). Geminin, an inhibitor of DNA replication, is degraded during mitosis Cell, 93, 1043-1053.

[Non-patent Document 14] Ishimi, Y., Komamura, Y., You, Z., Kimura, H. (1998). Biochemical function of mouse minichromosome maintenance 2 protein J Biol Chem., 273, 8369-8375.

[Non-patent Document 15] Ishimi, Y. (1997) A DNA helicase activity is associated with an MCM4, -6, and -7 protein complex J. Biol. Chem., 272, 24508-24513.

[Non-patent Document 16] Gozuacik, D., Chami, M., Lagorce, D., Faivre, J., Murakami, Y., Poch, O., Biermann, E., Knippers, R., Brechot, C. and Paterlini-Brechot, P. (2003) Identification and functional characterization of a new member of the human Mcm protein family: hMcm8 Nucleic Acids Res., 31, 570-579.

[Non-patent Document 17] Sato, N., Arai, K., Masai, H. (1997). Human and *Xenopus* cDNAs encoding budding yeast Cdc7-related kinases: in vitro phosphorylation of MCM subunits by a putative human homologue of Cdc7 EMBO J. 16, 4340-4351.

[Non-patent Document 18] Bernstein, H. S., Coughlin, S. R. (1998). A mammalian homolog of fission yeast Cdc5 regulates G2 progression and mitotic entry. J Biol Chem., 273, 4666-4671.

[Non-patent Document 19] Kubota, Y., Takase, Y., Komori, Y., Hashimoto, Y., Arata, T., Kamimura, Y., Araki, H., Takisawa, H. (2003). A novel ring-like complex of *Xenopus* proteins essential for the initiation of DNA replication. Genes Dev., 17, 1141-1452.

[Non-patent Document 20] Kukimoto, I., Igaki, H. and Kanda, T. (1999). Human CDC45 protein binds to minichromosome maintenance 7 protein and the p70 subunit of DNA polymerase alpha. Eur J Biochem. 265, 936-943.

[Non-patent Document 21] Stadlbauer, F., Brueckner, A., Rehfuess, C., Eckerskorn, C., Lottspeich, F., Forster, V., Tseng, B. Y. and Nasheuer, H. P. (1994). DNA replication in vitro by recombinant DNA-polymerase-alpha-primase. Eur J Biochem. 222, 781-793.

[Non-patent Document 22] Bochkarev, A., Pfuetzner, R. A., Edwards, A. M. and Frappier, L. (1997). Structure of the single-stranded-DNA-binding domain of replication protein A bound to DNA. Nature., 385, 176-181.

[Non-patent Document 23] Erdile, L. F., Wold, M. S. and Kelly, T. (1990). The primary structure of the 32-kDa subunit of human replication protein A J. Biol. Chem, 265, 3177-3182.

[Non-patent Document 24] Krishna, T. S., Kong, X. P., Gary, S., Burgers, P. M. and Kuriyan, J. (1996). Crystal structure of the eukaryotic DNA polymerase processivity factor PCNA. Cell., 79, 1233-1243.

[Non-patent Document 25] Barnes, D. E., Johnston, L. H., Kodama, K., Tomkinson, A. E., Lasko, D. D. and Lindahl, T. (1990). Human DNA ligase I cDNA: cloning and functional expression in *Saccharomyces cerevisiae*. Proc Natl Acad Sci USA., 87, 6679-6683.

[Non-patent Document 26] Poot, R. A., Dellaire, G., Hulsmann, B. B., Grimaldi, M. A., Corona, D. F., Becker, P. B., Bickmore, W. A. and Varga-Weisz, P. D. (2000). HuCHRAC, a human ISWI chromatin remodelling complex contains hACF1 and two novel histone-fold proteins. EMBO J., 19, 3377-3387.

[Non-patent Document 27] D'Arpa, P., Machlin, P. S., Ratrie, H. 3rd, Rothfield, N. F., Cleveland, D. W. and Earnshaw, W. C. (1988). cDNA cloning of human DNA topoisomerase I: catalytic activity of a 67.7-kDa carboxyl-terminal fragment. Proc Natl Acad Sci USA., 85, 2543-2547.

[Non-patent Document 28] Pouliot, J. J., Yao, K. C., Robertson, C. A., Nash, H. A. (1999). Yeast gene for a Tyr-DNA phosphodiesterase that repairs Topoisomerase I complex Science, 286, 552-555.

[Non-patent Document 29] Cheng, T. J., Rey, P. G., Poon, T. and Kan, C. C. (2002). Kinetic studies of human tyrosyl-DNA phosphodiesterase, an enzyme in the topoisomerase I DNA repair pathway. Eur J Biochem., 269, 3697-3704.

[Non-patent Document 30] Merkle, C. J., Karnitz, L. M., Henry-Sanchez, J. T. and Chen J. (2003). Cloning and characterization of hCTF18, hCTF8, and hDCC1. Human homologs of a *Saccharomyces cerevisiae* complex involved in sister chromatid cohesion establishment J Biol Chem., 278, 30051-30056. Epub 2003 May 23.

[Non-patent Document 31] Sumara, I., Vorlaufer, E., Gieffers, C., Peters, B. H. and Peters, J. M. (2000). Characterization of vertebrate cohesin complexes and their regulation in prophase. J Cell Biol., 151, 749-762.

[Non-patent Document 32] Shiloh, Y. (2001). ATM and ATR: networking cellular responses to DNA damage. Curr Opin Genet Dev., 11, 71-77.

[Non-patent Document 33] Sanchez, Y., Wong, C., Thoma, R. S., Richman, R., Wu, Z., Piwnica-Worms, H., Elledge, S. J. (1997). Conservation of the Chk1 checkpoint pathway in mammals: linkage of DNA damage to Cdk regulation through Cdc25. Science., 277, 1497-1501.

[Non-patent Document 34] Carney, J. P., Maser, R. S., Olivares, H., Davis, E. M., Le Beau, M., Yates, J R. 3rd, Hays, L., Morgan, W. F. and Petrini, J. H. (1998). The hMre11/hRad50 protein complex and Nijmegen breakage syndrome: linkage of double-strand break repair to the cellular DNA damage response. Cell., 93, 477-486.

[Non-patent Document 35] Volkmer, E. and Karnitz, L. M. (1999). Human homologs of *Schizosaccharomyces pombe* rad1, hus1, and rad9 form a DNA damage-responsive protein complex. J Biol Chem., 274, 567-70.

[Non-patent Document 36] Parker, A. E., Van de Weyer, I., Laus, M. C., Oostveen, I., Yon, J., Verhasselt, P. and Luyten, W. H. (1998). A human homologue of the *Schizosaccharomyces pombe* rad1+checkpoint gene encodes an exonuclease. J Biol Chem., 273, 18332-18339.

[Non-patent Document 37] Koken, M. H., Reynolds, P., Jaspers-Dekker, I., Prakash, L., Prakash, S., Bootsma, D., and Hoeijmakers, J. H. (1991). Structural and functional conservation of two human homologs of the yeast DNA repair gene RAD6. Proc Natl Acad Sci USA. 88, 8865-8869.

[Non-patent Document 38] Xin, H., Lin, W., Sumanasekera, W., Zhang, Y., Wu, X. and Wang, Z. (2000). The human RAD18 gene product interacts with HHR6A and HHR6B. Nucleic Acids Res., 28, 2847-2854.

[Non-patent Document 39] Kim, J., Kim, J. H., Lee, S. H., Kim, D. H., Kang, H. Y., Bae, S. H., Pan, Z. Q. and Seo, Y. S. (2002). The novel human DNA helicase hFBH1 is an F-box protein. J Biol Chem., 277, 24530-24537. Epub 2002 Apr. 15.

[Non-patent Document 40] Masutani, C., Sugasawa, K., Yanagisawa, J., Sonoyama, T., Ui, M., Enomoto, T., Takio, K., Tanaka, K., van der Spek, P. J., Bootsma, D., et al. (1994). Purification and cloning of a nucleotide excision repair complex involving the xeroderma pigmentosum group C protein and a human homologue of yeast RAD23. EMBO J., 13, 1831-1843.

[Non-patent Document 41] Schauber, C., Chen, L., Tongaonkar, P., Vega, I., Lambertson, D., Potts, W. and Madura, K. (1998). Rad23 links DNA repair to the ubiquitin/proteasome pathway. Nature., 391, 715-8.

[Non-patent Document 42] Henning, K. A., Li, L., Iyer, N., McDaniel, L. D., Reagan, M. S., Legerski, R., Schultz, R. A., Stefanini, M., Lehmann, A. R., Mayne, L. V., et al. (1995). The Cockayne syndrome group A gene encodes a WD repeat protein that interacts with CSB protein and a subunit of RNA polymerase II TFIIH. Cell., 82, 555-564.

[Non-patent Document 43] Selby, C. P. and Sancar, A. (1997). Human transcription-repair coupling factor CSB/ERCC6 is a DNA-stimulated ATPase but is not a helicase and does not disrupt the ternary transcription complex of stalled RNA polymerase II. J Biol Chem., 272, 1885-1890.

[Non-patent Document 44] O'Donovan, A., Davies, A. A., Moggs, J. G., West, S. C. and Wood, R. D. (1994). XPG endonuclease makes the 3' incision in human DNA nucleotide excision repair. Nature., 371, 432-435.

[Non-patent Document 45] Sijbers, A. M., de Laat, W. L., Ariza, R. R., Biggerstaff, M., Wei, Y. F., Moggs, J. G., Carter, K. C., Shell, B. K., Evans, E., de Jong, M. C., Rademakers, S., de Rooij, J., Jaspers, N. G., Hoeijmakers, J. H. and Wood, R. D. (1996). Xeroderma pigmentosum group F caused by a defect in a structure-specific DNA repair endonuclease. Cell., 86, 811-822.

[Non-patent Document 46] Keeney, S., Chang, G. J. and Linn, S. (1993). Characterization of a human DNA damage binding protein implicated in xeroderma pigmentosum E. J Biol Chem., 268, 21293-21300.

[Non-patent Document 47] Nakatsu, Y., Asahina, H., Citterio, E., Rademakers, S., Vermeulen, W., Kamiuchi, S., Yeo, J. P., Khaw, M. C., Saijo, M., Kodo, N., Matsuda, T., Hoeijmakers, J. H. and Tanaka, K. (2000). XAB2, a novel tetratricopeptide repeat protein involved in transcription-coupled DNA repair and transcription. J Biol Chem., 275, 34931-34937.

[Non-patent Document 48] Olsen, L. C., Aasland, R., Wittwer, C. U., Krokan, H. E. and Helland, D. E. (1989). Molecular cloning of human uracil-DNA glycosylase, a highly conserved DNA repair enzyme. EMBO J., 8, 3121-3125.

[Non-patent Document 49] Hendrich, B. and Bird, A. (1998). Identification and characterization of a family of mammalian methyl-CpG binding proteins. Mol Cell Biol., 18, 6538-6547.

[Non-patent Document 50] Aspinwall, R., Rothwell, D. G., Roldan-Arjona, T., Anselmino, C., Ward, C. J., Cheadle, J. P., Sampson, J R., Lindahl, T., Harris, P. C. and Hickson, I. D. (1997). Cloning and characterization of a functional human homolog of *Escherichia coli* endonuclease III. Proc Natl Acad Sci USA., 94, 109-114.

[Non-patent Document 51] Hazra, T. K., Kow, Y. W., Hatahet, Z., Imhoff, B., Boldogh, I., Mokkapati, S. K., Mitra, S. and Izumi, T. (2002). Identification and characterization of a novel human DNA glycosylase for repair of cytosine-derived lesions. J Biol Chem., 277, 30417-30420. Epub 2002 Jul. 3.

[Non-patent Document 52] Morland, I., Rolseth, V., Luna, L., Rognes, T., Bjoras, M. and Seeberg, E. (2002). Human DNA glycosylases of the bacterial Fpg/MutM superfamily: an alternative pathway for the repair of 8-oxoguanine and other oxidation products in DNA. Nucleic Acids Res., 30, 4926-4036.

[Non-patent Document 53] Hadi, M. Z., Ginalski, K., Nguyen, L. H. and Wilson, D. M. 3rd. (2002). Determinants in nuclease specificity of Ape1 and Ape2, human homologues of *Escherichia coli* exonuclease III. J Mol Biol., 316, 853-866.

[Non-patent Document 54] Ikejima, M., Noguchi, S., Yamashita, R., Ogura, T., Sugimura, T., Gill, D. M. and Miwa, M. (1990). The zinc fingers of human poly(ADP-ribose) polymerase are differentially required for the recognition of DNA breaks and nicks and the consequent enzyme activation. Other structures recognize intact DNA. J Biol Chem., 265, 21907-21913.

[Non-patent Document 55] Jilani, A., Ramotar, D., Slack, C., Ong, C., Yang, X. M., Scherer, S. W. and Lasko, D. D. (1999). Molecular cloning of the human gene, PNKP, encoding a polynucleotide kinase 3'-phosphatase and evidence for its role in repair of DNA strand breaks caused by oxidative damage. J Biol Chem., 274, 24176-24186.

[Non-patent Document 56] Jezewska, M. J., Galletto, R. and Bujalowski, W. (2002). Dynamics of gapped DNA recognition by human polymerase beta. J Biol Chem., 277, 20316-20327. Epub 2002 Mar. 23.

[Non-patent Document 57] Fishel, R., Ewel, A. and Lescoe, M. K. (1994). Purified human MSH2 protein binds to DNA containing mismatched nucleotides. Cancer Res., 54, 5539-5542.

[Non-patent Document 58] Yuan, Z. Q., Gottlieb, B., Beitel, L. K., Wong, N., Gordon, P. H., Wang, Q., Puisieux, A., Foulkes, W. D. and Trifiro, M. (2002). Polymorphisms and HNPCC: PMS2-MLH1 protein interactions diminished by single nucleotide polymorphisms. Hum Mutat., 19, 108-113.

[Non-patent Document 59] Wilson, D. M. 3rd, Carney, J. P., Coleman, M. A., Adamson, A. W., Christensen, M. and Lamerdin, J. E. (1998). Hex1: a new human Rad2 nuclease family member with homology to yeast exonuclease 1. Nucleic Acids Res., 26, 3762-3768.

[Non-patent Document 60] Vaisman, A., Tissier, A., Frank, E. G., Goodman, M. F. and Woodgate, R. (2001). Human DNA polymerase iota promiscuous mismatch extension. J Biol Chem. 2001 Aug. 17; 276(33):30615-22. Epub 2001 Jun. 11.

[Non-patent Document 61] Tombline, G. and Fishel, R. (2002). Biochemical characterization of the human RAD51 protein. I. ATP hydrolysis. J Biol Chem. 277, 14417-14425. Epub 2002 Feb. 11.

[Non-patent Document 62] Tombline, G., Shim, K. S. and Fishel, R. (2002). Biochemical characterization of the human RAD51 protein. II. Adenosine nucleotide binding and competition. J Biol Chem., 277, 14426-14433. Epub 2002 Feb. 11.

[Non-patent Document 63] Tombline, G., Heinen, C. D., Shim, K. S. and Fishel, R. (2002). Biochemical characterization of the human RAD51 protein. III. Modulation of DNA binding by adenosine nucleotides. J Biol Chem., 277, 14434-14442. Epub 2002 Feb. 11.

[Non-patent Document 64] Masson, J. Y., Tarsounas, M. C., Stasiak, A. Z., Stasiak, A., Shah, R., McIlwraith, M. J., Benson, F. E. and West, S. C. (2001). Identification and purification of two distinct complexes containing the five RAD51 paralogs. Genes Dev., 15, 3296-3307.

[Non-patent Document 65] Johnson, R. D., Liu, N. and Jasin, M. (1999). Mammalian XRCC2 promotes the repair of DNA double-strand breaks by homologous recombination. Nature., 401, 397-399.

[Non-patent Document 66] Kanaar, R., Troelstra, C., Swagemakers, S. M., Essers, J., Smit, B., Franssen, J. H., Pastink, A., Bezzubova, O. Y., Buerstedde, J. M., Clever, B., Heyer, W. D. and Hoeijmakers, J. H. (1996). Human and mouse homologs of the Saccharomyces cerevisiae RAD54 DNA repair gene: evidence for functional conservation. Curr Biol; 6, 828-838.

[Non-patent Document 67] Yarden, R. I., Pardo-Reoyo, S., Sgagias, M., Cowan, K. H. and Brody, L. C. (2002). BRCA1 regulates the G2/M checkpoint by activating Chk1 kinase upon DNA damage. Nat Genet., 30, 285-289. Epub 2002 Feb. 11.

[Non-patent Document 68] Mimori, T., Ohosone, Y., Hama, N., Suwa, A., Akizuki, M., Homma, M., Griffith, A. J. and Hardin, J. A. (1990). Isolation and characterization of cDNA encoding the 80-kDa subunit protein of the human autoantigen Ku (p70/p80) recognized by autoantibodies from patients with scleroderma-polymyositis overlap syndrome. Proc Natl Acad Sci USA., 87, 1777-1781.

[Non-patent Document 69] Li, Z., Otevrel, T., Gao, Y., Cheng, H. L., Seed, B., Stamato, T. D., Taccioli, G. E. and Alt, F, W. (1995). The XRCC4 gene encodes a novel protein involved in DNA double-strand break repair and V(D)J recombination. Cell., 83, 1079-1089.

[Non-patent Document 70] Kim, S. H., Kaminker, P. and Campisi, J. (1999). TIN2, a new regulator of telomere length in human cells. Nat Genet., 23, 405-412.

[Non-patent Document 71] Afshar, G. and Murnane, J. P. (1999). Characterization of a human gene with sequence homology to Saccharomyces cerevisiae SIR2. Gene., 234, 161-168.

[Non-patent Document 72] Koike, G., Maki, H., Takeya, H., Hayakawa, H. and Sekiguchi, M. (1990). Purification, structure, and biochemical properties of human O6-methylguanine-DNA methyltransferase. J Biol Chem., 265, 14754-14762.

[Non-patent Document 73] Ladner, R. D., McNulty, D. E., Can, S. A., Roberts, G. D. and Caradonna, S. J. (1996). Characterization of distinct nuclear and mitochondrial forms of human deoxyuridine triphosphate nucleotidohydrolase. J Biol Chem., 271, 7745-7751.

[Non-patent Document 74] Sangoram, A. M., Saez, L., Antoch, M. P., Gekakis, N., Staknis, D., Whiteley, A., Fruechte, E. M., Vitaterna, M. H., Shimomura, K., King, D. P., Young, M. W., Weitz, C. J. and Takahashi, J. S. (1998). Mammalian circadian autoregulatory loop: a timeless ortholog and mPer1 interact and negatively regulate CLOCK-BMAL1-induced transcription. Neuron., 21, 1101-13.

[Non-patent Document 75] Hiraoka, L. R., Harrington, J. J., Gerhard, D. S., Lieber, M. R. and Hsieh, C. L. (1995). Sequence of human FEN-1, a structure-specific endonuclease, and chromosomal localization of the gene (FEN1) in mouse and human. Genomics., 25, 220-225.

[Non-patent Document 76] Liu, L., Mo, J., Rodriguez-Belmonte, E. M. and Lee, M. Y. (2000). Identification of a fourth subunit of mammalian DNA polymerase delta. J Biol Chem., 275, 18739-18744.

[Non-patent Document 77] Li, Y., Pursell, Z. F. and Linn, S. (2000). Identification and cloning of two histone fold motif-containing subunits of HeLa DNA polymerase epsilon. J Biol Chem., 275, 23247-23252.

[Non-patent Document 78] Hofmann, R. M. and Pickart, C. M. (1999). Noncanonical MMS2-encoded ubiquitin-conjugating enzyme functions in assembly of novel polyubiquitin chains for DNA repair. Cell., 96, 645-653.

[Non-patent Document 79] Neddermann, P. and Jiricny, J. (1993). The purification of a mismatch-specific thymine-DNA glycosylase from HeLa cells. J Biol Chem., 268, 21218-21224.

[Non-patent Document 80] Budd, M. E., Choe, W. C. and Campbell, J. L. (1995). DNA2 encodes a DNA helicase essential for replication of eukaryotic chromosomes. J Biol Chem., 270, 26766-26769.

[Non-patent Document 81] Budd, M. E. and Campbell, J. L. (1995). A yeast gene required for DNA replication encodes a protein with homology to DNA helicases. Proc Natl Acad Sci USA., 92, 7642-7646.

[Non-patent Document 82] Tang, J. and Chu, G. (2002). Xeroderma pigmentosum complementation group E and UV-damaged DNA-binding protein. DNA Repair (Amst)., 1, 601-616.

[Non-patent Document 83] Martin-Lluesma, S., Stucke, V. M. and Nigg, E. A. (2002). Role of Hec1 in spindle checkpoint signaling and kinetochore recruitment of Mad1/Mad2. Science., 297, 2267-2270.

DISCLOSURE OF THE INVENTION

An objective of the present invention is to provide cancer cell-specific apoptosis-inducing agents. More specifically, an objective of the present invention is to provide cancer cell-specific apoptosis-inducing agents having as an active ingredient a compound which inhibits chromosome stabilization, a compound which inhibits expression of a gene involved in chromosome stabilization, or a compound which inhibits a function of a protein encoded by the gene, and methods of screening for the apoptosis-inducing agents. Another objective of the present invention is to provide methods for producing an apoptosis-inducing agent as a pharmaceutical composition.

To achieve the above objectives, the present inventors examined whether apoptosis is induced cancer cell-specifically by abnormalities in various functions relating to chromosome stabilization in cells. The following functions that are deeply involved in chromosome stabilization were selected as cellular chromosome stabilization-associated functions: (a) genes associated with human chromosomal instability disorders, (b) chromosomal DNA replication reaction including initiation of chromosomal DNA replication and progression of replication fork, (c) DNA damage checkpoints, (d) sister chromatid agglutination and separation, (e) base excision repair, (f) mismatch excision repair, (g) nucleotide excision repair, (h) homologous recombination repair, (i) non-homologous end joining repair (non-homologous recombination repair), (j) double-strand DNA break repair, (k) DNA post-replication repair (DNA damage tolerance), (l) DNA crosslink damage repair, (m) DNA-protein crosslink damage repair, (n) DNA polymerase, (O) nuclease, (p) nucleotide cleansing, (q) chromatin structure maintenance, and (r) telomere structure maintenance.

The present inventors examined the cancer cell apoptosis-inducing effects of various genes involved in each of the aforementioned functions using siRNA having expression inhibitory effects on the genes. As a result, it was found that apoptosis was induced in cancer cells when the expression of a plurality of genes involved in each of the aforementioned functions were inhibited, and that this brought about an inhibition of cancer cell proliferation. The present inventors also discovered that induction of apoptosis does not occur with respect to normal cells (wild-type cells) even if the expression of these genes were inhibited. These genes are considered to be target molecules for preparing highly superior anticancer agents (carcinostatics) having few adverse side effects.

The above results suggested that inhibition of the expression of genes involved in each of the aforementioned functions would be able to induce apoptosis. In addition, these genes are deeply involved in each of the aforementioned functions, and inhibition of the expression of the genes generally prevents the functions from working normally in cells. Thus, the aforementioned findings made by the present inventors indicates none other than the fact that cancer cell-specific apoptosis is induced to due to abnormalities in each of the aforementioned functions. Accordingly, compounds that inhibit the aforementioned functions are considered to have the action of inducing cancer cell-specific apoptosis.

In addition, abnormalities in the aforementioned functions are known to destabilize chromosomes. Thus, chromosome destabilization in cells is considered to trigger induction of cancer cell-specific apoptosis. Namely, compounds that inhibit chromosome stabilization in cells, or compounds that inhibit the function of genes involved in chromosome stabilization, are expected to serve as cancer cell-specific apoptosis-inducing agents.

The present invention provides cancer cell-specific apoptosis-inducing agents having as an active ingredient a compound which inhibits chromosome stabilization, a compound which inhibits expression of a gene involved in chromosome stabilization, or a compound which inhibits the function of a protein encoded by said gene, and methods of screening for said apoptosis-inducing agents. More specifically, the present invention provides the following:

[1] a cancer cell-specific apoptosis-inducing agent, comprising a compound that inhibits chromosome stabilization;

[2] the apoptosis-inducing agent of [1], wherein inhibition of chromosome stabilization is due to the inhibition of any one of the following functions (a) to (r):

(a) genes associated with human chromosomal instability disorders, (b) chromosomal DNA replication reaction including initiation of chromosomal DNA replication and progression of replication fork, (c) DNA damage checkpoints, (d) sister chromatid agglutination and separation, (e) base excision repair, (f) mismatch excision repair, (g) nucleotide excision repair, (h) homologous recombination repair, (i) non-homologous end-joining repair (non-homologous recombination repair), (j) double-strand DNA break repair, (k) DNA post-replication repair (DNA damage tolerance), (l) DNA crosslink damage repair, (m) DNA-protein crosslink damage repair, (n) DNA polymerases, (o) nucleases, (p) nucleotide cleansing, (q) chromatin structure maintenance, and (r) telomere structure maintenance;

[3] a cancer cell-specific apoptosis-inducing agent, comprising a compound that inhibits expression of a gene involved in any one of the functions of (a) to (r) described in [2];

[4] a cancer cell-specific apoptosis-inducing agent, comprising as an active ingredient a compound that inhibits expression of any one of the following genes:

APE2, ATR, BRCA1, Chk1, Cdc5, Cdc6, Cdc7, Cdc45, Cdt1, CSA, CSB, Ctf18, DDB1, DDB2, DNA2, DUT, Elg1, EndoV, Esp1, Exonuclease1, FBH1, FEN1, Geminin, Hus1, KNTC2 (NDC80), Ku80, Ligase1, Mad2, MBD4, Mcm3, Mcm4, Mcm5, Mcm6, Mcm7, Mcm8, Mcm10, MGMT, MLH3, Mms4, MPG, MSH2, Mus81, NBS1, NEIL2, NEIL3, NTH1, Orc1, Orc3, PARP1, PCNA, Pif1, PMS1, PMS2, PNK, Pola p180, Pola p70, Pola Spp1(Prim2a), Polb, Pold p125, Pole Dpb3, Pole Dpb4, Pole Pol2, Poli, Poll, Polm, Psf1, Psf2, Psf3, Rad1, Rad18, Rad23A, Rad23B, Rad51, Rad51D, Rad54, Rad6A, RPA34, RPA70, Scc1, Scc3, Sir2, SIRT1 (Sirtuin), TDG, TDP1, TIMELESS, Tin2, Topoisomerase I, Topoisomerase IIIa, Topoisomerase IIIb, Ubc13, UNG, XAB2, XPC, XPF, XPG, Xrcc2, and XRCC4;

[5] the apoptosis-inducing agent of [4], wherein nucleotide sequence of each gene described in [4] is selected from the group consisting of the nucleotide sequences described in SEQ ID NOs: 1 to 637 and 810 to 908;

[6] the apoptosis-inducing agent of [4], wherein the compound that inhibits expression of any one of the genes described in [4] is a double-strand RNA having an RNAi effect (siRNA) on said gene;

[7] the apoptosis-inducing agent of [6], wherein the double-strand RNA is a double-strand RNA comprising a sense RNA consisting of a sequence homologous with arbitrary 20 to 30 contiguous bases in an mRNA of any one of the genes described in [4], and an antisense RNA consisting of a sequence complementary to said sense RNA,

[7b] the apoptosis-inducing agent of [6], wherein the double-strand RNA having an RNAi effect is a double-strand RNA in which one strand of the double strand is a nucleotide sequence described in SEQ ID NOs: 724 to 809 (this strand of the double strand is composed of a region excluding the terminal TT from the sequence) or a nucleotide sequence described in SEQ ID NOs: 974 to 1063, and the other strand is a nucleotide sequence complementary to said nucleotide sequence,

[7c] the apoptosis-inducing agent of [6], wherein the double-strand RNA having an RNAi effect is a double-strand RNA in which one strand of the double strand is a nucleotide sequence with one or a small number of nucleotide additions, deletions, or substitutions to a nucleotide sequence described in SEQ ID NOs: 724 to 809 (this strand of the double strand is composed of a region excluding the terminal TT from the sequence) or SEQ ID NOs: 974 to 1063, and the other strand is a nucleotide sequence complementary to said nucleotide sequence, wherein the double-strand RNA has a function to inhibit expression of any of the genes described in [4] above,

[7d] the cancer cell-specific apoptosis-inducing agent comprising as an active ingredient a molecule having a structure in which one end of the double-strand RNA is closed (forming a hairpin),

[8] a cancer cell-specific apoptosis-inducing agent, comprising as an active ingredient a DNA able to express a double-strand RNA having an RNAi effect on any one of the genes described in [4];

[9] the apoptosis-inducing agent of [4], wherein the compound that inhibits expression of any one of the genes described in [4] is the following (a) or (b):

(a) an antisense nucleic acid against a transcription product of said gene or a portion thereof, or (b) a nucleic acid having ribozyme activity which specifically cleaves a transcription product of said gene;

[10] a cancer cell-specific apoptosis-inducing agent comprising as an active ingredient a compound that inhibits the function of a protein encoded by any one of the genes described in [4];

[11] the apoptosis-inducing agent of [10], wherein the compound that inhibits the function of a protein encoded by any one of the genes described in [4] is a compound of any one of the following (a) to (c):

(a) a mutant protein having a dominant negative trait with respect to a protein encoded by said gene;

(b) an antibody which binds to a protein encoded by said gene; and, (c) a low molecular weight compound that binds to a protein encoded by said gene;

[12] an anticancer agent, comprising as an active ingredient an apoptosis-inducing agent of any one of [1] to [11];

[13] a method of screening for a cancer cell-specific apoptosis-inducing agent, comprising the following steps (a) to (c):

(a) contacting a test compound with a protein encoded by any one of the genes described in [4], or a partial peptide of the protein;

(b) measuring the binding activity between the protein, or partial peptide thereof, and the test compound; and (c) selecting a compound which binds to the protein encoded by said gene, or the partial peptide of the protein;

[14] a method of screening for a cancer cell-specific apoptosis-inducing agent, comprising the following steps (a) to (c):

(a) contacting a test compound with a cell that expresses any one of the genes described in [4], or a cell extract thereof;

(b) measuring the expression level of said gene; and (c) selecting a compound which lowers said expression level as compared to a level measured in the absence of the test compound;

[15] a method of screening for a cancer cell-specific apoptosis-inducing agent, comprising the following steps (a) to (c):

(a) contacting a test compound with a cell comprising a DNA having a structure in which the transcriptional regulatory region of any one of the genes described in [4] is operably linked to a reporter gene, or with a cell extract thereof;

(b) measuring the expression level of the reporter gene; and (c) selecting a compound which lowers the expression level as compared to a level measured in the absence of the test compound;

[16] a method of screening for a cancer cell-specific apoptosis-inducing agent, comprising the following steps (a) to (c):

(a) contacting a test compound with a protein encoded by any one of the genes described in [4], or a cell that expresses said protein, or a cell extract thereof;

(b) measuring the activity of the protein; and (c) selecting a compound which lowers the activity of the protein as compared to an activity measured in the absence of the test compound; and

[17] a method for producing the apoptosis-inducing agent of [4] or [10] as a pharmaceutical composition, comprising the following steps (a) and (b):

(a) screening for a compound by a method of any one of [13] to [16]; and (b) mixing said compound with a pharmaceutically acceptable carrier.

In addition, a specific embodiment of the present invention provides a cancer cell-specific apoptosis-inducing agent containing as its active ingredient an siRNA molecule having as one of the strands of the double-strand RNA a nucleotide sequence described in any of SEQ ID NOs: 724 to 809 and 974 to 1063 (siRNA molecule composed of a nucleotide sequence described in any of SEQ ID NOs: 724 to 809 and 974 to 1063, and a strand complementary thereto),

(18) a method for inducing apoptosis of target cells comprising a step of administering (contacting) any of the apoptosis-inducing agents to the cells,

(19) a method for treating cancer comprising a step of administering the apoptosis-inducing agent or anticancer agent to an individual (e.g., a cancer patient),

(20) use of a compound which inhibits chromosome stabilization (for example, a compound which inhibits expression of any of the genes described in (4) above or inhibits the function of a protein encoded by said genes) to produce an apoptosis-inducing agent, and

(21) use of the apoptosis-inducing agent to produce an anticancer agent.

BRIEF DESCRIPTION OF THE DRAWINGS

FIG. 1 shows the names of genes used in Examples, accession numbers, siRNA sequences, SEQ ID NOs, inhibition of gene expression in HeLa cells, MTT assay (HeLa cells), results of the TUNEL method, inhibition of gene expression in TIG3 cells, and MTT assay (TIG3 cells).

The column entitled "Inhibition of gene expression in HeLa cells" indicates the results of respectively introducing siRNA for each gene into HeLa cells, and quantifying expression of each mRNA by Taqman PCR 48 hours after introduction.

The column entitled "MTT assay (HeLa cells)" indicates the results of respectively introducing siRNA for each gene into HeLa cells, and investigating the cell survival rates by an MTT assay 4 days after introduction.

The column entitled "TUNEL method" shows YES if staining has been observed, i.e., when it was apoptosis-positive.

The column entitled "Inhibition of gene expression in TIG3 cells" indicates the results of respectively introducing siRNA for each gene into TIG3 cells and quantifying expression of mRNA 72 hours later by Taqman PCR. ND stands for "not detectable".

The column entitled "MTT assay (TIG3 cells)" indicates the results of respectively introducing siRNA for each gene into TIG3 cells and investigating the cell survival rates 4 days later by an MTT assay.

The genes were grouped according to their respective functions.

FIG. 2 is a continuation of FIG. 1.
FIG. 3 is a continuation of FIG. 2.
FIG. 4 is a continuation of FIG. 3.

Figure 5:
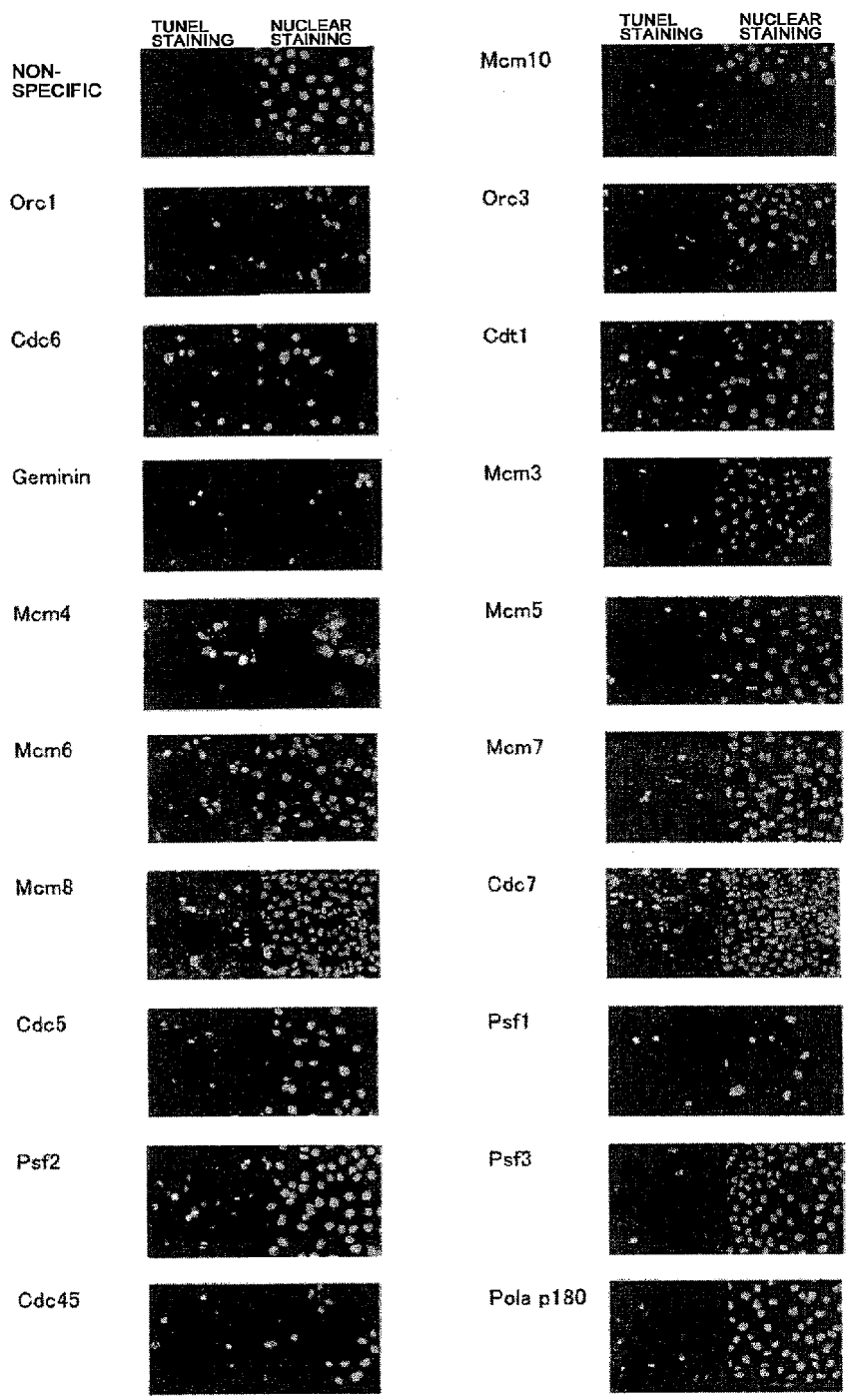

FIG. 5 shows photographs indicating induction of apoptosis by inhibition of mRNA expression of each gene in HeLa cells. The photographs show the results of respectively introducing siRNA for each gene into HeLa cells and examining induction of apoptosis in the HeLa cells 48 hours after introduction using the TUNEL method. The green color on the left side of each panel (black-and-white photographs are shown) indicates apoptotic nuclei, and the right side indicates nuclei of cells present in the field of view.

Figure 6:
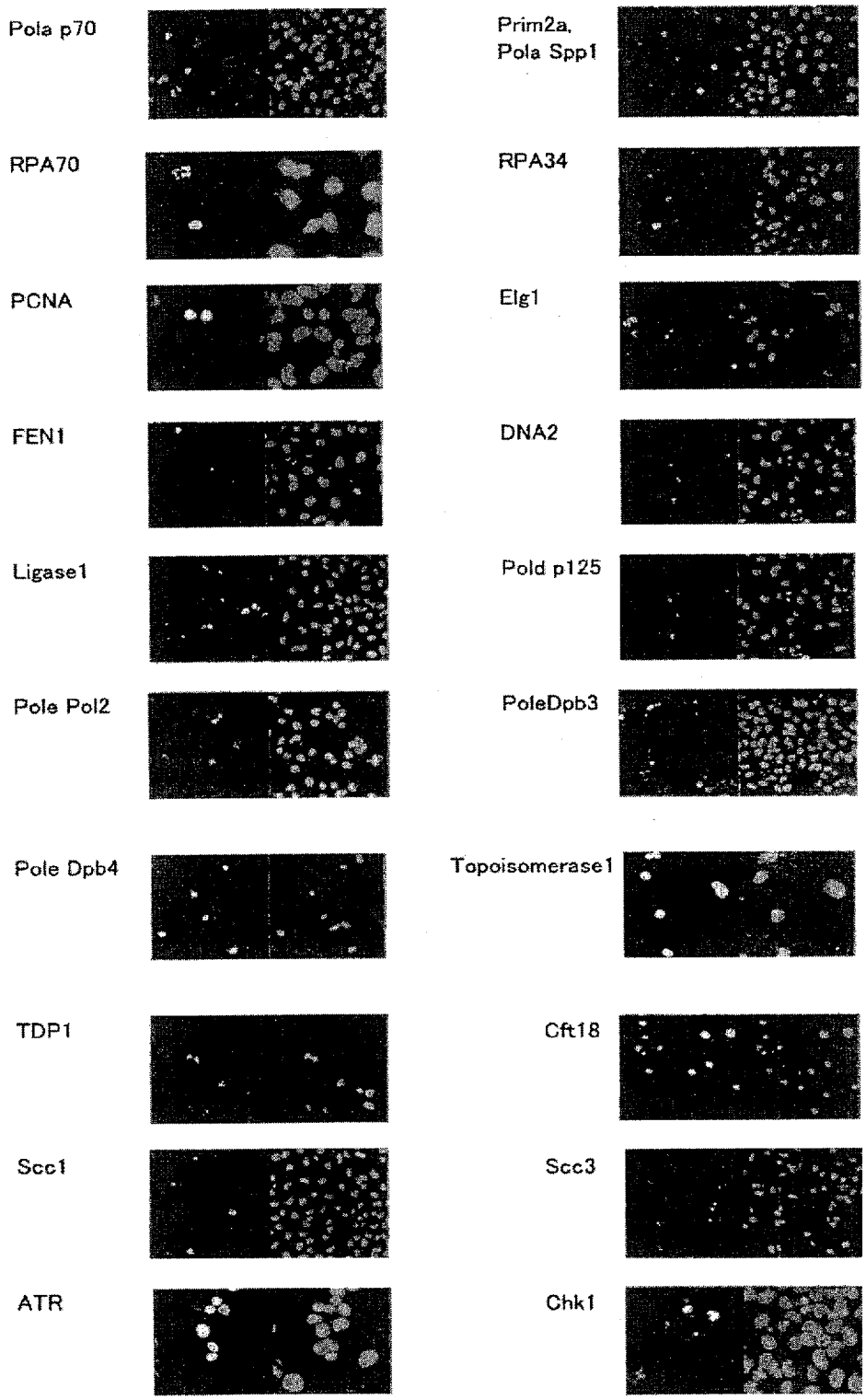
Figure 7:
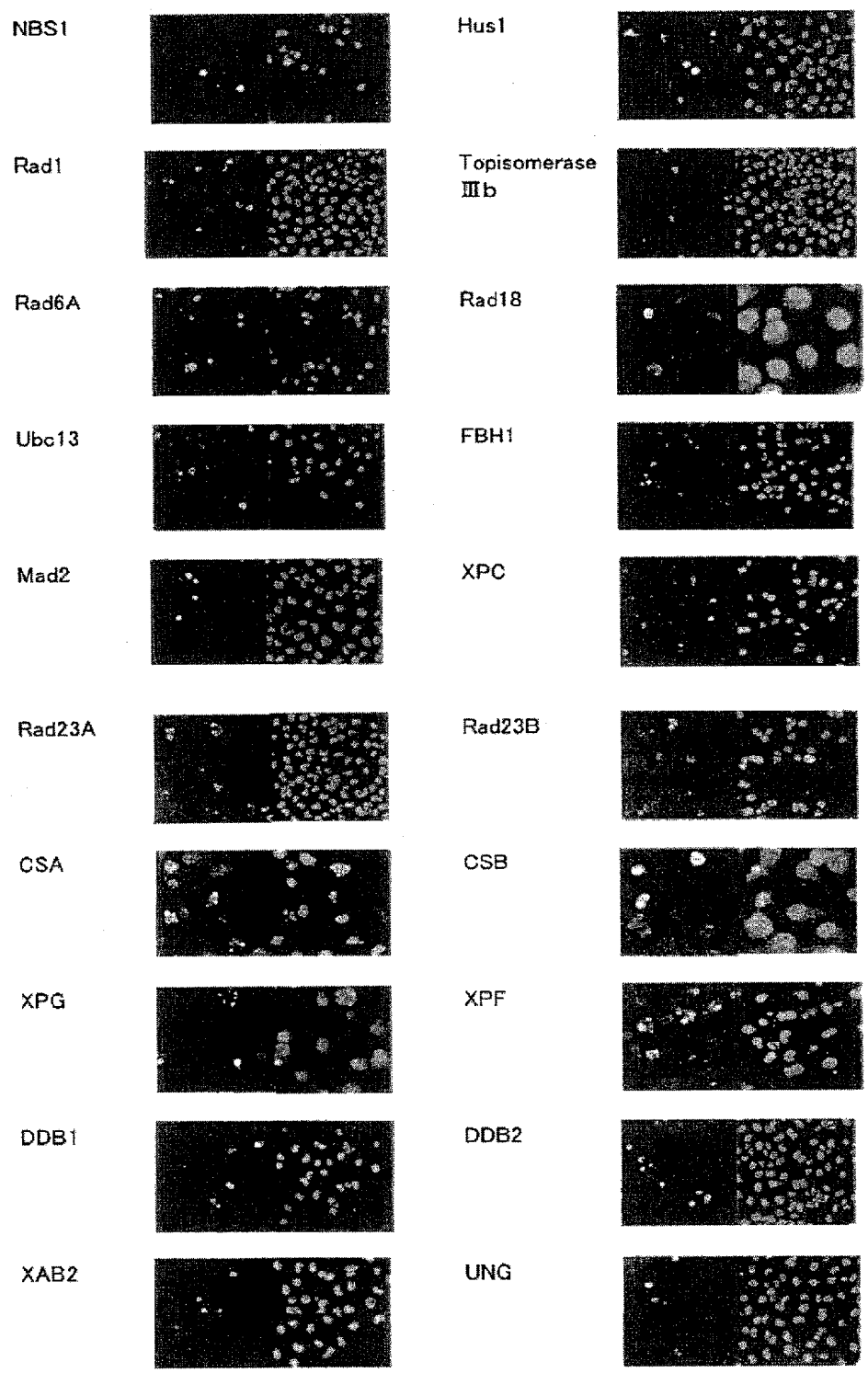
Figure 8:
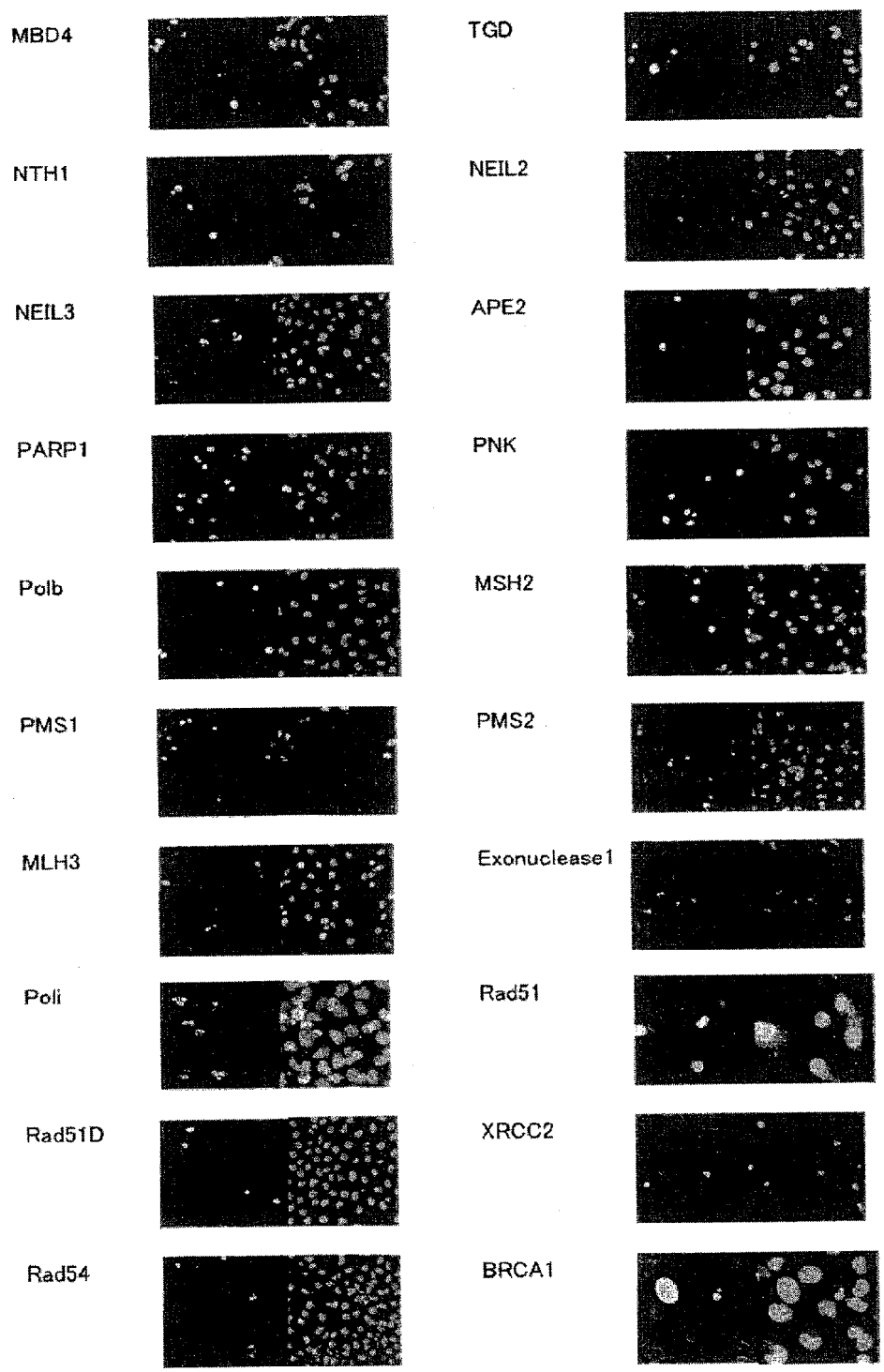

FIG. 6 is a continuation of FIG. 5.
FIG. 7 is a continuation of FIG. 6.
FIG. 8 is a continuation of FIG. 7.
FIG. 9 is a continuation of FIG. 8.

Figure 10:
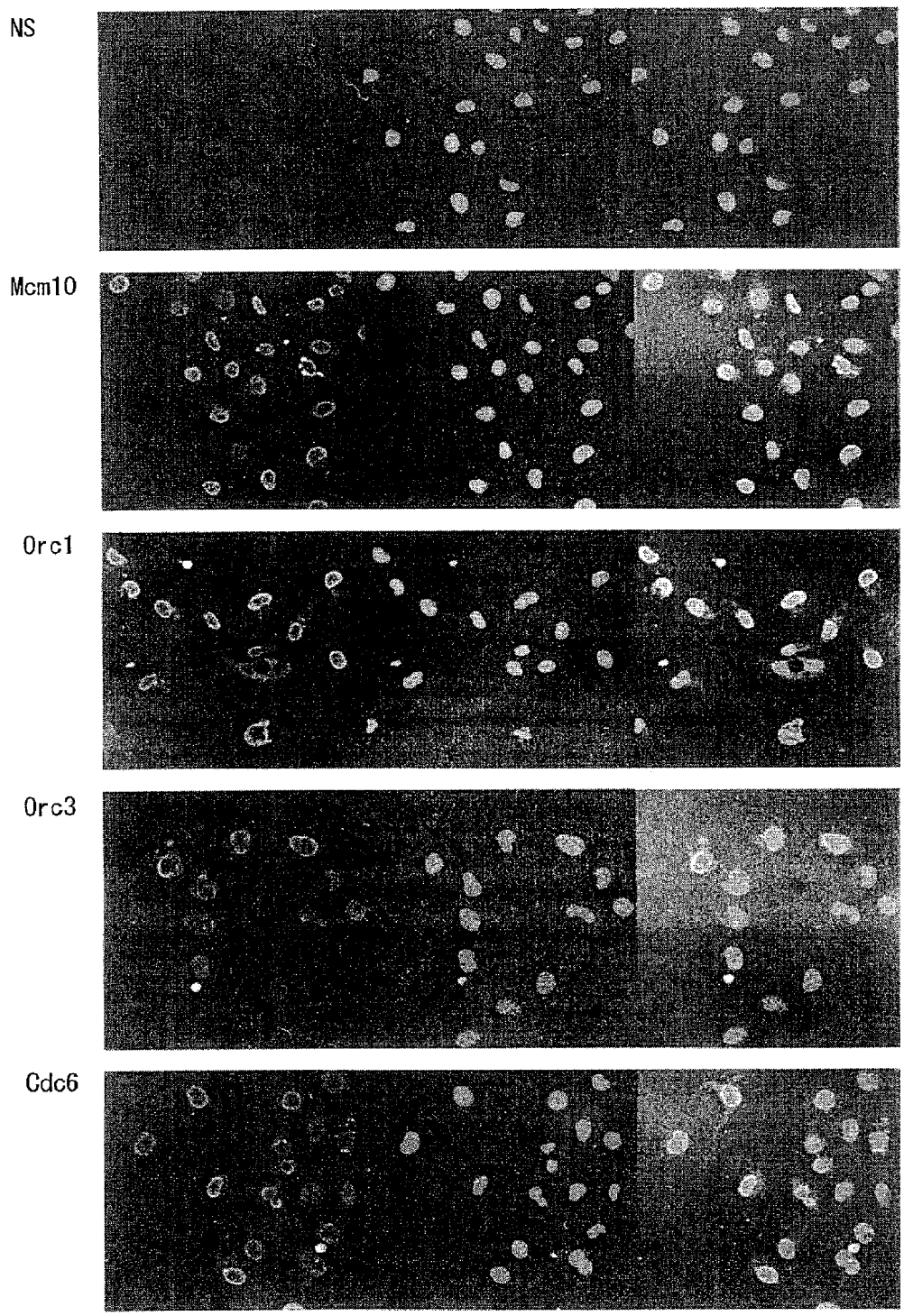

FIG. 10 shows photographs indicating the results of immunostaining the regions in which single-strand DNA is exposed in chromosomal DNA using anti-ssDNA antibody. Three photographs are shown for each gene. Starting from the left, an anti-ssDNA image, nuclear staining image, and superimposed image, are shown.

Figure 11:
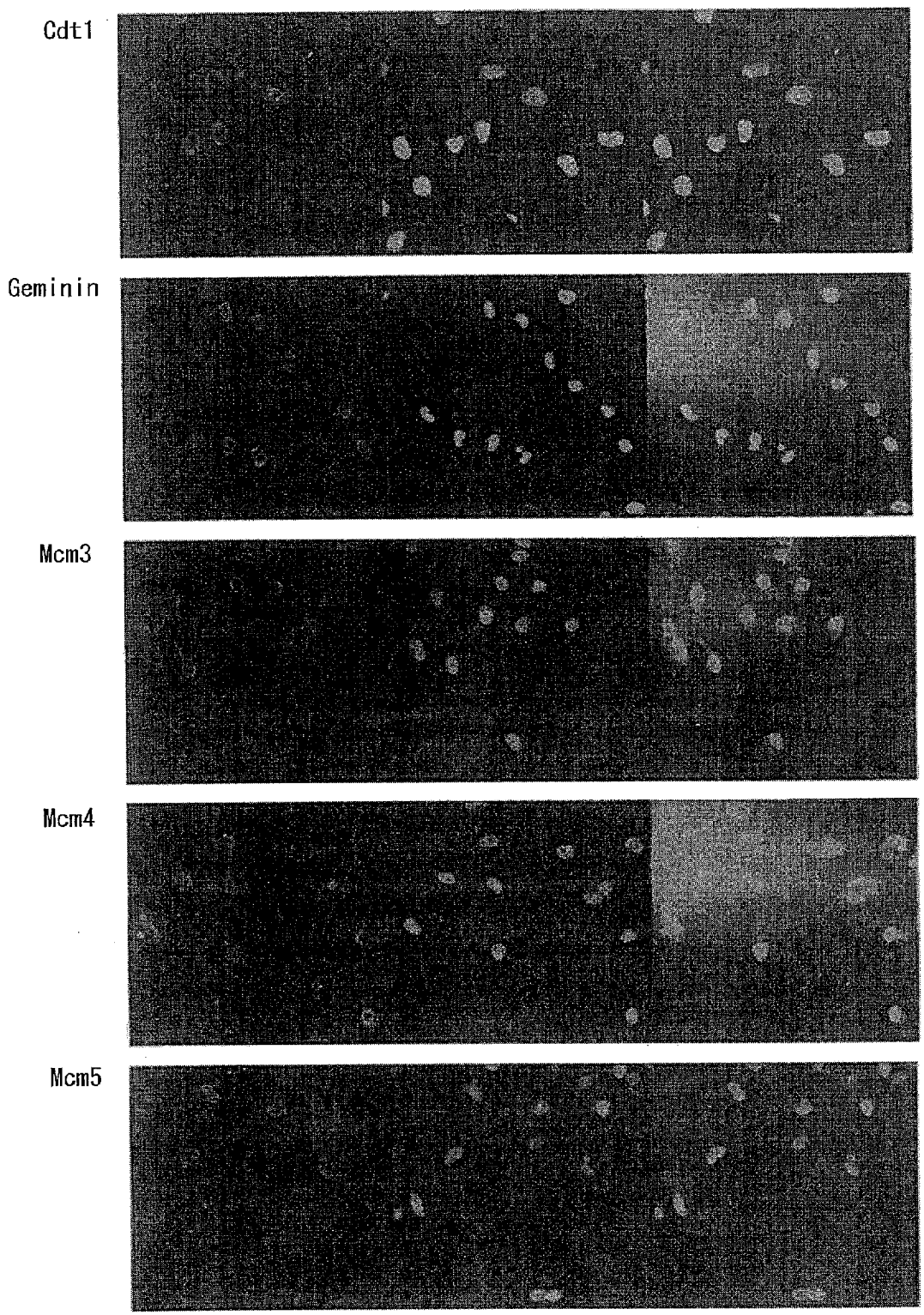
Figure 13:
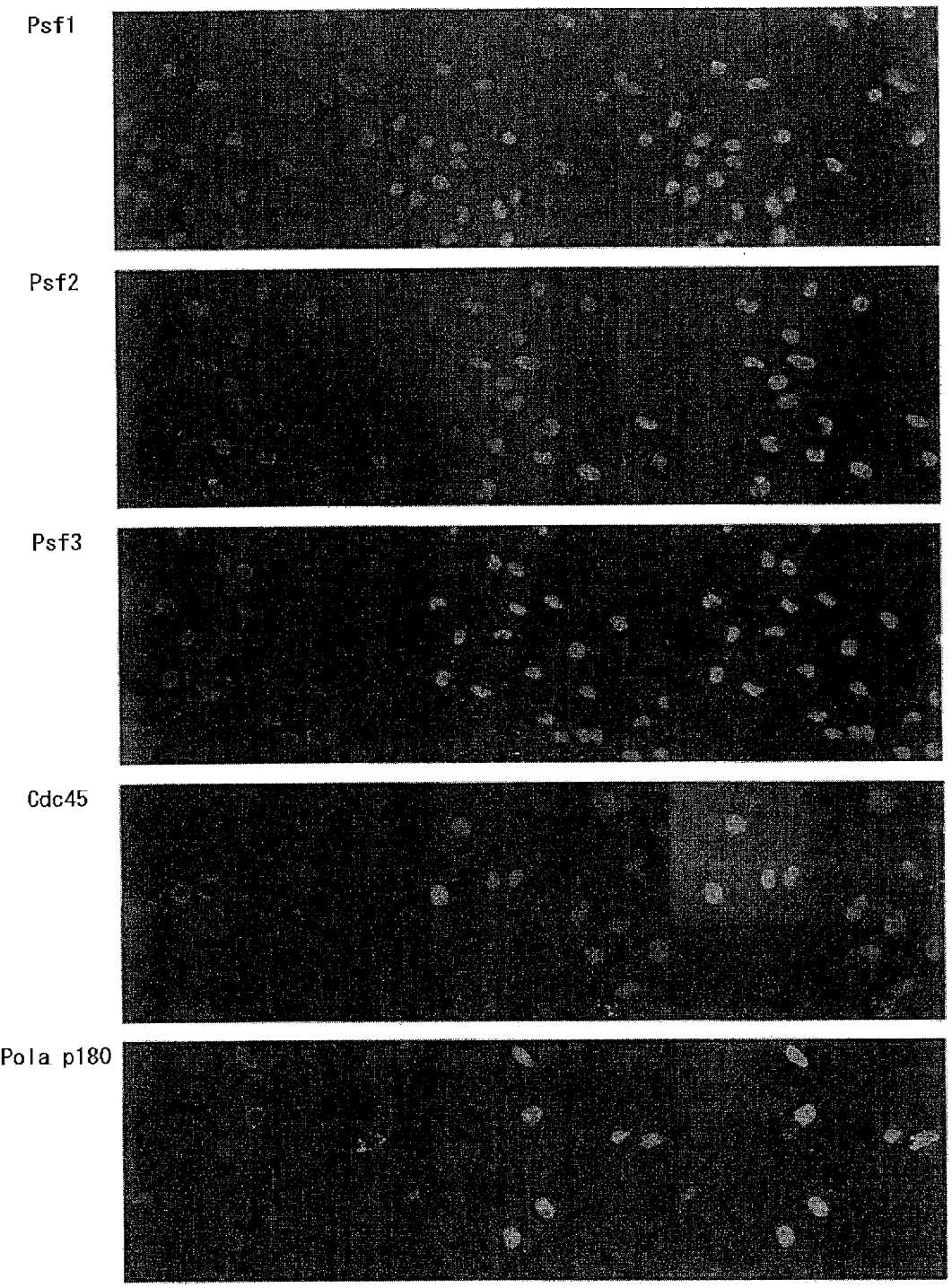
Figure 14:
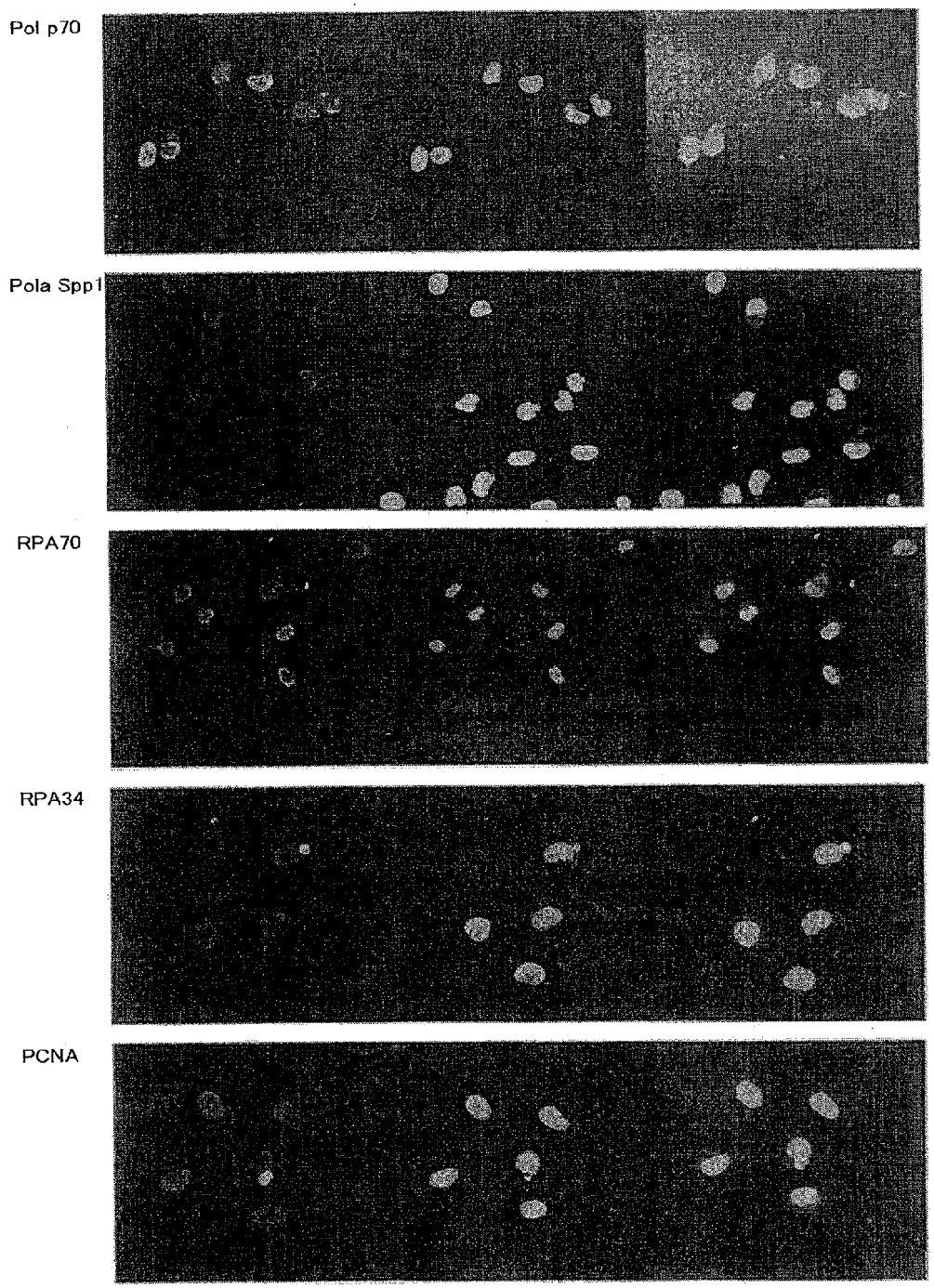
Figure 15:
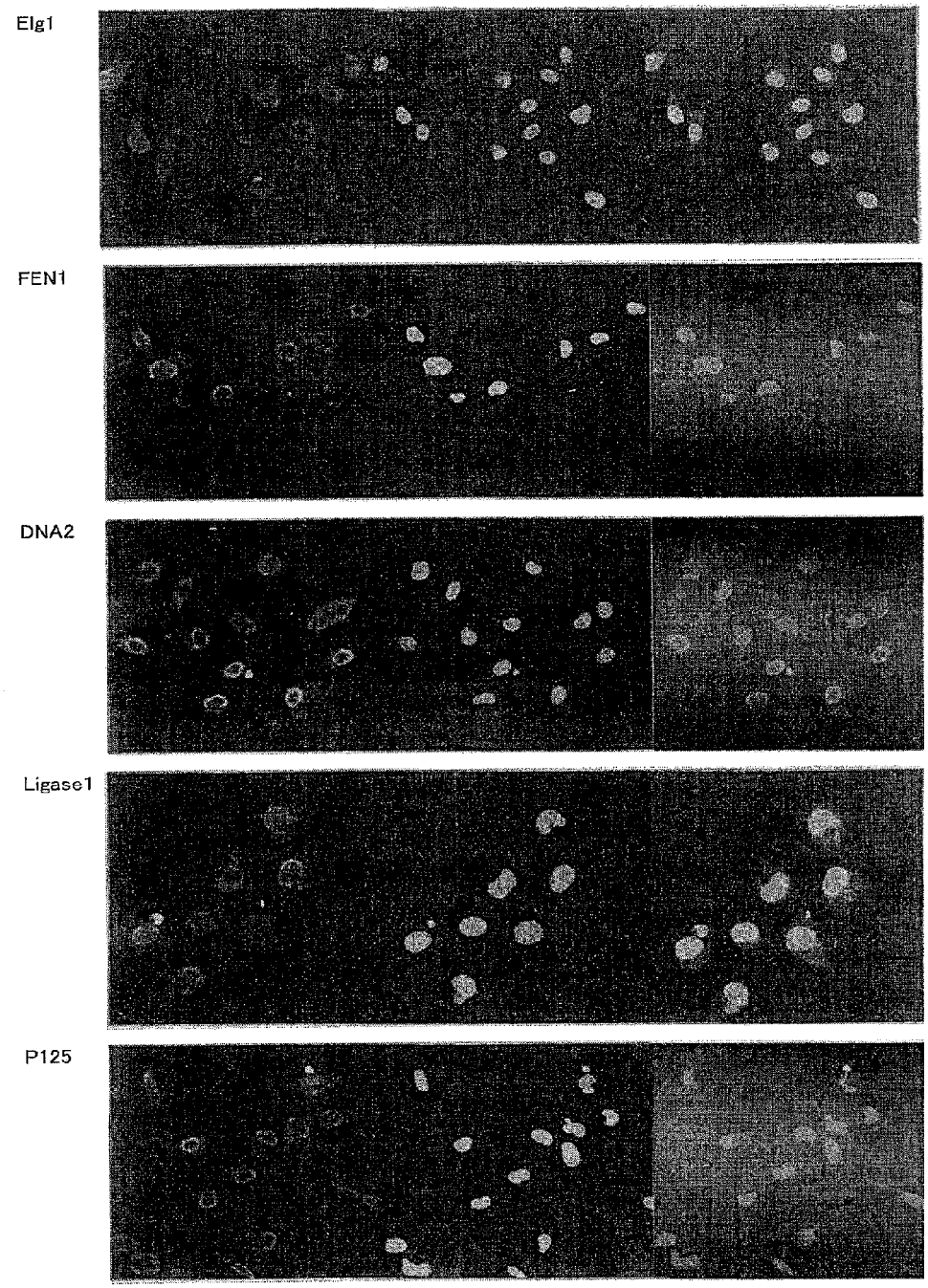
Figure 16:
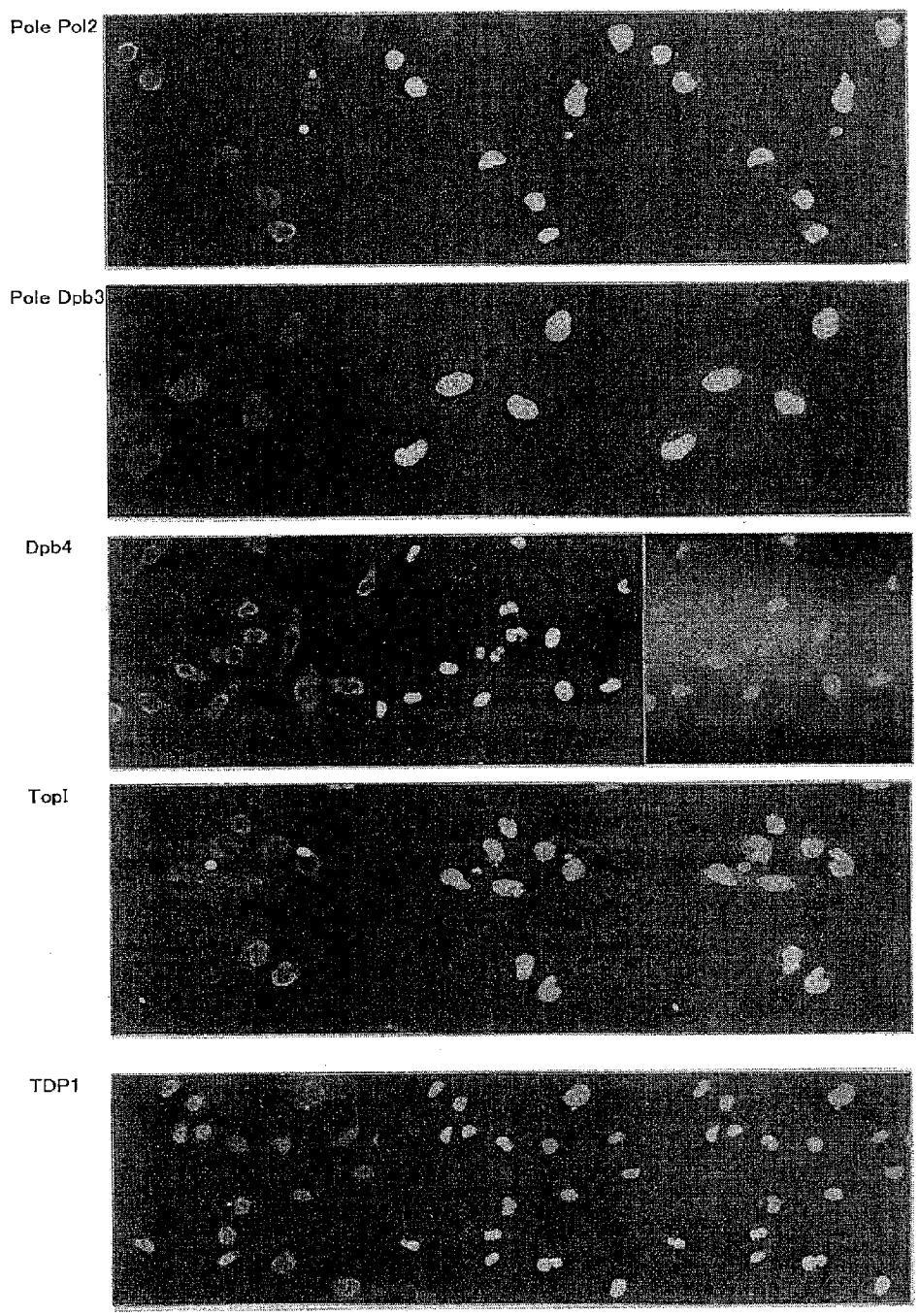
Figure 17:
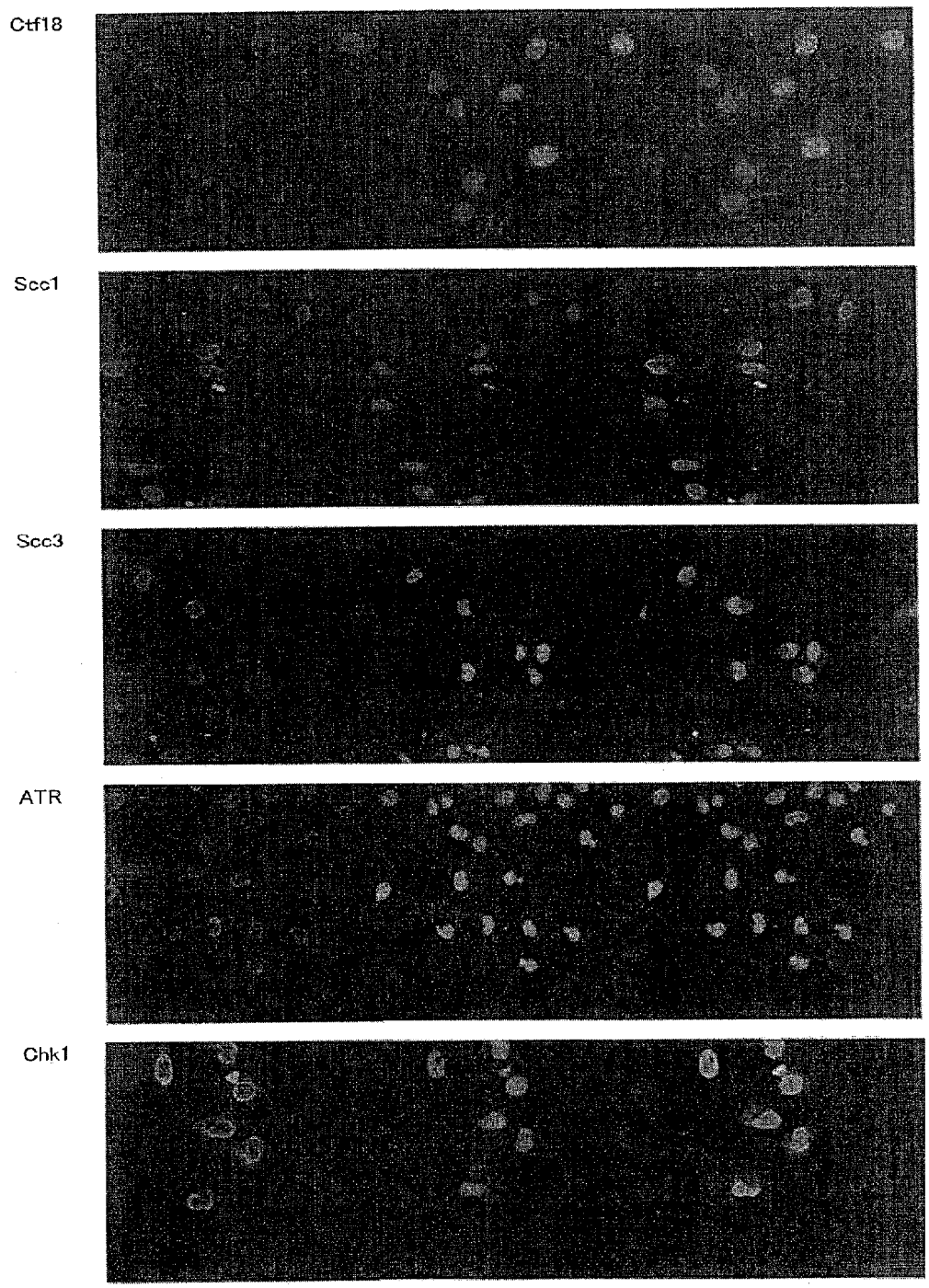
Figure 18:
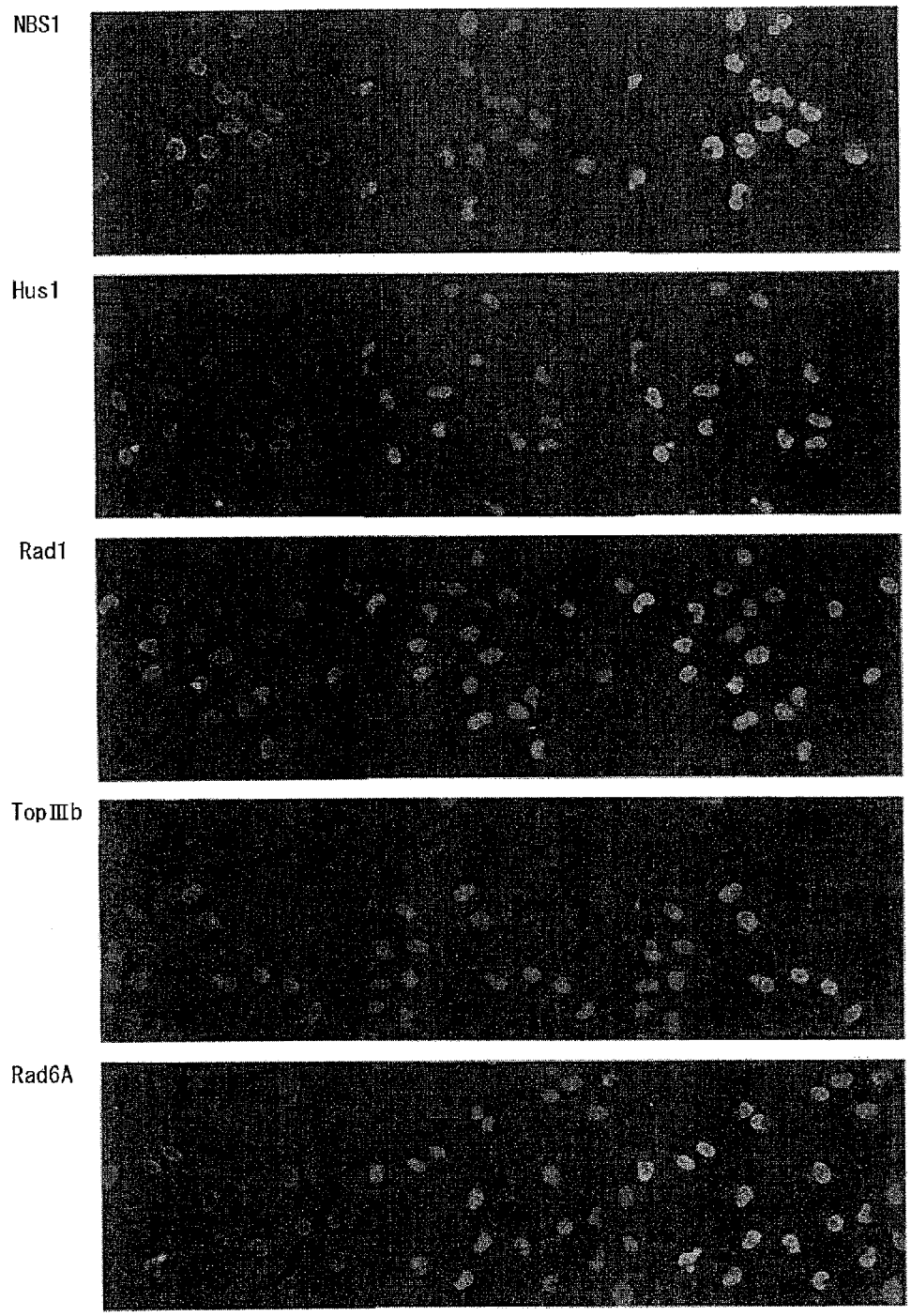
Figure 21:
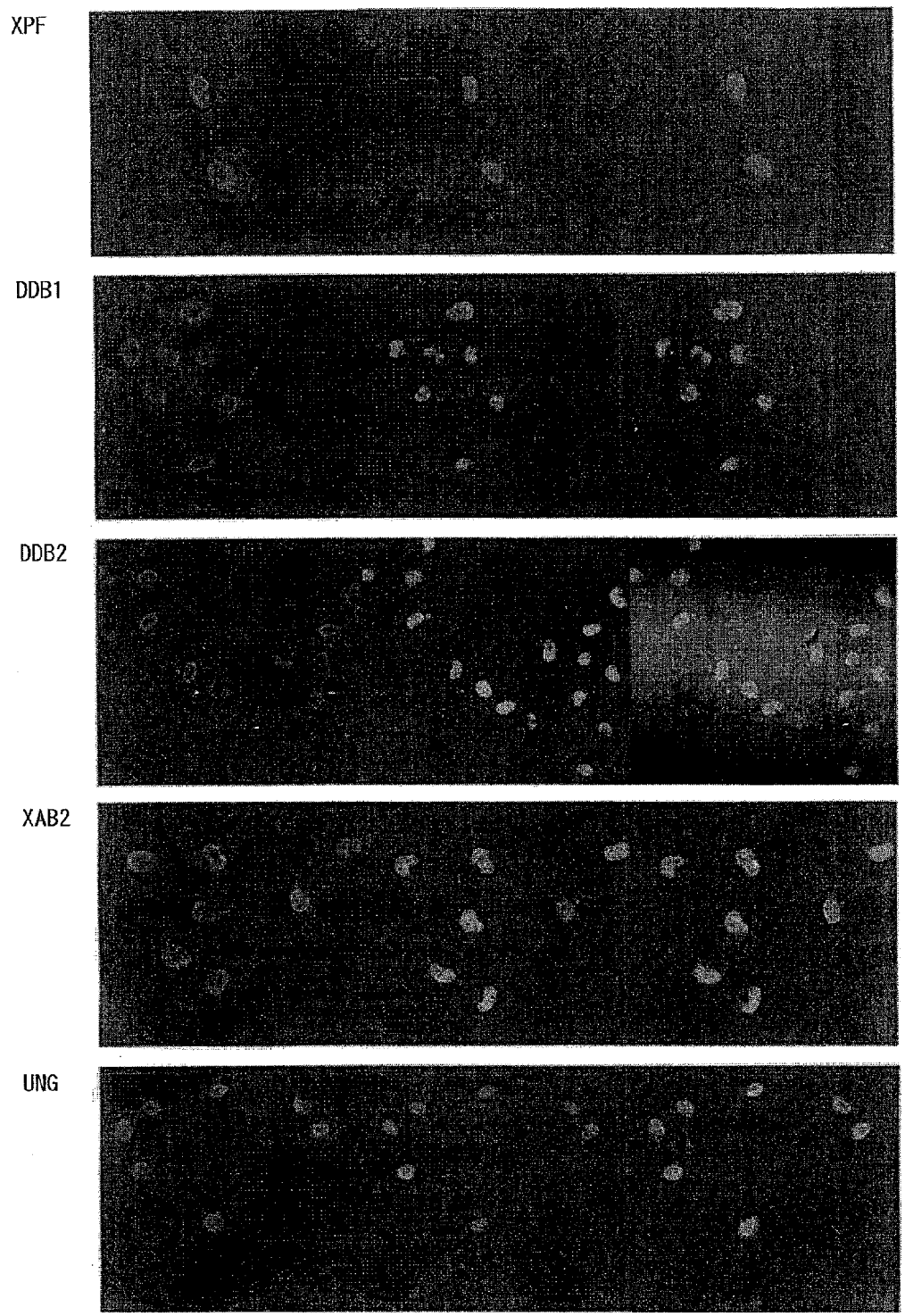
Figure 22:
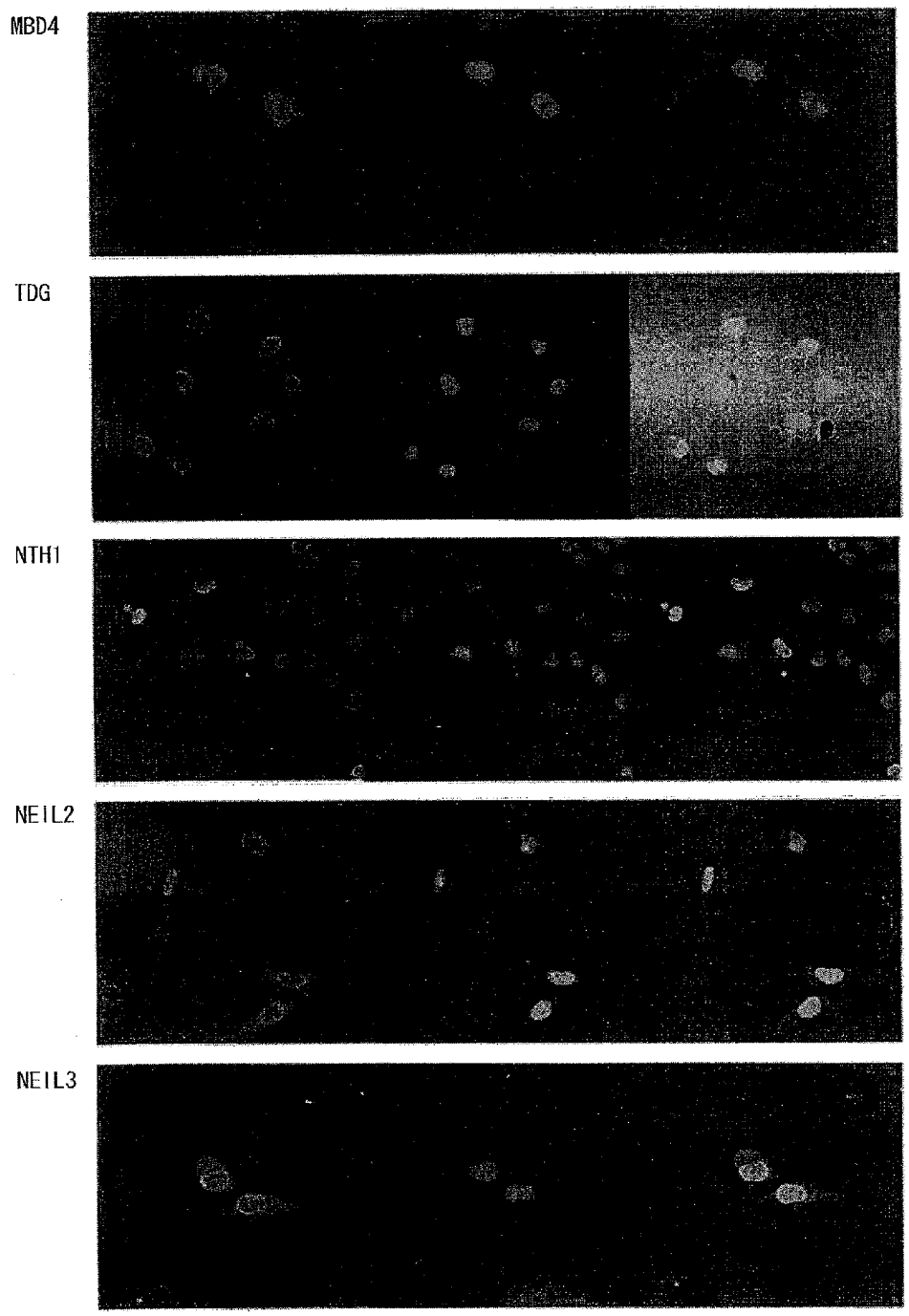
Figure 26:
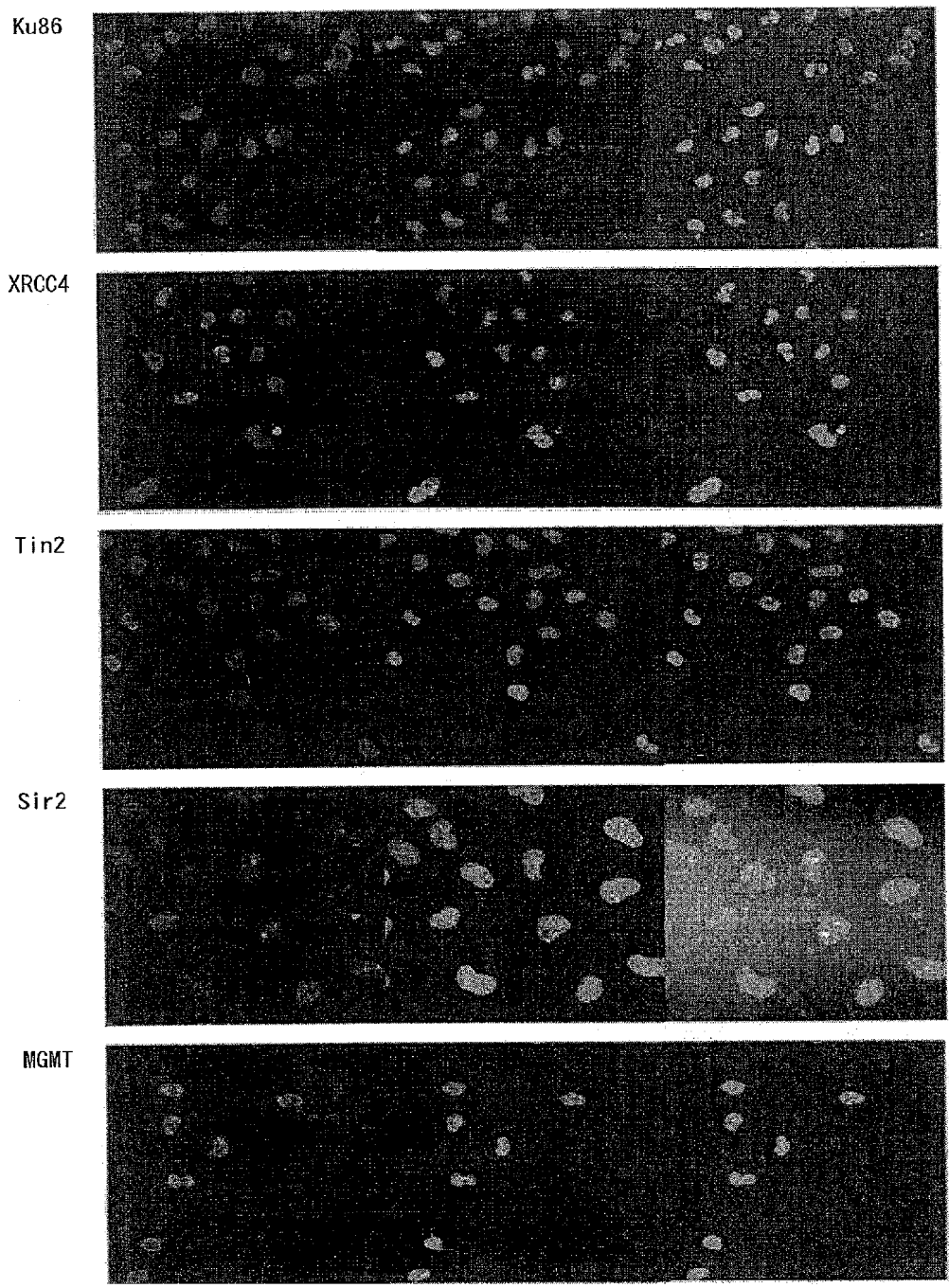
Figure 27:
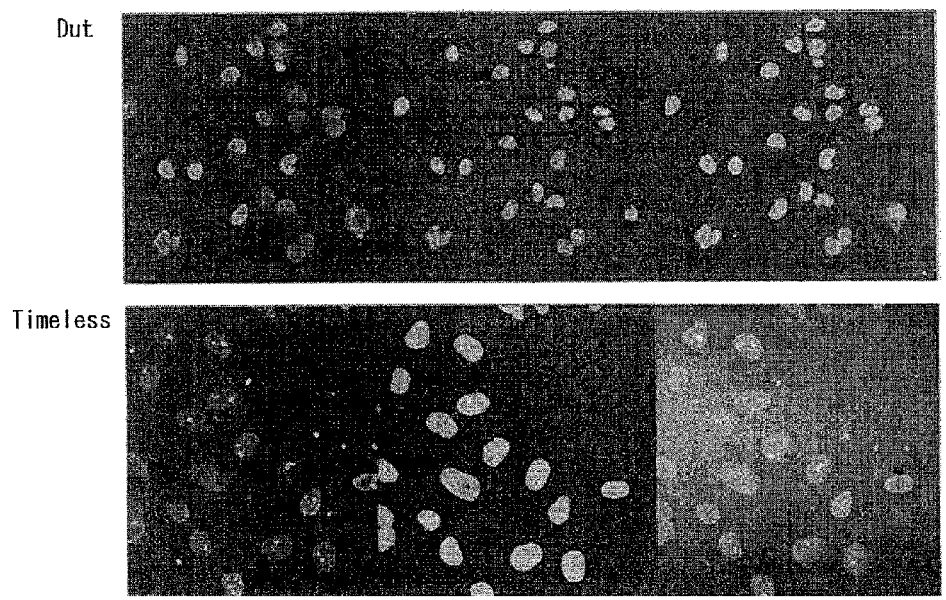

FIG. 11 is a continuation of FIG. 10.
FIG. 12 is a continuation of FIG. 11.
FIG. 13 is a continuation of FIG. 12.
FIG. 14 is a continuation of FIG. 13.
FIG. 15 is a continuation of FIG. 14.
FIG. 16 is a continuation of FIG. 15.
FIG. 17 is a continuation of FIG. 16.
FIG. 18 is a continuation of FIG. 17.
FIG. 19 is a continuation of FIG. 18.
FIG. 20 is a continuation of FIG. 19.
FIG. 21 is a continuation of FIG. 20.
FIG. 22 is a continuation of FIG. 21.
FIG. 23 is a continuation of FIG. 22.
FIG. 24 is a continuation of FIG. 23.
FIG. 25 is a continuation of FIG. 24.
FIG. 26 is a continuation of FIG. 25.
FIG. 27 is a continuation of FIG. 26.

FIG. 28 shows the names of genes used in Examples, accession numbers, other accession numbers, siRNA sequences, SEQ ID NOs, inhibition of gene expression in HeLa cells, inhibition of proliferation in HeLa cells, inhibition of gene expression in TIG3 cells, and inhibition of proliferation in TIG3 cells.

The column entitled "Inhibition of gene expression in 40 nM HeLa cells" indicates the results of respectively introducing an siRNA sequence for each gene into HeLa cells, and quantifying the expression of each mRNA by Taqman PCR 48 hours after introduction.

The column entitled "Inhibition of proliferation in 40 nM HeLa cells" indicates the results of respectively introducing an siRNA sequence for each gene into HeLa cells, and investigating the cell survival rates by an MTT assay 4 days after introduction.

The column entitled "Inhibition of gene expression in 40 nM TIG3 cells" indicates the results of respectively introducing siRNA for each gene into TIG3 cells, and quantifying the expression of mRNA 72 hours later by Taqman PCR. The symbol "**" indicates "not determined".

The column entitled "Inhibition of proliferation in 40 nM TIG3 cells" indicates the results of respectively introducing an siRNA sequence for each gene into TIG3 cells, and investigating the cell survival rates by an MTT assay 4 days after introduction.

The genes were grouped according to their respective functions.

FIG. 29 is a continuation of FIG. 28.
FIG. 30 is a continuation of FIG. 29.

FIG. 31 shows alternative names for KNTC2 (NDC80) gene, accession number, mRNA registrations, siRNA IDs, siRNA sequences, SEQ ID NOs, mRNA expression in HeLa cells, inhibition of proliferation in HeLa cells, apoptosis in HeLa cells, mRNA expression in HDF cells, inhibition of proliferation in HDF cells, and apoptosis in HDF cells.

The column entitled "mRNA expression" in HeLa cells indicates the results of respectively introducing an siRNA sequence for KNTC2 (NDC80) gene into HeLa cells, and quantifying expression of each mRNA by Taqman PCR 48 hours after introduction.

The column entitled "Inhibition of proliferation" in HeLa cells indicates the results of respectively introducing an siRNA sequence for KNTC2 (NDC80) gene into HeLa cells, and investigating the cell survival rates by an MTT assay 4 days after introduction.

The column entitled "Apoptosis" in HeLa cells shows YES if staining was observed, i.e., when it was apoptosis-positive.

The column entitled "mRNA expression" in HDF cells indicates the results of respectively introducing an siRNA sequence for KNTC2 (NDC80) gene into HDF cells, and quantifying the expression of each mRNA by Taqman PCR 48 hours after introduction.

The column entitled "Inhibition of proliferation" in HDF cells indicates the results of respectively introducing an siRNA sequence for KNTC2 (NDC80) gene into HDF cells, and investigating the cell survival rates by MTT assay 4 days after introduction.

The column entitled "Apoptosis" in HDF cells shows YES if staining was observed, i.e., when it was apoptosis-positive.

FIG. 32 shows the names of genes used in Examples, siRNA IDs, siRNA sequences, SEQ ID NOs, mRNA expression in HeLa cells, inhibition of proliferation in HeLa cells, apoptosis in HeLa cells, mRNA expression in HDF cells, inhibition of proliferation in HDF cells, and apoptosis in HDF cells.

The column entitled "Expression" of mRNA in HeLa cells indicates the results of respectively introducing an siRNA sequence for each gene into HeLa cells, and quantifying expression of each mRNA by Taqman PCR 48 hours after introduction.

The column entitled inhibition of "Proliferation" in HeLa cells indicates the results of respectively introducing an siRNA sequence for each gene into HeLa cells, and investigating the cell survival rates by an MTT assay 4 days after introduction.

The column entitled "Apoptosis" in HeLa cells shows "+" if staining was observed, i.e., when it was apoptosis-positive.

The column entitled "Expression" of mRNA in HDF cells indicates the results of respectively introducing an siRNA sequence for each gene into HDF cells, and quantifying expression of each mRNA by Taqman PCR 48 hours after introduction.

The column entitled inhibition of "Proliferation" in HDF cells indicates the results of respectively introducing an siRNA sequence for each gene into HDF cells, and investigating the cell survival rates by MTT assay 4 days after introduction.

The column entitled "Apoptosis" in HDF cells shows "+" if staining was observed, i.e., when it was apoptosis-positive, and shows "−" when it was apoptosis-negative.

Figure 33:
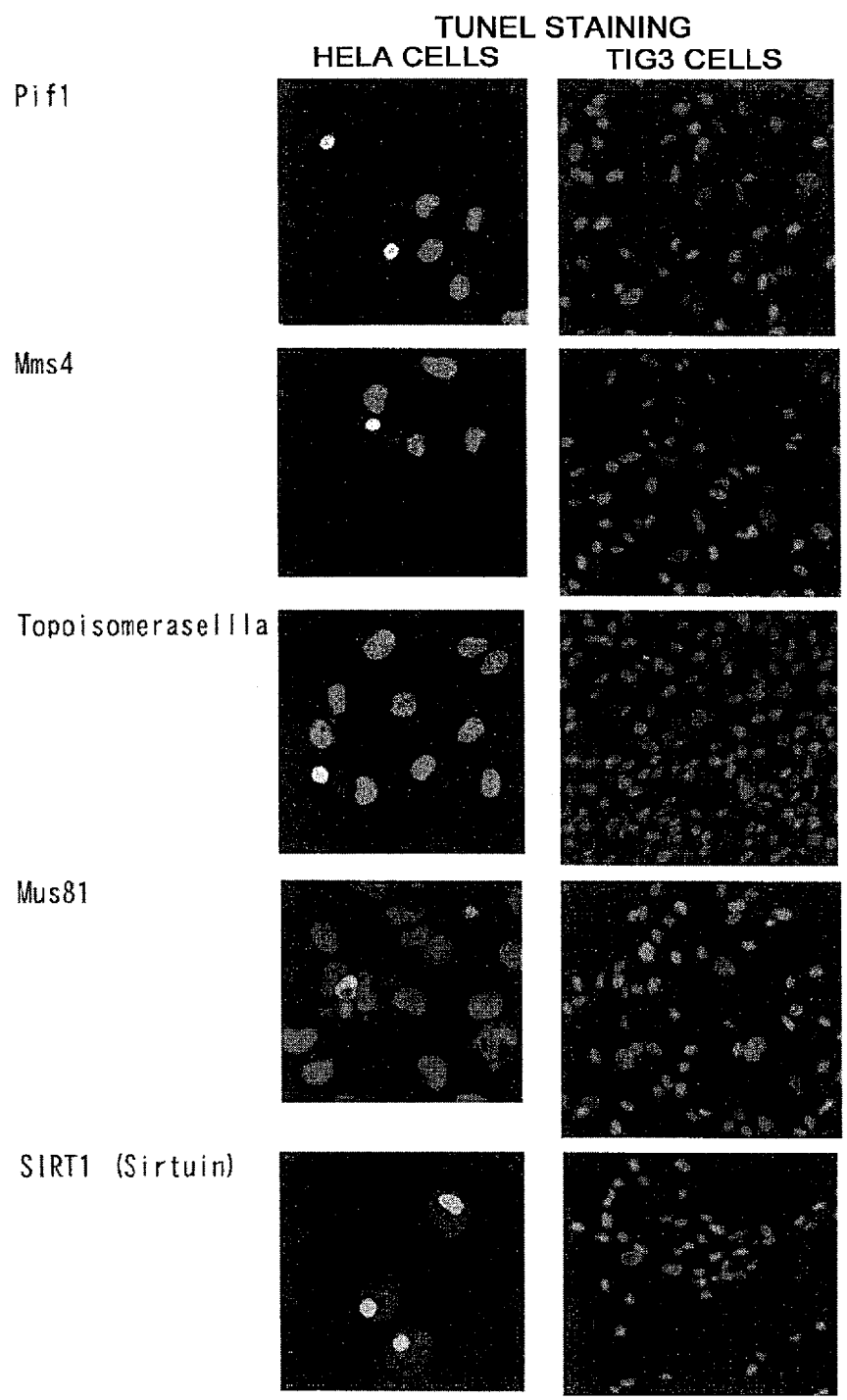

FIG. 33 shows photographs indicating induction of apoptosis by inhibiting the mRNA expression of Pif1, Mms4, Topoisomerase IIIa, Mus81, SIRT1 (Sirtuin), Esp1, MPG, Polι, Polm, and EndoV gene in HeLa cells and TIG3 cells. The photographs show the results of respectively introducing siRNA for each gene into HeLa cells and TIG3 cells, and examining the induction of apoptosis in HeLa cells 48 hours after introduction and in TIG3 cells 72 hours after introduction using the TUNEL method.

FIG. 34 shows photographs continuing from FIG. 33.

Figure 35:
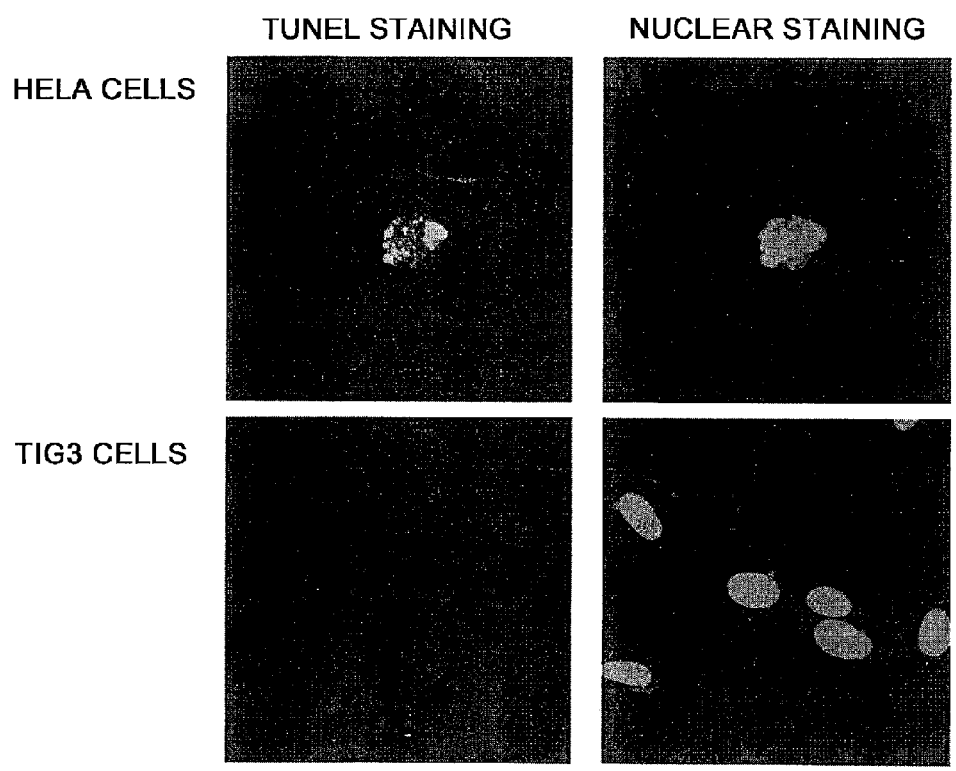

FIG. 35 shows photographs indicating induction of apoptosis by inhibiting the mRNA expression of KNTC2 (NDC80) gene in HeLa cells and TIG3 cells. The photographs show the results of respectively introducing siRNA for KNTC2 (NDC80) gene into HeLa cells and TIG3 cells, and examining the induction of apoptosis in HeLa cells 48 hours after introduction and in TIG3 cells 72 hours after introduction using the TUNEL method. The photographs on the left side depict apoptotic nuclei. The photographs on the right depict nuclei of cells present in the field of view.

Figure 36:
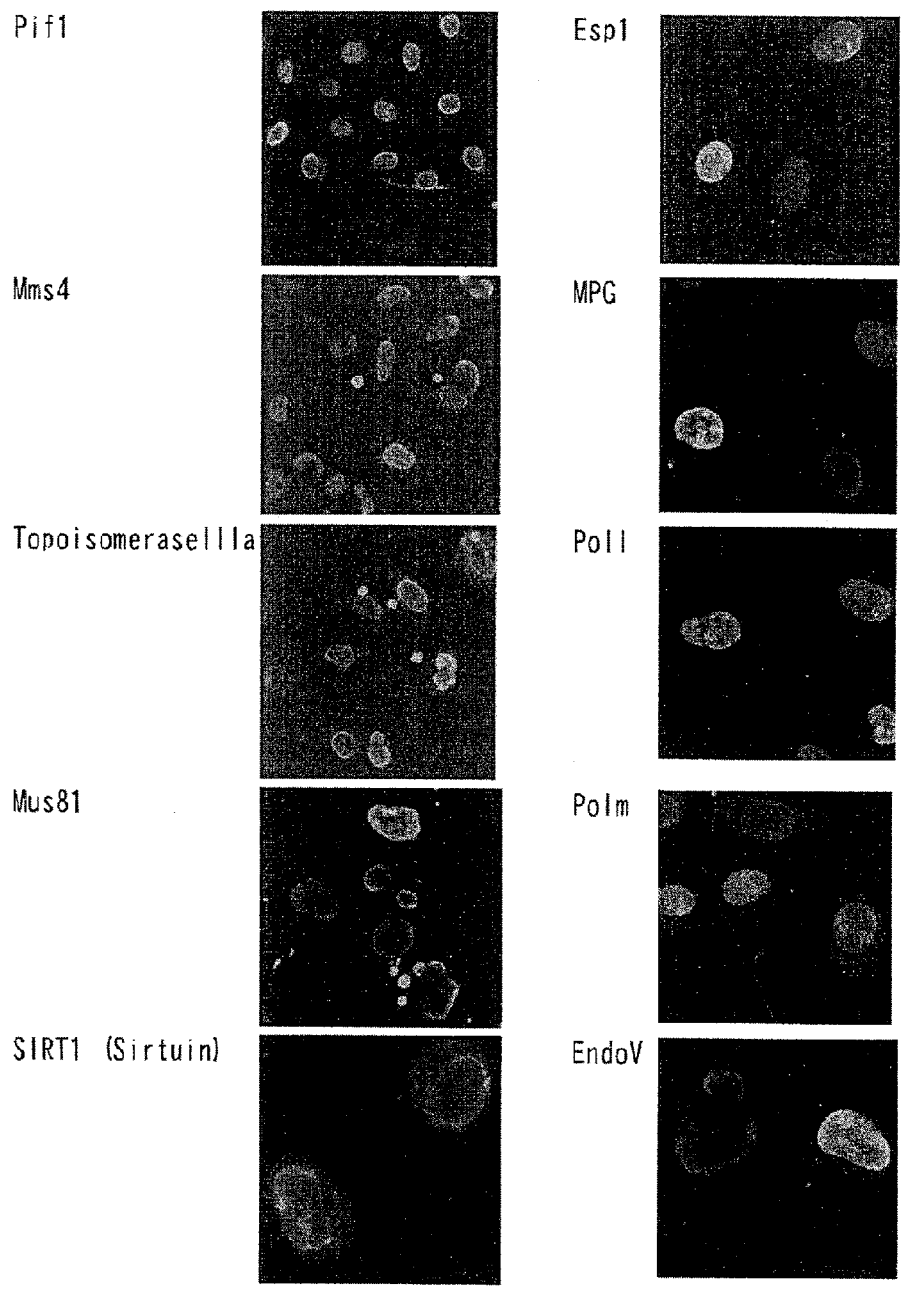

FIG. 36 shows photographs indicating the results of immunostaining the regions in which single-strand DNA is exposed in chromosomal DNA using an anti-ssDNA antibody.

BEST MODE FOR CARRYING OUT THE INVENTION

The present inventors found that inhibition of chromosome stabilization induces cancer cell (tumor cells)-specific apoptosis.

First, the present invention provides cancer cell-specific (anti-cancer cell) apoptosis-inducing agents comprising a compound that inhibits chromosome stabilization.

The apoptosis-inducing agents of the present invention are characterized in that they have an action to selectively induce apoptosis in cancer cells. In the present invention, "cancer cell-specific" means that the agent substantially demonstrates an apoptosis-inducing action in cancer cells without demonstrating a substantial apoptosis-inducing action in normal cells. Preferably, it means that the agent has an apoptosis-inducing action against cancer cells without showing an apoptosis-inducing action against normal cells.

The term "apoptosis" generally refers to cell death actively induced by the cell itself due to a physiological condition. Morphological features of apoptosis include, for example, chromosome condensation in the cell nucleus, nuclear fragmentation, loss of microvilli on the cell surface, and cytoplasmic shrinkage. Thus, as used herein, the term "apoptosis-inducing action" refers to, for example, the action of inducing in cells any of the above-described morphological features of apoptosis, but is not limited to those described above. One skilled in the art can appropriately assess whether apoptosis induction is taking place in cells or not.

The cancer cell-specific apoptosis-inducing agents of the present invention are considered to be, for example, anticancer agents (carcinostatics) having an apoptosis-inducing action as a mechanism of function. Since the apoptosis-inducing agents of the present invention specifically induce apoptosis in cancer cells but do not induce apoptosis in normal cells, they are expected to be safe anticancer agents having few adverse side effects.

The "anticancer agent" as used herein, may also be referred to as a "carcinostatic agent". The "anticancer agent" may also be expressed as an "antitumor agent", "antitumor pharmaceutical", "antitumor pharmaceutical composition", etc.

In the present invention, "inhibition of chromosome stabilization" indicates, for example, reaching a state in which unrepaired damage remaining in chromosomal DNA has accumulated, and more specifically, a state in which regions with exposed single strand chromosomal DNA have accumulated, or a state in which a large number of breaks in double-strand DNA have appeared; however, "inhibition of chromosome stabilization" is not necessarily limited to these states.

In the present invention, "chromosome stabilization" is maintained, for example, by the following functions in cells. Thus, inhibition of the following functions inhibits chromosome stabilization.

(a) genes associated with human chromosomal instability disorders,
(b) chromosomal DNA replication reaction including initiation of chromosomal DNA replication and progression of replication fork,
(c) DNA damage checkpoints,
(d) sister chromatid agglutination and separation,
(e) base excision repair,
(f) mismatch excision repair,
(g) nucleotide excision repair,
(h) homologous recombination repair,
(i) non-homologous end joining repair (non-homologous recombination repair),
(j) double-strand DNA break repair,
(k) DNA post-replication repair (DNA damage tolerance),
(l) DNA crosslink damage repair,
(m) DNA-protein crosslink damage repair,
(n) DNA polymerase,
(o) nuclease,
(p) nucleotide cleansing,
(q) chromatin structure maintenance, and
(r) telomere structure maintenance.

In a preferred embodiment of the present invention, inhibition of chromosome stabilization includes inhibition of any of the aforementioned functions (a) to (r).

Namely, a preferred embodiment of the present invention relates to cancer cell-specific apoptosis-inducing agents containing a compound which inhibits any of the aforementioned functions (a) to (r).

In the present invention, in order to inhibit any of the aforementioned functions (a) to (r), for example, the expression of a gene associated with the function (which may also be referred to as a "chromosome stabilization-associated gene" in the present specification) may be inhibited, or the function (activity) of a protein encoded by the gene may be inhibited.

Although examples of genes associated with each of the aforementioned functions are provided below, there are no particular limitations so long as they are genes associated with each of the aforementioned functions.

(a) Genes Associated with Human Chromosomal Instability Disorders

Examples of human chromosomal instability disorders include xeroderma pigmentosum, Cockayne syndrome, Nijmegen breakage syndrome, ataxia telangiectasia, Fanconi's anemia, and progeria. Genes associated with these diseases are described below.

Xeroderma pigmentosum: (a1) XPB, (a2) XPD, (a3) XPG, (a4) XPF, (a5) XPC, (a6) RAD23B, (a7) CETN2, (a8) RAD23A, (a9) ERCC1
Cockayne syndrome: (a10) CSA, (a11) CSB, (a12) XAB
Nijmegen breakage syndrome: (a13) NBS1
Ataxia telangiectasia: (a14) ATM
Fanconi's anemia: (a15) FANCA, (a16) FANCC, (a17) FANCD2, (a18) FANCE, (a19) FANCF, (a20) FANCG
Progeria: (a21) WRN, (a22) BLM, (a23) RTS (b) Chromosomal DNA Replication Reaction Including Initiation of Chromosomal DNA Replication and Progression of Replication Fork (b1) Mcm10, (b2) Orc1, (b3) Orc3, (b4) Cdc6, (b5) Cdt1, (b6) Geminin, (b7) Mcm3, (b8) Mcm4, (b9) Mcm5, (b10) Mcm6, (b11) Mcm7, (b12) Mcm8, (b13) Cdc7, (b14) Cdc5, (b15) Psf1, (b16) Psf2, (b17) Psf3, (b18) Cdc45, (b19) Pola p180, (b20) Pola p70, (b21) Pola Spp1(Prim2a), (b22) RPA70, (b23) RPA34, (b24) PCNA, (b25) Elg1, (b26) Ligase1, (b27) Pole Pol2, (b28) Pole Dpb3, (b29) Topoisomerase I, (b30) TDP1, (b31) Orc2, (b32) Orc4, (b33) Orc5, (b34) Orc6, (b35) Mcm2, (b36) Dbf4, (b37) TopBP1, (b38) Sld5, (b39) Pola Spp2, (b40) RFC1, (b41) RFC2, (b42) RFC3, (b43) RFC4, (b44) RFC5, (b45) Pif1, (b46) Pold p50, (b47) Pole Dpb2, (b48) Topoisomerase Iia, (b49) Topoisomerase Iib, (b50) RPA14, (b51) FEN1, (b52) DNA2, (b53) Pold p125, (b54) Pold p68, (b55) Pold p12, (b56) Pole Dpb4

(c) DNA Damage Checkpoints (c1) ATR, (c2) Chk1, (c3) NBS1, (c4) Hus1, (c5) Rad1, (c11) Mad2, (c12) BubR1, (c12) ATM, (c13) Rad50, (c14) Mre11, (c15) Mdc1, (c16) 53BP1, (c17) Rad17, (c22) BubR1, (c23) ATRIP, (c24) Chk2, (c25) H2AX, (c26) RFC1, (c27) RFC2, (c28) RFC3, (c29) RFC4, (c30) RFC5, (c31) ATM, (c32) BRCA1, (c33) Chk1, (c34) Chk2, (c35) 14-3-3eta, (c36) 14-3-3sigma, (c37) cdc25A, (c38) cdc25c, (c39) wee1, (c40) ATR, (c41) ATRIP, (c42) Rad17, (c43) RFC2, (c44) RFC3, (c45) RFC4, (c46) RFC5, (c47) HUS1, (c48) Rad1, (c49) Rad9, (c50) P53, (c51) Rad50, (c52) Mre11, (c53) NBS1, (c54) TopBP1, (c55) 53BP1, (c56) H2AX (d) Sister Chromatid Agglutination and Separation (d1) Ctf18, (d2) Scc1, (d3) Scc3, (d4) Dcc1, (d5) Trf4-1, (d6) Trf4-2, (d7) Smc1, (d8) Smc3, (d9) Pds1(Securin), (d10) Mad2, (d11) BubR1, (d12) Esp1

(e) Base Excision Repair (e1) UNG, (e2) MBD4, (e3) TDG, (e4) NTH1, (e5) NEIL2, (e6) NEIL3, (e7) APE2, (e8) PARP1, (e9) PNK, (e10) Polb, (e11) OGG1, (e12) APE1, (e13) XRCC1, (e14) Ligase3, (e15) SMUG1, (e16) TDG, (e17) MYH, (e18) MPG, (e19) NEIL1, (e20) ADPRT, (e21) ADPRTL2, (e22) MGMT, (e23) ABH1, (e24) ABH2, (e25) ABH3

(f) Mismatch Excision Repair (f1) MSH2, (f2) PMS1, (f3) PMS2, (f4) MLH3, (f5) Exonuclease1, (f6) MSH3, (f7) MSH6, (f8) MSH5, (f9) MLH1, (f10) MSH4, (f11) PMS2L3, (f12) Trex1, (f13) Trex2, (f14) PMS2L4

(g) Nucleotide Excision Repair (g1) XPC, (g2) Rad23A, (g3) Rad23B, (g4) CSA, (g5) CSB, (g6) XPG, (g7) XPF, (g8) DDB1, (g9) DDB2, (g10) XAB2, (g11) XPB, (g12) ERCC1, (g13) XPD, (g14) XPA, (g15) DDB2, (g16) Mms19, (g17) CETN2, (g18) RPA70, (g19) RPA34, (g20) RPA14, (g21) GTF2H1, (g22) GTF2H2, (g23) GTF2H3, (g24) GTF2H4, (g25) CDK7, (g26) CCNH, (g27) MNAT1, (g28) Ligase1, (g29) CSA, (g30) CSB (h) Homologous Recombination Repair (h1) Rad51, (h2) Rad51L1, (h3) Rad51C, (h4) Rad51L3, (h5) DMC1, (h6) XRCC2, (h7) XRCC3, (h8) Rad52, (h9) Rad54L, (h10) Rad54B, (h11) BRCA1, (h12) BRCA2, (h13) Rad50, (h14) Mre11, (h15) NBS1, (h16) TopoisomeraseIIIa, (h17) TopoisomeraseIIIb, (h18) WHIP, (h19) WRN, (h20) BLM, (h21) RecQ1, (h22) RecQ5

(i) Non-Homologous End Joining Repair (Non-Homologous Recombination Repair)

(i1) Ku70, (i2) Ku80, (i3) DNA-pk, (i4) Ligase4, (i5) XRCC4, (i6) Artemis, (i7) WRN (j) Double-Strand DNA Break Repair (j1) Rad51, (j2) Rad51D, (j3) Xrcc2, (j4) Rad54, (j5) BRCA1, (j6) Ku80, (j7) XRCC4, (j8) Rad52, (j9) Rad51C, (j10) Dmc1, (j11) Rad54B, (j12) DNA-pk, (j13) Ku70, (j14) Ligase4, (j15) Rad51B, (j16) XRCC3, (j17) BRCA2, (j18) Artemis (k) DNA Post-Replication Repair (DNA Damage Tolerance)

(k1) Rad6A, (k2) Rad6B, (k3) Rad18, (k4) Ubc13, (k5) FBH1

(l) DNA Crosslink Damage Repair (l1) FANCA, (l2) FANCC, (l3) FANCD2, (l4) FANCE, (l5) FANCF, (l6) FANCG (m) DNA-Protein Crosslink Damage Repair (m1) TDP1

(n) DNA Polymerase (n1) Poli, (n2) Polh, (n3) Polq, (n4) Polk, (n5) Polz(REV3), (n6) Poll, (n7) Polm, (n8) Rev1, (n9) Polb, (n10) Polg, (n11) Pold p50, (n12) Pole Pol2, (n13) REV7, (n14) Poln, (n15) Pola P180, (n16) Pola p70, (n17) Pola Spp1, (n18) Pola Spp2, (n19) Pold p68, (n20) Pold p12, (n21) Pole Dpb2, (n22) Pole Dpb3, (n23) Pole Dpb4

(o) Nuclease (o1) FEN1, (o2) TREX1, (o3) TREX2, (o4) Exonuclease1, (o5) SPO11, (o6) ENDO V, (o7) APE1, (o8) APE2, (o9) Mre11, (o10) Artemis (p) Nucleotide Cleansing (p1) MTH1, (p2) DUT, (p3) p53R2

(q) Chromatin Structure Maintenance (q1) H2AX, (q2) Sir2, (q3) SIRT1 (Sirtuin)

(r) Telomere Structure Maintenance (r1) Tin2, (r2) Sir2, (r3) hTert, (r4) TRF1, (r5) TRF2, (r6) Tankyrase, (r7) Pot1, (r8) Rap1, (r9) Pif1

Preferred examples of genes associated with each of the aforementioned functions (a) to (r) include the genes described in Examples below. More specifically, examples of such genes are as follows:

APE2, ATR, BRCA1, Chk1, Cdc5, Cdc6, Cdc7, Cdc45, Cdt1, CSA, CSB, Ctf18, DDB1, DDB2, DNA2, DUT, Elg1, EndoV, Esp1, Exonuclease1, FBH1, FEN1, Geminin, Hus1, KNTC2 (NDC80), Ku80, Ligase1, Mad2, MBD4, Mcm3, Mcm4, Mcm5, Mcm6, Mcm7, Mcm8, Mcm10, MGMT, MLH3, Mms4, MPG, MSH2, Mus81, NBS1, NEIL2, NEIL3, NTH1, Orc1, Orc3, PARP1, PCNA, Pif1, PMS1, PMS2, PNK, Pola p180, Pola p70, Pola Spp1(Prim2a), Polb, Pold p125, Pole Dpb3, Pole Dpb4, Pole Pol2, Poli, Poll, Polm, Psf1, Psf2, Psf3, Rad1, Rad18, Rad23A, Rad23B, Rad51, Rad51D, Rad54, Rad6A, RPA34, RPA70, Scc1, Scc3, Sir2, SIRT1 (Sirtuin), TDG, TDP1, TIMELESS, Tin2, Topoisomerase I, Topoisomerase IIIa, Topoisomerase IIIb, Ubc13, UNG, XAB2, XPC, XPF, XPG, Xrcc2, and XRCC4.

A preferred embodiment of the present invention provides a cancer cell-specific apoptosis-inducing agent comprising as an active ingredient a compound which inhibits the expression of a chromosome stabilization-associated gene (for example, any of the aforementioned genes), or inhibits the function of a protein encoded by the gene.

Since the gene names described in the present specification are names which are widely and generally known, those skilled in the art are able to suitably acquire data on the nucleotide sequences of said genes from a public reference database or gene database (e.g., GenBank) based on the gene name.

Specific examples of the nucleotide sequences of the aforementioned genes of the present invention and amino acid sequences of proteins encoded by the genes are listed in the Sequence Listing. NCBI accession numbers by which sequence data on the genes can be acquired, and the relationships between the nucleotide sequences of genes acquired using said numbers and SEQ ID NOs, are shown in Tables 1 to 16. In addition, examples of amino acid sequences of proteins encoded by the aforementioned genes of the present invention are also shown in the Sequence Listing.

TABLE 1

| Gene Name | Accession No. | SEQ ID NO Nucleotide Sequence | SEQ ID NO Amino Acid Sequence |
|---|---|---|---|
| Mcm10 | NM_182751 | 1 | 638 |
|  | NM_018518 | 2 |  |
|  | AB042719 | 3 |  |
|  | AL136840 | 4 |  |
|  | AK055695 | 5 |  |
|  | BC009108 | 6 |  |
|  | BC004876 | 7 |  |
|  | AF119869 | 8 |  |
| Orc1 | NM_004153 | 9 | 639 |
|  | U43416 | 10 |  |
|  | U40152 | 11 |  |
|  | BC011539 | 12 |  |
| Orc3 | NM_181837 | 13 | 640 |
|  | NM_012381 | 14 |  |
|  | BC035494 | 15 |  |
|  | AF125507 | 16 |  |
|  | AF135044 | 17 |  |
|  | AL080116 | 18 |  |
|  | AF093535 | 19 |  |
|  | BC047689 | 20 |  |
|  | U50950 | 21 |  |
|  | AK094135 | 22 |  |
| Cdc6 | NM_001254 | 23 | 641 |
|  | AF022109 | 24 |  |
|  | BC025232 | 25 |  |
|  | U77949 | 26 |  |
| Cdt1 | NM_030928 | 27 | 642 |
|  | BC008676 | 28 |  |
|  | AF321125 | 29 |  |
|  | AB053172 | 30 |  |
|  | BC000137 | 31 |  |
|  | BC008860 | 32 |  |
|  | BC009410 | 33 |  |
|  | BC049205 | 34 |  |
|  | BC021126 | 35 |  |

TABLE 1-continued

| Gene Name | Accession No. | SEQ ID NO Nucleotide Sequence | SEQ ID NO Amino Acid Sequence |
|---|---|---|---|
|  | AF070552 | 36 |  |
|  | BC014202 | 37 |  |
| Geminin | NM_015895 | 38 | 643 |
|  | BC005389 | 39 |  |
|  | BC005185 | 40 |  |
|  | AF067855 | 41 |  |
|  | AK021685 | 42 |  |
| Mcm3 | BC003509 | 43 |  |
|  | NM_002388 | 44 | 644 |
|  | BC001626 | 45 |  |
|  | AY032603 | 46 |  |
|  | X62153 | 47 |  |
|  | D38073 | 48 |  |
|  | U41843 | 49 |  |

TABLE 2

| Gene | Accession | Nuc SEQ ID | AA SEQ ID |
|---|---|---|---|
| Mcm4 | NM_005914 | 50 | 645 |
|  | XM_030274 | 51 |  |
|  | X74794 | 52 |  |
|  | NM_182746 | 53 |  |
|  | BC031061 | 54 |  |
|  | AK022899 | 55 |  |
| Mcm5 | NM_006739 | 56 | 646 |
|  | X74795 | 57 |  |
|  | BC003656 | 58 |  |
|  | BC000142 | 59 |  |
|  | D83986 | 60 |  |
|  | AK130620 | 61 |  |
|  | AK122853 | 62 |  |
| Mcm6 | NM_005915 | 72 | 647 |
|  | BC020268 | 73 |  |
|  | D84557 | 74 |  |
|  | BC032374 | 75 |  |
|  | U46838 | 76 |  |
|  | BC008774 | 77 |  |
| Mcm7 | NM_005916 | 65 | 648 |
|  | BC013375 | 63 |  |
|  | D55716 | 70 |  |
|  | AK096959 | 71 |  |
|  | X74796 | 68 |  |
|  | NM_182776 | 64 |  |
|  | D28480 | 66 |  |
|  | AK055379 | 67 |  |
|  | AY007130 | 69 |  |
|  | BC009398 | 78 |  |
|  | AF279900 | 79 |  |
| Mcm8 | NM_032485 | 80 | 649 |
|  | AJ439063 | 81 |  |
|  | BC008830 | 82 |  |
|  | AK027644 | 83 |  |
|  | NM_182802 | 84 |  |
|  | AY158211 | 85 |  |
|  | BC005170 | 86 |  |

TABLE 3

| Gene | Accession | Nuc SEQ ID | AA SEQ ID |
|---|---|---|---|
| Cdc7 | NM_003503 | 87 | 650 |
|  | AF015592 | 88 |  |
|  | AB003698 | 89 |  |
|  | AF005209 | 90 |  |
| Cdc5 | BC001568 | 91 |  |
|  | NM_001253 | 92 | 651 |
|  | U86753 | 93 |  |
|  | AK128737 | 94 |  |
|  | AB007892 | 95 |  |
|  | D85423 | 96 |  |
| Psf1 | NM_021067 | 97 | 652 |
|  | D80008 | 98 |  |
|  | BC012542 | 99 |  |

TABLE 3-continued

| | | | |
|---|---|---|---|
| Psf2 | BC010164 | 100 | |
| | NM_016095 | 101 | 653 |
| | AF151880 | 102 | |
| | AF125098 | 103 | |
| | AK001275 | 104 | |
| | AF201939 | 105 | |
| | BC022839 | 106 | |
| | BC003186 | 107 | |
| | BC062444 | 108 | |
| | AK091519 | 109 | |
| Psf3 | NM_022770 | 110 | 654 |
| | BC014437 | 111 | |
| | BC005879 | 112 | |
| | AK127454 | 113 | |
| | AK023974 | 114 | |
| | AL137379 | 115 | |
| Cdc45 | BC005879 | 112 | |
| | NM_003504 | 116 | 655 |
| | BC006232 | 117 | |
| | BT006792 | 118 | |
| | BC010022 | 119 | |
| | AF081535 | 120 | |
| | AF053074 | 121 | |
| | AY358971 | 122 | |
| | AF062495 | 123 | |
| | AJ223728 | 124 | |
| Pola p180 | NM_016937 | 125 | 656 |
| | X06745 | 126 | |
| | BX648513 | 127 | |
| Pola p70 | L24559 | 128 | |
| | BC002990 | 129 | |
| | NM_002689 | 130 | 657 |
| | BC001347 | 131 | |
| | BC018813 | 132 | |
| | BC018814 | 133 | |
| | AK025315 | 134 | |
| | AK094569 | 135 | |
| Pola Spp1(Prim2a) | NM_000947 | 136 | 658 |
| | X74331 | 137 | |
| | BC017833 | 138 | |

TABLE 4

| | | | |
|---|---|---|---|
| RPA70 | BC018126 | 139 | |
| | NM_002945 | 140 | 659 |
| | M63488 | 141 | |
| RPA34 | NM_002946 | 142 | 660 |
| | BC021257 | 143 | |
| | BC012157 | 144 | |
| | BC001630 | 145 | |
| | J05249 | 146 | |
| PCNA | NM_002592 | 147 | 661 |
| | NM_182649 | 148 | |
| | BC000491 | 149 | |
| | M15796 | 150 | |
| Elg1 | AJ314648 | 151 | |
| | NM_024857 | 152 | 662 |
| | AL832103 | 153 | |
| | AK022797 | 154 | |
| | BC015051 | 155 | |
| FEN1 | NM_004111 | 156 | 663 |
| | BC000323 | 157 | |
| | X76771 | 158 | |
| | L37374 | 159 | |
| | XM_209325 | 160 | |
| DNA2 | D42046 | 161 | |
| | XM_166103 | 162 | 664 |
| | BC063664 | 163 | |
| | BC053574 | 164 | |
| | BC041115 | 165 | |
| | BC028188 | 166 | |
| | BC017003 | 167 | |
| Ligase1 | NM_000234 | 168 | 665 |
| | M36067 | 169 | |
| Pold p125 | NM_002691 | 170 | 666 |
| | M80397 | 171 | |

TABLE 4-continued

| | | | |
|---|---|---|---|
| | BC008800 | 172 | |
| | M81735 | 173 | |
| Pole Pol2 | NM_006231 | 174 | 667 |
| | L09561 | 175 | |
| | U49356 | 176 | |
| | S60080 | 177 | |
| | BX647647 | 178 | |
| | BC007599 | 179 | |
| | BC021559 | 180 | |
| | AK093003 | 181 | |
| | AK025087 | 182 | |
| | BC011376 | 183 | |
| | AL080203 | 184 | |
| | AK128248 | 185 | |
| | NM_012332 | 186 | |
| | AF132950 | 187 | |

TABLE 5

| | | | |
|---|---|---|---|
| Pole Dpb3 | NM_017443 | 188 | 668 |
| | AK074762 | 189 | |
| | BC004170 | 190 | |
| | BC003166 | 191 | |
| | AK074629 | 192 | |
| | AF226077 | 193 | |
| | AK074782 | 194 | |
| | AK096050 | 195 | |
| | AK092840 | 196 | |
| Pole Dpb4 | AF261688 | 197 | |
| | BC031331 | 198 | |
| | NM_019896 | 199 | 669 |
| | AY034104 | 200 | |
| Topoisomerase I | NM_003286 | 201 | 670 |
| | J03250 | 202 | |
| | U07806 | 203 | |
| | U07804 | 204 | |
| | X16479 | 205 | |
| TDP1 | BC015474 | 206 | |
| | NM_018319 | 207 | 671 |
| | AK001952 | 208 | |
| | AF182002 | 209 | |
| | BX161451 | 210 | |
| | AK093235 | 211 | |
| | BC006083 | 212 | |
| | AL832288 | 213 | |
| | AF182003 | 214 | |
| | AK023514 | 215 | |
| Ctf18 | BC018184 | 216 | |
| | NM_022092 | 217 | 672 |
| | BC006278 | 218 | |
| | BC006437 | 219 | |
| | AK024476 | 220 | |
| | AK128869 | 221 | |
| Scc1 | BC050381 | 222 | |
| | NM_006265 | 223 | 673 |
| | D38551 | 224 | |
| | X98294 | 225 | |
| | AK098521 | 226 | |
| | AK097915 | 227 | |
| | BC001229 | 228 | |
| | AK125620 | 229 | |

TABLE 6

| | | | |
|---|---|---|---|
| Scc3 | NM_005862 | 230 | 674 |
| | Z75330 | 231 | |
| | BC017735 | 232 | |
| | BC040708 | 233 | |
| | AF070586 | 234 | |
| | BC001765 | 235 | |
| | NM_006603 | 236 | |
| | BX641003 | 237 | |
| | AK098737 | 238 | |
| | Z75331 | 239 | |
| | BX641002 | 240 | |

TABLE 6-continued

| | | | |
|---|---|---|---|
| | BX640970 | 241 | |
| | AL831939 | 242 | |
| | AK124202 | 243 | |
| | NM_012447 | 244 | |
| | AJ007798 | 245 | |
| | BC047490 | 246 | |
| | BC028684 | 247 | |
| ATR | NM_001184 | 248 | 675 |
| | Y09077 | 249 | |
| | U76308 | 250 | |
| | U49844 | 251 | |
| Chk1 | BC017575 | 252 | |
| | NM_001274 | 253 | 676 |
| | AF016582 | 254 | |
| | BC004202 | 255 | |
| | AF032874 | 256 | |
| NBS1 | NM_002485 | 257 | 677 |
| | AF051334 | 258 | |
| | AF058696 | 259 | |
| | BX640816 | 260 | |
| | BC040519 | 261 | |
| | BC005293 | 262 | |
| | BC016762 | 263 | |
| | AK001017 | 264 | |
| Hus1 | NM_004507 | 265 | 678 |
| | BC007013 | 266 | |
| | AF110393 | 267 | |
| | AF076844 | 268 | |
| | Y16893 | 269 | |
| | AJ227901 | 270 | |
| | AK097182 | 271 | |

TABLE 7

| | | | |
|---|---|---|---|
| Rad1 | BC037857 | 272 | |
| | BC009804 | 273 | |
| | NM_133377 | 274 | |
| | NM_002853 | 275 | 679 |
| | BC006837 | 276 | |
| | AK002112 | 277 | |
| | AF074717 | 278 | |
| | AF076841 | 279 | |
| | AF030933 | 280 | |
| | AF084512 | 281 | |
| | AF058392 | 282 | |
| | AF011905 | 283 | |
| | AJ004974 | 284 | |
| | BT006908 | 285 | |
| | AF073524 | 286 | |
| | NM_133282 | 287 | |
| | AF090170 | 288 | |
| | AF084513 | 289 | |
| | AF058393 | 290 | |
| | AJ004975 | 291 | |
| Topoisomerase IIIb | NM_003935 | 292 | 680 |
| | AF053082 | 293 | |
| | AF017146 | 294 | |
| | AF125216 | 295 | |
| | BC002432 | 296 | |
| | AL833505 | 297 | |
| | AK096695 | 298 | |
| | AF070585 | 299 | |
| | XM_066339 | 300 | |
| | BC051748 | 301 | |
| | NM_004618 | 302 | |
| | U43431 | 303 | |
| Rad6A | BC010175 | 304 | |
| | NM_003336 | 305 | 681 |
| | M74524 | 306 | |
| | NM_181777 | 307 | |
| | BC042021 | 308 | |
| | NM_181762 | 309 | |
| | BC005979 | 310 | |
| | BC008404 | 311 | |
| | BC008470 | 312 | |
| | NM_003337 | 313 | |

TABLE 7-continued

| | | | |
|---|---|---|---|
| | BT007071 | 314 | |
| | X53251 | 315 | |
| | M74525 | 316 | |
| Rad18 | NM_020165 | 317 | 682 |
| | AF169796 | 318 | |
| | AK023075 | 319 | |
| | AB035274 | 320 | |
| | BC001302 | 321 | |
| | AY004333 | 322 | |

TABLE 8

| | | | |
|---|---|---|---|
| Ubc13 | BC000396 | 323 | |
| | BC003365 | 324 | |
| | NM_003348 | 325 | 683 |
| | D83004 | 326 | |
| | BT006873 | 327 | |
| | XM_372257 | 328 | |
| | AK098233 | 329 | |
| FBH1 | NM_178150 | 330 | |
| | NM_032807 | 331 | 684 |
| | AF380349 | 332 | |
| | AF456237 | 333 | |
| | AK095343 | 334 | |
| | AF454502 | 335 | |
| | BC020266 | 336 | |
| | BC032674 | 337 | |
| | AK122753 | 338 | |
| | AK027496 | 339 | |
| | AK027381 | 340 | |
| | BC006430 | 341 | |
| | BC012762 | 342 | |
| | AL133069 | 343 | |
| | AL832251 | 344 | |
| Mad2 | NM_002358 | 345 | 685 |
| | BC000356 | 346 | |
| | BC005945 | 347 | |
| | U31278 | 348 | |
| | AJ000186 | 349 | |
| | U65410 | 350 | |
| | NG_002592 | 351 | |
| | AF394735 | 352 | |
| | XM_374193 | 353 | |
| XPC | BC016620 | 354 | |
| | NM_004628 | 355 | 686 |
| | D21089 | 356 | |
| | X65024 | 357 | |
| Rad23A | BC014026 | 358 | |
| | NM_005053 | 359 | 687 |
| | D21235 | 360 | |
| | M77024 | 361 | |
| | L37720 | 362 | |
| | BC020973 | 363 | |
| | NM_002874 | 364 | |
| | AY313777 | 365 | |
| | AK125226 | 366 | |
| | D21090 | 367 | |

TABLE 9

| | | | |
|---|---|---|---|
| Rad23B | NM_002874 | 364 | 688 |
| | D21090 | 367 | |
| | BC020973 | 363 | |
| | AK125226 | 366 | |
| | AY313777 | 365 | |
| | XM_067249 | 368 | |
| | BC014026 | 358 | |
| | NM_005053 | 359 | |
| | D21235 | 360 | |
| | AK122683 | 369 | |
| CSA | NM_000082 | 370 | 689 |
| | U28413 | 371 | |
| | AK056931 | 372 | |
| | BC009793 | 373 | |
| CSB | NM_000124 | 374 | 690 |
| | L04791 | 375 | |
| | AK130100 | 376 | |
| XPG | X69978 | 377 | |
| | NM_000123 | 378 | 691 |
| | BC031522 | 379 | |
| | AF462447 | 380 | |
| | BX647399 | 381 | |
| | L20046 | 382 | |
| | D16305 | 383 | |
| XPF | L77890 | 384 | |
| | NM_005236 | 385 | 692 |
| | U64315 | 386 | |
| | BC020741 | 387 | |
| DDB1 | NM_001923 | 388 | 693 |
| | U32986 | 389 | |
| | BC050530 | 390 | |
| | BC011686 | 391 | |
| | BC051764 | 392 | |
| | HSU18299 | 393 | |
| | AJ2955 | 394 | |
| | L40326 | 395 | |
| | BC021044 | 396 | |
| | BC032080 | 397 | |
| | AL831958 | 398 | |
| DDB2 | NM_000107 | 399 | 694 |
| | U18300 | 400 | |
| | BC000093 | 401 | |
| | BT007139 | 402 | |
| | BC001160 | 403 | |
| | BC050455 | 404 | |
| | AK091640 | 405 | |

TABLE 10

| | | | |
|---|---|---|---|
| XAB2 | NM_020196 | 406 | 695 |
| | AF226051 | 407 | |
| | BC007208 | 408 | |
| | AF258567 | 409 | |
| | AB026111 | 410 | |
| | AB033003 | 411 | |
| | BC008778 | 412 | |
| | AK025858 | 413 | |
| | AK074035 | 414 | |
| UNG | BC050634 | 415 | |
| | NM_003362 | 416 | 696 |
| | BC015205 | 417 | |
| | X15653 | 418 | |
| | NM_080911 | 419 | |
| | Y09008 | 420 | |
| MBD4 | NM_003925 | 421 | 697 |
| | AF072250 | 422 | |
| | AF114784 | 423 | |
| | AF532602 | 424 | |
| | BC034463 | 425 | |
| | BC011752 | 426 | |
| | U56428 | 427 | |
| | U56254 | 428 | |
| TDG | BC037557 | 429 | |
| | NM_003211 | 430 | 698 |
| | U51166 | 431 | |
| | BC019925 | 432 | |
| | BC010945 | 433 | |

TABLE 10-continued

| | | | |
|---|---|---|---|
| NTH1 | NM_002528 | 434 | 699 |
| | U79718 | 435 | |
| | AB001575 | 436 | |
| | U81285 | 437 | |
| | BC000391 | 438 | |
| | BC003014 | 439 | |
| | Y09687 | 440 | |
| NEIL2 | BC013964 | 441 | |
| | BC013952 | 442 | |
| | NM_145043 | 443 | 700 |
| | AK056206 | 444 | |
| | AB079070 | 445 | |
| | AK097389 | 446 | |
| | BX537529 | 447 | |
| | BC045822 | 448 | |
| NEIL3 | NM_018248 | 449 | 701 |
| | AK001720 | 450 | |
| | AB079071 | 451 | |
| | BC025954 | 452 | |
| APE2 | BC002959 | 453 | |
| | NM_014481 | 454 | 702 |
| | AJ011311 | 455 | |
| | AB021260 | 456 | |
| | AB049211 | 457 | |
| | AF119046 | 458 | |

TABLE 11

| | | | |
|---|---|---|---|
| PARP1 | NM_001618 | 459 | 703 |
| | M32721 | 460 | |
| | M18112 | 461 | |
| | J03473 | 462 | |
| | BC037545 | 463 | |
| | NG_002655 | 464 | |
| | M17081 | 465 | |
| | BC018620 | 466 | |
| | BC021045 | 467 | |
| | BC014206 | 468 | |
| | BC008660 | 469 | |
| | AK125650 | 470 | |
| | AF401218 | 471 | |
| | AJ236912 | 472 | |
| | AJ236876 | 473 | |
| | AK001980 | 474 | |
| | NM_005484 | 475 | |
| | AF085734 | 476 | |
| | BC033822 | 477 | |
| PNK | NM_007254 | 478 | 704 |
| | AF125807 | 479 | |
| | AF126486 | 480 | |
| | AF120499 | 481 | |
| | BC002519 | 482 | |
| | BC009339 | 483 | |
| | BC013034 | 484 | |
| Polb | NM_002690 | 485 | 705 |
| | D29013 | 486 | |
| | L11607 | 487 | |
| | M13140 | 488 | |
| MSH2 | NM_000251 | 489 | 706 |
| | BC021566 | 490 | |
| | L47581 | 491 | |
| | U04045 | 492 | |
| | L47577 | 493 | |
| | L47574 | 494 | |
| | L47582 | 495 | |
| | L47583 | 496 | |
| | U03911 | 497 | |
| | L47579 | 498 | |
| | L47578 | 499 | |
| | BX649122 | 500 | |
| | L47580 | 501 | |
| | L47576 | 502 | |
| | L47575 | 503 | |
| | BC001122 | 504 | |
| | BC012599 | 505 | |
| PMS1 | NM_000534 | 506 | 707 |
| | U13695 | 507 | |

TABLE 11-continued

| | | |
|---|---|---|
| | BC036376 | 508 |
| | BC008410 | 509 |
| | BT006947 | 510 |

TABLE 12

| | | | |
|---|---|---|---|
| PMS2 | NM_000535 | 511 | 708 |
| | U14658 | 512 | |
| | BC031832 | 513 | |
| | BC008400 | 514 | |
| | XM_208368 | 515 | |
| | AB116525 | 516 | |
| MLH3 | NM_014381 | 517 | 709 |
| | AF195657 | 518 | |
| | AB039667 | 519 | |
| Exonuclease1 | NM_003686 | 520 | |
| | AF091740 | 521 | |
| | AF042282 | 522 | |
| | NM_006027 | 523 | 710 |
| | BC007491 | 524 | |
| | NM_130398 | 525 | |
| | AF060479 | 526 | |
| | AF084974 | 527 | |
| | AL080139 | 528 | |
| Polι | AF140501 | 529 | |
| | NM_007195 | 530 | 711 |
| | BC032662 | 531 | |
| | AF245438 | 532 | |
| | AL136670 | 533 | |
| | BC032617 | 534 | |
| | BX649100 | 535 | |
| | AK093688 | 536 | |
| Rad51 | NM_002875 | 537 | 712 |
| | D14134 | 538 | |
| | D13804 | 539 | |
| | NM_133487 | 540 | |
| Rad51D | NM_002878 | 541 | 713 |
| | Y15572 | 542 | |
| | BC014422 | 543 | |
| | BX647297 | 544 | |
| | AB013341 | 545 | |
| | NM_133627 | 546 | |
| | AB016223 | 547 | |
| | AF034956 | 548 | |
| | BC002723 | 549 | |
| | NM_133628 | 550 | |
| | AL117459 | 551 | |
| | NM_133630 | 552 | |
| | AB016224 | 553 | |
| | NM_133629 | 554 | |
| | AB016225 | 555 | |
| | AK097811 | 556 | |
| | AB020412 | 557 | |
| | AB018363 | 558 | |
| | AB018360 | 559 | |
| | AB018362 | 560 | |
| | AB018361 | 561 | |

TABLE 13

| | | | |
|---|---|---|---|
| Xrcc2 | BC042137 | 562 | |
| | NM_005431 | 563 | 714 |
| | AF035587 | 564 | |
| | Y08837 | 565 | |
| Rad54 | NM_003579 | 566 | 715 |
| | X97795 | 567 | |
| BRCA1 | NM_007295 | 568 | 716 |
| | NM_007296 | 569 | |
| | NM_007294 | 570 | |
| | NM_007306 | 571 | |
| | NM_007302 | 572 | |
| | NM_007297 | 573 | |
| | U14680 | 574 | |
| | AF005068 | 575 | |
| | NM_007301 | 576 | |
| | NM_007300 | 577 | |
| | NM_007299 | 578 | |
| Ku80 | NM_021141 | 579 | 717 |
| | M30938 | 580 | |
| | BC019027 | 581 | |
| | J04977 | 582 | |
| | X57500 | 583 | |
| XRCC4 | NM_022550 | 584 | |
| | NM_003401 | 585 | 718 |
| | U40622 | 586 | |
| | NM_022406 | 587 | |
| | BC016314 | 588 | |
| | AB017445 | 589 | |
| | BC005259 | 590 | |
| | BT007216 | 591 | |
| | BC010655 | 592 | |
| Tin2 | NM_012461 | 593 | 719 |
| | AF195512 | 594 | |
| | BC019343 | 595 | |
| | BC005030 | 596 | |
| | AK023166 | 597 | |
| | BX161478 | 598 | |
| Sir2 | NM_012237 | 599 | 720 |
| | BC003012 | 600 | |
| | BC003547 | 601 | |
| | AK025876 | 602 | |
| | AF095714 | 603 | |
| | AF083107 | 604 | |
| | NM_030593 | 605 | |
| | AJ505014 | 606 | |
| | AK054642 | 607 | |
| | AF160214 | 608 | |
| | AF131800 | 609 | |
| | AK092940 | 610 | |

TABLE 14

| | | | |
|---|---|---|---|
| MGMT | NM_002412 | 611 | 721 |
| | X54228 | 612 | |
| | M60761 | 613 | |
| | BC000824 | 614 | |
| | M29971 | 615 | |
| | BT006714 | 616 | |
| | M31767 | 617 | |
| DUT | NM_001948 | 618 | 722 |
| | AB049113 | 619 | |
| | BC033645 | 620 | |
| | U62891 | 621 | |
| | U31930 | 622 | |
| | L11877 | 623 | |
| | M89913 | 624 | |
| | AK000629 | 625 | |
| | U90223 | 626 | |
| | NM_182746 | 53 | |
| | BC031061 | 54 | |
| | AK022899 | 55 | |
| TIMELESS | BC050557 | 627 | |
| | BC031514 | 628 | |
| | AB015597 | 629 | |
| | AF098162 | 630 | |
| | NM_003920 | 631 | 723 |
| | BC039842 | 632 | |
| | AK022702 | 633 | |
| | BX640990 | 634 | |
| | AK000721 | 635 | |
| | AY207390 | 636 | |
| | AY207391 | 637 | |

TABLE 15

| Gene Name | Accession No. | SEQ ID NO Nucleotide Sequence | Amino Acid Sequence |
|---|---|---|---|
| Pif1 | AF108138.1 | 810 | 909 |
| | BC033254.1 | 811 | |
| | AK026345.1 | 812 | 910 |
| | NM_025049.1 | 813 | 911 |
| | BC018978.2 | 814 | |
| Mms4 | NM_152463.1 | 815 | 912 |
| | AK021607.1 | 816 | |
| | BC016470.2 | 817 | 913 |
| | AK055926.1 | 818 | 914 |
| Topoisomerase IIIa | NM_004618.2 | 819 | 915 |
| | BC051748.1 | 820 | 916 |
| | AK126869.1 | 821 | |
| | U43431.1 | 822 | 917 |
| Mus81 | NM_025128 | 823 | 918 |
| | AK126820.1 | 824 | |
| | CR604400.1 | 825 | |
| | CR601399.1 | 826 | |
| | AL353934.1 | 827 | 919 |
| | AK024665.1 | 828 | 920 |
| | NM_025128.3 | 829 | 921 |
| | BC009999.2 | 830 | 922 |
| | AF425646.1 | 831 | 923 |
| | AK095326.1 | 832 | |
| SIRT1 (Sirtuin) | NM_012238.3 | 833 | 924 |
| | BX648554.1 | 834 | |
| | AF083106.2 | 835 | 925 |
| | AF235040.1 | 836 | 926 |
| | AL136741.1 | 837 | |
| | AK027686.1 | 838 | |
| | BC012499.1 | 839 | 927 |
| | AK074805.1 | 840 | |
| Esp1 | NM_012291 | 841 | 928 |
| | BC047603.1 | 842 | 929 |
| | AK128350.1 | 843 | |
| | AY455930.1 | 844 | 930 |
| | D79987.1 | 845 | 931 |
| MPG | NM_002434 | 846 | 932 |
| | M99626.1 | 847 | 933 |
| | NM_002434.1 | 848 | 934 |
| | CR619346.1 | 849 | |
| | CR612592.1 | 850 | |
| | CR606356.1 | 851 | |
| | CR600098.1 | 852 | |
| | CR598824.1 | 853 | |
| | L10752.1 | 854 | 935 |
| | M74905.1 | 855 | 936 |
| | X56528.1 | 856 | 937 |
| | BC014991.1 | 857 | 938 |
| | M71215.1 | 858 | 939 |
| | S51033.1 | 859 | 940 |

TABLE 16

| Gene Name | Accession No. | Nucleotide Sequence | Amino Acid Sequence |
|---|---|---|---|
| Polι | NM_013274 | 860 | 941 |
| | AK128521.1 | 861 | |
| | AK127896.1 | 862 | 942 |
| | BC068529.1 | 863 | 943 |
| | AJ131890.1 | 864 | 944 |
| | CR619817.1 | 865 | |
| | CR615868.1 | 866 | |
| | NM_013274.2 | 867 | 945 |
| | AF161019.1 | 868 | 946 |
| | AK021600.1 | 869 | 947 |
| | AK022476.1 | 870 | 948 |
| | AF218027.1 | 871 | 949 |
| | AF283478.1 | 872 | 950 |
| | BC003548.1 | 873 | 951 |
| | AK094956.1 | 874 | |
| Polμ | NM_013284 | 875 | 952 |
| | BC049202.1 | 876 | 953 |
| | BC062590.1 | 877 | 954 |
| | BC026306.1 | 878 | 955 |
| | AJ131891.2 | 879 | 956 |
| | CR620839.1 | 880 | |
| | CR606869.1 | 881 | |
| | NM_013284.1 | 882 | 957 |
| | AF176097.1 | 883 | 958 |
| | AK023002.1 | 884 | 959 |
| | AK092903.1 | 885 | |
| | AK092801.1 | 886 | 960 |
| | BC035685.1 | 887 | |
| EndoV | NM_173627 | 888 | 961 |
| | NM_173627.2 | 889 | 962 |
| | BC045824.1 | 890 | 963 |
| | BX647411.1 | 891 | |
| | AK123689.1 | 892 | 964 |
| | BC059781.1 | 893 | |
| | BC064545.1 | 894 | 965 |
| | CR617882.1 | 895 | |
| | CR599326.1 | 896 | |
| | AK056045.1 | 897 | |
| | AK096802.1 | 898 | |
| | AK096344.1 | 899 | 966 |
| | AK092539.1 | 900 | 967 |
| | BC037889.2 | 901 | 968 |
| KNTC2 (NDC80) | NM_006101 | 902 | 969 |
| | NM_006101.1 | 903 | 970 |
| | CR609890.1 | 904 | |
| | BC010171.2 | 905 | 971 |
| | BC005239.1 | 906 | |
| | BC035617.1 | 907 | 972 |
| | AF017790.1 | 908 | 973 |

Each of the aforementioned genes may be assigned multiple accession numbers even for the same gene due to the presence of polymorphisms in the nucleotide sequence or the like. These "polymorphisms" are not limited to single nucleotide polymorphisms (SNPs) including a mutation of a single nucleotide by substitution, deletion, or insertion, and also include substitutions, deletions, and insertion mutations of several contiguous nucleotides. Thus, the nucleotide sequences of the aforementioned genes are not necessarily limited to sequences acquired according to the accession numbers described in Tables 1 to 16, or to the sequences described in SEQ ID NOs. 1 to 637 and 810 to 908. Similarly, the amino acid sequences of proteins encoded by the aforementioned genes are not particularly limited to the amino acid sequences described in SEQ ID NOs. 638 to 723 and 909 to 973.

The aforementioned proteins of the present invention are not limited to the amino acid sequences described in SEQ ID NOs. 638 to 723 and 909 to 973, and include proteins comprising amino acid sequences in which one or more of the amino acid residues in said amino acid sequences have been added, deleted, substituted, or inserted, and which are functionally equivalent to the proteins described in SEQ ID NOs. 638 to 723 and 909 to 973.

The chromosome stabilization-associated genes of the present invention (e.g., the aforementioned various genes) are normally of animal origin, more preferably of mammalian origin, and most preferably of human origin, but they are not particularly limited thereto.

Namely, the present invention is not limited to apoptosis-inducing agents specific for human cancer cells, and also includes apoptosis-inducing agents for cancer cells of non-human animals. Thus, nonhuman-animal homolog (counterpart) genes of the aforementioned genes are included in the genes of the present invention. For example, endogenous genes (e.g., homologs) in other animals corresponding to genes comprising each of the nucleotide sequences described in SEQ ID NOs: 1 to 637 and 810 to 908 are included. Endogenous DNA of other animals corresponding to DNA comprising the nucleotide sequences generally has high homology with DNA described in the SEQ ID NOs above. High homology refers to homology of 50% or more, preferably 70% or more, more preferably 80% or more, and even more preferably 90% or more (for example, 95% or more, or further 96%, 97%, 98%, or 99% or more). The homology can be determined by the mBLAST algorithm (Altschul et al. (1990), Proc. Natl. Acad. Sci. USA 87: 2264-8; Karlin and Altschul (1993), Proc. Natl. Acad. Sci. USA 90: 5873-7). In addition, the homologous DNA is thought to hybridize under stringent conditions with DNA described in the above SEQ ID NOs if it has been isolated from the living body. Here, "stringent conditions" are, for example, "2×SSC, 0.1% SDS, 50° C.", "2×SSC, 0.1% SDS, 42° C.", or "1×SSC, 0.1% SDS, 37° C.", and more stringent conditions are "2×SSC, 0.1% SDS, 65° C.", "0.5×SSC, 0.1% SDS, 42° C.", or "0.2×SSC, 0.1% SDS, 65° C.". Those skilled in the art are able to suitably acquire data (such as sequence data) relating to endogenous genes corresponding to each of the aforementioned genes of the present invention in other animals based on the nucleotide sequences described in the Sequence Listing.

In addition, the present invention provides compounds which inhibit expression of chromosome stabilization-associated genes (for example, any of the aforementioned genes).

Preferred examples of compounds of the present invention which inhibit expression of chromosome stabilization-associated genes (for example, any of the aforementioned genes) include double-strand RNA having an RNAi (RNA interference) effect on said genes. In general, the term "RNAi" refers to a phenomenon where target gene expression is inhibited by inducing disruption of the target gene mRNA. This disruption is caused by introducing into cells a double-stranded RNA that comprises, a) a sense RNA comprising a sequence homologous to the target gene mRNA sequence, and b) an antisense RNA comprising a sequence complementary to the sense RNA.

While details of the RNAi mechanism remains unclear, it is thought that an enzyme called DICER (a member of the RNase III nuclease family) decomposes double-stranded RNA into small fragments called "small interfering RNA" or "siRNA", when it comes into contact with the double-stranded RNA. This siRNA is also included in the double-stranded RNA comprising RNAi activity of the present invention. Furthermore, DNAs that allow the expression of the double-stranded RNA of the present invention are also included in the present invention.

A preferred embodiment of the present invention provides a cancer cell-specific apoptosis-inducing agent comprising as an active ingredient a double-strand RNA capable of inhibiting expression of a chromosome stabilization-associated gene (for example, any of the aforementioned genes) by an RNAi effect (siRNA), where the double stranded RNA comprises a structure in which an RNA consisting of a nucleotide sequence described in any of SEQ ID NOs: 724 to 809 and 974 to 1063, is hybridized with an RNA consisting of a sequence complementary to said RNA.

For example, an example of a siRNA of the present invention comprising the nucleotide sequence described in SEQ ID NO: 724 (5'-ggaaaaucuggccacucucTT-3') is an RNA molecule having the structure shown below (SEQ ID NOs: 1064 and 1065).

(In the above structure, "|" indicates a hydrogen bond.)

Molecules having a structure in which one end of the above RNA molecule is closed, such as siRNA having a hairpin structure (shRNA), are also included in the present invention. Namely, molecules able to form a double-stranded RNA structure within the molecules are also included in the present invention.

For example, a molecule such as 5'-ggaaaaucuggccacucuc (xxxx)n gagaguggccagauuuucc-3' is also included in the present invention. (The above "(xxxx)n" represents a polynucleotide consisting of an arbitrary number of nucleotides or sequences.)

A preferred embodiment of the aforementioned siRNA is a double strand RNA able to inhibit expression of a chromosome stabilization-associated gene (for example, any of the aforementioned genes) by an RNAi effect (siRNA), comprising a structure in which an RNA consisting of a nucleotide sequence described in any of SEQ ID NOs: 724 to 809 and 974 to 1063 is hybridized with an RNA consisting of a sequence complementary to the RNA. However, double-strand RNA, for example, having a structure in which one or more ribonucleotides are added to or deleted from an end of the double-strand RNA, for example, is also included in the present invention.

Specifically, the present invention provides DNAs (vectors) that allow the expression of a double-stranded RNA of the present invention. These DNAs (vectors) that allow the expression of a double-stranded RNA of the present invention are typically DNAs comprising a structure where a DNA encoding one strand of the double-stranded RNA, and a DNA encoding the other strand of the double-stranded RNA, are operably linked to a promoter. Those skilled in the art can readily prepare an above-described DNA of the present invention with routinely used genetic engineering techniques. More specifically, expression vectors of the present invention can be prepared by appropriately inserting DNA encoding an RNA of the present invention into various known expression vectors.

Although RNA used for RNAi is not required to be completely identical (homologous) to a chromosome stabilization-associated gene (for example, any of the aforementioned genes) or a partial region of the gene, it is preferably completely identical (homologous).

The present invention's double-strand RNA having RNAi effects is normally double-strand RNA comprising sense RNA consisting of a sequence homologous with an arbitrary contiguous RNA region in the mRNA of a chromosome stabilization-associated gene (for example, any of the aforementioned genes), and an antisense RNA consisting of a sequence complementary to the sense RNA. The length of the "arbitrary contiguous RNA region" is normally 20 to 30 bases, and preferably 21 to 23 bases. An example includes, but is not necessarily limited to, the length of an siRNA, having as one of the strands, an RNA described in any of SEQ ID NOs: 724 to 809 and 974 to 1063. However, even in the case of a long-strand RNA that does not have RNAi effects as is, the length of the double-stranded RNA of the present invention is not limited since the long-stand is expected to be degraded into siRNA having RNAi effects in cells. In addition, long double-strand RNA corresponding to the entire length or nearly the entire length of the mRNA of a chromosome stabilization-associated gene (for example, any of the aforementioned genes) can be degraded in advance with, for example, DICER, and the resulting degradation product can be used as an apoptosis-inducing agent of the present invention. This degradation product is expected to contain a double-strand RNA molecule (siRNA) having RNAi effects. In this method, it is not particularly required to select an mRNA region that is expected to have an RNAi effect. Namely, it is not necessarily required to accurately define a region on mRNA of a chromosome stabilization-associated gene (for example, any of the aforementioned genes) that has an RNAi effect. However, the various types of siRNA used in the Examples described later are more preferred.

In general, double-strand RNA having an overhang of several nucleotides on an end is known to have strong RNAi effects. Double-stranded RNAs of the present invention preferably have an overhang of several nucleotides on an end. The length of the nucleotides which form the overhang is not particularly limited. This overhang may be DNA or RNA. For example, the overhang preferably has two nucleotides. In the present invention, double-strand RNA having an overhang comprises, for example, TT (two thymines), UU (two uracils), or other nucleotides (most preferably molecules having double-strand RNA consisting of 19 bases and an overhang consisting of 2 nucleotides (TT)) can be preferably used. Molecules in which the nucleotides forming the overhang in this manner are DNA, and sequences homologous to a target mRNA sequence, are also included in the double-strand RNA of the present invention.

Examples of siRNA molecules of the present invention where the nucleotides of the overhang portion are TT include molecules having TT added to the 3' side thereof, such as the molecule indicated below (SEQ ID NOs: 724 and 1068).

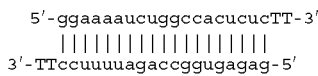

The aforementioned "double-strand RNA having an RNAi effect on a chromosome stabilization-associated gene" of the present invention can be suitably produced by those skilled in the art based on the nucleotide sequence of a chromosome stabilization-associated gene (for example, any of the aforementioned genes) targeted by said double-strand RNA. A nucleotide sequence of a chromosome stabilization-associated gene (for example, any of the aforementioned genes) can be easily acquired from a public gene database as described above. As an example, double-strand RNA of the present invention can be produced based on a nucleotide sequence described in any of SEQ ID NOs: 1 to 637 and 810 to 908. Namely, the selection of an arbitrary contiguous RNA region of mRNA, which is a transcription product of any of the nucleotide sequences described in SEQ ID NOs: 1 to 637 and 810 to 908, based on that sequence, and the production of double-strand RNA corresponding to that region, can be easily carried out by those skilled in the art. In addition, methods for selecting an siRNA sequence having more potent RNAi effects from an mRNA sequence which is a transcript of said sequences can be suitably carried out by those skilled in the art with reference to, for example, the following documents: Reynold et al. Nature biotechnology 22. 326-330 (2004), Ui-Tei et al. Nucleic Acids Res. 32. 936-948 (2004), Boese Q, Leake D, Reynolds A, Read S, Scaringe S A, Marshall W S, Khvorova A. Mechanistic insights aid computational short interfering RNA design. Methods Enzymol. 2005; 392:73-96, Snove O Jr, Nedland M, Fjeldstad S H, Humberset H, Birkeland O R, Grunfeld T, Saetrom P. Designing effective siRNAs with off-target control. Biochem Biophys Res Commun. 2004; 325(3):769-73, Yiu S M, Wong P W, Lam T W, Mui Y C, Kung H F, Lin M, Cheung Y T. Filtering of Ineffective siRNAs and Improved siRNA Design Tool. Bioinformatics. 200515; 21(2):144-51, Chalk A M, Wahlestedt C, Sonnhammer E L. Improved and automated prediction of effective siRNA. Biochem Biophys Res Commun. 2004; 319 (1):264-74, Amarzguioui M, Prydz H. An algorithm for selection of functional siRNA sequences. Biochem Biophys Res Commun. 2004; 316(4):1050-8, Sioud M, Leirdal M. Potential design rules and enzymatic synthesis of siRNAs. Methods Mol Biol. 2004; 252:457-69. In addition, if one of the strands has been determined (for example, a nucleotide sequence described in any of SEQ ID NOs: 724 to 809 and 974 to 1063), the nucleotide sequence of the other strand (complementary strand) can be easily determined by those skilled in the art. siRNA can be suitably produced by those skilled in the art using a commercially available nucleic acid synthesizer. To synthesize a desired RNA, custom synthesis services are also available.

All of the nucleotides in the siRNA of the present invention are not necessarily required to be ribonucleotides (RNA). Namely, in the present invention, one or more of the ribonucleotides which compose the siRNA may be the corresponding deoxyribonucleotides. This "corresponding" means that the nucleotides have identical base species (adenine, guanine, cytosine, and thymine (uracil)), but the structure of the sugar portion is different. For example, the deoxyribonucleotide corresponding to a ribonucleotide having adenine means a deoxyribonucleotide having adenine. In addition, the above "more" is not limited to a particular number but preferably means a small number around 2 to 5.

It is not essential to have information on the full-length nucleotide sequence of a gene (the target gene) from which the double-stranded RNA of the present invention is derived. It is enough that the arbitrary RNA region comprising consecutive nucleotides (for example, 20 to 30 nucleotides) which is to be selected has been identified. Thus, the double-stranded RNA of the present invention can be prepared based on the nucleotide sequence of a fragment of a gene, such as an Expressed Sequence Tag (EST), whose mRNA sequence has been determined partially, but not completely. The accession numbers and names of EST sequences in the GenBank database with a high homology to the aforementioned genes are shown below. However, this list includes only a few examples of the many EST sequences. Those skilled in the art can readily obtain sequence information on appropriate EST fragments from public databases.

Mcm10: BQ230201, CK000876, BX324498, BM466246, BI086715, BE561621, BM781578, BE397209, BM781561, BF797760, BE268770, AI133628, BI860489, CA488245, BE018388, BM794417, AI005288, AV759891, BE536223, AI078425, BI023355, CB120985, AA305452, BX324497, AI636632, CB143720, BM465842, BM833978, AI962581, BE206240, BE536858, BQ432059, BX099770, BX346400, BE890219, BU542039, AI750442, BU542210, BQ929138, BG323332, AA312197, BG942019, BM755471, AA091854, BX346399, BG493975, T97047, BU615340, BG777950, BU618352, BG323324

Orc1: BM556110, AL558857, AL528479, AL530422, AU125429, BQ229865, BX370588, AL563154, BU552785, BQ055912, CD642483, BE903488, BU854876, BM908744, BF205157, BX372245, BQ230059, BX110476, BM743410, BG821765, AL530421, BI222366, BU198520, BF796650, BM476715, AL552393, AU127396, BM740840, BE781976,

AL580583, BG391980, BM852299, CD654548, BQ423782, AW378723, AL582531, AL561250, BU194186, BQ048846, BG822626, AL552501, BU854819, BQ433201, BE782505, BG257286, BX281133, CF140351, BF795920, BG390855, BG831652, BF794915, BF797918, BG325714, AI651655, BM833692, BQ883238, BX474463, AI038384, AU129034, BP431296, BG328342, BP430683, H51719, AI739661, T96858, BE782390, BU630113, BG025019, BE937466, AA332534, AI343281, AU149094, BP430714, BI087773, AW393255, AU151220, BE076727, AI452809, AW877655, AI003527, AI391554, AW602975, AW877662, AA633915, BF108860, AU149996, T96859, R83277

Orc3: BM478060, BU509511, BQ718539, BU153003, AL533919, BQ220405, AU118962, BM550235, BG187255, AU117920, BQ719965, BQ716606, BQ953945, BU166296, AU119182, BI769170, BI819545, CD655888, BX409716, BI520392, BG214275, BI770086, BI091781, BM802602, BG187780, BU170385, BI769508, BX433033, BX507848, AU124361, BX488094, BM785800, BG205874, CD679490, BX490513, CB153029, AW967051, BM826548, AU139285, BG572634, AL533918, CB152486, AU136510, BE536929, BX352629, BQ102522, AW369628, AW449272, BF672680, BE882468, BX343146, BG943457, BF698289, CD702536, BF667912, AU280292, CA842624, BF674961, BF184165, BQ441255, BF794512, CD699734, AL600904, BX462706, BF215571, AL709158, AV753736, AI904063, CB123265, BX486937, BG214276, CD245870, BF059711, AI651375, BQ102253, AL711211, BF964587, AW500090, BM751168, CB963370, BI862225, AA442539, AW887723, AW801684, AV708200, BM152858, H17704, BF683230, BM848524, BQ772810, BQ361466, AL710982, CD242978, H11812, AA305227, AW607564, H94935, BU632641, BX328353, BI255412

Cdc6: AL562624, AL521818, BM465884, BQ064897, BX451346, BX349920, BU846236, BQ675107, BI260747, BU633837, BG256606, BM464160, BQ228599, BG252312, BM559225, AL521819, BE907412, BQ070080, BU619893, BF698043, BE741201, AL526150, BG765988, BU173127, BF699051, AA502608, BG165110, AU129648, CA488634, BM450676, BF028885, CB135870, BF185000, BG026757, CA429336, BF977528, BF240966, BG766090, AI478744, BM803439, AA045217, AA813386, BE565947, BF571756, AL710150, BF307679, AA723372, BG721945, AI433558, BF208758, BI559407, BX482661, BF102841, BE779410, BQ441118, N69246, BF310791, CF123750, BI006635, BQ775002, AA907374, BM011340, CA429634, W03300, BM845715, AA113790, BF210909, BM706052, H59204, BI255053, AI424746, H59203, AI052065, BE073887, BE550416, AI341585, BG025851, BF221502, T83032, T90351, BG720011, AI953729, AI699473, BF115521, BF223422, AI808683, BE085836, AI699980, BX355209, BE086769, AW518847, AA099980, BE965778, AA836395, AI766778, BE869748, AI802324, AA584340, BE693538, AI567411

Cdt1: BX332414, BQ935210, BU931977, BM811548, BU849056, BQ062875, BQ053758, BU187852, BX406047, AL555432, BQ278148, BX402195, BU845736, AL580756, BQ058496, AL581992, BX332413, AL557066, BU930971, BM016975, BX421258, BU190377, BQ960305, BG824304, AL520240, BM917547, BQ053108, AL582018, BG393757, AL520239, BF791881, BM019024, AL556319, BI092793, BI258203, AL559054, AL527465, AL558613, BU856820, AL524910, AL580393, BX333703, BQ063175, BG259986, BI335580, BG327660, BM556535, BI222927, BG251456, AL520887, BI224536, BI335105, AL524909, BQ053124, BI093258, BG745159, BX405984, AL515463, BE910713, AL518299, BQ054892, BQ053069, BI333817, AL518300, BU189533, BI260243, BF972427, BQ684815, BM695575, BQ652285, BQ649771, BQ647760, BQ647212, BQ645148, BG822442, AL581566, BQ652445, BQ649937, BE544515, AL577935, BX405983, BM927844, BE727635, AL515464, BU176676, BU931060, BU859159, BX366934, BX355022, BM800496, BM463356, BG389325, BU164161, BE388067, BX464574, BE778380, BF237902, BU158281, BM917445, BM809482

Geminin: BM550773, AL522354, BI092791, BX375519, BX414734, AL562503, BI861855, BM471496, AL518006, BQ430578, AL580178, BG577005, BG032232, AL525229, AL518005, AL522353, CA417249, AU118695, BQ645204, BG612964, BI855710, BQ718513, BG577324, BI086620, AL558330, BG776051, BG777134, BE893489, BF967933, BG776192, AW996997, BF666338, BQ015308, BQ064691, CD366250, BE910343, BM699599, BG776218, BF029154, BU629613, CB992796, BG825264, BE613337, CB131959, CB049968, BQ772723, BE564333, BI759810, BF666672, BF808421, BF700297, BG337926, BE565866, BG776386, CD367234, BF213350, CB136099, BI830428, BG612435, BE535264, BQ575533, BF667576, BG505022, AA447810, CA442918, BU623074, BF696555, AA393139, CD708137, BF699912, BF967209, BF056288, CA503202, CA312813, BG530534, BF109418, AV756510, BG778341, AA235222, BI093913, BF248391, AI968057, CD686529, BU685799, BG777305, AV734242, AV689368, BF240393, AW006287, AI828103, BF003138, CB049969, BF947954, BF594599, BE048465, BG429246, BG180421, AI803434, AV734302, BE219705

Mcm3: BM467763, AL551465, BQ066322, BQ061652, AL559830, BQ059704, BM471050, BU849776, AL545116, BQ063041, BU541430, BU860117, BM542415, AU124791, BU857116, BM453648, BQ056448, BM927480, BQ218351, BQ057647, BQ940737, AU119321, BX462455, BQ898140, CF995699, BI772155, AL549372, BQ214499, BU856617, BM007763, BI223143, BQ652945, BQ649476, BU509755, BQ058522, BQ641758, BQ064200, BG281527, AU133404, BE249947, BU601317, BU154249, BQ927115, BI457651, BX462766, BU558287, BQ051029, BM917594, AU134083, BM561561, CD656673, BQ422727, BQ058080, BM478599, BQ881515, BE795211, BI196606, BG034961, BE892181, BQ649956, BM479437, BG765473, AL527918, BE560376, BI261474, BI599305, BX348989, BE793456, BM461732, BE620320, BE783059, BE799563, BE561200, BQ064568, BE620857, BG681460, BE616575, AU124152, BM832703, BG392301, BG259417, AW083217, BI086286, BQ650935, BI259905, BG686972, CD642696, BI091236, CD655620, BI551396, BE778348, BG773437, BU193733, BE274144, BE891644, AW732422, AU131124, BG742232, BU178300, AU123260

Mcm4: BX363316, BM557639, BM479183, BU163628, BX341147, BQ956710, BQ689703, BU855555, BM423607, BQ689028, BQ684773, BU149764, BM917541, BQ877570, BQ962733, BQ213101, BQ679476, BQ931933, BQ670123, BQ680471, BQ878671, BU196152, BQ218770, BQ687458, BQ058022, BU838204, BQ231069, AU124599, BQ060869, AI936566, BQ066067, BQ066435, BU182872, BQ065206, BQ061896, AL710281, AU125558, BM560344, AU124716, AU130095, BX341146, BQ060907, BG683134, AU131502, BM909380, BI259276, BQ676347, BQ054534, BU601939, BQ056963, BQ883247, AU124662, AU134265, BQ681631, BI092911, AU124469, BU151359, AU131979, BU860012, BQ058401, AU126357, BE740475, BG772025, BU154598, BF058934, BQ670493, BI520579, BQ681697, CD643530, CD655257, BQ948077, BE796484, BQ681384, AI738700, BF569146, AU124670, BQ772225, BI117233, AI923706, BX100324, BF059052, BQ652623, AU131348, CF265157,

CF594355, BU940867, BG339157, BF116228, BQ682913, BG029854, BG421025, BG248645, BI223223, BE891270, BE741088, AU130533, BG684174, BQ675821, BI830911, AU136189

Mcm5: BX446933, BX443180, BU179314, BX465121, BX360307, BQ219621, BQ059059, BX374727, BM560991, BM802651, BU148505, BM478574, BM480184, BX407417, BM558890, BU538182, BX331301, BX465031, BQ893665, BQ671418, BM559170, BX331344, BU156108, BQ645833, BQ069574, BX458285, BQ895922, BQ057750, BQ054136, BQ957762, BX367432, BG767144, BQ065023, BQ055590, BM470663, BU839673, BQ065213, BX368805, BU192073, BQ065931, BQ232104, BM917136, BQ880654, BX346462, BU163845, BQ672003, BQ434878, BQ647973, BG770644, BU557340, BU165017, BG760478, BQ671606, BU541449, BQ670216, BQ649375, BI086963, BQ669996, BI909897, BQ935556, BM043366, BQ642797, BU195081, BQ222354, BU190738, BI869446, BX346537, BQ066237, BG770167, BU557310, BX465120, BX388269, BQ943544, BQ069268, BQ679299, BQ683703, BG576914, BX341163, BM051781, BM719141, BQ440728, BQ431588, BQ643976, BX381461, BU845031, BU839453, BQ213876, BX407118, AU131148, BG685544, BU178502, BQ929382, BU556785, BM457715, BU166135, BM927634, BE735173, BX428497, BX407353, BE253723

Mcm6: BM563815, BQ689609, BU178707, BU185218, BM917146, BU180530, BQ691498, BM917702, BQ721374, BQ430793, BQ710328, BQ276415, AU124829, BM551692, BM457121, BQ919455, BQ688139, BQ685964, BQ424418, BM453163, BQ671824, AU143594, BU542273, BU146898, BU178966, BQ072203, BM461535, AU131056, AU133299, AU125636, BU180371, BE383991, BU181929, BQ691761, AU125495, BG686841, CD242701, BG685821, AU117647, BX483567, BM564401, BG390247, AU133321, BI870675, BI084962, BE731324, BI084168, BG532524, AU126102, BM803211, BE734309, BM450955, BG419290, BU146822, BM013848, BG680470, CD643818, BU176030, BM917579, BM045567, BE733405, BG877987, BG538573, AU142944, AU130133, AU124506, BE796828, AU137338, BG253660, BQ879136, BG386500, BM048943, BG914034, AU124893, BX451899, BM012817, BG389994, BG030690, BE731558, BG877979, BE407913, BG878155, BX416717, BE385730, AU128720, BE618973, BE268695, BX118733, BG256582, BG878151, BE513514, BG877982, BG335342, BE281191, BE778969, BM842510, BG878152, BG877994, BU506698, BE280389

Mcm7: BX446600, BM916932, AL555833, BM451540, BX342306, BX424231, BQ279230, BM462954, BM468766, BU500250, BM803547, BM557336, BX443366, BQ070647, AL561620, BX355367, BM908241, BQ924446, BQ887320, BM912799, CD108811, BX324854, BQ643995, BM463747, BU183306, BM927622, BQ055649, BQ053452, BX428085, BQ673910, BM921077, BQ887860, BQ883251, BU147232, BQ071179, BQ935246, BQ652903, BQ883056, BQ674104, BQ641811, BQ053620, BM917214, BU162886, BQ052004, BQ891995, BQ878240, BQ953990, BQ063971, BX405959, BQ898941, BQ061151, BQ054401, BQ917453, BM564271, BU189313, BQ058499, BU161199, BM469583, BQ218009, BI522846, BU855416, BQ056795, BQ643247, BQ069037, BQ920442, AU125112, BU194965, BU854868, BU183465, BQ720104, BQ228405, BQ214543, BQ064840, BQ650571, BQ642612, AU125755, BQ956957, BU526752, BE740091, AL561593, BU165222, BE792286, BQ643233, BQ676107, BQ070446, BQ225752, BQ670399, BQ932333, BM810332, CD051232, BU527906, BU942698, BI335520, BQ057726, BM554740, BE799854, AU124962, BM914800, BI825746, BX324853

Mcm8: BQ055956, BQ070426, BM454681, BU556999, BM904262, BQ441929, BM559514, BM808018, BM459480, BM808016, BQ070219, BM009484, BQ940417, BU162199, BM558689, BM912457, BQ434761, BI862190, BM810194, CD642958, BG422937, BG338287, BM015340, BI859244, BG762185, BU509003, BG420680, BG023796, BF309111, BM453735, BM466057, CA495297, BF306586, BE513731, BI086506, BM009302, BX504348, BE898012, BG338630, AW955317, BE273079, BG827920, BG396259, BE269095, BM793002, CF137101, BF308208, BM913291, CA425682, AW960988, BX282225, BG168597, BF973469, BE278386, AV645497, AA325061, BE311854, BG339877, BF754616, W94454, CB136734, BI225492, BG434327, CA445505, BG761050, W25728, BM751186, BE842789, BM825974, BU955551, BF127844, BQ007416, CD299273, AI086063, BE928109, BF088599, AA225696, BQ071854, AA226268, AW440309, AA370141, AA193063, BQ334627, AW845751, W94336, AA609373, CA436668, AI609077, BQ320963, AA563920, AI537281, AI200790, BG259140, AI219139, AA192859

Cdc7: CA441701, BG170872, BM463748, AL044123, BE789148, AU120443, AU129167, AU116849, AW968900, AW574512, BI462237, AL602215, BM789148, CB959717, AL039323, AA814975, AA936081, BG721963, BU657893, CB216422, AU117631, AA768993, AA131310, BF366907, W76628, N40295, BF982876, AA488999, AW405542, AL044122, BF031756, BQ221549, AA291015, BX419687, BF696442, AA488783, CD523327, BG116756, D20593, CD689440, BG116838, BU568048, CD642993

Cdc5: BX350355, BU192616, BQ427813, BQ961587, BI222621, BQ962695, BX331396, CD107746, BQ427606, BE275179, BF982513, BU195085, BX483740, AL558731, BG431157, BM450338, BM925609, BU073210, BG028239, CB306835, AL706102, BG178910, BF025810, BX446071, BU508497, BM718344, BX349125, BQ423785, BM505336, BF977508, BI823054, CD103634, AL135197, AU135978, BF132826, CB160730, AL710914, AI679458, BE617311, BG390164, AW959030, BU933396, BF217466, BG502998, BM894208, AW268817, CF135420, BM146535, BU071659, BE884277, CD101983, BF035463, BG424071, AI143113, AA044750, CF143619, BG722285, BM127700, BG327622, AI122932, BM804765, AV682172, AW954903, AU279537, AL580487, BM894481, BE781164, CK024078, AV762357, BF744457, BM834441, BG121920, BE541230, BF679988, AA811533, AI221677, BG897659, CB052718, AU136923, BU623810, BG497404, CA448370, BF813646, BI048250, BF214089, AU131684, BG540599, BG942273, AA191036, BP429997, AA249176, AL710062, BE140574, AU127833, BG614948, BE140795, AI583919, AI909768, BI918547, BF795413

Psf1: BM458856, BU171017, BM450503, BX384069, BQ070512, AW499844, BM151985, AA860312, BF692084, BU430742, AI190765, BQ440331, BM152648, AA725561, AA383128, BM465819, BU659306, BI333600, AA355925, BG910353, BI223929, BF892016, AU099454, AL044646, AI184188, N39921, N39947, AU076561, AL597443

Psf2: BU597296, BU184963, BM449472, BM043804, BF683514, BF311745, BE514071, BE513254, BE382866, BQ277667, BQ229290, BG825252, BG772776, BG284180, BG104289, BF795157, AU126087, BF035586, BE796384, BE795838, BE795306, BE561044, BE274253, BE312319, AW249012, CK001498, AL560880, AL560669, BQ233393, BG420251, BE267495, BE258240, CA455226, BE251065, BU957713, BE791539, BE267221, BX415204, BI196248, BG118214, AL529785, BU595469, BF310321, BI257993, BF684568, BE561525, BE251621, BG475509, BG527542, BE793125, BE562088, BG519560, BG475384, BE259285,

BU601226, BG339264, BX456910, AV712739, BF312439, AL526847, BU603101, BE260083, BI832397, BU940719, BE255698, BE514978, AA521273, BG469677, BF209856, AL563552, AI828992, AI583174, AL582217, CB112523, BF238335, BG531588, CB129701, BF312015, BE878751, BU625683, AL582077, BE222543, AA262870, AL562756, AW958853, BU506537, BQ361100, AA251319, BM832297, BE296429, AI827298, AL560926, BE907417, BU729618, BE799212, BE268868, BM126492, BE262182, AA053046, AL582250

Psf3: BQ231741, BQ948256, BI489800, AL555105, AL524624, BM904357, AL525185, BX406244, AL529159, AL550963, AL524746, BI753591, BI770007, AL561070, BM016893, BG387533, BQ422835, BE782757, BF316873, BF797649, BG765190, BF796771, BM925118, BM722252, BG769825, CF141388, CD676320, BE749159, AL711201, BE297646, AW674872, BQ645203, BM926055, CD693113, BM804294, BG257517, CF552524, BM786881, BF797402, AU142374, BE208552, BF239248, BF310190, BQ890204, BE256868, BG249299, BE907809, W79671, BM754989, BX328153, BU939987, BE281396, CA430225, BQ304813, BQ027991, BM542908, BF769732, BG744402, AA353408, BP430213, BM564422

Cdc45: BM550683, BX366266, BX358668, BM478173, BX345270, BX355266, BX366366, BM557094, BM557313, BX358667, BX346442, BX371229, BX352708, BX366365, BX451104, BX352909, BX349664, BX331394, BX328445, BQ069733, BX448615, CA454819, BX448616, BX447114, BX349663, BU184174, BX328421, BQ427880, BX328446, BX451105, BX352910, BX334120, BX409672, BQ214084, BU171037, BQ233704, BX391089, BE747427, BX346464, BX428526, BX422691, BX331393, BX367431, BX367477, BX391088, BX367513, BX325504, BX352709, BX362080, BX367505, BF026159, BE869669, BX325558, BX366268, BE260534, CB124085, BX371230, BG122390, BG387745, BG252967, BG180337, BE897594, BX367410, BM917964, BX346526, BX328422, BQ674776, BM912689, BQ436443, BF965716, BX376594, BG720395, BF125841, BI546622, BQ216400, BU537659, AL711006, CF139190, BU618386, BX367472, BX328725, AI768340, CA454402, AW081615, BX366267, BM751026, BX328423, BE795241, BU618460, BE255146, BG386934, AI369688, BX367409, AW674262, BE903958, AW674908, AA700904, BX389190, CF141215, BE501602

Pola p180: BU508486, AL543898, AU121118, CB134498, AU132112, BX327138, BQ883339, CB121808, AW674983, CB149914, CB140712, CB152927, BQ882043, AL570197, BF210579, BE835570, BE818389, AA379019, BE837514, BQ312037, BE837504, AI354751, BM475170, CB122291, AL044294, BE771020, AA355814, BQ351870, AW589637, AA383406, BE717631, R72191, BX117096, AA828105, BF888988, AI261685, BE163167, BE817842, CD000139, CB999470, BF899310, BG926114

Pola p70: BU508486, AL543898, AU121118, CB134498, AU132112, BX327138, BQ883339, CB121808, AW674983, CB149914, CB140712, CB152927, BQ882043, AL570197, BF210579, BE835570, BE818389, AA379019, BE837514, BQ312037, BE837504, AI354751, BM475170, CB122291, AL044294, BE771020, AA355814, BQ351870, AW589637, AA383406, BE717631, R72191, BX117096, AA828105, BF888988, AI261685, BE163167, BE817842, CD000139, CB999470, BF899310, BG926114

Pola Spp1(Prim2a): AL556161, AL513776, BM546142, AL549894, BX401418, BU187783, BM459297, BU193561, BI523986, BI907286, BG034836, BG215267, CF595567, CA406143, BX280180, BM926617, BF572603, BQ947185, BX404971, BM852865, BM756079, BI547222, BF978626, AL578476, BF747008, BX401417, AL573915, BF745947, AV757142, CF140555, AI557036, T75233, BF745931, BF744295, BM464505, AA465014, T10253, BG183395, BE697488, BG205656, BG209815, BG195945, AA434502, CB113799, BG184433, BF746454, BE766105, AA361880, AA255550, BG191366, BE766167, BE766098, BE766038, BE765690, BE769157, N80963, AI216670, BX114039, AW951150, N80656, BE714429, AA255569, BE843957, R61073, BE714404, BF000349, AA093814, BE538394, T93658, R00642, F12922, BE543709, BF172325, T05292, BQ001605, CA411912, BX455830, BM551302

RPA70: BM456944, BQ222582, AU119564, AL576308, AU124434, AU125631, AU122638, BM556841, BQ222302, BM542894, BU177749, BU508590, BM456314, BM466291, BG108961, BX425090, BU633264, BU153418, BU184357, BU517134, BG251944, BG828190, BG764082, BI858388, BG758555, BG035161, BG287240, BF796027, BG036436, BG826869, BX488619, BF971387, BM790584, BG119012, BG765594, BG685852, BE292972, BG761657, BE898956, BE743787, BE897915, BF983057, BF665538, BM792560, BI253949, BG755233, AU125797, BE178302, BI093003, BG120570, BQ218906, BM743518, BM742537, BF698180, BE178464, CD579303, BM848213, BM844440, CF121414, BF344035, BM838207, BE927446, CB121597, BE542431, BF664182, CB115068, BM847443, CD580024, BM848384, BF028723, BM851538, BE927448, BE773962, BE773949, BF751549, BM016568, BQ214159, AA460805, BE764622, AU128580, BG029093, BF082772, BX339968, CB130706, BQ230034, BM711058, CB160550, BE927450, BU501405, BE932015, BE773964, BF699259, BF919259, BE932029, BM541370, BM462468, BE171973, BM845370, BX477548, AL553255

RPA34: BX333932, BQ064852, BX442975, BQ069120, BQ943330, BQ063763, BQ674220, AU118399, BQ059648, AU143441, BQ673815, BQ439053, BQ278675, BU856528, BE741729, BQ066157, BG825398, BQ668543, BI600038, BQ641985, BI757393, BG333934, BQ054635, BQ070050, BQ066715, BI518754, AI419040, BE271646, BQ063545, BQ058415, AI890508, BM543895, BG336979, BE898769, BI818496, BG421195, BE901546, BG469742, BE887147, AU134052, BI756891, BF308713, BM312218, BE902956, BG433978, BG334708, AI744901, BG254134, BU943380, AI929664, CA488595, BE298500, BG826547, BE394497, BI599375, CK002534, BG779099, BE313107, BE298150, BG501316, BG826213, AU129936, BQ059808, AU126353, BI113916, BE297131, BG424340, BQ642824, BI193274, BI546749, BG716673, BQ055902, BG777777, BG428439, BE019650, AV762431, CD687322, CA842220, BE898527, BE294795, BG616118, BG615827, BF791819, BE568731, BQ059622, BQ054654, BG436837, BF686542, CD702944, CD710078, BG479643, BE898609, BM698831, BQ924421, BE394931, AI961707, BX283385, AA641800, CB145745, BF692608

PCNA: BM464765, AL547405, BU162573, BQ233597, BM923901, BM475636, BM809424, BU506972, AL549034, AL549068, BI254350, BU187589, BG686220, BQ716438, BM477662, BM542830, AL572455, BM474328, BQ231284, BU195180, BU161781, BG774625, BQ681114, BQ649204, BU634227, BM474327, BI765443, BM979950, CD519986, BU626265, BQ682146, BI767353, BG707111, BQ679867, BG755768, CD367344, BI254540, BG166783, BQ014636, BI598197, BM977646, BU624262, BG686801, BM016212, CA442951, CA443088, BM976306, BU628431, BQ009665, BE889822, BE738456, AA910951, BQ218579, BI829094, BI226337, BQ050978, CD238945, BG503955, BE888544, CD367010, BQ429019, BM466077, AI348072, AA843679, BE739511, BG540339,

BF685141, BM842748, BM829821, AI125272, BU656120, AV717345, BU154500, BI831672, BG533644, BM850147, BQ016237, CB529827, CA446890, BQ447329, BM781704, BG503385, CD364739, BG614065, BG290688, BQ681737, BE887284, BE883191, BG613869, BE746433, CB529409, BQ016228, BQ003193, BG502601, BX473856, CA443057, AV649575, BM995025, BU154811, BG532459

Elg1: BX435523, CD643489, AW976468, CB161634, CB051111, BE551573, AW514252, BE042824, AI621250, AI623298, BF669931, AA651909, AW450012, BG389184, CD644045, AA972691, AU149697, BU509262, AA724028, AU126948, AI656767, BI094506, BU428574, BF243394, BE886708, BX102408, AA744478, W87913, BF212165, BE834403, AA857981, AA136031, AA703271, D29036, BE152409, BX109066, H456423, H68973, BE005696, BX461696, AA610813, BE834436, BM312382, AI078312, BG207827, N90506, BG197401, BM724358, CB051112, BE148289, AA806690, AW978010, BX108248, BX104136, AL712199, BG619264, BE163388, AA976805, AA707097, AA705010, AA702235, AA436301, AA436174, H59615, BU682299, BF993160

FEN1: BU538692, BX397634, BQ058498, BX424210, BX333531, BU170538, BX443166, BG860300, BQ888965, BQ880548, CA489528, BX433300, BM015629, BX448621, AL560007, AL531350, BX331605, BU535646, BQ957039, BU931957, BX445725, BG828048, BU167885, BM561765, BM560757, BG575417, BU931950, AL519300, BQ918754, BM546237, BX425258, BQ642352, BU538026, BQ641309, BU178840, BU553925, BQ690414, BU539094, BG574950, BX448789, BG337603, BM552061, BQ053379, BQ424018, BF686180, BU176039, BG676364, BQ064038, BU170972, CA454699, BU859837, BI116779, AL560377, AL560395, BE793493, BG576479, BE792164, BG756459, BG773958, BE311755, BE796307, BG474425, BI767742, BX394237, BM542385, BE795541, BI827898, BU931956, BE799080, BE397382, BQ050062, BE796569, BI117469, BQ227585, BI115669, BE780262, BE274648, BQ946363, CF131987, BM917670, BG825257, BU189559, BM803891, BU856251, BU165752, BE794075, BE793759, BQ777102, BI256835, BU541327, BU152651, BE799325, CD243456, BQ278519, BQ219034, BG287218, BI334366, BI116455, BE798996, BG472198

DNA2: BX390869, BX329314, AL527195, BG289876, BI869219, BX384719, CD644575, BG106738, BE866952, BG117032, BG036343, BG177711, BE748018, AW134972, AA284382, BG501340, BX384718, AW369063, AW369067, BU658975, BF213278, AW367239, AA282895, BE085640, BQ435874, C20980, BG944343, CD514528, AA974495, AA830575, AA767191, AA748680, AA282803, AW977920, AA732685, AW367310, BF089037, AI186294, AW361984, AI940759, AI940744, AA812151, BF357542, AI248069, W86421, AW378978, BG961093, R05855, BI091087, BI091081, BG505976

Ligase1: BI916625, BM555654, BX325045, BU154275, BM044202, BM548700, AL530699, BG743952, BG678604, BU168385, BG774713, BM015149, BG825382, BG681554, BI755126, BU152699, BU543078, BG744633, AU120968, BX329161, BE747873, BM472230, BG257399, BI856896, AU143382, BE794374, BE744087, BM763360, AU120985, BG327553, BE512655, BE873444, AL570759, AL042689, BG747144, BX325044, BE047619, BQ072622, BF038182, BU159409, BM013639, CD579385, BM794429, BF529953, BQ923144, BE297514, BE263744, BQ648677, BG257587, BX362172, BG251839, BF205184, AL558263, BI765243, BM917641, BE512703, AU128254, BE294485, BQ644838, BG024771, CB109099, BQ654248, AA306774, BM711430, BG177788, BX370252, BM846234,
CB270211, BI025622, BE257136, BM975458, BM819487, BE266691, BX475022, AL530700, BQ231386, BQ071175, AL710126, AL705975, AL705915, AL697933, BM749091, BI463850, AL602262, BG333926, BG116773, BE294757, BX362173, BM456382, BF797607, CB121210, BM458469, BX503423, BG685986, BM836632, BG469591, BE907368, BX475021, BM793401, BI829665

Pold p125: AL578715, BX382861, BX366475, AL560083, AL556466, BX366474, BX402885, AL525375, AL514720, BX350425, BM479873, BM905305, BQ920464, BU855691, BQ054258, BU527550, CA455120, BM008549, BQ070749, AL559084, BQ688129, BQ068026, BQ955289, BU542295, BM048573, BE311672, BQ958499, BM044191, BU859048, BI859768, BG744446, BQ936440, BU173332, BU931011, BG826841, AL580780, BU527075, BQ918345, BE737103, BM008621, CF125207, BG745091, BG472420, CA455000, BQ890540, BU154168, BI334420, BF205093, BG340726, BE798460, BI118205, BG683283, BE547846, BU185961, AL514719, BQ071299, BG258722, BE796517, CD101690, BE274988, BU844535, BE298157, BQ953920, BG390567, BE731346, CD615429, BG029434, BF346914, BG911621, BG281172, BU944555, BF206631, BE513504, BE391305, BG832159, CB321982, BG749237, BG285702, BQ343533, BF312202, BE901507, BU553455, BF304095, BU501677, CD615427, BI227211, BG120642, BE255898, BU161275, BM012106, BF529600, BQ232039, BU539859, BG115290, BM471494, BM742222, BF203965, BQ071659, BE514532, BF689201

Pole Pol2: BM799918, BX368245, CA489133, BX452508, AU124277, BX448917, BI524150, BX432893, BE613576, BX400486, BX448918, AI341337, AW629043, BX444300, BU617156, BF029073, BX280062, AW974329, AA448761, BE966475, AA709119, BX400487, BQ318645, BM784534, AI039222, BQ946037, BM454666, AW439589, BE782680, AA282380, BU742406, BM193890, AA448664, BM665497, BF738758, BF766844, BG473220, BM751106, AA333178, AW139478, AI636255, AW242762, BF766936, CA941526, CA941235, BM509588, BF766967, BF766969, BX384417, BM505194, AA812343, N53947, BF766934, BM751342, BG195865, BG185004, BX414432, BG219868, BG210945, BG207825, BG197398, BG193392, BG188146, BG195403, BG190325, BG207824, BG216817, BG216115, BG212524, BG209425, BG196918, BG190326, BG189205, BG188145, BG218864, BG203607, BG182912, BG215183, BG220834, BG216818, BG203604, BG195863, BG194393, BG194392, BG181396, BG212527, BG197926, BG195866, BG189206, M62099, BG214127, BG193903, BG192860, BG212525, BG207823, BG207822, BG204615, BG202577, BG202576, BG202042

Pole Dpb3: BX471071, AL544919, AL531155, CD171731, BX422049, BX403356, CB159628, CB152302, CA487866, BU956441, BU931411, BU844651, BU844620, BU193214, BU181445, BU178251, BU160282, BU153515, BQ956965, BQ932794, BQ896428, BQ883962, BQ691435, BQ688656, BQ643218, BQ437007, BQ425615, BQ421168, BQ227667, BQ224773, BQ220928, BQ057666, AL713425, AL711259, BM853361, BM830557, BM818099, BM811580, BM552527, BM478816, BM474837, BM465332, BM463844, BM451660, BI463584, BI224290, BI091613, BG181075, BG111071, BF978613, BE895839, BE883232, BE872164, AW246427, BE910559, BU161793, CD300569, AL542290, CB132298, BQ924495, BM920044, BM847093, BM451747, BM013495, BI668995, BG700033, BE781043, AL598822, AL550727, BM749328, BM477218, BI755256, BG720455, BG505578, BG387715, BF983616, BF978547, AL541402, BM557688, BM558417, BM193306, BG024009, BE543436, BI333822, BQ059205, BI561738, AU280159, AA524279, BM753932, BM014466, BE880199, BE242720, CD710143, BU959989, AW136187, W03622, BU571151, AI634435, AI991485, BI334810

Pole Dpb4: CD674888, BU597500, BU595433, BU594966, BM924454, BM555016, BM551010, BM009306, BG491874, AW081785, BE910607, CD107195, CA307504, BU520765, BQ233876, BM912894, BM809080, BM727074, BF237493, AI554783, AI436367, AI886832, BU597812, CA454961, BM929605, AI432454, BI667558, F26406, BQ954219, AI815728, BF025828, BE276764, BF764960, BM725423, BF107426, BG760830, BU740914, BG740141, BU077279, BU963250, BF237693, BG683544, AW970445, AA927473, AI142293, BM714678, BU739305, BM984649, BI599890, BU076938, AI797479, R07547, AI188727, BG682813, AI815926, AA513753, BP431280, BU537093, H27059, BP429067, BM677848, AA811357, BQ219306, AI833007, AI090223, AW368694, AI148002, AA676886, AA353038, AA740345, BQ640428, AI191303, BQ013037, BX112032, BU953216, AW955899, AA400317, BQ011449, BM688755, BM687694, AA368986, CD693537, AA400632, BF944449, BF378717, BE615920, BE408046, BF978324, BM723287, BM682293, AA536076, AI336523, AF202331, BG461940, AA639692, AI970899, CF529348, AI017725, AA468753, AA978356

Topoisomerase I: BU175449, BG574241, BQ918804, BQ720771, CA488073, BG506927, BM788013, BG546269, BM722996, CF137671, BX403047, BX391491, AI878932, BG493034, BU934394, BF977810, BE748187, BQ230349, BE733657, AW025108, CA487823, BE070282, BG401860, CB242988, BF912374, BG433599, BI561949, BG252538, BX406161, BI092973, CB959389, BF887734, CF145440, BG529331, BF594476, BF726053, BI087263, BG540279, BF002422, BF214159, AA765988, AA594329, R60159, AW368554, BF768633, BF923424, BF573926, D55538, BF105824, BF741104, AW854287, BF095014, AV708869, AI493041, CF127017, CD523275, AL559809, BU625720, BU195531, BQ950231, BQ718893, BG778556, F07589, BI834633, BU940860, BG169393, BE818064, BQ438538, BU429936, AI271876, BX389156, D54890, BX391490, BM541278, AA887955, BM699908, BF216295, AW368250, AW368275, AI479910, BG532987, BM720782, BF342838, BQ379859, AW003919, AA639463, BX403046, BE172121, BF924434, BG942263, BG611737, AI337284, AA987503, BF030802, BP430593, AI637947, BM985011, BF694314, BG569753, BF887735

TDP1: BM545366, BX357935, BX352942, BX368062, BU185781, BX336700, BQ214685, BQ233509, BX367994, BX368251, BQ689475, BQ049211, BU163540, CD654830, BI253420, BX388603, BX357934, BG291484, BQ277263, CD642861, BX336701, BU174608, CK000808, BE894450, BE613472, BI490906, BX352941, BM150331, BQ223905, BX472747, BX363837, AU136908, BX407827, BX461234, AW968944, BX368068, BX474790, BE387073, BE614223, BE786331, BI222338, BU429540, BG772310, AU135919, AW249271, BX367862, BU849335, BI822990, AL602103, BX477415, AL598723, BI861569, BI489958, AW962673, AL705760, BE909004, BE747879, BM712636, CA425849, BX401951, BE312937, AW849814, AW849937, BG475315, CD641965, AW007897, H49893, BQ010512, BE246145, W76100, AA332235, BF196744, BM462605, AW410205, AI480141, CD703683, BE247287, AA609339, BX475227, AA477148, AI209111, AW961554, AA330280, W72865, BU738356, AA336839, AA514317, AA620407, AW000979, AA504522, H49894, AU156926, AW129282, AA628378, AW589860, AI636696, AI989590, AA716609, AA489121, BF896143

Ctf18: BQ231004, BX447012, BM806765, AL562324, BX371387, BU553656, BE795677, AL516520, BQ962210, BQ650965, BE797877, BQ645686, BU845747, BQ646300, BE898071, BE901267, BU509771, BQ650789, BI457170, BI196074, BG481033, BI823171, BU625412, BU633872, BE888887, BI766695, AL516519, BE902046, BG168881, AL524240, BM674122, BQ648925, BQ651106, BQ646373, BM715777, BM127632, BF308850, AW973666, BG761379, BU845239, BM832965, BU616468, BF306837, BQ645867, BQ773121, BM127327, CA421425, BE262702, BU159091, BM703773, BM793661, BF513105, BM005987, BE314193, BF347314, BM906352, BE313266, BQ644028, BQ650233, BQ647544, AI831961, D61532, BG480239, BX117345, BE780529, AI650845, BE300859, AW196692, BM150350, BF093805, BQ367862, BQ073027, AA478378, AI824849, BE279389, AI620989, BU540454, AW236312, BG825945, AI918000, BE242499, AW662226, AA352175, AI355547, AI916173, BM701214, BF182688, AA610722, AI276362, BQ651661, AW149595, AW631061, BF434726, AW467884, BF091910, BG488804, AI401116, AW904596, AI689357, AI382635

Scc1: BM466374, BU146139, BU164770, BQ434145, BU190012, BQ222984, CF552154, BM474979, BM477931, AU130565, BU156118, BX390631, CD657694, CD654104, AU123599, AU131556, AU123557, BM927599, BI089741, AU124372, BI869474, BU625171, AU137268, BM920285, BM479826, AU138617, BM803806, BG779064, BG503734, AI905425, AU134242, AU130905, BU175990, BG289967, CB959416, BQ437529, BE870127, BU940947, AU135199, BQ229673, BF797759, BG254176, BU178041, CF619358, BM452576, BI093343, BE560508, AI627668, BG390625, BQ638398, BQ230670, BU509303, CD358988, BQ574279, BE867847, AW028126, BQ230181, BU181371, Z78332, BQ218011, BU598145, BF103682, CB143108, AL705581, CD557703, AU134649, AU125960, BM833822, BM749176, BM452530, BG505923, BU431249, Z78334, AI739002, BF540787, AU128854, BE895809, AL540173, AU133303, CF135927, BM907180, AU129400, BF091717, AA129353, AL558080, AL046011, BM833939, BM467920, AU135442, BF794442, AW500227, BM461566, BF590668, BE748270, AI017447, BI093513, AI367597, CB143109, AA699622, BM478563

Scc3: BQ946254, BQ224497, BG678247, AU131359, AU141951, BX643586, CA488740, AW993480, BG284625, BM468092, AL042846, BX506229, BI223205, AL582073, BQ229101, BF796496, BU431562, BG682345, BQ718426, BG114650, BE871224, AU132652, BE929374, BM799307, AL701691, AW499961, BX505839, BQ422046, BF085120, AW966123, BF085121, AW993214, AA311870, BE817052, BU430955, N25477, AW937839, AW501973, BX503773, CB988449, AL701626, BE541958, AL710194, BE817053, BF085130, BX505398, AW892743, CB963696, AL582049, BX643342, BX643410, AA179766, BI088302, CA454732, AL708036, AW999070, AW966631, BF367226, BE540683, AI064692, AL692142, AA334313, BG698257, BX473973, CD238866, BQ371413, BF330420, BE832149, BU431563, BE832148, AA385639, D78828, BE844082, AL710458, BE844095, AW993032, BX473971, BM751899, BG951313, AA249600, BG187519, AL603592, AU117247, BX102249, BX646186, BM718664, BX474425, BI771735, BM833941, AL600231, BE708022, BG536049, AI351861, BG899130, BF830533, BX437683, BG167708, H75808, BM561699, BG256800

ATR: BM452469, BU146099, BU193242, CD359676, AU133155, BQ226453, BU616550, AU138930, BU521017, CA771525, BG679313, BI259481, BE894977, BX476619, CB134903, CA771217, BU620031, BG770191, AI685264,

BE221326, BU676069, BQ432546, BM855140, BX646290, BX476608, BM141700, BX476618, BM129429, BM129718, BM141963, AW769028, AA453176, AL707012, BG768017AW029178, BG960271, BE646363, AU154536, AA746485, BQ025557, AW769551, BG960875, BE091396, BG026395, AU157822, BM796532, AI584172, BU431210, AI288527, BM459025, AA731840, BE859077, AL039634, AW976047, BF222914, AA825525, AV751232, AW390089, AW152454, BG392173, BG223235, AA551327, CD644383, BF094478, BF930497, AI962936, AI871554, AI279279, AA837410, AW978820, AI394218, AI285634, AI280393, AI127664, AI078770, AI027417, BU076885, BX497770, BG192205, BG189101, BG184889, AI088580, BU077225, AA215661, BG208865, BF110182, AW237573, BG210328, BG221227, BG201951, BG191706, BG182288, AI902747, BG194892, BG204028, BG208221, AA747410, AW390065, CD642306, AI689705

Chk1: BX384024, BX425856, BX352948, BM458297, BM803862, BX363020, BX384025, BX383978, BX363830, BX443777, BQ071454, AL515222, BQ919396, BX346314, BX363829, BX414303, BQ424951, BX345096, BM048703, BM478961, BU620586, BX386787, BX386786, BU181250, BG717056, BX440542, BG687019, AL523644, BG258170, CA441277, AI924526, BI088504, BF795495, AL708308, BG612596, BQ226720, BM968823, BG339614, BG944287, BE299090, BI521358, BX351192, BG828404, BQ223060, BF310022, BQ641604, BM558032, BG218896, BF242017, BF001625, BG470645, CB127107, BG192348, CB124258, BF204894, BG124369, BE464453, CB125201, BG256454, AL559804, BE298964, BX383977, CB124285, BG194802, CB998143, BE904400, AL559805, BG216281, BG191840, BX425855, BG215785, N99369, BG470702, BM193374, BX363019, BI197298, BE882051, BE297644, N53057, BE548526, BI824209, BG211479, BX346313, CB142976, AA224307, CD694666, BQ322635, AA962684, AI536947, BM455102, R86187, H67490, BF973418, AL515221, BF946916, N71469, AI750793, AL523643, H59530, BU927896

NBS1: BM542698, BX405940, BG182890, BU166634, BM461758, BG214621, BG388866, BG284646, CF593314, CB123692, BU517247, BU661996, BM014420, AW976050, AI796269, BG483074, AU118357, BG109073, AW978306, BG392111, CF994271, CB250418, AW183153, BF027776, BU620472, AI888159, BE694454, CB989468, BF511289, AL713597, BG292394, BI962748, BG202556, AW363125, BF028917, AI767797, BE142989, AV715636, BU686090, BE695861, AU144944, BF219376, AI478631, BF208284, AW237021, BF217323, AA535147, AL041061, AA741007, AA577530, N22869, BE694368, AA713939, BF222791, BE892618, BQ354782, BE566896, H98655, AW391193, BE694374, AW340253, BG197194, BF062731, BM835126, AI890179, AA807181, AW025671, AW593423, BE089552, BG194661, BG194211, BG187424, AA463450, BG184671, BG209170, BM833754, BE694416, BG198067, BG214402, AI478521, AA835830, BU172525, BQ380443, N36514, AI858133, AA907134, BF096050, N51586, BG196671, BU429506, BE694353, AI952672, AI377839, CF137847, BE142840, CB135538, R48068, AA535711, AW207441, BF219034

Hus1: BX510134, CD520767, AL554895, CD104810, BU933524, BU932644, BU600981, BU171912, BF185772, BG386353, BG286955, BE874516, BM462752, BU932377, BE568470, BE892098, BM546627, BF510091, BE543378, BG330719, BU193379, BG703514, BM906889, BE644764, BF796878, BM822628, BE566605, AA902233, AA280710, CA418558, BQ646867, CD678464, AI675254, AI968159, BG028551, BU680921, AI968626, AI750426, BU784416, BE891273, BF056974, AW518029, R29753, AW270395, CD357688, AI656993, BX115181, AI149713, AI538328, CB992757, AW965692, BU588470, BF222727, AI654498, AA693873, AA353895, AA828114, AA773515, AA897773, AA652723, BX500811, BF998283, AI968739, AI656972, BX370241, AW467865, BF211281, BU928301

Rad1: BX439078, BX362814, BM915064, BU508168, AU142492, BG325636, BG254417, BE739684, BU942019, CB997499, BG528822, BF305274, BU192569, BE379759, BX472344, BM453151, BG502187, CD365064, BI821006, AW779759, CD370483, BU567700, BE542464, BQ277303, BF381656, BF103945, AL697883, BG687436, BU431185, AI732815, AI870850, BE866735, AA486301, BM875591, BX362071, BU623683, CB126098, AW237104, BG687442, BF084168, BE565545, AI052547, AI628587, BX105685, CA432131, AW373219, CB306975, BU682777, BM875344, AW473643, AW473637, BM790461, BG777245, AW104439, AW001011, BF667027, BQ214495, BG108349, BQ433094, CD513520, AI685362, AI075030, CD672667, AA968417, AA029300, BF807890, BM264116, BG036263, BE843169, AW779236, AW819703, BX373966, CB218092, AA768474, BF242093, AW579006, AA464502, AA227739, BE930194, BF375637, BE549430, AA913007, BI862650, AI871190, BX369672, BX369671, AA228124, BF748944, AU157657, AU123712, BE928477, BX435862, BM015762, BE645342, BE379989, AI885817, AI734194, BG612563, AV711443, AA464501

Topoisomerase IIIb: BX424738, BX425419, BQ651682, BX403442, CD107506, BX446190, CA453925, BX346535, BX418504, BG763535, BM549973, BX403443, BX388297, BQ649447, BQ279059, BX353337, BX428354, BM562369, BX389266, BF690073, BM922961, BQ884077, BI254650, BG751464, BF348239, BG767127, BX375918, BI199856, BQ425197, BX333417, BQ939934, BG748897, BX418503, AI361851, BQ183439, BX428593, BM719837, BF689997, BG827105, BG180123, BX431485, BM020904, BX431486, BG251915, BF568363, BX430251, BM982636, BM542563, BX353336, BF839819, BX389265, BX456723, AW082912, BU739692, BM668058, AA581879, BM929485, BX375917, BF569140, BF840332, AW081400, BQ072301, BI908256, BI458744, BQ437166, BE262344, BX471363, BX333418, AI653725, BG281858, AI432376, BG910301, AI271458, BQ018902, AW594115, AW580188, BF683888, BQ052367, CB958279, BU733478, BU956077, CD656636, AA576862, BX425418, BQ925386, BG519835, BQ267454, AA789096, AI884361, BQ270362, BU194029, AI654571, AV724647, AI797309, BX088825, AI252649, AI368666, H30621, BG281907, BF971171

Rad6A: CF242862, AL556664, AL554264, AL551212, AL545489, AL527666, CD245975, BX420488, BU177002, BU176550, BU158774, BU155911, BQ938012, BM904536, BM671147, BM547988, BM460782, AL601372, BG477320, AL557798, AL552044, BU594647, BQ773667, BM127839, AU137774, BE873022, AI126625, BM128123, AL547443, AL547028, BG771586, AL561578, BU596427, BE893452, BG037200, BM128046, BM127780, AU135850, AI912983, AW051875, AA917931, BM172179, BE280929, BE504240, BF308088, AI367248, BM888354, BE465165, BI914734, BI562526, BG426078, BG399765, AU128974, BI117499, BG709332, BI223209, AU123986, AU126997, AL540766, AL545955, BQ717080, BX377743, BE276997, BG429673, AI830472, CB118540, CA398015, AU280101, AI367259, BE001808, CD673205, AU128994, BQ050943, BE934281, AA314005, BG249012, AW206875, AI984287, BM752230, AI097110, BF030505, CD299140, CB962261, BE867709, AW205767, AI371888, AI087376, BG680605,

AW139418, BP431686, BM741851, BE002061, BF694346, AA442497, T80555, CB127128, W77761, AA340148, R92832, AA808831

Rad18: AL515920, AL525404, AL562493, AL515921, BM479176, AL519429, BX327634, BU633444, AU130305, AU124369, AL519379, BQ878144, BX118224, BI260485, BX644573, CD657250, BQ002046, BG403172, BG187245, BG687139, BQ438688, AL519378, AL602096, BG501779, AV689196, BG434615, BX506345, BG528199, BU928268, BM827802, CB146761, BM783792, AU152279, AI674134, BM987526, BF062100, BE538599, AW024863, AW188470, AW852547, AI140776, BM739442, AI140772, AA625471, AA628928, BM820601, AA953817, AV689200, AL600012, AV689197, BI463280, AV689198, AI075759, BQ012909, BU588168, BE245247, AI826396, AW274711, R59255, AA311754, AI266146, BE715962, AI051483, BI060361, R59197, AI292169, BQ305165, H79432, CD643305, AA972797, AW607437, CD709390, BF241055, R42938, H79318, R17601, AI262720, BQ013328, AL044563, AA494524, AI536060, R18043, R13366, AW804426, AW607158, AW969432, AA745596, R40881, BI060362, AW804432, BG992485

Ubc13: CF130960, CD710574, CD692115, CD673025, AL543503, CD245362, CB988950, AU280192, CB215753, CB161684, CB161357, CB159339, CB158868, CB147566, BX110715, CA453274, CA310015, BU959707, BU942968, BU941352, BU935537, BU787955, BU509214, BU195662, BU177345, BQ670955, BQ651546, BQ438057, BQ434581, BQ431772, BQ278353, BQ233659, BQ233603, BQ233591, BQ220048, BQ212232, BQ071631, BQ053849, BQ053589, BM927363, BM920802, BM916123, BM810273, BM805692, BM548060, BM480191, BM456876, BM449746, BI830293, BI829065, BI822117, BI753449, BI603033, BI193140, BG759142, BG758336, BG720632, BG716212, BG701931, BG613290, BG548397, BG531270, BG503962, BG432626, BF974186, AU125145, AU119879, AV758049, BE747116, BE266994, BE314665, BE207615, AW246428, CD685196, CD558824, CB987518, BU940976, BU177313, BG715594, BG715088, BG714343, BG701027, BG615565, BG504869, AW950789, AW250538, BG716471, BE262841, AW673494, CD686244, CB957396, BI197667, BE313357, CD701933, AL583561, CD385216, BU596184, BX415171, BX400510, AL534723

FBH1: BQ668450, CD518455, BM475590, BQ073711, BX350417, BM556786, BX385835, BU171774, BM462614, CA976039, AL555827, BU527061, BG682347, BQ932104, BU184837, BM811347, CD513292, BM051895, CF552522, BF792094, BQ953076, BM469767, BU856754, BU507355, AL580250, BQ672631, BM541777, BG575794, BG396523, BM019265, BI462395, AL578234, BQ710339, BQ889679, BQ706264, CF125476, CA439526, BU535409, BM916651, BM014236, BF683805, BG104902, BG385761, BX369664, BG483429, BQ722509, BQ894882, BG028476, BG422497, CD722593, BE253172, BX483033, AL558429, BE513039, BG117837, AW369165, BQ437287, BG479586, BG830784, BQ129343, BM686491, BX117109, BE541008, BE736140, CA393619, BG109986, BG913455, BM717015, BX356080, BG323256, BF684368, AA045149, BE730963, BG682808, AL044721, BF349688, AW964614, BQ951138, BQ325260, BI006637, BM707421, CB113655, BQ898291, BE378693, AW963805, AA430290, CB159047, CB161429, CA438158, BX364723, BM707309, BM699811, AA428015, AW963835, BQ129349, CA395354, CB321675, BM798328, AI459539, CA945183

Mad2: BX092337, BU509241, BQ959603, BQ440642, BQ428342, BM472395, BM472304, BI766194, BU508933, BG532327, BQ425846, BG702724, BU509710, BG614828, BG505458, BX443383, BU963707, BX325759, BU198649, BM016150, BG503527, BX404037, BG679723, BG533781, BX449727, BX346251, BE270292, BU177716, BU662541, BG530972, BG531198, BG116166, BG527529, BE886793, BF305710, BU928412, CA489378, BG503886, BE311763, BX401098, BG496604, AW950858, BE778450, BE270518, BG613007, BF034523, BG504712, BG249673, AW411207, BG501915, BF219704, BE890707, BU598703, CA489522, BG504001, BF130567, BE296423, BF030667, BG531869, BF694258, BE295856, BQ277112, BE895923, BF666701, BI560148, BE543883, AW674988, CD700655, BU659357, BG169697, BE960883, BM458351, BG615578, BM837848, BG506388, BE870543, CA488467, AA490658, BF184132, BE567312, AV715949, BF667164, BG284883, BF666681, BM450737, BU661109, CB137773, CB137684, CB134844, BF698236, BU158230, BF701297, BF240809, BF185562, BF696854, BG613188, BE738000, BG290170, BF696888, BE270517

XPC: AL537156, BQ898206, BM556322, BQ918948, BU506961, AU125870, AU130697, BE260062, BQ892451, BG751164, CD643621, CK000090, BE730655, BF981364, BG748625, BG341433, BF972749, BG338028, BU602325, BF317427, BF306190, BI255928, BE278952, BM461420, BE733920, BE252615, BG752811, BI670281, AU120699, AU130155, BE254313, BX474915, BM729318, BG340238, BF314903, AU280283, BG489139, AA287404, BG337505, AU127391, CF995178, BG335426, BQ308142, BG259049, BQ649424, BQ307301, BX505750, BE260137, BF683997, CF140093, BF685974, BX470382, BE257840, AI123414, AU150414, BQ477814, CF141168, BM827376, AA657557, BE221715, BG571695, BX475123, BF090364, BF207269, AL709045, BM856351, BX497971, BM708556, AW504862, BM833387, BG178613, BG620310, BX283619, BG749233, CB269927, CB267080, BM700758, BX486869, AU143301, BX493543, BM852149, AU128095, AA190694, BE702371, BE074001, BX644722, BG396899, CD250721, AL710884, BE262208, AW903238, BF827957, BE766460, AV736879, BG116273, AA329947, BX476805, BM454293, AV734541, BM908255

Rad23A: BX386817, BM555668, AL556689, BM923938, BX462941, BQ226301, BX383110, AL518853, BM563676, BX346368, BX443456, BX458814, AL560403, BM800629, BM546406, BM450093, BX400223, BM905361, BQ067487, AL538737, BX448989, BX376642, BU182138, BU501586, BM460305, BM455101, BM553961, BX405327, BX439481, BQ959921, BG397266, BQ231221, AL528006, BQ649073, BU161613, CD516432, CD300604, BU161547, AL527519, BU170588, BQ922155, BM922503, BM806531, BM811343, BQ878719, BX416323, BQ431936, BX424587, BQ231191, BM553778, BU166711, BQ068184, BI115640, BX336880, BE743148, BU902824, BM543659, CD517476, BX440266, BM928421, BE793785, BM805413, BU663811, BM767302, BI771571, BU543634, BI488410, BI831370, BG828123, BM702259, BG826357, BQ671655, AU120562, BI756007, AL554211, BG575011, CD359531, BI092253, BQ923295, BG765676, CF146536, BE254829, BM764880, BI768800, BE254847, BU186368, AL548714, CD580418, BQ430734, AL708410, BU598395, BU160883, BI770418, BI458425, CB243750, CD300680, BE296271, BU624195, BE792673, BF982409

Rad23B: AL542437, BU508207, CF242874, BI761813, BX385070, BX344701, BX397027, BX406219, AL544467, AL540969, BG617563, AU135170, BM785167, BG681545, CD516576, BM846302, BI094479, AL532383, AL554483, AL549735, BI524081, BI086980, AW747914, BM843069, BF949974, AL570682, BE166667, BI460482, BF696085, BG290212, BE018477, BE566434, AW117407, AW631016,

AW629978, BM919879, AL516156, BE218017, AA460535, AA305019, BM845855, AW610521, BQ927520, BF082151, AL571657, AW080867, AI221288, BF239610, BF116028, BE218477, BG035090, BF238781, AW610520, BE926034, BG718045, CB995306, BM705797, AL569427, BX411441, BI868477, BF817189, AA316654, AW821231, BF433951, BF906503, AW578686, BF762435, AA932185, BG958581, CA406436, BX387819, AW389400, CA389879, BU959168, AI261824, AW991331, AW663949, BF374886, AW770657, AI703064, AW510997, BE925443, BE220051, BE674734, AW389398, CF553075, BF088680, BF762431, BF692478, BF111238, BX422214, AA359699, BF994844, BE613559, BQ929186, BE817876, BM480327, BF755677, BF795639, BX500679

CSA: BI918304, BM833676, BG611935, BM017684, BG722970, BG612963, BI458951, AI950957, BI601669, BU603353, BU533681, AA454500, AW954940, BI828404, BE540951, BF244952, BE567160, AL691658, CB160846, BG387575, AW388466, AW388282, BF206366, AW301277, BI850241, BF665074, CD687697, AW409745, W19086, BF790869, BM147057, BF665145, BG616128, BE568475, BQ218876, BX116922, AA129369, CD109410, BG032140, BG037177, BF588485, BF000147, CF552572, AA159858, BI561029, BM835908, BQ645232, AW418819, BF247700, AU100233

CSB: CD653749, AL039860, BG723092, BX644251, BX474980, BF508753, AL702189, BM759548, AL039851, BF094116, BG121679, BI020594, AU185158, BE763975, AV725351, AI418429, AU185476, CA502920, BX485503, BE841244, AA305555, BQ015647, BG259982

XPG: BX370344, AL537284, BQ215712, BM461711, BX383623, BI518401, AL537285, BG754702, CD243930, BU680238, BG574639, BQ002437, BI836225, CA503022, AW044617, BQ045373, BU608348, BG282989, CF619292, BQ014611, BI091747, BU624982, AA843311, CA418268, BM793974, AW772514, BU617777, BQ186957, BG400427, BU732780, BU608324, BQ221301, BM504121, BG391687, BG286779, BI711387, AI680931, BQ775943, AI417946, CA424453, BM875436, M797308, BE170510, AW317068, BF576042, BE552270, BM507072, BM750705, BM675983, AI885477, CB142083, AI623400, BQ614576, BM830049, BM875687, BE350942, AW854025, CD579376, BM677102, BF360483, BU740308, BQ002355, BM504348, D250763, AI768283, BG282957, AA548114, CB270753, BF515914, AW369265, AA312903, AI702437, BX471563, AA582936, AI907200, BQ215703, BM712460, AW504101, AI452675, BI459976, BE772886, AW576371, BM838528, AW401569, BE772887, AI218110, BE349982, BG723008, BM506721, AA592904, AI458250, AI272121, AW966715, AI572661, AI023105, BM831424, AI285500, AA808705, BU738082, AA506450

XPF: BI522552, CB956135, BG620282, BG181154, CF529228, BQ013114, BX503907, BQ310815, BM671280, BQ011470, AW977575, BM710111, BG724387, AL705565, BE818393, AA291199, AA770518, BE837466, CD674166, AA774566, AI431784, AA256859, AW271424, AA638976, AV685090, BE818447, AA255461, AW242081, AA723776, AV692790, BE814005, AI653508, AA721794, BX103000, AA834535, AA292809, AA808363, BI459712, AA284141, AA639091

DDB1: BM927667, BM545266, AL547974, BM559217, BM474381, BQ057079, BQ230722, BQ051604, BQ927173, BQ943701, BM799741, BU543084, BQ220481, BQ070702, BQ061047, AL521541, BU931018, BM469013, BU153954, BQ945468, BU165038, AL555048, BQ898580, BQ068618, BQ050859, BG764306, BQ057811, BU159948, BU508051, BQ065776, BM804642, BU845856, BM905933, BQ935651, BQ060859, BQ052770, BQ066316, BQ066118, AU125547, BM803322, BQ927550, BM552236, BM473607, AU121686, BG746666, BU535682, BM556709, BQ931953, BG831447, BG751027, BG677450, BQ683506, BQ642180, BM476800, BQ063089, AL549443, BM553844, BU178933, BI256821, BQ059091, CD652436, BQ962485, BU542556, BQ061252, BU156588, BQ642770, BU501977, BQ897254, BG762513, AU140587, BM046600, BQ070862, BI260236, BG747001, AU140248, BU154345, BQ060945, AU140289, BE743760, AU130230, BQ056360, BE794022, BG327224, BE747530, BI457215, AU140521, BM456004, BG481963, BG469259, BU943325, BQ943596, BQ213497, BM043469, BQ439584, AU140209, BG769813, CK000424, BQ279191, BQ438774, AU140418

DDB2: BX401847, BX400795, BM460187, BQ688926, BM563807, BU159281, BX384437, BM008599, BE792938, BG479004, BQ940060, BE797218, BM560871, BX117885, BM018420, BM455897, BI256001, BX360369, BI868487, BX385303, BE799933, BM009575, BM553220, CA487463, BU174903, BX366945, BM850079, CD518332, BI915455, BG756997, BM782789, BI915534, BM554617, BG118313, BE261143, BG913101, BE783395, AL566516, CB142981, BG035565, BX403426, BI838828, BG756904, BM885720, BX400794, BE018683, BI761524, BM746344, BX363265, AW247981, BM743623, BE536472, BE903342, AA309052, BG612441, BQ063694, BM744890, BX384436, BI255783, BM791178, BM924491, CD696204, BG106780, AL536826, BQ062583, BF974680, AW803143, BM783399, BF791778, BG759533, BX366944, BF974639, AL702736, AA278480, BG613246, BM840145, BM821166, AA311506, CD685541, BM920389, BF375336, BF576398, BX360368, BX384709, AL702729, BP431548, BI092193, BF382434, BQ001750, BI261116, BF184818, CF144601, AA128445, BE798846, AW802999, BF203187, BQ001644, BE247271, BQ003952, BQ575065

XAB2: BX356659, AL518679, AL519886, BX424193, BM922374, BX381810, BX381811, AL557238, AL535342, AL525436, AL538943, AL518678, BX342559, AL565880, BX397557, BX383379, BX383380, BX382204, BQ053451, BX383814, BQ643137, AL561830, BQ050225, AL519590, CA488373, BU845857, AL560324, AL521338, AL534944, BX370726, AL560477, BQ935369, BU153161, BM476327, BG488778, AL516161, BX538674, BX392023, BM806807, BX364648, BI771923, BQ927835, BG488879, BM917523, BI822736, AL514374, BQ227702, BU541210, BQ221081, BM451911, BI772072, BX446010, BU855544, BU179797, BI823391, BM913999, BX448905, BQ054530, BG744221, BI910746, BQ956926, BG480524, BI261656, BM469671, BX464425, BI767323, BE253641, BI768994, BG386812, BQ063543, BI911058, BI518767, BE799838, BQ212885, BI459403, BU528530, BQ073165, BM048645, BE898732, BG468301, BE531308, BF311851, BI561194, BI560801, BF569424, BF686448, CD672626, BG425290, AL559075, BU170853, BE728374, BE871613, BE274104, BF314780, BE280310, BM456485, BU856266, BM020680, BI911907, AW837892

UNG: BM926584, BM799989, BX438441, BX342506, BU165625, BU943452, BX378897, BM471137, BM928006, BQ228775, AL559968, BX379137, CF551970, BX378357, BX372231, BU161952, BU176423, BQ882986, BQ420300, BX361226, AV705903, BM919577, BX440252, BI823926, BQ048928, BM458045, BG105781, BQ962046, BU187892, CD643361, BX366166, BM541301, CD512104, CD686190, AU126319, BM718553, BE793197, BM449708, AI879177, BX429498, BE902908, BQ950839, BG326541, BG389571, BM012071, BQ670076, BF342799, AA290918, BG392330, BM799653, BX368057, BE734542, BG717638,

BI198939, BI226322, CA454788, BG176725, BX347126, BE882172, BG256273, H09366, BI226401, AL079771, BE781768, BQ348703, BG390499, BF701762, BG176633, BE559523, BG282433, AU279887, BQ365552, BE883671, BE270595, BQ917973, BE258817, BE546123, AW401453, BG106747, BE268637, BI259016, BU168154, BX346912, T78215, BG481771, BX346928, CB130269, CB129289, BE261638, BQ348874, AA573859, BP429782, CD672939, BM751245, R25268, AA356048, BI766031, BM825376, BE263990, BQ322779

MBD4: AL556619, BX372087, BM459663, BI767663, CD105484, BG032353, CD367008, BM690016, AL549313, BQ722669, BE561716, BI521142, BG032516, BI765468, BM465252, BI823689, BG686312, CA773665, BG716078, CD364595, CB989176, BF446103, BE622249, CA943572, BM314436, BI596708, AW964068, BI820928, BF033618, AW073379, BM857488, CA773226, AA741175, CA395073, CB136245, CA867841, BE541307, CB995679, AL578833, BM749974, AL553305, BE614377, CD557525, CB158348, AL553419, CB243592, BM462436, AU138081, AW138783, BU789775, AW193960, AA167425, AW195025, BG621850, BF509234, CA390195, BQ005967, BG613448, AW958704, AA939068, BF509053, AA167418, BU619480, BM476709, BM314740, BI462718, BM015493, BI544324, BF109031, AA905592, AA648364, BF109027, BF515981, AA167414, AI682256, AA011232, AI225045, BU153530, CA487592, BM857715, AA954283, BX390695, AW474165, AA825707, BI517400, BG742246, AA353798, CD678412, BG031116, BU732453, BM836637, BM709307, AI217321, AA247185, AA618259, BU678959, AW959666, CB144059, BI669635, AA171632

TDG: BM479641, BM905541, BX370775, BM456725, AU128073, CD652973, CD657696, BG621267, AV708234, BE779060, BX331941, BX483618, BX382383, BF033788, BM476558, BX385505, AV649391, AV649244, AV649186, AA477864, BE181979, BX338343, CB145292, CD642813, CD644103, BM729260, BI760123, AL600750, BX509348, BX492385, BX476996, CD110168, CB994452, CB961815, CB267807, AL701375, BM915474, BG114997, BF002914, AW590228, AW502250, AW136393, AL120270, AW051610, AI916834, AI868982, AI767246, AI669518, AI493141, AI360256, AI352697, AI332786, AA306938, AA257018, AA143198, AA131695, AA316331, CD109607, CD109351, CB989389, CB959951, AL699594, BF674842, BE502468, AI769788, BU566171, BX366012, AV654940, AL710869, BE784882, AI272154, BX340488, T34101, AW408102, BM457221, BF001989, AW138490, AW135094, H14409, BG940420, BU564446, AI869223, BE536675, BF241047, BE882613, AI435880, BF195990, BE080436, AW955279, CD050602, CA406412, AI272147, AI338205, BX646789, AA356499, BM556682, CB047650, CB047649, AI937774, AA360035

NTH1: BM553336, AL536460, BM921161, AL566343, BM803928, BM472681, BG760523, BX438358, BM019398, BQ052788, BG821962, BI868261, AL545181, BI199103, BG766177, BI832477, BQ216562, BI757515, BQ431466, BQ052774, BE799423, BG519584, BG490410, BG747350, BG472059, BE746343, BI839163, BI196060, BG468596, CA488808, BF794685, BU182347, BG388749, BI226382, BE792632, BG248655, BQ881995, BF525435, BE797167, BM917598, BM451836, BF315844, BF312887, BG468607, BE790928, BG114969, BF337743, BE878633, BM677868, BF205470, AL545152, BQ958991, BG827031, BE266472, BE314558, BM811237, BF219845, BM831407, BX445525, BM424115, BM916696, BE313626, BG678320, BE262196, BF220231, BG331307, CB142490, BQ647925, BU622908, BQ575671, BF303821, BE891721, BE744813, BG468617, BU535559, BU634434, BM982354, BM129563, BE250955, BM821556, BM851724, BM725444, AW246140, BG469318, BX444894, AI610226, BX379864, CA488850, BE256091, AI818303, BU957532, BM129299, BM831443, BU902454, BF002443, AI968475, AW732463, AI424835, BU849457, AW103041

NEIL2: BX401292, BX418848, BX386695, AL529804, AL530971, BX341864, BG759722, BQ942628, BG697467, BX427919, BI522685, BU158642, BX386994, BX333648, BI224185, AW411371, BE887573, BI113772, AL555248, BF305600, BI522781, BI520072, CB112109, BG700461, BM466367, BI601338, BU189576, CF145781, BM011284, CD558091, CF147070, BE736612, BE736412, CF139009, BF346473, AL524751, BF932051, CD671249, BF241652, BE153549, BI962581, BI793306, Z43722, BX340965, BI548326, Z46109, BU165567, BU193072, CB126915, BM729333, BM450046, BI789116, AI968247, BF761462, BF529055, BI793006, BU168329, BE153640, BI439197

NEIL3: AL528028, BU170388, BX391576, BM458786, BU173488, BX112923, BQ687469, AU133212, BQ054308, BQ220911, BX348730, AL528027, BF700528, BG397668, BX391575, BE885006, BG026947, BF664630, BG758440, BF030084, BG495300, BF103925, BF217043, BQ441413, BE882646, BE865481, BF183915, BU689565, BG122779, BQ422423, T85431, AA373561, BG388415, AI307746, AA815079, CB145683, AU154583, AA677552

APE2: BX325338, AL556617, AL519979, BQ277791, AL561128, BX395132, AL531548, BX433301, BQ050352, BM541964, AL559217, BX385097, AL528954, BI093915, BU931498, BM016132, BI859309, BQ921050, BI086544, AL582410, BQ428526, BE531337, BU553240, BM015733, BE737187, BI767790, BU184166, BU164122, CA495324, BE794688, CA495346, BI196397, BI912615, BX325337, BI669515, BQ229782, BM807966, BG709216, BX382166, BI333249, AL527692, BI909503, AL561839, BE616906, BM016478, BM726096, BE547006, BU942097, BE885110, BI837686, AL527693, BG024450, BE794496, BI915874, BX452361, BI911544, BG752268, BG386237, BF203315, BI858986, AL578831, BX394096, BI859870, BI256178, BF308964, BF310943, BF307805, BI223857, BI160978, BI160236, BE548576, BF981813, AL580878, BQ328004, BF931957, CB993692, BE280661, BI033411, AL711190, BE729174, CF146056, AL564091, BM682530, AL528953, BG438154, BX374269, BE265083, BX392349, CD366445, CD514757, BE795242, AI547012, BU540750, BE076387, AI547003, BG897167, AW386829, BI094006, AI907885, BF792036

PARP1: BX425285, BM474368, BM473858, BM458759, BM458491, BQ216584, BM468375, BU164317, BM924278, BU149272, BM474022, BM905935, BG281447, AL542989, BQ946216, BQ918876, BU849139, BX438143, BX443246, BX420713, BU166033, BM012504, BM454330, BQ438889, BI091452, BX395490, BU844993, BM472955, BM555163, BX368206, BU171470, BM472260, BG280821, BX464445, BI833606, BQ882633, AU124412, BM463285, CK000195, CD653823, CF552559, AU124072, BE740909, AU131873, BQ213230, CK000758, BQ954235, BU156802, BX460089, BX450439, BI253230, BM450940, BM478605, BI334768, BQ222114, BM805846, CD651914, CD108986, BX462212, AU125041, BQ708310, BM043633, BM452637, BX388560, BM012492, CD521009, BF976506, BX431987, AU138067, BX421686, BM469381, BU942653, BM545681, AL517083, BG499313, BG533818, BU177793, BE270913, BU178223, BI908423, BE783663, BI087079, BE270845, BE899131, BE561235, BG177824, BG031594, BG393066, BE560200,

CK000604, BE744678, BM799547, BM453457, BI093436, BG259918, BQ691997, BI113824, BG123019, AA401836, BM472073

PNK: AL577752, AL542181, AL529432, AL578082, BX440754, AL529433, AL531397, AL563677, AL563673, BM552937, AL530233, AL555192, BM811617, BI523512, AL562615, BX385339, BM047190, AL582405, BI761490, BI765355, BG519795, BU957084, AL518252, BU541073, AL561123, BG912156, AL531398, AL529487, AL555795, BI488573, BQ943952, AL518253, AL555631, BI908075, BF971606, AL525997, BX331554, BU552518, BF314736, BI522840, BE312745, AL530223, BM011630, BI489474, BQ219713, BI766984, BI199796, AL519579, AL563456, BQ877856, BI834426, BG252407, BE799855, BQ055605, BQ067892, AL519578, BF315056, AL042657, BU956990, BI820868, BM045471, BM710277, BE394572, BG330783, BI909140, CB529741, BU527521, BM974879, BU619715, AV655619, BM917371, BI907002, AL526117, BU543115, BG118159, BE313034, BM982849, BI599430, CA425985, BM910694, BQ772660, BI770327, BE734945, BU622816, BG939419, AL525953, BI116338, BM923265, CF594119, BI822801, CA439970, BI827695, BE272050, BM819357, BE266096, BM687914, BE260690, AI984026, BX279591, AI830883

Polb: AL572526, AL547658, BU157194, BG743462, BX383155, BU166001, BG251605, BI761008, BM790436, BQ430835, BQ434342, BG032291, AL705932, BI753835, BI915120, BI559405, AL558615, BX646755, BE394043, CD641318, BM928122, BX395185, CA314334, CD671591, CA313995, AU121247, AA916271, CD579745, BF131951, BQ188410, AI654868, CA439409, BI598628, AA130183, AL580395, BG506123, BU188474, CB125716, CB141008, AA172068, CB130159, AL702696, AA706903, BG025809, BU933432, AI827117, BM852849, BE280856, AL702481, AA172228, AA130175, BF693388, AI124907, AW957764, AW102789, AI825920, BM725613, BM678092, BX115761, BU934294, BF245489, AW070694, AI014834, BQ053443, BI461358, AW402160, AI689323, AA315716, BF219035, AI034273, AA856902, BM931013, BM684499, AA977230, BG339593, CB144384, AA809775, BQ574627, BM979958, BF590500, AW269977, AL120608, AI128173, AI057605, AI032461, AI017499, BF507649, AI087793, AW887363, AI949400, BG196141, AA723600, BG209074, BQ186692, BQ184899, BG212204, BE889161, CD110437, BG220062, BG200837

MSH2: BM479882, AL528268, BX461033, BM557852, BM457765, BX431195, CD247876, BM543463, AU125214, AU125592, BQ878410, BQ225922, BI256610, CD655479, AU118136, BI090516, BU154902, BG756122, AU123630, CD656123, AU133361, CD519566, AU133333, BG773440, BI769598, BU178986, CB955666, AU131598, AU124367, AL563106, BX436686, BM475467, BI093054, AU120648, BU182908, BE792530, BQ223894, BI757481, AU131477, AU124664, CD656999, CD652376, CD657313, BG716960, BQ431632, BM834569, CD557029, CD693039, BE778241, BU934097, CD653693, BE779907, BG773429, BQ643544, BQ422633, BG388582, BG759539, BE894244, BG721947, BE268484, BE297145, BF033549, BQ221216, BI561347, BG773147, BE870260, AU123223, AA502616, AI792246, BX436685, AU126323, BF205395, AU144782, AU129482, AI823868, AU151529, BE254661, AU123102, BQ334510, BX413346, AW951649, BF834144, AU129404, BM788022, BM455023, CA843563, BU620631, AV693408, BU600314, AA287480, BE897216, AW402832, AA219060, AV732547, CB135442, AW003984, BE550379, BG499470, AW515731, CB143683

PMS1: BX353664, BM479838, BX328949, BX327629, BM553209, BX117693, BM800196, BG193431, CB157373, BG168340, BQ429685, BX435290, BI464618, BG536475, BM723144, BF666456, BG163660, BG776017, BX452128, AL043809, AW945172, CB161021, BF699885, AL705101, CB131671, BG292439, BX419980, CB136057, CB268969, BG120880, BM677668, BQ771615, BF978494, BU599098, BM742128, BI545790, BG401461, CA415469, AI811371, CB852984, BG827501, BG719470, BG772717, BU623174, AL043785, AI458470, BE779274, AI636100, AA278390, BM820659, AI076038, BE350913, BG222592, AA781041, BX353663, BF056020, BG716188, AA833518, Z36291, BM009631, BU597828, BE350907, BG614286, BI438347, BM996496, AV730735, BE972698, CB144057, BF210947, AW269877, AA573397, AA393893, BQ574496, AA573406, AI660351, BF570703, BU854630, BG196186, AI367805, AA210907, AA393809, BG215472, BG207030, AA092955, AI277404, BG195153, AI278080, AA297925, BQ220187, BG182167, AW661801, BG209122, AV732009, AV731296, BP431712, AI828829, AI655707, AL600680, BU561560, AA282075

PMS2: BQ951503, BM474394, BU153042, BQ881303, BU178449, BQ069438, AU140605, BG829980, BQ644101, BG720607, BQ436841, BU153051, AL708946, BU622416, BF568181, BU171754, BE884933, BQ221907, BM012037, BQ369274, BM701781, AL699728, AU280501, BE763779, BF840656, BG177103, BQ045117, BE304459, BX385541, BI548246, BM669686, BM144251, BX283912, BF674494, BU193656, BQ775383, AL701903, BQ232687, BI544939, BX283370, BM967072, BM148437, BE090126, BM967300, BI912345, BG565558, BU665027, BM147147, BX385540, BE090067, AL702122, BF114739, CB111334, BG708195, AA151500, BI752285, BF697242, BU934799, BU728992, BF381825, BM698903, AV655809, BQ322673, BQ050630, BG776255, AA428236, BU604958, AI096500, AA256227, AI147872, AA256169, BM893955, BI037161, BF840055, AI539402, BM893782, BX095320, BQ221253, BE675175, BQ368913, BI829104, BE676031, CF124711, BU622696, BU620584, AI831722, BQ644699, AI341574, BM714146, BQ129192, BG398558, BF216419, AA297413, CB306237, AA707711, AA458667, AA206606, AA078218, AA418026, AW968473

MLH3: AU121422, BQ878851, BQ716451, BG499557, BM551767, BU939998, BU183004, BM019183, CD103565, BX105329, CB118745, BM272299, Z78340, BM910096, BI752941, AV716905, AW340308, AW362032, BM738947, BE702562, AA679054, AA910059, CD701194, BM977366, AA766226, CD691614, BF540730, AI694991, AI792373, BG531828, BF207616, AA128984, H14680, BG119667, T08142, AV763342, AV764126, AA128983, BF364343, BQ002635, BQ008613, CA423918, BM792789, CA417441, CA418772, Z78339, W90440, N28386, D59901, R24851, BM684959, BM931907, AI685618, BG621929, AW007533, CA440408, AI768447, Z42933, AW385347, AI743250, AA649171, BF593505, AI683070, BQ316181, BM989024, AW896052, BM021521, AA682848, BQ428064, BM021241, AI768554, N99774, AI769320, BF197240, BF475901, BM023592, AW814434, BM146299, R20012, AL709475, BM023291, BF197600, AU147242, AA043269, AA043268, BM148801, CD678743, AI147056, N20033, AI825216, BF507953, AI934949, AI452776, W90107, AI857356, N71335, AA403079, N71385, AA249090

Exonuclease1: AL561030, BX416336, BU159140, AU124774, BU166252, AL582335, AL517937, BU190454, BG762651, BG764476, BU179240, BU163048, BG120654, BE780022, BE260617, AA486526, AL043793, BE385439, BM788680, AL517936, AL530611, BG111229, BM837022, BX280790, AV712138, BU616763, AL530610, CA419695, W79628, BF793400, AW390232, BE538507, BU178737, BX437336, BQ576087, BE082055, BM988542, CA446317, BQ776150, BM983504, BU617051, AW390243, BQ015148, BG251725, BU619316, BF435309, CD644038, AI693533, AW665143, BE464836, BF240758, BM479145, AL043794, AA489549, BM465399, BF478070, AA703000, AW977979, AI768937, AA485938, AU148568, BF979589, AA122095, AA122096, N74770, W79484, AI653837, AA972063, BE737930, AI968408, AA578654, AI859579, BE738387, BF870905, AI683464, AA812220, BU623456, CA430743, BE154204, BQ012304, BE274208, AI357911, AA485921, BF870910, AW663404, AI005418, AI023645, AA622919, BE085798, AW080921, AI040508, AI084836, AW664078, AA909643, AA832160, BI494500, BI494499, BG527833, BX470325, BF435984

Poli: BX360120, BX370036, BX329075, BX436380, BM453196, BX370037, BM470558, BM450274, BG428228, BG532401, CD642641, BX378703, BG564733, BQ316794, BX360119, BM788353, BM714817, BG724156, BI560521, AA156839, BU958811, W60418, BG678675, BF219796, BG718281, CA431039, BI465231, BX378704, BE895738, BQ438265, AW852908, AW247603, CA418634, C18134, BQ086307, BM979833, BQ429462, BM918353, CA447232, BQ365259, CA446505, BU688625, C18844, BQ365051, CB243862, BU624232, BX386327, AW974469, AA878207, BQ102388, N57090, AA812734, AA856713, AA156602, AW418676, AW857684, R37923, AA648538, BM559425, AW150751, AA383550, AW880052, AW269829, AI634894, AW468818, BF111492, AA825419, AW070469, AA890447

Rad51: AL541688, AL524788, AL530472, BQ053625, BM808716, BQ070341, AL526587, AL526399, BU182612, BX364160, BX349297, BQ438308, BU553012, BM910438, BM558629, AI347079, BM810067, BG826929, BG774318, BU508719, BI827729, BE262785, BU164989, AL563696, BQ278437, BE256767, BQ424388, BI826961, BF969466, BM804639, BQ918872, BU624430, BF311612, BF313593, AU118946, AL563755, BF970732, BG325079, AL524787, BM791694, BM018810, BG338607, AL530290, BE312219, BM011814, BM745228, BE883694, BG474115, BU931527, BF982698, AL526641, BG420079, AW732525, BF203788, BM557367, BG480368, BM972210, BE514829, BF684891, AU123935, BF313295, AL569030, AL526670, BE394150, BI197901, BQ070384, BG469700, AW006523, AA568782, AU145391, BG774691, AI419710, CF139164, BE280848, BI193363, BG470554, BM147841, BX475529, BX494877, BE890859, BU596395, BM555611, BM796675, AI670798, BQ224221, AW103435, AA873056, BE779265, BX475478, BE926933, BE186007, BQ316481, BQ316480, BF683589, BF764274, AI018041, AW392597, AU100170, BM145097, BQ316451

Rad51D: BX443779, BM915550, BU681257, AL559564, BI915527, BI254468, BG829674, BI823883, BM476837, BU521767, BQ961661, BI916871, BG475664, CD387861, AI692982, AA707504, BX327473, AL581158, BE382759, AL597240, BI915277, AW631291, N57184, BU786480, AU098391, AA352205, AA868613, BQ576251, AA868612, D59413, BU784751, BI561390, BX111725, BF905526, CA423187, BF905698, BM559794, BE827486, AW948521

Xrcc2: BQ068576, BX283699, BQ430896, AW795339, BX490624, AL575509, CD365380, CD364971, CD299443, BX452455, CD103503, CB998612, CB241699, CB161449, CB160341, BX112725, CA436504, CA433495, BU681335, BU677265, BU508799, BQ771572, BQ229516, BQ217842, BQ030362, BQ028254, BQ026904, BQ017903, BQ000324, BM992214, BM710721, BM707110, BM353061, BM312475, BM054681, BM047586, BM023098, BI911022, BI907991, BI222447, BG621955, BG259639, BG121288, BF695702, BF573900, BF475941, BE962487, AV713355, BE768228, BE768138, BE716250, BE674520, BE617958, BE617517, BE243767, BE046093, BE044165, AW856234, AW795333, AW469111, AW338249, AW272847, AW192175, AW152595, AW081629, AI921359, AI866980, AI859056, AI812052, AI807730, AI761522, AI693828, AI636343, AI587436, AI469779, AI458271, AI423414, AI401226, AI357497, AI347767, AI346854, AI346825, AI343926, AI304763, AI304314, AI299263, AI223196, AI222728, AI220037, AI219853, AI140511, AI125306, AI094986, AI089590, AI051303, AI021980, AI018616, AA928999, AA782270, AL574032

Rad54: BX403014, BX333113, BX363903, BQ277879, BU552753, BU932120, BX363304, BU553867, BX402970, BG679516, BU170678, BU173543, AL520104, BX414817, BU160045, BU932121, BQ225695, BX403013, AU124617, BG471582, BX363902, BI819429, BX363303, BG393630, BX386730, BU553362, BQ048878, BE797412, BG763599, BG258318, BF689785, BU855314, BM789908, BM720371, BE378872, BE397391, BE270285, BG768944, BM739336, BG030016, BX414818, BF304094, BM795109, BE742863, BU633988, BQ224151, BF308260, BM821481, BF663661, BX483240, BG323434, BF690175, BE614490, BX329613, BU634286, BG740710, CD696837, BE872543, CA414068, AI818766, BM754736, AI061463, AL040507, BG395239, BM773411, BM825772, AA313874, BG944997, BG827295, BU934008, BM772100, BF769132, AW516286, BM745768, BM765732, BG720800, AU148441, BM746228, BM678712, AA227600, AW236802, AA582917, BG114710, BM753165, AI990748, BM753679, BM745825, AA724587, BU849113, BX106292, AL520105, BI255111, BE613982, AI372035, BM857179, BF913956, BE708827, AA227900, BM801845, AW003486

BRCA1: BQ679749, BQ068830, BU194336, BU155689, AU122476, BM452288, BQ683955, BU552955, BU163307, AU142729, BQ878445, BU171200, BG681276, BQ676829, BU163141, BQ681242, CF121736, BQ422380, AU125312, BF508987, BF791668, BM042892, BU147444, BQ677666, BQ215100, CB155501, BG178466, BF983078, BG777447, AI992040, AL704228, AI589028, BF794879, BG257190, AL135363, AA608570, BG530796, BM800251, BM042282, CB118225, BE264293, AW295197, AW968546, AA205436, BE043993, AW968720, AI915085, CB158976, AA804632, AW504244, AU148997, BE018878, BE206562, AA702344, BQ214737, AW514868, AA812019, BE564528, AI684595, BU617173, AA486004, BU679389, BX102233, CB150491, AA814998, AA484941, CF142324, CF138586, CB136844, CB108172, AA773331, AI680547, BU677011, BM755214, CF596982, CF143993, AA111870, CF144118, AI040685, BM988066, BF447679, BF028959, BQ308670, BX644276, H90415, AW673569, BM755305, AA086435, BF795489, AW408596, BQ378479, AW575729, BQ378695, AW964452, BE560149, BX497486, AI217721, AL043576, AA205474, AA917008

Ku80: AL542654, AL537322, AL556485, AL552210, BM927751, AL557736, BX418952, BM801948, AL541582, AL516832, BX425176, BM905671, BX458362, BU193782, AL540737, BQ679008, AL550730, BM471778, BX446693, BU146999, BM560171, AL548391, BQ213485, BQ220595, AL542266, BU542616, BQ651471, AL541946, BM803480, BX439845, BQ899268, BQ672013, BM800555, BX419500, BX415043, BM543372, AU131739, BQ679661, BU188691, BQ059109, BM451420, BQ880232, BQ645929, BM467250, BM453905, BQ650072, AU142506,

BU188386, BM451883, AU124221, BU168862, BQ649861, BU170704, BU155107, BU146251, BQ226372, AU125704, BU177113, CF552735, BX439846, BQ424597, BM549064, BU509423, BM809313, BI259161, BQ878391, BU158765, BQ226911, BX421454, AU119267, BQ898623, BQ425827, BG827810, BQ642849, BU177743, CD107663, CF265072, BM466124, AU141293, CD243745, AL575698, BQ921196, BQ427943, BM470728, AU131108, BG576028, AU131971, BU150184, AU132099, BU176974, BQ223936, BX447056, BU153309, BM466876, AU132244, AU122435, BQ229983, BQ881903, BM454471, BQ924231

XRCC4: BX362079, BX340876, AL543920, BM471375, AL551668, BI760531, AL558342, BI770803, CD580212, BG682493, BI758185, BG699970, BG505339, BI822602, BI463813, BG772422, BM465969, BU664243, BG776379, CA394395, BI464058, BQ226357, BI828556, BQ233170, BF183927, CB962180, BE748849, BE748380, CB146884, BF211589, BX281210, BQ421318, AW950192, BF572503, BM846671, AA314379, BF669890, CD706606, AL580186, AA447878, BX279574, AL575167, AA258143, CB144620, BG500252, BF247013, BG499117, AA448976, BF107431, BF214359, R19860, AV717223, CA453949, BG497598, AA065267, BE254850, BU171074, BM564730, AU099389, BE781259, BE780721, BE778165, AA398779, BE781955, BE783342, AA398935, AV743689, AL570210, BF895164, BF242563, BX362078, R14027, CD358588, AI795996, BG282107, BG206341, BG204714, BG199056, BG193494, BG219448, BG218328, BX389897, BG221405, BG208423, BG204713, BG201112, BG196512, BG187196, BG192946, BG214239, BG211030, BG208424, BG203200, BG198531, BG198530, BG186701, BG186093, BG181983, BG213659, BG214740

Tin2: BM911894, BQ941808, BX398174, BM915062, BQ066985, BX430064, BX347075, BX387627, BI837194, BQ423479, BX347045, BI871294, BE747943, BX429614, BX347087, BX337436, BU942629, CD244144, BX388585, BF793349, BX346850, BX388520, BX423719, BX367761, BG420146, BE903807, BE727299, BX388767, BX428959, BX430065, BX326045, BX346831, BX355414, BX428954, BX367991, BI193188, BX388709, BX398173, BX394341, BX442338, BX326233, BX432669, BQ707785, CK005692, BE562849, BU187043, BX429889, BM541314, BX444001, BX474320, BX386120, BX355792, BX395024, BQ218393, BE408455, BX381411, BX423718, BQ222471, BF125394, BE410701, BX388630, BI909268, BX374920, BX375500, BX368189, BF125791, BM549897, BF125418, BE743717, BX333804, BX450403, BI754471, BI760932, BX388787, BX356844, BI518422, BI488522, BQ707493, AA428113, AV686147, BQ720769, BM545840, BE383960, BI764031, BI767028, CB216205, BG824273, AW402903, BI835774, BQ707958, BM452819, BI833476, BI755739, BM919172, BX326360, AV693747, BI116486, BX368042, BE882159, BI821458

Sir2: BM544569, BX445007, BI834120, BM547962, BQ228980, BU507144, AL550142, BX367337, BQ072979, BI766740, CD624348, BQ052789, BU182713, BQ068262, BM920249, BQ951302, BE379525, BI862361, BX375262, CF264878, BF528797, BM462565, BX340941, BM806242, BI518634, CD515474, BX453795, BU195684, BQ068338, BQ058696, BE798693, BQ645221, BG437042, CD517619, BX380923, BQ068347, AL519386, BU197397, BM903578, BI554088, CD624352, BQ221442, BM473470, AL533183, BM924936, BI766260, BI918160, BI762157, BF034485, CD674710, BQ653076, BI603360, BG723057, BG339784, BM546244, BQ929517, CD624347, BI523850, BX428185, BG339736, BG468891, BG386360, BI838558, BI771058, CD624353, BF345522, BI823957, CD558177, BI766390, BI768954, BI768415, AL549311, BI907256, BM906233, BG819884, BI910251, BI760600, BI517372, BM805816, BF529638, AL561653, BQ430510, BQ339694, CB150996, BF975840, BG032959, BF531032, BI756237, BF975705, BU196170, BI763858, BI918541, BI524122, BG332544, BG328012, CD624351, BF686436, BG288542, BI838925, BE867361

MGMT: BU931774, BU859113, BU172662, BQ641434, BQ220709, BI771279, BI520278, BG753063, BU850242, BQ228817, BQ710379, BI520938, BG764104, BX094941, BQ279107, BI226276, BU858086, BX509195, BM759902, BI520029, BU154192, AL520114, BM974121, CF130478, BM738844, CB992752, BI772512, BG436862, AL520115, BM973348, BG249568, BI520980, AL524961, CB993639, BM009017, BU845865, BM970224, BX373012, BU616455, CB055208, BI225271, BI333401, BX376972, CB055209, BU947266, CB997161, BE858532, BM972582, AI719186, BM670373, BU845870, AA978354, BM744653, BG340352, BQ222473, BM758658, CD369999, BG183775, BX351398, BE541556, CD249663, BM744647, BU737340, BM754382, BG181704, AW168149, BM712082, AI963126, AW274265, BF109578, BE464809, BM711175, AI016474, AA126722, AI143841, AA948354, BU786059, BM049297, AA779559, AI052155, W58681, N95214, AA988766, BU566480, BX349121, BQ072274, AI057145, BM823702, AI040746, W25247, AA677158, AA136191, BX383619, AI123988, R72558, BQ217761, AW804292, AA565025, BE774145, AA868690

DUT: AL576853, AL519489, BM757904, CD247125, BM457507, BI091680, BQ440183, BM915011, BM740990, BU600705, BE386365, AL532465, AI686520, BM475441, AW968574, BF338018, BF206146, AI680930, BG682494, BI836025, BE221492, BI255334, AI951891, BI868234, AW968748, BM470935, BG700386, BE897174, CB529208, BU677683, BU677665, BU620392, AL554011, BQ777742, BE254729, CA777885, BU597092, AU119115, BU623296, BG717317, BG655751, AW162006, BI670458, BG705392, BE902236, BG717215, BG53201, BG610639, BG677850, AI635074, AI261871, BI091131, BG163981, BG113287, BE706306, AA056738, BE644721, CB110414, BF317403, BE551158, AA737006, BM554499, BE222283, AL532464, BM840182, AA256721, AI373097, AW629827, CA778151, CB117412, BE549576, BG505144, BE218639, BF058963, AW341118, AW967946, AA278799, BE504213, AI191219, BI860728, AW962792, AI697600, CB137303, CB133275, BE502892, AA291243, AI199667, AA446533, BE673841, AI937879, AA434589, AI986329, AA433910, CA488337, BF938984, BU608498, BM559498, BU683317, BG403290, BM817453

TIMELESS: BM467715, BM927658, BM541298, BM801216, BQ052552, BQ945096, AL560919, BQ068552, BU845242, BQ071352, BU930918, BU854737, BQ068451, BQ961203, BQ055183, BU500665, BX390921, BX401304, BQ962781, BQ672871, BG749383, BX346012, BU521442, CF242984, BU552412, CD653932, AU125640, BU543485, BQ927368, BQ051381, BI222498, BG822789, BQ944034, BM046877, BU146750, BU956003, BQ670516, BQ061549, BG757741, BE797452, CA430803, BG819936, BE746308, BU187951, BE794062, BM013386, BE795708, BU553769, BM552373, BQ424129, CD654639, BM910771, BG388233, BE729276, BM013167, BE791318, BE514198, BM740568, BX350660, BG110568, BX110927, BI087328, BQ958679, BE727460, BG823400, BE729002, BG289919, BF971197, BM048813, BE514731, BE314800, BQ887260, BE745259, BE408808, BE208475, CA489086, BG478136, BU188642, CD673319, BE389356, AW382754, BE793649, BQ214512, AW383633, BM793905, BM789297,

BQ221649, AW383534, AW673493, BM018763, CB990372, AW383548, BQ937242, BQ678339, BU172010, BU167922, BU163559, BQ679317, BQ679254, BQ679251

Pif1: AI655645.1, AI280491.1, AI654749.1, AI333976.1, AA743647.1, AA872541.1, AA279102.1, AA278838.1, AI827264.1, AI652391.1, AW004048.1, CN358868.1, CN358870.1, T85126.1, T88870.1, CN358869.1, T54683.1, T54599.1, CN358871.1, CN265097.1, AA464521.1, BG231673.1, AA642924.1, BX109827.1, AI696210.1, AI745642.1, AI984536.1, AW170361.1, AW590310.1, AW663962.1, AW801494.1, BF516453.1, BG951026.1, BI116535.1, BM043514.1, W60651.1, W60880.1, BM888249.1, BQ061682.1, BQ065272.1, BQ958807.1, BU502486.1, CA310274.1, AA464522.1, BE280562.1, BF316643.1, AA827755.1, CN259034.1, CN277199.1, AA973831.1, CN259037.1, CN259036.1, BX283578.1, AI889087.1, BG323851.1, BI063248.1, BI063942.1, BQ315498.1, BE148134.1

Mms4: BI918962.1, BE613887.1, AW672839.1, R86709.1, R85191.1, H80469.1, CN290252.1, CN281043.1, CN342824.1, R83093.1, BX333338.2, BX327691.2, D25658.1, AW955836.1, BE378681.1, BE542457.1, CN484982.1, R87430.1, BE887145.1, BE895828.1, BE897152.1, AU118079.1, BF244395.1, BE547467.1, BG028794.1, BG000465.1, BG167025.1, BG167838.1, BG255030.1, BG256327.1, BG436043.1, BG393362.1, BG498016.1, BI084419.1, BI088431.1, BF793987.1, BG996952.1, BI255051.1, BI256195.1, BI258650.1, BM462968.1, BM800592.1, BM802118.1, BM809503.1, BM906256.1, BM918347.1, BQ072173.1, BG992888.1, BQ216341.1, BQ218372.1, BQ230208.1, BQ232225.1, BG116791.1, BG120099.1, AA243757.1, AA443229.1, AA481119.1, AA774064.1, BX108233.1, BX333337.2, BX443561.2, BX328975.1, AI305107.1, BP429202.1, BX509606.1, BP430970.1, AW250729.1, BP430731.1, CK023740.1, CN482590.1, BQ082456.1

TopoisomeraseIIIa: BM462184.1, BQ226006.1, BQ215187.1, AI933546.1, AI694682.1, AW005757.1, AI871758.1, AI627306.1, AI357363.1, CN431712.1, CN431714.1, AI131044.1, CN431713.1, CN431717.1, CN431715.1, AI863107.1, N21546.1, AI652693.1, AI637907.1, AI917456.1, AW370762.1, AW375839.1, AW411282.1, AW411283.1, AW449041.1, AW449710.1, AW450373.1, CK300631.1, CD619024.1, CD619023.1, AW513442.1, AW748535.1, AW954652.1, BE062796.1, BE062799.1, BE062870.1, BE062878.1, BE275290.1, BE294390.1, BE297536.1, BE383990.1, BE384385.1, BE388003.1, BE389807.1, BE408865.1, BE410098.1, BE886538.1, AU125151.1, AU130137.1, BF307775.1, BF345890.1, AW601235.1, BF060985.1, AU148874.1, AU152155.1, BF772443.1, BF913078.1, AL555800.3, AL578214.3, BG281391.1, BG333658.1, BM046431.1, BM046548.1, BM049492.1, BM553540.1, BM683614.1, BM804018.1, BM817686.1, BM910465.1, BQ187307.1, BQ334676.1, BQ342906.1, BQ673046.1, BM929666.1, BQ883495.1, BQ897944.1, BQ929795.1, BU159208.1, AL601602.1, BU542042.1, BU191611.1, BU902730.1, AA307047.1, AA325934.1, AI206124.1, AI206134.1, CB123137.1, R45840.1, AL040785.1, BX394136.2, BX359327.2, BX359328.2, BX348607.2, AI969044.1, AI978571.1, BX499775.1, AW270386.1, AW351792.1, AW370749.1, AW370750.1, AW370754.1, AW370756.1, AW370757.1, AW370758.1, BU169620.1

Mus81: BI828324.1, BI822910.1, BI772783.1, BI766615.1, BI551731.1, BE313033.1, BF317447.1, BG912942.1, BG388554.1, BG336401.1, BM926996.1, BG334598.1, BG330488.1, BG328798.1, BG327203.1, BG165822.1, BM561952.1, BM795493.1, BI871701.1, BI909656.1, W05036.1, BM787599.1, BM015068.1, BM762869.1, BM715429.1, W46505.1, BM051590.1, BM193717.1, BM820646.1, BM673914.1, W46441.1, W46397.1, W46466.1, D81040.1, D81583.1, N66260.1, BI083900.1, BI084569.1, BI058696.1, N74665.1, BI015411.1, BI225125.1, BI261175.1, BI334628.1, BI520226.1, BI520852.1, BI495735.1, BI495736.1, N99229.1, BI818186.1, BI818415.1, BI821127.1, BI816797.1, AA278513.1, CA426286.1, CA428478.1, CA439511.1, CA488369.1, AA310067.1, AA321039.1, AA325265.1, AA353351.1, AA361208.1, AA361844.1, AA410784.1, AA412362.1, AA425903.1, AA483867.1, T24587.1, AA588568.1, AA742229.1, AA742315.1, R07365.1, AA767217.1, AA808486.1, AA811878.1, AA830456.1, AA831614.1, AA935774.1, BM828633.1, W86124.1, BQ004754.1, BQ007168.1, W94929.1, W92200.1, W96213.1, W96307.1, BQ219750.1, BQ421044.1, BQ673374.1, BQ716313.1, BM147893.1, BQ951454.1, BQ787518.1, BU626130.1, BU630449.1, AA195097.1, AA195293.1, AA235399.1, BU855063.1, AA256727.1, AA258031.1, AA261839.1, AA262485.1, AA262698.1, CB989437.1, CB995814.1, BX329339.2, BX363788.2, BX363789.2, BX364239.2, BX364240.2, BX376440.2, BX376441.2, BX352736.2, BX352737.2, BX400774.2, BX393197.2, AW008546.1, Z46145.1, Z41778.1, AW080590.1, AW081005.1, CF130974.1, AW057824.1, AI174987.1, CF272441.1, AW292451.1, AW296475.1, AA989261.1, AI004770.1, AI027750.1, AI078127.1, AI161039.1, BX117949.1, AI223161.1, AI198223.1, AI289132.1, AI291347.1, AI312012.1, AI423724.1, AI355186.1, AI444946.1, AI565701.1, AI568723.1, AI401565.1, AI589837.1, AI561084.1, AI696162.1, AI701699.1, AI708157.1, AI796616.1, AI809463.1, BE843407.1, AV683439.1, AV684455.1, AV692941.1, AV695347.1, BE871764.1, AV706138.1, AV737334.1, AV749817.1, D53819.1, BF337818.1, BF340725.1, BF345411.1, AA836608.1, H70568.1, BF594105.1, BF594519.1, BF742954.1, BF801584.1, BG026984.1, BF940759.1, AL535449.3, AL535450.3, BG393857.1, AW387757.1, CF995326.1, AW469599.1, CD632462.1, CD632461.1, AW905089.1, AW954207.1, CN336481.1, CN336479.1, CN336477.1, CN336478.1, CN336480.1, AW967947.1, CN422010.1, CN422011.1, CN422012.1, AW978460.1, CV028339.1, BE328203.1, H25803.1, BE379473.1, BE396264.1, BE396772.1, BE513701.1 BE564111.1, AW365100.1, AW365101.1

SIRT1 (Sirtuin): AI037953.1, AA236993.1, N23557.1, H98832.1, R86123.1, AA044634.1, AI381553.1, AA608812.1, AI378978.1, AI367389.1, CN357085.1, AI972705.1, H12698.1, AI217748.1, CN357086.1, BE072031.1, BE081871.1, BE245026.1, BE463430.1, AV660110.1, AV660133.1, D59300.1, BE883278.1, D62968.1, AV704288.1, AV704956.1, AV750129.1, BF445130.1, BF692058.1, BF848464.1, BF848494.1, AW615289.1, AV718812.1, AV720195.1, BF590111.1, BF796692.1, BG026102.1, BG036612.1, BF999696.1, BG178600.1, BG282746.1, BG283059.1, BG496097.1, BG498089.1, N68314.1, BI091351.1, BG705339.1, BG717615.1, BI258271.1, AL599794.1, BI520244.1, BI869083.1, BI918557.1, BM273130.1, BM475115.1, BM697223.1, BM905888.1, BM980158.1, BM986798.1, BQ025488.1, BQ219206.1, BQ226337.1, BQ631955.1, BQ632248.1, BM152225.1, BU186744.1, BM452557.1, AA251252.1, AA382573.1, AA452304.1, AA460952.1, AA461259.1, AA828109.1, BX105044.1, AI751813.1, AI751814.1, AI807525.1, AL042303.1, CD110682.1, AW007728.1, AW020605.2, AW021852.1, BX505161.1, AW504399.1, CK820052.1, CK820053.1, AW967429.1, AW996552.1, BU935054.1

Esp1: BM456594.1, BM051112.1, BM049903.1, BM044277.1, BM013405.1, BI262337.1, BI117483.1, BI200147.1, BI195989.1, BI023133.1, BG821987.1, BG767950.1, BG760762.1, BG756617.1, BG684814.1, BG493667.1, BG490228.1, BG480927.1, BG479609.1, BG469946.1, BG386315.1, BG337498.1, BG328178.1, BF932278.1, BF973206.1, BF972380.1, BF764335.1, BF742768.1, AA780037.1, AA581005.1, AA580948.1, AA548572.1, T86767.1, AA455415.1, T86675.1, AA339975.1, AA248889.1, BU856483.1, BU855930.1, BU844826.1, BQ958098.1, BQ939849.1, BQ894059.1, BQ893225.1, BQ882493.1, BQ881349.1, BF924624.1, BQ361233.1, BQ069829.1, BQ052875.1, BQ052507.1, BQ014621.1, BM905149.1, BM837056.1, BM797577.1, BM468940.1, AW207246.1, CF137736.1, CF137709.1, CF137594.1, CF135495.1, BX483646.1, CD579284.2, AW009863.1, AW008862.1, CD359905.1, CD299902.1, BX415621.2, AI816969.1, AL046060.1, AI800823.1, R42883.1, AI458447.1, AI446360.1, AI283098.1, AI268609.1, AI214569.1, AI127437.1, R21501.1, AA928961.1, AI023991.1, AI023899.1, AI022797.1, AA948058.1, BF512245.1, BF698487.1, BF697145.1, BF686746.1, BF683733.1, AA694341.1, BF314077.1, BF155328.1, BF154952.1, BF154938.1, BE538398.1, BE467107.1, CR746800.1, BE019694.1, CN356489.1, CN356487.1, CN356486.1, CN356485.1, CN356484.1, CN356488.1CN356495.1, CN356494.1, CN356493.1, CN356492.1, CN356491.1, CN356490.1, AW867242.1, AW497592.1

MPG: BE567173.1, BF678850.1, BG769688.1, BM663214.1, BM690361.1, BM707428.1, BM750136.1, BM771938.1 BM796074.1, BM796301.1, BM822805.1, BM823382.1, BM823606.1, BM825519.1, BM831379.1, W69334.1, W69335.1, BM852297.1, BM909194.1, BM914408.1, W76127.1, BM922561.1, BM970297.1, BQ053339.1, BQ224541.1, AA010929.1, AA011317.1, BQ416588.1, BQ416589.1, BQ416891.1, BQ416892.1, BQ430971.1, BF174738.1, BG469815.1, BG479289.1, BG574541.1, BG686214.1, BG779735.1, BG746848.1, BG763639.1, BG823448.1, BG830627.1, BI253826.1, BI259059.1, BI524092.1, N90880.1, N91934.1, BI552950.1, BI713520.1, BI759543.1, BI818264.1, BI820665.1, BI791744.1, BI870400.1, BI858760.1, BI964886.1, BI906325.1, W17097.1, BM194361.1, BM471029.1, BM543869.1, BM552363.1, BM556912.1, BU565588.1, BU631253.1, AA187311.1, AA187412.1, BU684880.1, BU687924.1, BU858254.1, BU860310.1, BU956115.1, CA337274.1, CA423548.1, CA438664.1, CA441991.1, CA488184.1, CA488371.1, AA299077.1, AA285256.1, AA491244.1, AA503832.1, AA527886.1, AA568795.1, AA578450.1, AA603076.1, AA621361.1, AA732078.1, AA761676.1, AA767201.1, AA768478.1, AA768552.1, AA806008.1, AA853981.1, AA857130.1, AA026824.1, AA026957.1, BQ447759.1, BQ668747.1, BQ675987.1, BQ676108.1, BQ676179.1, BQ676405.1, BQ678708.1, BQ678722.1, BQ680099.1, BQ682489.1, BQ684616.1, BQ686780.1, BQ773643.1, BM147473.1, BM149314.1, BQ888825.1, BQ921148.1, BQ927180.1, BQ945550.1, AA065084.1, AA064997.1, BU195384.1, BU149567.1, BU157028.1, BU168113.1, BU172290.1, AA113980.1, AA113972.1, AA115941.1, AA122238.1, AI695611.1, AI739369.1, AI750356.1, AI754347.1, AI765874.1, AI798386.1, CB267218.1, BX281276.1, AI817691.1, AI913581.1, AI922106.1, AI928586.1, CB997674.1, BX395164.2, CD105357.1, BX353976.2, BX372753.2, BX392614.1, BX357530.2, BX391673.2, AI961117.1, CD368856.1, AW007326.1, AW072347.1, AW083039.1, AW131829.1, AW149104.1, AJ573841.1, AJ573842.1, AW204546.1, AW206735.1, AA971357.1, AI015443.1, AI037999.1, AI089498.1, AI131317.1, AI143697.1, CB044049.1, CB044050.1, CB048492.1, CB048493.1, CB048779.1, CB049248.1, CB049249.1, AI149080.1, AI188471.1, AI205596.1, AI208926.1, AI209171.1, CB128954.1, AI203215.1, AI345964.1, AI350908.1, AI382391.1, AI453105.1, AI457314.1, AI521404.1, AI553664.1, AI569449.1, AI580320.1, AI679185.1, AI695608.1, BF001487.1, BF002356.1, T28409.1, BF109116.1, BF219424.1, AA862053.1, BF664362.1, BF669361.1, BF526924.1, BF572325.1, BF790595.1, BG033001.1, BG033146.1, BF974328.1, BF940863.1, BG165742.1, BG153198.1, AL520051.3, AL520052.3, AL521514.3, AL521515.3, N26769.1, AL524386.3, AL524387.3, AL527543.3, AL527544.3, AL530961.3, AL530962.3, N30855.1, BG284431.1, BG430698.1, F04542.1, AW291955.1, CF993786.1, AW452798.1, AW590115.1, AW593038.1, CK902061.1, CN266626.1, CN266627.1, CN266628.1, CN266629.1, CN266630.1, CN266631.1, CN266632.1, AW973756.1, BE045501.1, BE207420.1, BE275484.1, BE385924.1, BE394756.1, BE408565.1, BE465105.1, BE502294.1, BE538276.1, BE733520.1, BE735753.1, BE780181.1, AV694099.1, BE908188.1, BE909470.1, BF000140.1, BF000556.1, CB114652.1, CN276703.1, N41382.1, BQ694950.1

Polι: BQ052050.1, BQ072779.1, BQ232853.1, BG823706.1, BE264721.1, BI758654.1, BE539840.1, BE541711.1, BG389885.1, BG331116.1, BI770175.1, BE880092.1, BM544877.1, BI825514.1, BE974036.1, BI827122.1, BI910222.1, BI906881.1, BI909106.1, BI906886.1, BI772047.1, BG945087.1, BI091406.1, BG770791.1, BG764790.1, BG763955.1, BG751184.1, BG749688.1, BG490202.1, BF171635.1, AL562678.3, AL541662.3, AL526446.3, BG149290.1, BG024414.1, BF807384.1, BF591938.1, BF476040.1, BF475279.1, AA807380.1, AA742404.1, T81701.1, CA406519.1, CA405484.1, BU855318.1, AA234405.1, BU618135.1, BU194042.1, BU184350.1, BU191914.1, BU159682.1, BQ957310.1, BQ932866.1, BM148925.1, M145476.1, BG118565.1, BG056482.1, BQ311579.1, BQ276405.1, AL702021.1, AL702011.1, AL698041.1, M923533.1, BM908370.1, W69888.1, BM824844.1, BM801377.1, BM354225.1, BM273229.1, BI912822.1, BI909369.1, AW406239.1, AW418802.1, AW377370.1, AW377335.1, AW377300.1, AW377298.1, AW377264.1, AW377257.1, AW367852.1, CF147037.1, CF140209.1, CF140207.1, BX426881.2, BX372137.1, BX384565.2, BX384564.2, AA991853.1, AA927738.1, AA922738.1, CA976110.1, CB151800.1, CB131141.1, AI538103.1, AI922500.1, BX333693.2, BX351220.1, BX361517.2, BX382774.2, BX398077.2, BX398078.2, BX400678.2, BX374468.2, BX390819.1, BE144586.1, BE162920.1, BP871239.1, CV025896.1, BE392666.1, BE562674.1, BE744935.1, BE819364.1, BE905104.1, BE938379.1, BE938389.1, AV705731.1, AU118033.1, AU122737.1, AU141478.1, AU144697.1, BF433511.1, AW673654.1, AW731648.1, AW752914.1, AW752922.1, AW768836.1, AW769721.1, CK820138.1, CK820139.1, CN304569.1, CN304570.1, CN304571.1, CN304572.1, CN304573.1, CN304574.1, CN304575.1, CN304576.1, H11886.1, CD243848.1, BX448084.2, BG488800.1, BI027900.1, BI460283.1,

BM479907.1, BM541632.1, BM563437.1, BQ232479.1, BQ923975.1, BQ954336.1, BU195355.1

Polm: BI914097.1, BI908863.1, BI907196.1, BI858799.1, BG700584.1, BM920340.1, BI769194.1, BG483069.1, BG499408.1, BG910514.1, BI029339.1, BI001584.1, BI752559.1, BI838830.1, BI857029.1, BM739081.1, BM739884.1, BM739966.1, BM744174.1, AV692664.1, AV697631.1, AV697781.1, AV699741.1, BF102699.1, AU129189.1, AA694217.1, AA766124.1, AW613566.1, BF530871.1, BF819685.1, BF895261.1, BG253328.1, AL523598.3, AL529987.2, AL529988.3, AL562232.3, BG231904.1, BG386713.1, BM148157.1, BM148944.1, BM149019.1, BM151641.1, BU517199.1, BU520948.1, AA077726.1, CA388951.1, CA487306.1, CA487434.1, AA298793.1, CA944555.1, AA507121.1, AA605050.1, AA769270.1, AA814924.1, AA815032.1, AA832314.1, AA917987.1, BM744180.1, BM747399.1, BM752457.1, BM755685.1, BM756419.1, BM756478.1, BM804478.1, BM808078.1, BM853841.1, BM911482.1, BM911832.1, AL700896.1, BQ015336.1, BQ214851.1, BQ686436.1, AA046576.1, AA046663.1, BG116876.1, BM147833.1, BX390956.2, BX350666.1, BX385063.2, BX385064.2, CD109226.1, BX354131.1, BX354132.2, BX351215.2, BX376517.2, BX376518.2, BX395027.2, BX335337.2, BX335338.2, BX383403.1, BX383404.2, BX383221.2, BX402828.2, BX402829.2, BX384388.2, AI025113.1, AA928729.1, AI057140.1, AI208523.1, AA910584.1, AI365238.1, AI365240.1, AI392687.1, AI419960.1, AI458707.1, AI459543.1, AI469103.1, AI627311.1, AI652512.1, AI654109.1, AI738949.1, AI767982.1, AI638032.1, CB990757.1, BE241524.1, BE241656.1, BE241950.1, BE242681.1, BE242829.1, BE242932.1, BE243489.1, BE244287.1, BE247085.1, BE247483.1, CR735361.1, BE503442.1, BE789823.1, AV685517.1, AV688018.1, AV688777.1, AV689313.1, AV689923.1, AV691130.1, BX393262.2, BX435165.2, BX419627.2, CD252488.1, BX477278.1, AW070683.1, AW137352.1, AW182301.1, CF529830.1, AW207742.1, AW296010.1, AW361738.1, AW402473.1, AW575118.1, AW578625.1, AW592532.1, CN480773.1, CN304577.1, CN304578.1, CB104684.1, AI438940.1, CB266611.1, CN293022.1, AA078383.1

EndoV: BQ279208.1BM554738.1, BM911430.1, BI830073.1, BI829389.1, BG681481.1, BG819544.1, BI117355.1, BI551407.1, BQ287914.1, BQ050806.1, BQ024655.1, BQ021027.1, W87446.1, BM926784.1, BM128679.1, BM128571.1, BM128352.1, AA720808.1, AA452047.1, AA363057.1, AA351281.1, BU621053.1, BU553848.1, BU527982.1, BQ957094.1, AA056490.1, BQ923151.1, BQ923003.1, BQ772531.1, BQ435901.1, BQ429806.1, BQ429804.1, BQ427432.1, BQ417371.1, BQ342726.1, R14533.1, CB143295.1, AI370900.1, BX334744.2, BX355957.2, Z41683.1, AW157406.1, CK819308.1, CN288502.1, CN310874.1, CN310875.1, CN310876.1, AW975617.1, H09974.1, BE619534.1, BE905153.1, BE938460.1, BF686490.1, BF477753.1, AL541721.3, AL569045.3, BG749082.1, BI549266.1, BI550542.1, BI550562.1, BI837982.1, BI917934.1, BM007984.1, BM008131.1, BM043073.1, BM047737.1, BX092874.1, AI219827.1, AI249283.1, AA926664.1, AI223657.1, AI290823.1, AI300416.1, AI311040.1, AI349370.1, AI393803.1, AI307620.1, AI571214.1, AI635870.1, AI660440.1, AI681370.1, AI702794.1, AW001931.1, AW136860.1, AW204051.1, AW438764.1, BE041666.1, BE043347.1, BE049112.1, BE219425.1, BE219749.1, BE672512.1, BF194919.1, BF196166.1, BF718311.1, BF840896.1, BM662670.1, BM665527.1, BM671155.1, BM684408.1, BM689003.1, BM710007.1, BM711618.1, BM930887.1, AA451847.1, AA593804.1, AA617805.1, T96971.1

KNTC2(NDC80): BG612856.1, BG532554.1, BG531886.1, BI093871.1, BG500282.1, BI825656.1, BE561023.1, BE564344.1, BE565202.1, BE566742.1, BE903220.1, BQ233581.1, BQ425406.1, BF029347.1, CD557751.1, BU507911.1, BF977553.1, BF976962.1, BF700934.1, BF219086.1, BF244797.1, BF700668.1, BF246890.1, BF684028.1, BF667950.1, BF666100.1, BF665251.1, AU151690.2, BF540908.1, AU099103.1, BF576929.1, BG403284.1, BF589484.1, AL583281.3, AL583241.3, AL531915.3, AL531914.3, AL527360.3, BF984727.1, AL527307.3, BG257162.1, BF899120.1, BF994346.1, BF978548.1, BU633554.1, AA188980.1, AA188981.1, AA189047.1, AA211359.1, BU943322.1, AA249583.1, AA249666.1, CA311030.1, CA446863.1, AA312280.1, T89463.1, AA492580.1, AA628019.1, AA639709.1, AA700427.1, AA857356.1, AA878068.1, BG679506.1, BI087094.1, BI260526.1, N88235.1, BI861865.1, BM194061.1, BM453009.1, BM476696.1, BM806248.1, BM828736.1, BM995677.1, W72679.1, AL711170.1, AL710845.1, BQ307283.1, BQ307306.1, BQ776047.1, BQ776118.1, CN294243.1, CN294241.1, CN294240.1, CN294239.1, CN294238.1, CN294237.1, AW821289.1, AW955129.1, AW573107.1, AW449014.1, BP430527.1, AW069561.1, AI979323.1, BX453617.2, AI955047.1, AI954614.1, BX431751.2, BX372554.2, BX353230.2, BX351284.2, BX333981.2, AI913466.1, AI866885.1, BX284007.1, BF246242.1, AI660156.1, AI380253.1, BP369219.1, BF218992.1, BP282259.1, AU129601.1, BP283529.1, AI341287.1, BF084870.1, BP290528.1, BP242960.1, BP239153.1, CV030676.1, CN294245.1, CN294236.1, BF082771.1, BE503512.1, AI341285.1, BF038467.1, BE543964.1, CB150849.1, CB160181.1, BF001266.1, BE672102.1, CN294234.1, CN294233.1, R94766.1, CV363738.1, BE927464.1, AA911686.1, AV718407.2, BE940500.1, BE857720.1, BE889796.1, AV718036.1, BF687621.1, BF447144.1, CN294232.1, CN294235.1, CN294244.1, R92253.1

A preferred embodiment of the present invention provides an apoptosis-inducing agent comprising double-strand RNA having RNAi effects and having as one of the strands thereof a contiguous RNA region of mRNA corresponding to a chromosome stabilization-associated gene (for example, any of the aforementioned genes) or any of the aforementioned ESTs.

As described above, each of the aforementioned genes may contain various polymorphisms even for the same gene. Those skilled in the art can suitably design an RNA sequence expected to have RNAi effects for any of the nucleotide sequences described in SEQ ID NOs: 1 to 637 and 810 to 908 or the aforementioned EST sequences by incorporating data from, for example, a public polymorphism database relating to any of the aforementioned genes. An apoptosis-inducing agent comprising such an RNA is also included in the present invention. In addition, RNA having optimum RNAi effects can be suitably selected by those skilled in the art from several types of double-strand RNA produced in the present invention to obtain an apoptosis-inducing agent.

Specific examples of the aforementioned "double-strand RNA having RNAi effects" of the present invention include siRNA molecules having as one of the strands of the double-strand RNA a nucleotide sequence described in FIGS. 1 to 4 and FIGS. 28 to 32 (a nucleotide sequence described in any of SEQ ID NOs: 724 to 809 and 974 to 1063) (siRNA molecules composed of a nucleotide sequence described in any of SEQ ID NOs: 724 to 809 and 974 to 1063, and a complementary strand thereto). Namely, an embodiment of the present invention provides a cancer cell-specific apoptosis-inducing agent comprising as its active ingredient an siRNA molecule in which one of the strands of the double-strand RNA having RNAi effects comprises a nucleotide sequence described in any of SEQ ID NOs: 724 to 809 and 974 to 1063 (an siRNA molecule composed of a nucleotide sequence described in any of SEQ ID NOs: 724 to 809 and 974 to 1063, and a complementary strand thereto).

In addition, one of the RNA sequences of a double strand region in the aforementioned siRNA molecule is not necessarily limited to that which is completely identical to a nucleotide sequence described in any of the aforementioned SEQ ID NOs: 724 to 809 and 974 to 1063. For example, the aforementioned siRNA molecule may be an siRNA molecule having as one of the strands of the double-strand RNA a nucleotide sequence in which one or more nucleotides in the nucleotide sequence have been altered, as long as it has a function which inhibits expression of a gene of the present invention.

Namely, in a preferred embodiment of the present invention, double-strand RNA having RNAi effects is double-strand RNA having a function which inhibits expression of a gene of the present invention, in which one of the strands of the double strand is a nucleotide sequence having one or more nucleotide additions, deletions or substitutions to a nucleotide sequence described in any of SEQ ID NOs: 724 to 809 and 974 to 1063, and the other strand is a nucleotide sequence complementary to the nucleotide sequence. The above "more" usually refers to a small number, and more specifically, refers to 2 to 10, preferably 2 to 5, and more preferably 2 to 3.

In addition, a preferred embodiment of the present invention provides an apoptosis-inducing agent in which the compound which inhibits expression of a chromosome stabilization-associated gene (for example, any of the aforementioned genes) is (a) or (b) below:

(a) an antisense nucleic acid to a transcription product, or a portion thereof, of a chromosome stabilization-associated gene of the present invention (for example, any of the aforementioned genes), or (b) a nucleic acid having ribozyme activity which specifically cleaves a transcription product of a chromosome stabilization-associated gene of the present invention (for example, any of the aforementioned genes).

As used herein, the term "nucleic acid" refers to RNA and DNA. Methods well known to those skilled in the art for inhibiting (suppressing) the expression of a specific endogenous gene include those using antisense technology. Multiple factors contribute to the inhibition of a target gene expression by an antisense nucleic acid. These factors include, for example, inhibition of transcription initiation through triplex formation; inhibition of transcription through hybrid formation with a sequence at the site of a local open loop structure made by RNA polymerase; inhibition of transcription through hybrid formation with the RNA being synthesized; inhibition of splicing through hybrid formation with a sequence at an intron-exon junction; inhibition of splicing through hybrid formation with a sequence at the site of spliceosome formation; inhibition of transfer from the nucleus to the cytoplasm through hybrid formation with mRNA; inhibition of splicing through hybrid formation with a sequence at the capping site or poly(A) site; inhibition of translation initiation through hybrid formation with a sequence at the site of binding of the translation initiation factor; inhibition of translation through hybrid formation with a sequence at the ribosome binding site near the initiation codon; inhibition of peptide chain elongation through hybrid formation with a sequence at the site of the translational region or polysome binding site of the mRNA; and inhibition of gene expression through hybrid formation with a sequence at the site of interaction between the expression regulatory region and the transcriptional regulatory factor. Thus, an antisense nucleic acid inhibits target gene expression by inhibiting various processes, such as transcription, splicing, and translation (Hirashima and Inoue, Shin Seikagaku Jikkenkoza 2 (New Lecture for Experimental Biochemistry 2), Kakusan IV (Nucleic Acid IV), Replication and Expression of Genes; Ed., Japanese Biochemical Society, Tokyo Kagaku Dozin Co., Ltd., pp. 319-347, 1993).

Antisense nucleic acids used in the present invention may inhibit the expression of a chromosome stabilization-associated gene (e.g., any of the aforementioned genes) through any one of the actions described above. In one embodiment, an antisense sequence is designed to be complementary to the 5'-untranslated region of a chromosome stabilization-associated gene (e.g., any of the aforementioned genes) mRNA. Thus such an antisense sequence is expected to effectively inhibit translation of that gene. A sequence complementary to the coding region or 3'-untranslated region can also be used for this purpose. Thus, a nucleic acid comprising the antisense sequence corresponding to the sequence of the translated as well as the untranslated regions of the chromosome stabilization-associated gene (e.g., any of the aforementioned genes) can be included as an antisense nucleic acid used in the present invention. The antisense nucleic acid to be used is ligated downstream of an appropriate promoter and preferably ligated with a sequence comprising a transcription termination signal at the 3' end. The antisense nucleic acid to be used for clinical applications is typically a synthetic oligomer. Such synthetic oligomers include the widely used S-oligo (phosphorothioate oligo nucleotide) in which S (sulfur) has been substituted for O (oxygen) at the phosphate ester bond, thus reducing sensitivity to nuclease digestion and maintaining antisense nucleic acid activity. S-oligo is currently being tested as an antisense drug in clinical trials where it is administered directly to affected areas. This S-oligo is also suitable for use in the present invention. It is preferable that the antisense nucleic acid sequence is complementary to the target gene sequence or a portion thereof; however perfect complementarity is not necessary as long as the antisense nucleic acid effectively suppresses target gene expression. The transcribed RNA has preferably 90% or higher complementarity, and most preferably 95% or higher complementarity to the target gene transcript. The length of the antisense nucleic acid used to effectively suppress target gene expression is at least 15 nucleotides or longer, preferably 100 nucleotides or longer, and more preferably 500 nucleotides or longer.

The inhibition of chromosome stabilization-associated gene (e.g., any of the aforementioned genes) expression can also be achieved using a ribozyme or ribozyme-encoding DNA. The term "ribozyme" refers to an RNA molecule comprising catalytic activity. Ribozymes can have a variety of activities, and can be designed to have the activity of cleaving RNA in a site-specific fashion. Ribozymes such as group I intron-type ribozymes and M1 RNA, which are RNase P ribozymes, are 400 nucleotides or more in length. Others such as hammerhead and hairpin ribozymes have active sites comprising about 40 nucleotides (M. Koizumi and E. Otsuka, Tanpakushitsu Kakusan Koso (Protein, Nucleic acid, and Enzyme), 1990, 35, 2191).

For example, the autolytic domain of a hammerhead ribozyme cleaves the 3' side of C15 in the sequence G13U14C15. Base pairing between U14 and A9 plays an important role in this activity, and A15 or U15 can be cleaved instead of C15 (Koizumi, M. et al., FEBS Lett, 228: 228, 1988). A restriction enzyme-like RNA-cleaving ribozyme that recognizes the target RNA sequences UC, UU, or UA can be produced by designing the ribozyme such that the substrate binding site complements the RNA sequence near the target site (Koizumi, M. et al., FEBS Lett, 239: 285, 1988; M. Koizumi and E. Otsuka, Tanpakushitsu Kakusan Koso (Protein, Nucleic acid, and Enzyme), 35:2191, 1990; and Koizumi, M. et al., Nucl. Acids Res., 17: 7059, 1989).

The hairpin ribozyme can also be used for the purposes of the present invention. This ribozyme is found, for example, in the minus strand of tobacco ring spot virus satellite RNA (Buzayan, J. M., Nature, 323: 349, 1986). A target specific RNA-cleaving ribozyme can also be produced from a hairpin ribozyme (Kikuchi, Y. and Sasaki, N., Nucl. Acids Res., 19: 6751, 1991; Kikuchi, H., Kagaku to Seibutsu (Chemistry and Biology), 30: 112, 1992). Thus, the expression of a chromosome stabilization-associated gene of the present invention can be inhibited by specifically digesting the gene transcript using a ribozyme.

The present invention also relates to a cancer cell-specific apoptosis-inducing agent comprising as its active ingredient a compound which inhibits the function (activity) of a protein encoded by a chromosome stabilization-associated gene (for example, any of the aforementioned genes).

A protein encoded by a chromosome stabilization-associated gene of the present invention includes mutant proteins or homolog proteins of a protein encoded by a chromosome stabilization-associated gene. Such mutant proteins or homolog proteins are functionally equivalent to the protein encoded by a chromosome stabilization-associated gene, and have an amino acid sequence with one or more amino acid deletions, substitutions, or additions to the amino acid sequence of the protein. Here, a "functionally equivalent protein" refers to a protein having a function which is similar to the function (for example, any of the functions of the aforementioned (a) to (s)) of a protein encoded by a chromosome stabilization-associated gene (for example, any of the aforementioned genes).

Alternatively, a protein having, for example, 90% or more, desirably 95% or more, and more desirably 99% or more homology with the amino acid sequence of a protein encoded by a chromosome stabilization-associated gene (for example, any of the aforementioned genes) can be indicated as a protein functionally equivalent to a protein encoded by a chromosome stabilization-associated gene.

A preferred embodiment of the present invention provides an apoptosis-inducing agent in which a compound which inhibits the function (activity) of a protein encoded by a chromosome stabilization-associated gene (for example, any of the aforementioned genes) is a compound described in any of (a) to (c) below. These compounds are thought to have an apoptosis-inducing action against cancer cells by inhibiting (decreasing) the function or activity of a protein encoded by a chromosome stabilization-associated gene (for example, any of the aforementioned genes).

(a) Mutant proteins having dominant negative traits with respect to a protein encoded by a chromosome stabilization-associated gene of the present invention (for example, any of the aforementioned genes).

(b) Antibodies which bind to a protein encoded by a chromosome stabilization-associated gene of the present invention (for example, any of the aforementioned genes).

(c) Low molecular weight compounds which bind to a protein encoded by a chromosome stabilization-associated gene of the present invention (for example, any of the aforementioned genes).

The "mutant proteins having dominant negative traits" in above (a) refer to mutants of a protein encoded by a chromosome stabilization-associated gene (for example, any of the aforementioned genes) having a function to deactivate or decrease the activity of an endogenous wild-type protein.

The "antibodies" in above (b) can be prepared according to methods known to those skilled in the art. Polyclonal antibodies, for example, can be obtained in the following manner. Serum is obtained from a small animal such as a rabbit immunized with a protein encoded by a naturally-occurring or recombinant chromosome stabilization-associated gene (for example, any of the aforementioned genes) or a protein encoded by a recombinant chromosome stabilization-associated gene expressed in microorganisms such as Escherichia coli as a fusion protein with GST, or a partial peptide thereof. This serum is then purified by, for example, ammonium sulfate precipitation, protein A column and protein G column, DEAE ion exchange chromatography, or an affinity column coupled with a protein or synthetic peptide encoded by a chromosome stabilization-associated gene. In addition, monoclonal antibodies can be prepared by, for example, immunizing a small animal such as a mouse with a protein, or a partial peptide thereof, encoded by a chromosome stabilization-associated gene (for example, any of the aforementioned genes), excising the spleen from the mouse, gently grinding the excised spleen to separate the cells, fusing the cells with mouse myeloma cells using a reagent such as polyethylene glycol, and selecting from the resulting fusion cells (hybridomas) those clones that produce an antibody which binds to the protein encoded by a chromosome stabilization-associated gene. Next, a hybridoma thus obtained is transplanted into the mouse abdominal cavity, peritoneal fluid is recovered from the mouse. The resulting monoclonal antibody can then be purified by, for example, ammonium sulfate precipitation, protein A column and protein G column, DEAE ion exchange chromatography, or an affinity column coupled with a protein or a synthetic peptide encoded by a chromosome stabilization-associated gene.

There are no particular restrictions on the antibody of the present invention so long as it is able to bind to a protein encoded by a chromosome stabilization-associated gene of the present invention (for example, any of the aforementioned genes). In addition to the aforementioned polyclonal antibody and monoclonal antibody, the antibody includes human antibodies, humanized antibodies obtained by genetic recombination, and antibody fragments and antibody modification products thereof.

There are no limitations on the animal species as the source of a protein encoded by a chromosome stabilization-associated gene of the present invention (for example, any of the aforementioned genes), which is used as a sensitizing antigen for acquiring antibody; however, a protein of mammalian origin, such as that from a mouse or human, is preferable, and a protein of human origin is particularly preferable.

Proteins to be used as a sensitizing antigen in the present invention may be intact proteins as well as partial peptides derived from those proteins. Such partial protein peptides include, for example, protein amino (N)-terminal fragments and carboxyl (C)-terminal fragments. As used herein, "antibody" usually refers to an antibody which reacts with a full-length protein or a fragment thereof.

In addition to obtaining the above-described hybridomas by immunizing non-human animals with an antigen, hybridomas producing a desired human antibody having binding activity with the protein can also be prepared in vitro by sensitizing human lymphocytes, for example, human lymphocytes infected with EB virus, with the protein, cells expressing the protein, or a lysate of those cells, and fusing these sensitized lymphocytes with immortalized human myeloma cells, for example, U266 cells. When an antibody of the present invention is intended to be administered into human bodies (antibody therapy), a human antibody or humanized antibody is preferable to reduce the immunogenicity.

Examples of compounds which are already known to bind to proteins encoded by chromosome stabilization-associated genes include monoclonal or polyclonal antibodies directed to a protein encoded by any of the aforementioned genes.

Compounds which inhibit the expression of a chromosome stabilization-associated gene (for example, any of the aforementioned genes) of the present invention or inhibit the function (activity) of a protein encoded by the gene may be naturally-occurring or artificial compounds. They are typically compounds which can be produced, obtained, or isolated using a method known to those skilled in the art. Examples of such compounds include single compounds such as organic compounds, inorganic compounds, nucleic acids, proteins, peptides, and sugars, as well as compound libraries, gene library expression products, cell extracts, cell culture supernatants, microbial fermentation products, marine organism extracts, plant extracts, and compounds isolated and purified from the extracts.

The present invention also provides methods of screening for cancer cell-specific apoptosis-inducing agents.

A preferred embodiment of the aforementioned methods of the present invention is a method which uses as an index the binding activity between a protein encoded by a chromosome stabilization-associated gene (for example, any of the aforementioned genes), or a partial peptide thereof, and a test compound. Normally, a compound which binds to a protein encoded by a chromosome stabilization-associated gene, or a partial peptide thereof, is expected to have inhibitory effects on the function of a protein encoded by a chromosome stabilization-associated gene (for example, any of the aforementioned genes).

In the aforementioned method of the present invention, a protein encoded by a chromosome stabilization-associated gene (for example, any of the aforementioned genes), or a partial peptide thereof, is first contacted with a test compound. The protein encoded by a chromosome stabilization-associated gene, or partial peptide thereof, can be, for example, in a purified form of the protein encoded by a chromosome stabilization-associated gene, or partial peptide thereof, or in a form expressed within or outside cells, or in a form bound to an affinity column, depending on the index for detecting its binding to the test compound. Test compounds used in this method can be used after being suitably labeled as necessary. Examples of labels include radioactive labels and fluorescent labels.

In the present method, the binding activity between the protein encoded by the chromosome stabilization-associated gene, or partial peptide thereof, and the test compound, is then measured. Binding activity between the protein encoded by the chromosome stabilization-associated gene, or partial peptide thereof, and the test compound can be measured by, for example, a label attached to the test compound bound to the protein encoded by the chromosome stabilization-associated gene or partial peptide thereof. In addition, binding activity can also be measured using as an index a change in the activity of the protein encoded by the chromosome stabilization-associated gene expressed within or outside cells, or partial peptide thereof, which occurs due to binding of the test compound to the protein or partial peptide thereof.

In the present method, a test compound is then selected which binds to a protein encoded by a chromosome stabilization-associated gene (for example, any of the aforementioned genes), or partial peptide thereof.

There is no limitation as to the type of test compound used in the present invention. Such compounds include, but are not limited to, for example, single unmixed compounds of organic compounds, inorganic compounds, nucleic acids, proteins, peptides, sugars, natural compounds, and such; or compound libraries, expression products of gene libraries, cell extracts, cell culture supernatants, products of fermenting microorganisms, marine organism extracts, and plant extracts; and artificially synthesized compounds.

In an alternative embodiment of the screening method of the present invention, first, a test compound is contacted with cells that express a chromosome stabilization-associated gene (for example, any of the aforementioned genes), or with a cell extract prepared from such cells. The phrase "cells that express a chromosome stabilization-associated gene" described above includes cells expressing an endogenous chromosome stabilization-associated gene, and cells into which an exogenous chromosome stabilization-associated gene has been introduced and in which that gene is expressed. The cells in which an exogenous chromosome stabilization-associated gene is expressed can typically be prepared by introducing into host cells an expression vector which contains the gene. Those skilled in the art can prepare such an expression vector using routine genetic engineering techniques. In the screening methods of the present invention, cells expressing a chromosome stabilization-associated gene preferably include various tumor cells, for example, MCF7 (breast cancer), A549 (lung cancer), U2OS (osteogenic sarcoma), C33A (cervical cancer), HT1080 (fibrosarcoma), PA-1 (ovarian teratocarcinoma), Tera2 (embryonal carcinoma), T24 (bladder cancer), K562 (chronic myelocytic leukemia), Molt4 (acute lymphoblastic leukemia), A172 (glioblastoma), HeLa (cervical cancer), HepG2 (hepatic cancer), ACC62 (melanoma), KP4 (pancreas cancer), CaKi-1 (kidney cancer), MKN45 (gastric cancer), LNcap (prostate cancer), MDA-MB435 (breast cancer), EJ 1 (bladder cancer), and OVCAR3 (ovarian cancer).

Typically, but without limitation, a test compound is contacted with cells expressing a chromosome stabilization-associated gene by adding the test compound to a culture medium of the cells expressing the chromosome stabilization-associated gene (for example, any of the aforementioned genes). When the test compound is a protein, the contact can be achieved by introducing into the cells a DNA vector that allows protein expression.

The next step of this method comprises determining the expression level of the chromosome stabilization-associated gene. Herein, the phrase "gene expression" refers to both transcription and translation. The gene expression level can be determined using a method known to those skilled in the art. For example, mRNA can be extracted from cells expressing the chromosome stabilization-associated gene according to a conventional method, and by using this mRNA as a template, the transcriptional level of the gene can be determined using Northern hybridization or RT-PCR. Alternatively, the translational level of the gene can be determined by collecting protein fractions from the cells expressing the chromosome stabilization-associated gene, and then detecting the expression of the protein encoded by the gene using an electrophoresis method such as sodium dodecyl sulfate-polyacrylamide gel electrophoresis (SDS-PAGE). Furthermore, the translational level of the gene can be determined by detecting the expression of the encoded protein by Western blotting analysis using an antibody against the protein. There is no limitation as to the type of antibody used for detecting the protein encoded by the gene, as long as the protein can be detected. Such antibodies include, for example, both monoclonal and polyclonal antibodies.

In this method, a compound that it causes a reduction in expression level when compared to the expression level measured in the absence of a test compound (control) is then selected. The compound selected by the above-described procedure is expected to have the action of inducing apoptosis in cancer cells. This compound may be used as a carcinostatic (an anticancer agent) whose mode of action is based on apoptosis induction.

In an alternative embodiment of the screening method of the present invention, a compound that reduces the expression level of a chromosome stabilization-associated gene (for example, any of the aforementioned genes) of the present invention is selected using a reporter gene.

In this method, a test compound is first contacted with cells (or an extract of those cells) that comprise a DNA having a structure where a reporter gene is operably linked to a transcriptional regulatory region of a chromosome stabilization-associated gene (for example, any of the aforementioned genes). As used herein, the phrase "operably linked" means that the transcriptional regulatory region of the chromosome stabilization-associated gene is linked to a reporter gene in such a way as to induce reporter gene expression when a transcriptional factor binds to the transcriptional regulatory region of the gene. Thus, even when the reporter gene is connected with another gene and thus forms a fusion protein with that gene product, such a case is included in the meaning of "operably linked", as long as the expression of the fusion protein is induced when the transcriptional factor binds to the transcriptional regulatory region of the gene. Using a known method and based on the cDNA nucleotide sequence for a chromosome stabilization-associated gene (for example, any of the aforementioned genes), those skilled in the art can obtain the transcriptional regulatory region of that gene within the genome.

There is no limitation as to the type of reporter gene used in this method, as long as the expression of the reporter gene can be detected. Such reporter genes include, for example, the CAT gene, lacZ gene, luciferase gene, and GFP gene. The "cells that comprise a DNA having a structure where a reporter gene is operably linked to a transcriptional regulatory region of a chromosome stabilization-associated gene" include, for example, cells into which a vector with a structure where a reporter gene is operably linked to a transcriptional regulatory region of a chromosome stabilization-associated gene (for example, any of the aforementioned genes) has been introduced. Those skilled in the art can prepare the above-described vector using routine genetic engineering techniques. The introduction of such a vector into cells can be achieved using a conventional method, for example, using calcium phosphate precipitation, electroporation, the lipofectamine method, microinjection, etc. "Cells that comprise a DNA having a structure where a reporter gene is operably linked to a transcriptional regulatory region of a chromosome stabilization-associated gene" also includes cells in which that structure has been inserted into the chromosome. A DNA structure can be inserted into a chromosome by using a method routinely used by those skilled in the art, for example, a random integration or gene transfer method using homologous recombination.

An "extract of cells that comprise a DNA having a structure where a reporter gene is operably linked to a transcriptional regulatory region of a chromosome stabilization-associated gene" includes, for example, a mixture prepared by adding a DNA to a cell extract included in a commercially available in vitro transcription/translation kit, where that added DNA comprises a structure where a reporter gene is operably linked to a transcriptional regulatory region of a chromosome stabilization-associated gene (for example, any of the aforementioned genes).

In this method, the "contact" can be achieved by adding a test compound into a culture medium of "cells that comprise a DNA having a structure where a transcriptional regulatory region of a chromosome stabilization-associated gene is operably linked to a reporter gene", or by adding a test compound into the above-described commercially available cell extract, which contains the DNA. However, the method of contact is not limited to the methods described above. When the test compound is a protein, the contact can also be achieved, for example, by introducing into the cells a DNA vector that directs the expression of the protein.

The next step of this method comprises determining the level of reporter gene expression. The expression level of the reporter gene can be determined by a method that depends on the type of the reporter gene and which is known to those skilled in the art. For example, when the reporter gene is the CAT gene, expression level can be determined by detecting the acetylation of chloramphenicol, mediated by the CAT gene product. When the reporter gene is the lacZ gene, expression level can be determined by detecting color development in a chromogenic compound, mediated by the catalytic action of the lacZ gene expression product. When the reporter gene is the luciferase gene, the level can be determined by detecting the fluorescence of a fluorescent compound, mediated by the catalytic action of the luciferase gene expression product. Alternatively, when the reporter gene is the GFP gene, the level can be determined by detecting the fluorescence of the GFP protein.

The next step of this method comprises selecting compounds that reduce reporter gene expression level as compared to expression level determined in the absence of a test compound. The compounds selected by the above-described procedure can be cancer cell-specific apoptosis inducing agents.

Another embodiment of the method of the present invention is a method of screening for compounds by using as an index the activity of a protein encoded by a chromosome stabilization-associated gene (for example, any of the aforementioned genes) of the present invention.

In this method, a protein encoded by a chromosome stabilization-associated gene (for example, any of the aforementioned genes) or cells expressing the protein, or a cell extract thereof, is first contacted with a test compound. Next, the activity of the protein is measured. Examples of the activity of the protein include the functions (activities) indicated in the aforementioned (a) to (r). Those skilled in the art are able to suitably acquire information on the functions (activities) of proteins used as indexes in screening and information on methods for evaluating (measuring) the functions (activities) from, for example, a reference database.

For example, when the protein used as an index is Mcm10, the function of the protein can be evaluated (measured) by detecting the behavior of ARS (autonomously replicating sequences) with two-dimensional electrophoresis (MCB (1997) 3261-3271).

When the protein used as an index is Orc1, the function of the protein can be evaluated (measured) by, for example, detecting the formation of a complex of Orc1-6 which contains the protein or by detecting a change in the electrophoretic mobility of an Orc1-6 complex in the presence of CaCl$_2$ (JBC (1998) 273, 32421-32429).

When the protein used as an index is Orc3, the function of the protein can be evaluated (measured) by, for example, detecting the formation of a complex of Orc1-6 which contains the protein or by detecting Ori-specific binding of the protein (JCB (1998) 273, 32421-32429).

When the protein used as an index is Cdc6, the function of the protein can be evaluated (measured) by, for example, using a cell-free DNA replication assay (EMBO (1998) 17, 7219-7229).

When the protein used as an index is Cdt1, the function of the protein can be evaluated (measured) by, for example, detecting binding of the protein with Geminin, or by using a cell-free DNA replication assay (Science (2000) 290, 2309-2312).

When the protein used as an index is Geminin, the function of the protein can be evaluated (measured) by, for example, detecting DNA replication inhibitory activity using a cell-free DNA replication assay (Cell (1998) 93, 1043-1053).

When the protein used as an index is Mcm3, the function of the protein can be evaluated (measured) by, for example, detecting the activity of an Mcm2,3,5 complex containing the protein which inhibits the helicase activity of Mcm4,6,7 (JBC (1998) 273, 8369-8375).

When the protein used as an index is Mcm4, the function of the protein can be evaluated (measured) by, for example, detecting the ssDNA binding activity, ATPase activity, and helicase activity of an Mcm4,6,7 complex containing the protein (JBC (1997) 272, 24508-24513).

When the protein used as an index is Mcm5, the function of the protein can be evaluated (measured) by, for example, detecting the inhibitory activity on the helicase activity of Mcm4,6,7 by an Mcm2,3,5 complex containing the protein (JBC (1998) 273, 8369-8375).

When the protein used as an index is Mcm6, the function of the protein can be evaluated (measured) by, for example, detecting the ssDNA binding activity, ATPase activity, and helicase activity of an Mcm4,6,7 complex containing the protein (JBC (1997) 272, 24508-24513).

When the protein used as an index is Mcm7, the function of the protein can be evaluated (measured) by, for example, detecting the ssDNA binding activity, ATPase activity, and helicase activity of an Mcm4,6,7 complex containing the protein (JBC (1997) 272, 24508-24513).

When the protein used as an index is Mcm8, the function of the protein can be evaluated (measured) by, for example, detecting binding between the protein and an Mcm4,6,7 complex (Nucleic Acids Res. (2003) 31, 570-579).

When the protein used as an index is Cdc7, the function of the protein can be evaluated (measured) by, for example, detecting the phosphorylation activity of the protein using an MCM complex as the substrate (EMBO (1997) 16, 4340-4351).

When the protein used as an index is cdc5, the function of the protein can be evaluated (measured) by, for example, detecting the transcription activation ability of the protein (JBC (1998) 273, 4666-4671).

When the protein used as an index is Psf1, the function of the protein can be evaluated (measured) by, for example, detecting the formation of a GINS complex between Psf1-4 containing the protein and Sld5, or by detecting binding of Dpb1, Sld3, and Cdc47 to the Ori sequence by GINS (Genes & Dev. (2003) 17, 1153-1165).

When the protein used as an index is Psf2, the function of the protein can be evaluated (measured) by, for example, detecting the formation of a GINS complex between Psf1-4 containing the protein and Sld5, or by detecting binding of Dpb11, Sld3, and Cdc47 to the Ori sequence by GINS (Genes & Dev. (2003) 17, 1153-1165).

When the protein used as an index is Psf3, the function of the protein can be evaluated (measured) by, for example, detecting the formation of a GINS complex between Psf1-4 containing the protein and Sld5, or by detecting binding of Dpb11, Sld3, and Cdc47 to the Ori sequence by GINS (Genes & Dev. (2003) 17, 1153-1165).

When the protein used as an index is Cdc45, the function of the protein can be evaluated (measured) by, for example, detecting binding of the protein to Mcm7 and Polα p70 (Eur. J. Biochem. 265, 936-943).

When the protein used as an index is Polα p180, the function of the protein can be evaluated (measured) by, for example, detecting the formation of a tetramer composed of Polα p180, p70, p58, and p48 containing the protein, or by detecting the primase or polymerase activity of this complex (Eur. J. Biochem. 222, 781-793).

When the protein used as an index is Polα p70, the function of the protein can be evaluated (measured) by, for example, detecting the formation of a tetramer composed of Polα p180, p70, p58, and p48 containing the protein, or by detecting the primase or polymerase activity of this complex (Eur. J. Biochem. 222, 781-793).

When the protein used as an index is Polα Spp1 (p58), the function of the protein can be evaluated (measured) by, for example, detecting the formation of a tetramer composed of Polα p180, p70, p58, and p48 containing the protein, or by detecting the primase or polymerase activity of this complex (Eur. J. Biochem. 222, 781-793).

When the protein used as an index is RPA70, the function of the protein can be evaluated (measured) by, for example, detecting the binding of the protein to ssDNA (Nature (1997) 385, 176-181).

When the protein used as an index is RPA34, the function of the protein can be evaluated (measured) by, for example, detecting binding of the protein to ssDNA or by using an in vitro replication assay including the protein (JBC (1990) 265, 3177-3182).

When the protein used as an index is PCNA, the function of the protein can be evaluated (measured) by, for example, using an in vitro replication assay including the protein (JBC (1990) 265, 3177-3182).

When the protein used as an index is Ligase 1, the function of the protein can be evaluated (measured) by, for example, the DNA ligation activity involving the protein (PNAS (1990) 87, 6679-6683).

When the protein used as an index is Polε Pol2, the function of the protein can be evaluated (measured) by, for example, detecting the DNA synthesis activity of a Polε purified preparation containing the protein (PNAS (1990) 87, 6664-6668).

When the protein used as an index is Polε Dpb3, the function of the protein can be evaluated (measured) by, for example, detecting the DNA synthesis activity of a purified Polε preparation containing the protein (PNAS (1990) 87, 6664-6668).

When the protein used as an index is Topoisomerase 1, the function of the protein can be evaluated (measured) by, for example, detecting the relaxing activity of the protein using plasmid DNA as the substrate (PNAS (1988) 85, 2543-2547).

When the protein used as an index is TDP1, the function of the protein can be evaluated (measured) by, for example, detecting the activity of the protein which liberates a tyrosine residue bound to the 3' end of ssDNA (Science (1999) 286, 552-555).

When the protein used as an index is FEN1, the function of the protein can be evaluated (measured) by, for example, detecting the flap structure removal activity using as the substrate double-strand DNA having a 5'-overhanging flap structure (Genomics (1995) 25, 220-225).

When the protein used as an index is Polδ P125, the function of the protein can be evaluated (measured) by, for example, detecting the formation of a heterotetramer by the protein and Polδ P68, P50, and P12 (Biochemistry 2002 41(44): 13133-13142).

When the protein used as an index is Polε Dpb4, the function of the protein can be evaluated (measured) by, for example, detecting the DNA synthesis activity of a purified Polε preparation containing the protein (PNAS (1990) 87, 6664-6668).

When the protein used as an index is DNA2, the function of the protein can be evaluated (measured) by, for example, detecting ssDNA binding ability and ATPase activity (PNAS (1995) 92, 7642-7646).

When the protein used as an index is ATR, the function of the protein can be evaluated (measured) by, for example, binding the protein to double-strand DNA having a UV-damaged site, or by detecting phosphorylation by the protein using p53 protein as the substrate (PNAS (2002) 99, 6673-6678).

When the protein used as an index is Chk1, the function of the protein can be evaluated (measured) by, for example, detecting phosphorylation by the protein using p53 protein as the substrate (Genes Dev. (2000) 14, 289-300).

When the protein used as an index is NBS1, the function of the protein can be evaluated (measured) by, for example, detecting the formation of a complex of the protein with Mre11/Rad50 in response to DNA damage (Cell (1998) 93, 477-486).

When the protein used as an index is Hus1, the function of the protein can be evaluated (measured) by, for example, detecting the formation of a complex of the protein with Rad1 and Rad9 in response to DNA damage (JCB (1999) 274, 567-570).

When the protein used as an index is Rad1, the function of the protein can be evaluated (measured) by, for example, detecting the formation of a complex of the protein with Rad1 and Rad9 in response to DNA damage (JCB (1999) 274, 567-570).

When the protein used as an index is Mad2, the function of the protein can be evaluated (measured) by, for example, detecting the formation of a complex of the protein and Mad1 (Science 274 (1996) 246-248).

When the protein used as an index is Ctf18, the function of the protein can be evaluated (measured) by, for example, detecting the formation of a complex of the protein with Ctf8 and Dcc1 (JBC (2003) 30051-30056).

When the protein used as an index is Scc1, the function of the protein can be evaluated (measured) by, for example, detecting the formation of a 14S cohesin complex of the protein with Smc1, Smc3, and Scc1 (JCB (2000) 151, 749-761).

When the protein used as an index is Scc3, the function of the protein can be evaluated (measured) by, for example, detecting the formation of a 14S cohesin complex of the protein with Smc1, Smc3, and Scc1 (JCB (2000) 151, 749-761).

When the protein used as an index is UNG, the function of the protein can be evaluated (measured) by, for example, detecting glycosylase activity using deoxyuridine in ssDNA as the substrate (EMBO (1989) 8, 3121-3125).

When the protein used as an index is MBD4, the function of the protein can be evaluated (measured) by, for example, detecting the binding activity of the protein to a methylated CpG sequence (MCB (1998) 18, 6538-6547).

When the protein used as an index is NTH1, the function of the protein can be evaluated (measured) by, for example, detecting the glycosylase activity and AP lyase activity of the protein (PNAS (1997) 94, 109-114).

When the protein used as an index is NEIL2, the function of the protein can be evaluated (measured) by, for example, detecting the AP lyase activity of the protein using DNA having a damaged base as the substrate (JBC (2002) 277, 30417-30420).

When the protein used as an index is NEIL3, the function of the protein can be evaluated (measured) by, for example, detecting the AP lyase activity of the protein using DNA containing an 8-oxo, AP site, and 5-hydroxycytosine as the substrate (Nucleic Acids Res. (2002) 316, 853-866).

When the protein used as an index is APE2, the function of the protein can be evaluated (measured) by, for example, detecting the AP endonuclease activity of the protein (JMB (2002) 316, 853-866).

When the protein used as an index is PARP1, the function of the protein can be evaluated (measured) by, for example, detecting the ADP-ribose polymerase activity of the protein on nicked DNA using ADP-ribose as the substrate (JBC (1990) 35, 21907-21913).

When the protein used as an index is PNK, the function of the protein can be evaluated (measured) by, for example, detecting the polynucleotide kinase activity using oligo(dT) as the substrate (JBC (1999) 274, 24176-24186).

When the protein used as an index is Polβ, the function of the protein can be evaluated (measured) by, for example, detecting the gap-filling polymerase activity of the protein (Biochemistry (1988) 901-909).

When the protein used as an index is MGMT, the function of the protein can be evaluated (measured) by, for example, detecting a reaction in which a methyl group is transferred from methylated DNA by the protein (JBC (1990) 265, 14754-14762).

When the protein used as an index is TDG, the function of the protein can be evaluated (measured) by, for example, detecting the mismatched thymidine-cleaving activity of the protein (JBC (1993) 268, 21218-21224).

When the protein used as an index is MSH2, the function of the protein can be evaluated (measured) by, for example, detecting binding of the protein to double-strand DNA containing a mismatch (Cancer Res. (1994) 54, 5539-5542).

When the protein used as an index is PMS1, the function of the protein can be evaluated (measured) by, for example, detecting DNA binding ability and ATPase activity of the protein (Nucleic Acids Res. (2003) 31, 2025-2034).

When the protein used as an index is PMS2, the function of the protein can be evaluated (measured) by, for example, detecting the interaction of the protein with MLH1 (Hum. Mutat. 19, 108-113).

When the protein used as an index is Exonuclease 1, the function of the protein can be evaluated (measured) by, for example, detecting the exonuclease activity of the protein (Nucleic Acids Res. (1998) 26, 3762-3768).

When the protein used as an index is XPC, the function of the protein can be evaluated (measured) by, for example, detecting the binding ability of the protein to ssDNA (EMBO (1994) 15, 1831-1843).

When the protein used as an index is Rad23A, the function of the protein can be evaluated (measured) by, for example, detecting the interaction of its N terminal with the 26S proteasome and binding of its C terminal with Rad4 (Nature (1998) 391, 715-718).

When the protein used as an index is Rad23B, the function of the protein can be evaluated (measured) by, for example, detecting the interaction of its N terminal with the 26S proteasome and binding of its C terminal with Rad4 (Nature (1998) 391, 715-718).

When the protein used as an index is CSA, the function of the protein can be evaluated (measured) by, for example, detecting the interaction of the protein with CSB and TFIIH (Cell (1995) 82, 555-564).

When the protein used as an index is CSB, the function of the protein can be evaluated (measured) by, for example, detecting the DNA-dependent ATPase activity of the protein (JBC (1997) 272, 1885-1890).

When the protein used as an index is XPG, the function of the protein can be evaluated (measured) by, for example, detecting the endonuclease activity of the protein using a partial duplex having a bubble structure as the substrate (Nature (1994) 371, 423-425).

When the protein used as an index is XPF, the function of the protein can be evaluated (measured) by, for example, detecting the formation of a complex between the protein and ERCC1, and the endonuclease activity of the protein using DNA having a stem-loop structure as the substrate (Cell (1996) 86, 811-822).

When the protein used as an index is DDB1, the function of the protein can be evaluated (measured) by, for example, detecting the binding of the protein to UV-irradiated DNA (JBC (1993) 268, 21293-21300).

When the protein used as an index is XAB2, the function of the protein can be evaluated (measured) by, for example, detecting the interaction of the protein with XPA, CSA, CSB, and RNA polymerase II (JBC (2000) 275, 34931-34937).

When the protein used as an index is DDB2, the function of the protein can be evaluated (measured) by, for example, detecting the binding activity of the protein to UV-damaged DNA (DNA Repair (2002) 6, 601-616).

When the protein used as an index is Topoisomerase IIIb, the function of the protein can be evaluated (measured) by, for example, detecting the interaction with RecQ5 helicase (Nucleic Acids Res. (2000) 28, 1647-1655).

When the protein used as an index is Rad51, the function of the protein can be evaluated (measured) by, for example, detecting the ssDNA-dependent ATPase activity of the protein (JBC (2002) 277, 14417-14425).

When the protein used as an index is Rad51D, the function of the protein can be evaluated (measured) by, for example, detecting the ssDNA-binding ability of a Rad51B/Rad51C/Rad51D/Xrcc2 complex containing the protein, and detecting the ssDNA-dependent ATPase activity (Genes Dev. (2001) 15, 329-3307).

When the protein used as an index is XRCC2, the function of the protein can be evaluated (measured) by, for example, detecting the ssDNA-binding ability of a Rad51B/Rad51C/Rad51D/Xrcc2 complex containing the protein, and the ssDNA-dependent ATPase activity (Nature (1999) 401, 397-399).

When the protein used as an index is Rad54, the function of the protein can be evaluated (measured) by, for example, detecting the DNA-dependent ATPase activity of the protein (Curr. Biol (1996) 6, 828-838).

When the protein used as an index is BRCA1, the function of the protein can be evaluated (measured) by, for example, detecting the E3 ubiquitin ligase activity of the protein (EMBO J. (2002) 21, 6755-6762).

When the protein used as an index is Ku80, the function of the protein can be evaluated (measured) by, for example, detecting the binding of the protein to a DNA terminal and the formation of a complex with Ku70 (PNAS (1990) 87, 1777-1781).

When the protein used as an index is XRCC4, the function of the protein can be evaluated (measured) by, for example, detecting binding of the protein to Ligase4 and the DNA binding of the protein (Cell (1995) 83, 1079-1089).

When the protein used as an index is Ubc13, the function of the protein can be evaluated (measured) by, for example, detecting the ubiquitin conjugating activity of the protein (Cell (1999) 96, 645-653).

When the protein used as an index is Rad6A, the function of the protein can be evaluated (measured) by, for example, detecting the formation of a complex of the protein with Rad18 (PNAS (1991) 88, 8865-8869).

When the protein used as an index is Rad18, the function of the protein can be evaluated (measured) by, for example, detecting DNA binding of the protein (Nucleic Acids Res. (2000) 28, 2847-2854).

When the protein used as an index is FBH1, the function of the protein can be evaluated (measured) by, for example, detecting the helicase activity of the protein (JCB (2002) 277, 24530-24537).

When the protein used as an index is Poli, the function of the protein can be evaluated (measured) by, for example, detecting the activity of carrying out primer extension from mismatched partial duplex DNA (JBC (2001) 276, 30615-30622).

When the protein used as an index is DUT1, the function of the protein can be evaluated (measured) by, for example, detecting the dUTPase activity of the protein (J. Biol. Chem. (1996) 271, 7745-7751).

When the protein used as an index is Tin2, the function of the protein can be evaluated (measured) by, for example, detecting the interaction between the protein and TRF1 (Nat Genet (1999) 23, 405-412).

When the protein used as an index is Sir2, the function of the protein can be evaluated (measured) by, for example, a histone deacetylation assay for the protein (Gene (1999) 234, 161-168).

When the protein used as an index is Elg1, the function of the protein can be evaluated by, for example, detecting the formation of a complex of the protein with RFC2, RFC3, RFC4, and RFC5 (EMBO J. (2003) 22, 4304-4313).

When the protein used as an index is TIMELESS, the function of the protein can be evaluated (measured) by, for example, detecting the formation of a complex of the protein with mammalian clock period proteins (mPERs) (Science (2003) 302, 439-442).

When the protein used as an index is Pif1, the function of the protein can be evaluated (measured) by, for example, detecting the ATP-dependent helicase activity and DNA-dependent ATPase activity of the protein.

When the protein used as an index is Mms4, the function of the protein can be evaluated (measured) by, for example, detecting the endonuclease activity of a complex of the protein with Mus81 protein (JBC (2003) 278, 21715-21720).

When the protein used as an index is Topoisomerase IIIa, the function of the protein can be evaluated (measured) by, for example, detecting the topoisomerase activity of the protein (Nucleic Acids Res. (2002) 30, 4823-4829).

When the protein used as an index is Mus81, the function of the protein can be evaluated (measured) by, for example, detecting the endonuclease activity of a complex of the protein with Mms4 protein (JBC (2003) 278, 21715-21720).

When the protein used as an index is SIRT1, the function of the protein can be evaluated (measured) by, for example, detecting the NAD-dependent histone deacetylase of the protein (Nature (2000) 403, 795-800).

When the protein used as an index is ESP1, the function of the protein can be evaluated (measured) by, for example, detecting the protease activity of the protein (FEBS Lett. (2002) 528, 246-250).

When the protein used as an index is MPG, the function of the protein can be evaluated (measured) by, for example, detecting the glycosylase activity of the protein (Carcinogenesis (1996) 17, 2177-2182).

When the protein used as an index is Poll, the function of the protein can be evaluated (measured) by, for example, detecting the DNA polymerase activity of the protein (J Biol Chem. (2000) 275, 31233-31238).

When the protein used as an index is Polm, the function of the protein can be evaluated (measured) by, for example, detecting the DNA polymerase activity of the protein (J Biol Chem. (2002) 277, 44582-44587).

When the protein used as an index is EndoV, the function of the protein can be evaluated (measured) by, for example, detecting the endonuclease activity of the protein.

When the protein used as an index is KNTC2 (NDC80), the function of the protein can be evaluated (measured) by, for example, detecting the formation of a complex of the protein with human Nuf2 protein (Mol Biol Cell. (2005) 16, 519-531).

Next, a compound is selected which lowers the activity of a protein encoded by a chromosome stabilization-associated gene as compared to that measured in the absence of the test compound. Although a protein encoded by the gene used in this method is preferably an unmutated full-length protein, it may be a protein in which a portion of the amino acid sequence has been substituted and/or deleted so long as it has activity equivalent to that of the protein.

The present invention also provides anticancer agents (pharmaceutical compositions for treating cancers) which comprise as an active ingredient a cancer cell-specific apoptosis inducing agent of the present invention.

The present invention also provides methods for producing apoptosis inducing agents or anticancer agents as pharmaceutical compositions. In this method a compound for the cancer cell-specific apoptosis inducing agent is first selected using a screening method of the present invention. Then, the selected compound is combined with a pharmaceutically acceptable carrier. Such a pharmaceutically acceptable carrier can include, but is not limited to, for example, detergents, excipients, coloring agents, flavoring agents, preservatives, stabilizers, buffers, suspensions, isotonizing agents, binders, disintegrating agents, lubricants, fluidizing agents, and correctives. Other conventional carriers can be also used appropriately.

The agents such as apoptosis inducing agents and anticancer agents of the present invention can be formulated by adding the above-indicated carriers as required and according to conventional methods. More specifically, such carriers include: light anhydrous silicic acid, lactose, crystalline cellulose, mannitol, starch, carmellose calcium, carmellose sodium, hydroxypropyl cellulose, hydroxypropylmethyl cellulose, polyvinylacetaldiethylamino acetate, polyvinylpyrrolidone, gelatin, medium chain triglyceride, polyoxyethylene hydrogenated castor oil 60, saccharose, carboxymethyl cellulose, cornstarch, and inorganic salts.

The dosage forms for the agents described above include, for example, oral forms, such as tablets, powders, pills, dispersing agents, granules, fine granules, soft and hard capsules, film-coated tablets, pellets, sublingual tablets, and pastes; and parenteral forms, such as injections, suppositories, endermic liniments, ointments, plasters, and liquids for external use. Those skilled in the art can select the optimal dosage form depending on the administration route, subject, and such. Viral vectors such as retrovirus, adenovirus, and Sendai virus vectors, and non-viral vectors such as liposomes, may be used to introduce, into the living body, DNAs expressing proteins encoded by chromosome stabilization-associated genes (for example, the aforementioned genes), or DNAs expressing antisense RNAs, ribozymes, or siRNAs that suppress chromosome stabilization-associated genes. Alternatively, non-viral vectors such as liposomes, polymer micelles, or cationic carriers, may be used to introduce, into the living body, synthetic antisense nucleic acids or synthetic siRNAs that suppress chromosome stabilization-associated genes. The introduction methods include, for example, in-vivo and ex-vivo methods.

The present invention also includes pharmaceutical compositions comprising the above-described apoptosis-inducing action.

Ultimately, the dose of an agent or pharmaceutical composition of the present invention can be appropriately determined by a physician considering the dosage form, administration method, patient's age, weight, symptoms, etc.

The present invention also relates to methods for inducing apoptosis in desired cancer cells. A preferred embodiment of these methods is a method for inducing apoptosis in cells in which one wishes to induce apoptosis (target cells), comprising a step of administering (contacting) an apoptosis-inducing agent of the present invention to the cells. For example, when the active ingredient of an apoptosis-inducing agent of the present invention is a nucleic acid, that ingredient (the nucleic acid) is preferably introduced into the target cells.

Moreover, the present invention relates to a method for treating cancer comprising a step of administering an apoptosis-inducing agent or anticancer agent of the present invention to an individual (e.g., cancer patient).

The "individual" in the aforementioned treatment method normally refers to a cancer patient, and although there are no particular limitations, it is preferably a human. In general, administration to an individual can be carried out by a method known to those skilled in the art, examples of which include intraarterial injection, intravenous injection, and subcutaneous injection. Although the dosage varies depending on the weight and age of the patient, administration method, and so on, a suitable dosage can be appropriately selected by those skilled in the art. In addition, if the compound can be encoded by DNA, gene therapy can also be carried out by incorporating the DNA in a vector for gene therapy. Examples of vectors for gene therapy include viral vectors such as retroviral vectors, adenoviral vectors, and adeno-associated viral vectors, and non-viral vectors such as liposomes. A desired DNA can be administered to a patient by an ex vivo method or in vivo method using such a vector. In addition, a nucleic acid of the present invention can also be administered directly to an individual.

The present invention also relates to the use of a compound that inhibits chromosome stabilization (for example, a compound which inhibits expression of a gene of the present invention, or inhibits the function of a protein encoded by the gene) for producing an apoptosis-inducing agent or anticancer agent.

All prior art documents cited in the present specification are incorporated herein by reference.

EXAMPLES

The present invention will be described in detail below with reference to Examples, but is not to be construed as being limited thereto.

In the Examples, genes used as "chromosome stabilization-associated genes" are the following 97 genes:

APE2, ATR, BRCA1, Chk1, Cdc5, Cdc6, Cdc7, Cdc45, Cdt1, CSA, CSB, Ctf18, DDB1, DDB2, DNA2, DUT, Elg1, EndoV, Esp1, Exonuclease1, FBH1, FEN1, Geminin, Hus1, KNTC2 (NDC80), Ku80, Ligase1, Mad2, MBD4, Mcm3, Mcm4, Mcm5, Mcm6, Mcm7, Mcm8, Mcm10, MGMT, MLH3, Mms4, MPG, MSH2, Mus81, NBS1, NEIL2, NEIL3, NTH1, Orc1, Orc3, PARP1, PCNA, Pif1, PMS1, PMS2, PNK, Polα p180, Polα p70, Polα Spp1(Prim2a), Polβ, Polδ p125, Polε Dpb3, Polε Dpb4, Polε Pol2, Polι, Polλ, Polμ, Psf1, Psf2, Psf3, Rad1, Rad18, Rad23A, Rad23B, Rad51, Rad51D, Rad54, Rad6A, RPA34, RPA70, Scc1, Scc3, Sir2, SIRT1 (Sirtuin), TDG, TDP1, TIMELESS, Tin2, Topoisomerase I, Topoisomerase IIIa, Topoisomerase IIIb, Ubc13, UNG, XAB2, XPC, XPF, XPG, Xrcc2, and XRCC4.

Example 1

Cell Culturing

HeLa (human cervical carcinoma cells) and TIG3 (normal diploid fibroblasts) cells were used as human cultured cells. These human cultured cells were cultured in Dulbecco's modified Eagle's medium containing 10% fetal calf serum and 50 μg/ml gentamicin under conditions of 37° C. and 5% $CO_2$.

Example 2

Study of Chromosome Stabilization-Associated Gene Expression Inhibition's Effects on Cancer Cell Proliferation siRNA was selected for each of the aforementioned genes for the purpose of studying the effects of chromosome stabilization-associate gene expression inhibition on cancer cell proliferation. Synthesis of siRNA was carried out at Qiagen (Tokyo) and Dhamacon, Inc. (Colorado, USA).

The siRNA sequences for the aforementioned genes are shown in the column entitled "siRNA sequence" of FIGS. 1 to 4. Only the sense strands are shown in the Sequence Listing, and the corresponding antisense strands are omitted. In addition, the "dTdT" sequence of each siRNA sequence is abbreviated as "TT" in the Sequence Listing.

These siRNAs were introduced into human cervical carcinoma HeLa cells. More specifically, HeLa cells were inoculated and grown in a 24-well plate 24 hours prior to transfection of siRNA, and then transfection was performed at 20 to 50% confluence. Oligofectamine (Invitrogen) was used as the transfection reagent, and transfection was carried out according to the attached manual. mRNA expression of each gene was quantified by Taqman PCR 48 hours after introduction.

More specifically, total RNA was extracted from the cells 48 hours after transfection of siRNA using the RNeasy Mini Kit (Qiagen). The ABI PRISM 7000 Sequence Detection System (Applied Biosystems) was used for quantitative PCR. RT-PCR primers and TaqMan probes for each of the aforementioned genes and β-actin gene were purchased from Applied Biosystems. The TaqMan One-Step RT-PCR Master Mix Reagents Kit (Applied Biosystems) was used as the RT-PCR reaction reagents, and RT-PCR was carried out according to the attached manual. Comparative quantifications were carried out using β-actin as a standard.

The expression of each mRNA in cells to which each siRNA was introduced was compared to a value of 100% representing the expression of each mRNA in cells to which the control RNA (NS) was introduced. The siRNA for each gene was found to efficiently inhibit expression of each mRNA as shown in the column entitled "Inhibition of gene expression in HeLa cells" of FIGS. 1 to 4.

Example 3

Survival Rates of HeLa Cells

The siRNA for each of the aforementioned genes selected in Example 2 was respectively introduced into HeLa cells followed by an investigation of the cell survival rates 4 days later by an MTT assay. The number of viable cells 96 hours after introduction was measured using the viable cell measurement reagent SF (Nacalai Tesque).

As a result, prominent decreases in the survival rates were observed in HeLa cells to which siRNA of each of the aforementioned genes was introduced, as shown in the column entitled "MTT assay (HeLa cells)" of FIGS. 1 to 4.

Example 4

Apoptosis-Inducing Effects of siRNA in HeLa Cells

An investigation was made as to whether or not the decreases in survival rates in HeLa cells into which siRNA for each of the aforementioned genes was introduced occurred due to apoptosis. siRNA for each gene was introduced into HeLa cells, and apoptosis induction in the HeLa cells 48 hours after introduction was studied using the TUNEL method.

As a result, apoptosis was observed to be prominently induced in all HeLa cells to which siRNA for each of the aforementioned genes was introduced, as shown in the column entitled "TUNEL method" of FIGS. 1 to 4 and in the photographs of FIGS. 5 to 9. On the other hand, induction of apoptosis was not observed in HeLa cells to which the control RNA (NS) was introduced (upper left panel "Non-specific" in FIG. 5).

Namely, it was revealed that effective induction of apoptosis occurs as a result of inhibiting the expression of each of the aforementioned genes of the present invention.

Example 5

Effects of siRNA on Normal Cell Proliferation

A study was conducted on the effects of siRNA for each of the aforementioned genes on the proliferation of normal cells, human fetal lung-derived diploid fibroblast TIG3 cells. Lipofectamine 2000 (Invitrogen) was used as the transfection reagent, and siRNA for each of the aforementioned genes was respectively introduced into TIG3 cells followed by measurement of mRNA expression of each gene by Taqman PCR 48 hours after introduction. In this experiment, expression of each mRNA in TIG3 cells into which each siRNA was introduced was compared to a value of 100% representing the expression of each mRNA in TIG3 cells into which control RNA (NS) was introduced.

As a result, mRNA expression of each of the aforementioned genes in TIG3 cells to which each siRNA was introduced was inhibited considerably as compared with expression of these mRNA in TIG3 cells to which the control RNA (NS) was introduced, as shown in the column entitled "Inhibition of gene expression in TIG3 cells" of FIGS. 1 to 4.

Example 6

Survival Rates of TIG3 Cells

The aforementioned siRNAs were respectively introduced into TIG3 cells followed by an investigation of the cell survival rates 4 days later by MTT assay. As a result, the survival rates of TIG3 cells to which siRNA for each of the aforementioned genes was introduced were comparatively higher than the survival rates of HeLa cells to which the same siRNA was introduced, and there were no prominent decreases in survival rates observed, as shown in the column entitled "MTT assay (TIG3 cells)" of FIGS. 1 to 4.

From these results, it is thought that apoptosis is induced cancer cell-specifically through the inhibition of the expression of genes of the present invention.

Example 7

Analysis of Genome Breakdown Process Using Anti-Single-Strand DNA Antibody

Anti-single-strand DNA (anti-ssDNA) antibody is an antibody which specifically recognizes single-strand DNA. It is said that if the genomic structure of DNA, which are originally composed of double strands, is broken down due to a chromosome destabilization such as DNA damage, a single strand region will be partially exposed. Thus, the use of this antibody makes it possible to specifically recognize and visualize this genome breakdown process.

HeLa cells were inoculated on a slide glass and transfected with siRNA for each of the aforementioned genes. The cells were then fixed in formalin about 30 hours after siRNA introduction, and reacted with anti-ssDNA antibody as the primary antibody. The cells were then observed with a confocal laser microscope using a fluorescent-labeled antibody against the anti-ssDNA antibody as the secondary antibody. As a result, nuclei having single-strand DNA were stained green as shown in FIGS. 10 to 27.

Namely, DNA damage including single-strand DNA formation was confirmed to occur due to inhibition of expression of each of the aforementioned genes.

Example 8

Cell Culturing

The 11 genes indicated below were used as "chromosome stabilization-associated genes" in the following Examples.

Pif1, Mms4, Topoisomerase IIIa, Mus81, SIRT1 (Sirtuin), Esp1, MPG, Polι, Polm, EndoV, and KNTC2 (NDC80)

In addition to the HeLa cells and TIG3 cells described in Example 1, normal human skin-derived diploid fibroblasts (HDF cells) were used as human cultured cells. Culturing was carried out under the same conditions as Example 1.

Example 9

Study of Chromosome Stabilization-Associated Gene Expression Inhibition's Effects on Cancer Cell Proliferation siRNA for each of the aforementioned genes was selected for the purpose of studying the effects of inhibition of the expression of the aforementioned 11 chromosome stabilization-associated genes on proliferation of cancer cells. siRNA synthesis was carried out in the same manner as Example 2.

The siRNA sequences of the aforementioned 11 genes are shown in the column entitled "siRNA sequence" of FIGS. 28 to 32. Only the sense strands are shown in the Sequence Listing, and the corresponding antisense strands are omitted.

These siRNAs were introduced into HeLa cells, specifically under the same conditions as described in Example 2. mRNA expression of the aforementioned 11 genes was quantified by Taqman PCR 48 hours after introduction. Quantification was carried out using the same method as Example 2.

The expression of each mRNA in cells to which each siRNA was introduced was compared to a value of 100% representing the expression of each mRNA in cells to which the control RNA (NS) was introduced. The siRNA for each gene was found to have efficiently inhibited expression of each mRNA as shown in the column entitled "Inhibition of gene expression in 40 nM HeLa cells" of FIGS. 28 to 30, the column entitled "mRNA Expression" in HeLa cells of FIG. 31, or the column entitled "Expression" in HeLa cells of FIG. 32.

Example 10

Survival Rate of HeLa Cells

The siRNA for each of the aforementioned 11 genes was respectively introduced into HeLa cells followed by investigation of the cell survival rates by MTT assay 4 days after introduction. The number of viable cells at 96 hours after introduction was measured using viable cell measurement reagent SF (Nacalai Tesque).

As a result, prominent decreases in survival rates were observed in HeLa cells to which siRNA for each of the aforementioned genes was introduced, as indicated in the column entitled "Inhibition of proliferation in 40 nM HeLa cells" of FIGS. 28 to 30, the column entitled "Inhibition of proliferation" in HeLa cells of FIG. 31, or the column entitled "Proliferation" in HeLa cells of FIG. 32.

Example 11

Apoptosis-Inducing Effects of siRNA in HeLa Cells

An investigation was made as to whether or not the decreases in survival rates in HeLa cells to which siRNA for each of the aforementioned 11 genes was introduced occurred due to apoptosis. siRNA for each gene was introduced into HeLa cells, and apoptosis induction in the HeLa cells 48 hours after introduction was studied using the TUNEL method.

As a result, apoptosis was observed to be prominently induced in all HeLa cells to which siRNA for each of the aforementioned genes was introduced, as shown in the column entitled "Apoptosis" in HeLa cells of FIG. 31, the column entitled "Apoptosis" in HeLa cells of FIG. 32, the photographs entitled "HeLa cells" of FIGS. 33 and 34, and the photograph of TUNEL staining of HeLa cells of FIG. 35.

Namely, it was clarified that effective induction of apoptosis occurs as a result of inhibiting the expression of each of the aforementioned genes of the present invention.

Example 12

Effects of siRNA on Normal Cell Proliferation

A study was conducted on the effects of siRNA for each of the aforementioned 11 genes on the proliferation of normal cells, human fetal lung-derived diploid fibroblast TIG3 cells or human skin fibroblast HDF cells. Lipofectamine 2000 (Invitrogen) was used as the transfection reagent, and siRNA for each of the aforementioned genes was respectively introduced into the TIG3 cells or HDF cells followed by measurement of mRNA expression of each gene by Taqman PCR 48 hours after introduction. In this experiment, expression of each mRNA in TIG3 cells or HDF cells to which each siRNA was introduced was compared to a value of 100% representing the expression of each mRNA in TIG3 cells or HDF cells to which control RNA (NS) was introduced.

As a result, mRNA expression of each of the aforementioned genes in TIG3 cells or HDF cells to which each siRNA was introduced was inhibited considerably as compared with expression of these mRNA in TIG3 cells or HDF cells to which the control RNA (NS) was introduced, as shown in the column entitled "Inhibition of gene expression in 40 nM TIG3 cells" of FIGS. 28 to 30, the column entitled "mRNA Expression" in HDF cells of FIG. 31, or the column entitled "Expression" in HDF cells of FIG. 32.

Example 13

Survival Rates of TIG3 Cells and HDF Cells siRNA for each of the aforementioned 11 genes was respectively introduced into TIG3 cells or HDF cells followed by an investigation of the cell survival rates 4 days later by MTT assay. As a result, the survival rates of TIG3 cells or HDF cells to which siRNA for each of the aforementioned genes was introduced were comparatively higher than the survival rates of HeLa cells to which the same siRNA was introduced, and there were no prominent decreases in survival rates observed, as shown in the column entitled "Inhibition of proliferation in 40 nM TIG3 cells" of FIGS. 28 to 30, the column entitled "Inhibition of proliferation" in HDF cells of FIG. 31, or the column entitled "Proliferation" in HDF cells of FIG. 32.

From these results, it is thought that apoptosis is cancer cell-specifically induced through the inhibition of the expression of genes of the present invention.

Example 14

Analysis of Genome Breakdown Process Using Anti-Single-Strand DNA Antibody

HeLa cells were inoculated onto a slide glass and transfected with siRNA for each of the genes of Pif1, Mms4, Topoisomerase IIIa, Mus81, SIRT1 (Sirtuin), Esp1, MPG, Polι, Polm, and EndoV. The cells were then fixed in formalin for about 30 hours after introduction of siRNA, and reacted with anti-ssDNA antibody as the primary antibody. The cells were then observed with a confocal laser microscope using a fluorescent-labeled antibody against the anti-ssDNA antibody as the secondary antibody. As a result, nuclei having single-strand DNA were stained green as shown in FIG. 36.

Namely, DNA damage including single-strand DNA formation was confirmed to occur due to inhibition of expression of each of the aforementioned genes.

INDUSTRIAL APPLICABILITY

The present invention's compounds which inhibit chromosome stabilization in cells or compounds which inhibit the function of a chromosome stabilization-associated gene have an action to induce cancer cell-specific apoptosis. Pharmaceutical compositions comprising such compounds are believed to become anticancer agents having apoptosis-induction as the mechanism of action, while also having few adverse side effects. The present invention provides, for the first time, cancer cell-specific anticancer agents which have apoptosis-induction as the mechanism of action and which target chromosome stabilization-associated genes.

Even if certain compounds are found to have an apoptosis-inducing action, it is difficult to use the compounds as pharmaceuticals when their apoptosis-inducing actions in normal cells are unknown. This is because there may be a risk of adverse effects when the compounds have apoptosis-inducing actions in normal cells. In other words, if the compounds have apoptosis-inducing actions not specific to cancer cells, in general, it is practically difficult to use the compounds as pharmaceuticals. Accordingly, the agents (the compounds) of the present invention are very practical and effective because their apoptosis-inducing actions are specific to cancer cells.

The mechanism by which apoptosis is induced cancer cell-specifically by inhibition of chromosome stabilization can be explained in the following manner based on findings of the present inventors.

Numerous cancer cells are known to have mutations or deletions in the cancer suppressor gene p53. In addition, oncogenesis is known to take place in some cases due to the occurrence of an abnormality in a DNA damage checkpoint mechanism. If the expression of functional chromosome stabilizing genes is inhibited by siRNA or the like and their functions are blocked in cancer cells having an abnormality in p53 or a DNA damage checkpoint mechanism, the chromosome stabilization mechanism will fail and it would no longer be possible to repair chromosomal DNA. In such cells, it is thought that apoptosis will be induced due to the residual DNA damage that has not been repaired. On the other hand, it is thought that in normal cells such as diploid fibroblasts, if the expression of functional chromosome stabilizing genes is inhibited by siRNA or the like and their functions are blocked, the cell cycle will be temporarily interrupted by the action of p53 and the DNA damage checkpoint mechanism, thereby enabling damage in chromosomal DNA to be repaired.

In addition to providing cancer cell-specific apoptosis-inducing agents, the present invention provides extremely useful academic findings for elucidating the mechanism of cancer cell-specific apoptosis induction.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08470798B2). An electronic copy of the "Sequence Listing" will also be available from the USPTO upon request and payment of the fee set forth in 37 CFR 1.19(b)(3).

The invention claimed is:

1. A cancer cell-specific apoptosis-inducing agent, comprising as an active ingredient a double-strand RNA that inhibits expression of a Poli gene, wherein the double-strand RNA comprises: a sense RNA consisting of the sequence of SEQ ID NO: 797; and an antisense RNA consisting of a sequence complementary to said sense RNA.

2. A cancer cell-specific apoptosis-inducing agent, comprising as an active ingredient a DNA encoding a double-strand RNA comprising a sense RNA consisting of the sequence of SEQ ID NO: 797, excluding the terminal TT; and an antisense RNA consisting of a sequence complementary to said sense RNA.

3. An anticancer agent, comprising as an active ingredient an apoptosis-inducing agent of claim 1.

4. An anticancer agent, comprising as an active ingredient an apoptosis-inducing agent of claim 2.

5. A double-strand RNA comprising: a sense RNA consisting of the sequence of SEQ ID NO: 797; and an antisense RNA consisting of a sequence complementary to said sense RNA.

6. A vector comprising a DNA encoding a double-strand RNA comprising a sense RNA consisting of the sequence of SEQ ID NO: 797, excluding the terminal TT; and an antisense RNA consisting of a sequence complementary to said sense RNA.

7. A method for inducing apoptosis of a target cell comprising a step of administering the apoptosis-inducing agent of claim 1 to the cell.

8. A method for inducing apoptosis of a target cell comprising a step of administering the apoptosis-inducing agent of claim 2 to the cell.

9. A method for treating cancer comprising a step of administering the apoptosis-inducing agent of claim 1 to an individual.

10. A method for treating cancer comprising a step of administering the apoptosis-inducing agent of claim 2 to an individual.

* * * * *

UNITED STATES PATENT AND TRADEMARK OFFICE
CERTIFICATE OF CORRECTION

PATENT NO. : 8,470,798 B2  
APPLICATION NO. : 13/473328  
DATED : June 25, 2013  
INVENTOR(S) : Motoki Takagi et al.

Page 1 of 1

It is certified that error appears in the above-identified patent and that said Letters Patent is hereby corrected as shown below:

Title Page, Item (75):
"Motoki Takagi, Shinagawa-ku (JP); Kazunobu Futami, Fujisawa (JP); Akira Shimamoto, Hiroshima (JP); Yasuhiro Furuichi, Kamakura (JP)" should read, --Motoki Takagi, Shinagawa-ku (JP); Kazunobu Futami, Fujisawa-shi (JP); Akira Shimamoto, Hiroshima-shi (JP); Yasuhiro Furuichi, Kamakura-shi (JP)--.

Title Page 2, Item (56), Under Other Publication:
"Machida et al., "Hepatitis C virus induces a mutator phenotype. Enhanced mutations of immunoglobulin and protooncogenes," *PNAS 101*(12):4262-4267, 2004." should read, --Machida et al., "Hepatitis C virus induces a mutator phenotype: Enhanced mutations of immunoglobulin and protooncogenes," *PNAS 101*(12):4262-4267, 2004.--.

In the Specification:

Column 1, Lines 23-29:
"The Sequence Listing associated with this application is provided in text format in lieu of a paper copy, and is hereby incorporated by reference into the specification. The name of the text file containing the Sequence Listing is 390081_402D1_SEQUENCE_LISTING.txt. The text file is 3 MB, was created on May 7, 2012, and is being submitted electronically via EFS-Web." should read, --The Sequence Listing associated with this application is provided in text format in lieu of a paper copy, and is hereby incorporated by reference into the specification. The name of the text file containing the Sequence Listing is 390081_402D1_SEQUENCE_LISTING.txt. The text file is 3.1 MB, was created on November 12, 2013, and is being submitted electronically via EFS-Web.--.

Signed and Sealed this  
Twenty-second Day of April, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,470,798 B2
APPLICATION NO. : 13/473328
DATED : June 25, 2013
INVENTOR(S) : Motoki Takagi et al.

It is certified that error appears in the above-identified patent and that said Letters Patent is hereby corrected as shown below:

On the Title Page:

Item (56):
"Christensen, T. et al., "*Drosophila* Mcm10 Interacts with Members of the Prereplication Complex and Is Required for Proper Chromomsome Condensation," *Molecular Biology of the Cell 14*: 2206-2215, June 2003." should read, --Christensen, T. et al., "*Drosophila* Mcm10 Interacts with Members of the Prereplication Complex and Is Required for Proper Chromosome Condensation," *Molecular Biology of the Cell 14*: 2206-2215, June 2003.--.

Item (56):
"Collis, S. et al., "Enhanced Radiation and Chemothereapy-mediated Cell Killing of Human Cancer Cells by Small Inhibitory RNA Silencing of DNA Repair Factors," *Cancer Research 63*: 1550-1554, April 1, 2003." should read, --Collis, S. et al., "Enhanced Radiation and Chemotherapy-mediated Cell Killing of Human Cancer Cells by Small Inhibitory RNA Silencing of DNA Repair Factors," *Cancer Research 63*: 1550-1554, April 1, 2003.--.

Item (56):
"Fishel, R. et al., "Purified Human MSH2 Proteing Binds to DNA Containing Mismatched Nucleotides," *Cancer Research 54*: 5539-5542, November 1, 1994." should read, --Fishel, R. et al., "Purified Human MSH2 Protein Binds to DNA Containing Mismatched Nucleotides," *Cancer Research 54*: 5539-5542, November 1, 1994.--.

Item (56):
"Yuan, Z. et al., "Polymorhphisms and HNPCC: PMS2-MLH1 Protein Interactions Diminished by Single Nucleotide Polymorphisms," *Human Mutation 19*: 108-113, 2002." should read, --Yuan, Z. et al., "Polymorphisms and HNPCC: PMS2-MLH1 Protein Interactions Diminished by Single Nucleotide Polymorphisms," *Human Mutation 19*: 108-113, 2002.--.

Signed and Sealed this
Twenty-ninth Day of April, 2014

Michelle K. Lee
*Deputy Director of the United States Patent and Trademark Office*